(12) United States Patent
Burgard et al.

(10) Patent No.: US 8,470,582 B2
(45) Date of Patent: Jun. 25, 2013

(54) METHODS AND ORGANISMS FOR THE GROWTH-COUPLED PRODUCTION OF 1,4-BUTANEDIOL

(75) Inventors: Anthony P. Burgard, Bellefonte, PA (US); Stephen J. Van Dien, Solana Beach, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 13/065,303

(22) Filed: Mar. 18, 2011

(65) Prior Publication Data

US 2011/0201071 A1    Aug. 18, 2011

Related U.S. Application Data

(63) Continuation of application No. 11/891,602, filed on Aug. 10, 2007, now Pat. No. 7,947,483.

(51) Int. Cl.
*C12N 1/20* (2006.01)
(52) U.S. Cl.
USPC .................................. 435/252.8; 435/252.33
(58) Field of Classification Search
None
See application file for complete search history.

(56) References Cited

U.S. PATENT DOCUMENTS

| | | |
|---|---|---|
| 4,048,196 A | 9/1977 | Broecker et al. |
| 4,301,077 A | 11/1981 | Pesa et al. |
| 4,430,430 A | 2/1984 | Momose et al. |
| 4,652,685 A | 3/1987 | Cawse et al. |
| 4,876,331 A | 10/1989 | Doi |
| 5,164,309 A | 11/1992 | Gottschalk et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,413,922 A | 5/1995 | Matsuyama et al. |
| 5,461,139 A | 10/1995 | Gonda et al. |
| 5,475,086 A | 12/1995 | Tobin et al. |
| 5,478,952 A | 12/1995 | Schwartz |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |
| 5,602,321 A | 2/1997 | John |
| 5,608,146 A | 3/1997 | Frommer et al. |
| 5,610,041 A | 3/1997 | Somerville et al. |
| 5,650,555 A | 7/1997 | Somerville et al. |
| 5,663,063 A | 9/1997 | Peoples et al. |
| 5,674,978 A | 10/1997 | Tobin et al. |
| 5,705,626 A | 1/1998 | Tobin et al. |
| 5,747,311 A | 5/1998 | Jewell |
| 5,750,848 A | 5/1998 | Krüger et al. |
| 5,770,435 A | 6/1998 | Donnelly et al. |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,156,852 A | 12/2000 | Asrar et al. |
| 6,159,738 A | 12/2000 | Donnelly et al. |
| 6,204,341 B1 | 3/2001 | Asrar et al. |
| 6,228,579 B1 | 5/2001 | Zyskind et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |

(Continued)

FOREIGN PATENT DOCUMENTS

| | | |
|---|---|---|
| GB | 1230276 | 4/1971 |
| GB | 1314126 | 4/1973 |

(Continued)

OTHER PUBLICATIONS

Abe et al., "Biosynthesis from gluconate of a random copolyester consisting of 3-hydroxybutyrate and medium-chain-length 3-hydroxyalkanoates by *Pseudomonas* sp. 61-3," *Int. J. Biol. Macromol.* 16(3):115-119 (1994).
Aberhart and Hsu, "Stereospecific hydrogen loss in the conversion of [2H7]isobutyrate to beta-hydroxyisobutyrate in *Pseudomonas putida*. The stereochemistry of beta-hydroxyisobutyrate dehydrogenase," *J. Chem. Soc. Perkin1.* 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.* 46(10):1724-1734 (2005).
Adams and Kletzin, "Oxidoreductase-type enzymes and redox proteins involved in fermentative metabolisms of hyperthermophilic Archaea," *Adv. Protein Chem.* 48:101-180 (1996).
Aevarsson et al., "Crystal structure of2-oxoisovalerate and dehydrogenase and the architecture of 2-oxo acid dehydrogenase multienzyme complexes," *Nat. Struct. Biol.* 6:785-792 (1999).

(Continued)

*Primary Examiner* — Michele K Joike
(74) *Attorney, Agent, or Firm* — Jones Day

(57) ABSTRACT

The invention provides a non-naturally occurring microorganism comprising one or more gene disruptions, the one or more gene disruptions occurring in genes encoding an enzyme obligatory to coupling 1,4-butanediol production to growth of the microorganism when the gene disruption reduces an activity of the enzyme, whereby the one or more gene disruptions confers stable growth-coupled production of 1,4-butanediol onto the non-naturally occurring microorganism. The microorganism can further comprise a gene encoding an enzyme in a 1,4-butanediol (BDO) biosynthetic pathway. The invention additionally relates to methods of using microorganisms to produce BDO.

6 Claims, 9 Drawing Sheets
(6 of 9 Drawing Sheet(s) Filed in Color)

U.S. PATENT DOCUMENTS

| | | |
|---|---|---|
| 6,329,183 B1 | 12/2001 | Skraly et al. |
| RE37,543 E | 2/2002 | Krüger et al. |
| 6,361,983 B1 | 3/2002 | Ames |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,314,974 B2 | 1/2008 | Cao et al. |
| 7,393,676 B2 | 7/2008 | Gokarn et al. |
| 7,504,250 B2 | 3/2009 | Emptage et al. |
| 7,858,350 B2 | 12/2010 | Burk et al. |
| 7,947,483 B2 | 5/2011 | Burgard et al. |
| 8,067,214 B2 | 11/2011 | Burk et al. |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0203459 A1 | 10/2003 | Chen et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |
| 2005/0164342 A1 | 7/2005 | Tobin |
| 2005/0170480 A1 | 8/2005 | Huisman |
| 2005/0221466 A1 | 10/2005 | Liao et al. |
| 2005/0239179 A1 | 10/2005 | Skraly et al. |
| 2005/0287655 A1 | 12/2005 | Tabata et al. |
| 2006/0041152 A1 | 2/2006 | Cantrell et al. |
| 2006/0046288 A1 | 3/2006 | Ka-Yiu et al. |
| 2006/0073577 A1* | 4/2006 | Ka-Yiu et al. ............... 435/106 |
| 2006/0084155 A1 | 4/2006 | Huisman et al. |
| 2006/0134760 A1 | 6/2006 | Rieping |
| 2006/0141594 A1 | 6/2006 | San et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0120732 A1 | 5/2008 | Elliot |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |
| 2009/0047719 A1 | 2/2009 | Burgard et al. |
| 2009/0075351 A1 | 3/2009 | Burk et al. |
| 2009/0100536 A1 | 4/2009 | Adams et al. |
| 2009/0158452 A1 | 6/2009 | Johnson et al. |
| 2009/0253192 A1 | 10/2009 | Emptage et al. |
| 2010/0099925 A1 | 4/2010 | Kharas |
| 2010/0184171 A1 | 7/2010 | Jantama et al. |
| 2010/0304453 A1 | 12/2010 | Trawick et al. |
| 2010/0330634 A1 | 12/2010 | Park et al. |
| 2011/0014669 A1 | 1/2011 | Madden et al. |
| 2011/0045575 A1 | 2/2011 | Van Dien et al. |
| 2011/0129904 A1 | 6/2011 | Burgard et al. |
| 2011/0190513 A1 | 8/2011 | Lynch |

FOREIGN PATENT DOCUMENTS

| | | |
|---|---|---|
| GB | 1344557 | 1/1974 |
| GB | 1512751 | 6/1978 |
| JP | 62285779 | 12/1987 |
| KR | 1020060011345 A | 2/2006 |
| KR | 100676160 B1 | 1/2007 |
| KR | 100679638 B1 | 1/2007 |
| KR | 1020070021732 A | 7/2007 |
| KR | 1020070096348 A | 10/2007 |
| KR | 10-2009-0025902 | 3/2009 |
| WO | WO 82/03854 | 11/1982 |
| WO | WO 91/00917 | 1/1991 |
| WO | WO 92/19747 | 11/1992 |
| WO | WO 93/02187 | 2/1993 |
| WO | WO 93/02194 | 4/1993 |
| WO | WO 93/06225 | 4/1993 |
| WO | WO 94/11519 | 5/1994 |
| WO | WO 94/12014 | 6/1994 |
| WO | WO 95/11985 | 5/1995 |
| WO | WO 99/06532 | 2/1999 |
| WO | WO 99/14313 | 3/1999 |
| WO | WO 00/61763 | 10/2000 |
| WO | WO 02/55995 | 7/2002 |
| WO | WO 02/061115 | 8/2002 |
| WO | WO 03/008603 | 1/2003 |
| WO | WO 03/106998 | 12/2003 |
| WO | WO 2004/018621 | 3/2004 |
| WO | WO 2004/029235 | 4/2004 |
| WO | WO 2005/026338 | 3/2005 |
| WO | WO 2005/052135 | 6/2005 |
| WO | WO 2007/030830 | 3/2007 |
| WO | WO 2007/141208 | 12/2007 |
| WO | WO 2008/018930 | 2/2008 |
| WO | WO 2008/027742 | 6/2008 |
| WO | WO 2008/115840 | 9/2008 |
| WO | WO 2008/131286 | 10/2008 |
| WO | WO 2008/144626 | 11/2008 |
| WO | WO 2009/011974 | 1/2009 |
| WO | WO 2009/023493 | 2/2009 |
| WO | WO 2009/049274 | 4/2009 |
| WO | WO 2009/094485 | 7/2009 |
| WO | WO 2009/103026 | 8/2009 |
| WO | WO 2009/111513 | 9/2009 |
| WO | WO 2009/131040 | 10/2009 |
| WO | WO 2010/085731 | 7/2010 |
| WO | WO 2011/137192 | 11/2011 |

OTHER PUBLICATIONS

Aidoo et al., "Cloning, sequencing and disruption of a gene from *Streptomyces clavuligerus* Involved in clavulanic acid biosynthesis," *Gene* 147(1):41-46 (1994).

Alber et al., "Malonyl-coenzyme A reductase in the modified 3-hydroxypropionate cycle for autotrophic carbon fixation in archaeal *Metallosphaera* and *Sulfolobus* spp.," *J. Bacteriol.* 188:8551-8559 (2006).

Alberty, "Biochemical thermodynamics," *Biochem. Biophys. Acta.* 1207:1-11 (1994).

Alhapel et al., "Molecular and functional analysis of nicotinate catabolism in *Eubacterium barkeri*," *Proc. Natl. Acad. Sci. USA* 103(33)12341-12346 (2006).

Allen et al., "DNA sequence of the putA gene from *Salmonella typhimurium*: a bifunctional membrane-associated dehydrogenase that binds DNA," *Nucleic Acids Res.* 21:1676 (1993).

Amarasingham and Davis, "Regulation of alpha-ketoglutarate dehydrogenase formation in *Escherichia coli*," *J. Biol. Chem.* 240: 3664-3668 (1965).

Amos and McInerey, "Composition of poly-.beta.-hydroxyalkanoate from *Syntrophomonas wottei* grown on unsaturated fatty acid substrates," *Arch. Microbiol.* 155:103-106 (1991).

Amuro et al., "Isolation and characterization of the two distinct genes for human glutamate dehydrogenase," *Biochem. Biophys. Acta.* 1049:216-218 (1990).

Andersen and Hansen, "Cloning of the lysA gene from *Mycobacterium tuberculosis*," *Gene* 124:105-109 (1993).

Andersen et al., "A gene duplication led to specialized gamma-aminobutyrate and beta-alaine aminotransferase in yeast," *FEBS J.* 274(7):1804-1817 (2007).

Andre and Jauniaux, "Nucleotide sequence of the yeast UGA1 gene encoding GABA transaminase," *Nucleic Acids Res.* 18:3049 (1990).

Aneja and Charles, "Poly-3-hydroxybutyrate degradation in *Rhizobium* (*Sinorhizobium*) *meliloti*: isolation and characterization of a gene encoding 3-hydroxybutryate dehydrogenase," *J. Bacteriol.* 181(3):849-857 (1999).

Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68(5):557-562 (2000).

Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).

Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).

Aragon and Lowenstein, "A survey of enzymes which generate or use acetoacetyl thioesters in rat liver," *J. Biol. Chem.* 258(8):4725-4733 (1983).

Arikawa et al., "Soluble fumarate reductase isoenzymes from *Saccharomyces cerevisiae* are required for anaerobic growth," *FEMS Microbiol. Lett.* 165:111-116 (1998).

Asano and Kato, "Crystalline 3-methylaspartase from a facultative anaerobe, *Escherichia coli* strain YG1002," *FEMS Microbiol. Lett.* 118(3):255-258 (1994).

Asano et al., "Alteration of substrate specificity of aspartase by directed evolution," *Biomol. Eng.* 22:95-101 (2005).

Asaoka et al., "Production of 1,4-butanediol from bacillus which is fermented on sugar substrate, from which production is recovered," *Chiyoda Chem. Eng. Constr. Co.* (Official Publication Date 1987). Database WPI Week 198804 Thomson Scientific, London, GB; AN 1988-025175.

Asuncion et al., "Overexpression, purification, crystallization and data collection of 3-methylaspartase from *Clostridium tetanomorphum*," *Acta Crystallogr.D. Biol. Crystallogr.* 57:731-733 (2001).

Asuncion et al., "The Structure of 3-Methylaspartase from *Clostridium tetanomorphum* Functions via the Common Enolase Chemical Step," *J. Biol. Chem.* 277(10):8306-8311 (2002).

Atsumi et al., "Non-fermentative pathways for synthesis of branched-chain higher alcohols as biofuels," *Nature* 451(7174):86-89 (2008).

Baba et al., "Construction of *Escherichia coli* K-12 in-frame, single-gene knockout mutants: the Keio collection," *Mol. Syst. Biol.* 2:2006. 0008 (2006).

Baker and van der Drift, "Purification and properties of L-erythro-3,5-diaminohexanoate dehydrogenase from *Clostridium sticklandii*," *Biochemistry* 13(2):292-299 (1974).

Baker et al., "Purification and properties of L-erythro-3,5-diaminohexanoate dehydrogenase from a lysine-fermenting *Clostirdium*," *J. Biol. Chem.* 247(23):7724-7734 (1972).

Barker et al., "Butyryl-CoA:acetoacetate CoA-transferase from a lysine-fermenting *Clostridium*," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrowman et al , "Immunological comparison of microbial TPP-dependent non-oxidative alpha-keto acid decarboxylase," *FEMS Microbiology Lett.* 34:57-60 (1986).

Barthelmebs et al., "Expression of *Escherichia coli* of Native and Chimeric Phenolic Acid Decarboxylases with Modified Enzymatic activites and Method for Scrreening recombinant *E. coli* Strains Expressing These Enzymes," *Appl. Environ. Microbiol.* 67:1063-1069 (2001).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172:7035-7042 (1990).

Baum et al., "A plant glutamate decarboxylase containing a calmodulin binding domain, Cloning, sequence, and functional analysis," *J. Biol. Chem.* 268:19610-19617 (1993).

Benachenhou-Lahfa et al., "PCR-mediated cloning and sequencing of the gene encoding glutamate dehydrogenase from the archaeon *Sulfolobus shilbatae*: Identification of putative amino-acid signatures for extremophilic adaptation," *Gene* 140:17-24 (1994).

Berg et al., "A 3-Hydroxypropionate/4-Hydroxybutyrate Autotrophic Carbon Dioxide Assimilation Pathway in Archaea," *Science* 318:1782-1786 (2007).

Bergquist and Gibbs, "Degenerate oligonucleotide gene shuffling," *Methods Mol. Biol.* 352:191-204 (2007).

Bergquist et al., "Degenerate oligonucleotide gene shuffling (DOGS) and random drift mutagenesis (RNDM): two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. USA* 101:15870-15875 (2004).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Biellmann et al., "Aspartate-beta-semialdehyde dehydrogenase from *Escherichia coli*. Purification and general properties," *Eur. J. Biochem.* 104(1):53-58 (1980).

Binstock and Shulz, "Fatty acid oxidation complex from *Escherichia coli*," *Methods Enzymo.* 71 PtC:403-411 (1981).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Bisswanger, "Substrate Specificity of the Pyruvate Dehydrogenase Complex from *Escherichi coli*," *J. Biol. Chem.* 256(2):815-822 (1981).

Blanco et al., "Critical catalytic functional groups in the mechanims of aspartate-β-semialdehyde dehydrogenase," *Acta Crystallogr. D. Biol. Crystallogr.* 60:1808-1815 (2004).

Blanco et al., "The role of substrate-binding roups in the mechanism of asparte-β-semialdehyde dehydrogenase," *Acta Crystallogr. D. Biol. Crystallog.* 60:1388-1395 (2004).

Blattner et al., "The complete genome sequence of *Escherichia coli* K-12," *Science* 277:1453-1462 (1997).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).

Bonnarme et al., "Itaconate biosynthesis in *Aspergillus terreus*," *J. Bacteriol.* 177(12):3573-3578 (1995).

Bonner and Bloch, "Purification and Properties of Fatty Acyl Thiesterase I from *Escherichia coli*," *J. Biol. Chem.* 247(10) 3123-3133 (1972).

Botsford et al., "Accumulation of glutamate by *Salmonella typhimurium* in response to osmotic stress," *Appl. Environ. Microbiol.* 60:2568-2574 (1994).

Botting et al., "Substrate Specificity of the 3-Methylaspartate Ammonia-Lyase Reaction: Observation of Differential Relative Reaction rates for Substrate-Product Pairs," *Biochemistry* 27:2953-2955 (1988).

Bower et al., "Cloning, Sequencing, and Characterization of the *Bacillus subtilis* Biotin Biosynthetic Operon," *J. Bacteriol.* 178(14):4122-4130 (1996).

Boynton et al., "Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824," *J. Bateriol.* 178(11):3015-3024 (1996).

Brandl et al., "Ability of the phototrophic bacterium *Rhodospirillum rubrum* to produce various poly (beta-hydroxyalkanoates): potential sources for biodegradable polyesters," *Int. J. Biol. Macromol.* 11:49-55 (1989).

Branlant and Branlant, "Nucleotide sequence of the *Escherichia coli* gap gene. Differente evolutionay behaviour of the Nad+-binding domain and of the catalytic domain of D-glyceraldehyde-3-phosphate dehydrogenase," *Eur. J. Biochem.* 150(1):61-66 (1985).

Brasen and Schonheit, "Unusual ADP-forming acetyl-coenzyme a synthetases from the mesophilic halophilic eurarchaeon *Haloarcula marismortui* and from the hyperthermophilic crenarchaeon *Pyrobaculum aerophilum*," *Arch. Microbiol.* 182:277-287 (2004).

Bravo et al., "Reliable, sensitive, rapid and quantitative enzyme-based assay for gamma-hydroxybutyric acid (GHB)," *J. Forensic Sci.* 49:379-387 (2004).

Breitkreuz et al., "A novel gamma-hydroxybutyrate dehydrogenase: identification and expression of an *Arabidopsis* cDNA and potential role under oxygen deficiency," *J. Biol. Chem.* 278:41552-41556 (2003).

Bremer, "Pyruvate Dehydrogenase, Substrate Specificity and Product Inhibition," *Eur. J. Biochem.* 8:535-540 (1969).

Bridger et al., "The subunits of succinyl-coenzyme. A synthetase—function and assembly," In Krebs' Citric Acid Cycle-Half a Century and Still Turning, *Biochem. Soc. Symp.* 54:103-111 (1987).

Brosch et al., "Genome plasticity of BCG and impact on vaccine efficacy," *Proc. Natl. Acad. Sci. U.S.A.* 104(13):5596-5601 (2007).

Bu et al., "Two human glutamate decarboxylases, 65-kDa GAD and 67-kDa GAD, are each encoded by a single gene," *Proc. Natl. Acad. Sci. U.S.A.* 89(6):2115-2119 (1992).

Bu, et al., "The exon-intron organization of the genes (GAD1 and GAD2) encoding two human glutamate decarboxylases (GAD67 and GAD65) suggests that they derive from a common ancestral GAD," *Genomics* 21:222-228 (1994).

Buck and Guest, "Overexpression and site-directed mutagenesis of the succinyl-CoA synthetase of *Escherichia coli* and nucleotide sequence of a gene (g30) that is adjacent to the suc operon," *Biochem. J.* 260(3):737-747 (1989).

Buck et al., "Primary Structure of the Succinyl-CoA Synthetase of *Escherichia coli*," *Biochemistry* 24:6245-6252 (1985).

Buck et al., "Cloning and expression of the succinyl-CoA synthetase genes of *Escherichia coli* K12," *J. Gen. Microbiol.* 132(6):1753-1762 (1986).

Buckel et al., "Glutaconate CoA-Transferase from *Acidaminococcus fermentans*," *Eur. J. Biochem.* 118:315-321 (1981).

Bult et al., "Complete genome sequence of the methanogenic archaeon, *Methanococcus jannaschii*," *Science* 273:1058-1073 (1996).

Burgard and Maranas, "Probing the Performance Limits of the Escherichia coli Metabolic Network Subject to Gene Additions or Deletions," *Biotechnol. Bioeng.* 74(5):364-375 (2001).

Burgard et al., "Minimal reaction sets for *Escherichia coli* metabolism under different growth requirements and uptake environments," *Biotechnol. Prog.* 17(5):791-797 (2001).

Burgard et al., "Optknock: a bilevel programming framework for identifying gene knockout strategies for microbial strain optimization," *Biotechnol. Bioeng.* 84(6):647-657 (2003).

Burke et al, "The Isolation, Characterization, and Sequence of the Pyruvate Kinase Gene of *Saccharomyces cerevisiae*," *J. Biol. Chem.* 258(4):2193-2201 (1983).

Buu et al., "Functional Characterization and Localization of Acetyl-CoA Hydrolase, Ach1p, in *Saccharomyces cerevisiae*," *J. Biol. Chem.* 278(19):17203-17209 (2003).

Campbell et al., "A new *Escherichia coli* metabolic competency: growth on fatty acids by a novel anaerobic β-oxidation pathway," *Mol. Microbiol.* 47(3):793-805 (2003).

Cary et al., "Cloning and expression of *Clostridium acetobutylicum* ATCC 824 acetoacetyl-coenzyme A:acetate/butyrate:coenzyme A-transferase in *Escherichia coli*," *Appl. Environ. Microbiol.* 56(6):1576-1583 (1990).

Cary et al., "Cloning and expression of *Clostridium acetobutylicum* phosphotransbutyrylase and butyrate kinase genes in *Escherichia coli*," *J. Bacteriol.* 170(10):4613-4618 (1988).

Caspi et al., "MetaCyc: a multiorganism database of metabolic pathways and enzymes," *Nucleic Acids Res.* 34(Database issue):D511-D516 (2006).

Causey et al., "Engineering *Escherichia coli* for efficient conversion of glucose to pyruvate," *Proc. Natl. Acad. Sci. U.S.A.* 101:2235-2240 (2004).

Cha and Parks, Jr., "Succinic Thiokinase. I. Purification of the Enzyme from Pig Heart," *J. Biol. Chem.* 239:1961-1967 (1964).

Chandra Raj et al., "Pyruvate decarboxylase: a key enzyme for the oxidative metabolism of lactic acid by *Acetobacter pasteruianus*," *Arch. Microbiol.* 176:443-451 (2001).

Chavez et al., "The NADP-glutamate dehydrogenase of the cyanobacterium Synechocystis 6803: cloning, transcriptional analysis and disruption of the gdhA gene," *Plant Mol. Biol.* 28:173-188 (1995).

Chen and Hiu, "Acetone-Butanol-Isopropanol Production by *Clostridium beijerinckii* (Synonym, *Clostridium butylicum*)," *Biotechnology Letters* 8(5):371-376 (1986).

Chen and Lin, "Regulation of the adhE gene, which encodes ethanol dehydrogenase in *Escherichia coli*," *J. Bacteriol.* 173(24):8009-8013 (1991).

Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).

Chicco et al., "Regulation of Gene Expression of Branched-chain Keto Acid Dehydrogenase Complex in Primary Cultured Hepatocytes by Dexamethasone and cAMP Analog," *J. Biol. Chem.* 269(30):19427-19434 (1994).

Chirpich et al., "Lysine 2,3-Aminomutase. Purification and properties of a pyridoxal phosphate and S-adenosylmethionine-activated enzyme," *J. Biol. Chem.* 245(7):1778-1789 (1970).

Cho et al., "Critical residues for the coenzyme specificity of NAD+-deptendent 15-hydroxyprtaglandin dehydrogenase," *Arch. Biochem. Biophys.* 419(2): 139-146 (2003).

Chowdhury et al., "Cloning and Overexpression of the 3-Hydroxyisobutyrate Dehydrogenase Gene from *Pseudomonas putida* E23," *Biosci. Biotechnol. Biochem.* 67(2):438-441 (2003).

Chowdhury et al., "3-Hydroxyisobutyrate dehydrogenase from *Pseudomonas putida* E23: purification and characterization," *Biosci. Biotechnol. Biochem.* 60(12):2043-2047 (1996).

Christenson et al., "Kinetic analysis of the 4-methylideneimidazole-5-one-containing tyrosine aminomutase in enediyne antitumor antibiotic C-1027 biosynthesis," *Biochemistry* 42(43):12708-12718 (2003).

Chu et al., "Enzymatically active truncated cat brain glutamate decarboxylase: expression, purification, and absorption spectrum," *Arch. Biochem. Biophys.* 313:287-295 (1994).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-hydroxyacid dehydrogenase with new substrate specificity," *Biochem. Biophys. Res. Commun.* 148:15-23 (1987).

Clausen et al., "PAD1 encodes phenylacrylic acid decarboxylase which confers resistance to cinnamic acid in *Saccharomyces cerevisiae*," *Gene* 142:107-112 (1994).

Cock et al., "A nuclear gene with many introns encoding ammonium-inductible chloroplastic NADP-specific glutamate dehydrogenase(s) in *Chlorella sorokiniana*," *Plant Mol. Biol.* 17:1023-1044 (1991).

Coco et al., "DNA shuffling method for generating highly recombined genes and evolved enzymes," *Nat. Biotechnol.* 19(4):354-359 (2001).

Cogoni et al., "*Saccharomyces cerevisiae* has a single glutamate synthase gene coding for a plant-like high-molecular-weight polypeptide," *J. Bacteriol.* 177:792-798 (1995).

Colby and Chen, "Purification and properties of 3-Hydroxybutyryl-Coenzyme A Dehydrogenase from *Clostridium beijerinckii* (*Clostridium butylicum*:) NRRL B593," *Appl. Environ. Microbiol.* 58:3297-3302 (1992).

Cole et al., "Deciphering the biology of *Mycobacterium tuberculosis* from the complete genome sequence," *Nature* 393:537-544 (1998).

Coleman et al., "Expression of a glutamate decarboxylase homologue is required for normal oxidative stress tolerance in *Saccharomyces cerevisiae*," *J. Biol. Chem.* 276:244-250 (2001).

Cooper, "Glutamate-γ-aminobutyrate transaminase," *Methods Enzymol.* 113:80-82 (1985).

Corthesy-Theulaz et al., "Cloning and characterization of *Helicobacter pylori* succinyl CoA:acetoacetate CoA-transferase, a novel prokaryotic member of the CoA-transferase family," *J. Biol. Chem.* 272(41):25659-25667 (1997).

Creaghan and Guest, "Succinate dehydrogenase-dependent nutritional requirement for succinate in mutants of *Escherichia coli* K12," *J. Gen. Microbiol.* 107(1):1-13 (1978).

Cukalovic et al., "Feasibility of production method for succinic acid derivatives: a marriage of renewable resources and chemical technology," *Biofuels Bioprod. Bioref.* 2:505-529 (2008).

Cunningham and Guest, "Transcription and transcript processing in the sdhCDAB-sucABCD operon of *Escherichia coli*," *Microbiology* 144:2113-2123 (1998).

Darlison et al., "Nucleotide sequence of the sucA gene encoding the 2-oxoglutarate dehydrogenase of *Escherichia coli* K12," *Eur. J. Biochem.* 141(2):351-359 (1984).

Das et al, "Characterization of a corrinoid protein involved in the C1 metabolism of strict anaerobic bacterium *Moorella thermoacetica*," *Proteins* 67:167-176 (2007).

Datsenko and Wanner, "One-step inactivation of chromosomal genes in *Escherichia coli* K-12 using PCR products," *Proc. Natl. Acad. Sci. U.S.A.* 97(12):6640-6645 (2000).

Davie et al., "Expression and Assembly of a Functional E1 Component (α2β2) of Mammalian Branched-Chain α-Ketoacid Dehydrogenase Complex in *Escherichia coli*," *J. Biol. Chem.* 267:16601-16606 (1992).

De Biase et al., "Isolation, overexpression, and biochemical characterization of the two isoforms of glutamic acid decarboxylase from *Escherichia coli*," *Protein Expr. Purif.* 8:430-438 (1996).

De la Torre et al., "Identification and functional analysis of prokaryotic-type aspartate aminotransferase: implications for plant amino acid metabolism," *Plant J.* 46(3):414-425 (2006).

Deana, "Substrate specificity of a dicarboxyl-CoA: dicarboxylic acid coenzyme A transferase from rat liver mitochondria," *Biochem. Int.* 26(4):767-773 (1992).

Deckert et al., "The complete genome of the hyperthermophilic bacterium *Aquifex aeolicus*," *Nature* 392:353-358 (1998).

Diao et al., "Crystallization of butyrate kinase 2 from *Thermotoga maritima* medicated by varpor diffusion of acetic acid," *Acta Crystallogr. D. Crystallogr.* 59:1100-1102 (2003).

Diaz et al., "Gene cloning, heterologous overexpression and optimized refolding of the NAD-glutamate dehydrogenase from haloferax mediterranei," *Extremophiles* 10(2):105-115 (2006).

Diderichsen et al., "Cloning of aldB, which encodes alpha-acetolactate decarboxylase, an exoenzyme from *Bacillus brevis*," *J. Bacteriol.* 172(8):4315-4321 (1990).

Diruggiero et al., "Expression and in vitro assembly of recombinant glutamate dehydrogenase from the hyperthermophilic archaeon *Pyrococcus furiosus*," *Appl. Environ. Microbiol.* 61:159-164 (1995).

Doi et al., "Biosynthesis and characterization of poly(3-hydroxybutyrate-co-4-hydroxybutyrate) in *Alcaligenes eutrophus*," *Int. J. Biol. Macromol.* 12:106-111 (1990).

Doi et al., "Nuclear Magnetic Resonance Studies on Unusual Bacterial Copolyesters of 3-Hydroxybutyrate and 4-Hydroxybutyrate," *Macromolecules* 21:2722-2727 (1988).

Doi, "Microbial Synthesis, Physical Properties, and Biodegradability of Polyhydroxyalkanoates," *Macromol. Symp.* 98:585-599 (1995).

Dombek and Ingram, "Ethanol production during batch fermentation with *Saccharomyces cerevisiae*: changes in glycolytic enzymes and internal pH," *Appl. Environ. Microbiol.* 53:1286-1291 (1987).

Donnelly and Cooper, "Succinic semialdehyde dehydrogenases of *Escherichia coli*: their role in the degradation of p-hydroxyphenylacetate and gamma-aminobutyrate," *Eur. J. Biochem.* 113(3):555-561 (1981).

Donnelly and Cooper, "Two succinic semialdehyde dehydrogenases are induced when *Escherichia coli* K-12 is grown on gamma-aminobutyrate," *J. Bacteriol.* 145:1425-1427 (1981).

Dover et al., "Genetic analysis of the gamma-aminobutyrate utilization pathway in *Escherichia coli* K12," *J. Bacteriol.* 117(2):494-501 (1974).

Doyle et al., "Structural basis for a change in substrate specificity: crystal structure of S113E isocitrate dehydrogenase in a complex with isopropylmalate, $Mg^{2+}$, and NADP," *Biochemistry* 40(14):4234-4241 (2001).

Drake, "Acetogenesis, acetogenic bacteria, and the acetyl-CoA "Wood/Ljungdahl" pathway: past and current perspectives," In H.L. Drake (ed.), *Acetogenesis* pp. 3-60 Chapman and Hall, New York. (1994)

Drewke et al., "4-O-Phosphoryl-L-threonine, a substrate of the pdxC(serC) gene product involved in vitamin $B_6$ biosynthesis," *FEBS Lett.* 390:179-182 (1996).

Duncan et al., "Acetate utilization and butyryl coenzyme A (CoA):acetate-CoA transferase in butyrate-producing bacteria from the human large intestine," *Appl. Environ. Microbiol.* 68(10):5186-5190 (2002).

Duncan et al., "Purification and properties of NADP-dependent glutamate dehydrogenase from *Ruminococcus flavefaciens* FD-1," *Appl. Environ. Microbiol.* 58:4032-4037 (1992).

Dürre et al., "Solventogenic enzymes of *Clostridium acetobutylicum*: catalytic properties, genetic organization, and transcriptional regulation," *FEMS Microbiol. Rev.* 17(3):251-262 (1995).

Edwards and Palsson, "Systems properties of the *Haemophilus influenzae* Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).

Edwards et al., "In Silico Predictions of *Escherichia coli* metabolic capabilities are Consistent with Experimental Data," *Nat. Biotechnol.* 19(2):125-130 (2001).

Eggen et al., "The glutamate dehydrogenase-encoding gene of the hyperthermophilic archaeon *Pyrococcus furiosus*: sequence, transcription and analysis of the deduced amino acid sequence," *Gene.* 132:143-148 (1993).

Eikmanns et al., "The phosphoenolpyruvate carboxylase gene of *Corynebacterium glutamicum*: Molecular cloning, nucleotide sequence, and expression," *Mol. Gen. Genet.* 218:330-339 (1989).

Ekiel et al., "Acetate and CO2 assimilation by *Methanothrix concilii*," *J. Bacteriol.* 162(3):905-908 (1985).

Enomoto et al., "Cloning and sequencing of the gene encoding the soluble fumarate reductase from *Saccharomyces cerevisiae*," *DNA Res.* 3:263-267 (1996).

Estevez et al., "X-ray crystallographic and kinetic correlation of a clinically observed human fumarase mutation," *Protein Sci.* 11:1552-1557 (2002).

Faehnle et al., "A New Branch in the Family: Structure of Aspartate-β-semialdehyde dehydrogenase from *Methanococcus jannaschii*," *J. Mol. Biol.* 353:1055-1068 (2005).

Feist et al., "The growing scope of applications of genome-scale metabolic reconstructions using *Escherichia coli*," Nat. Biotechnol. 26(6):659-667 (2008).

Fell and Small, "Fat Synthesis in Adipose Tissue. An Examination of Stoichiometric Constraints," *Biochem. J.* 238(3):781-786 (1986).

Fernandez-Valverde et al., "Purification of Pseudomonas putida Acyl coenzyme a Ligase Active with a Range of Aliphatic and Aromatic Substrates," *Appl. Environ. Microbiol.* 59:1149-1154 (1993).

Filetici et al., "Sequence of the GLT1 gene from *Saccharomyces cerevisiae* reveals the domain structure of yeast glutamate synthase," *Yeast* 12:1359-1366 (1996).

Fischer and Sauer, "Metabolic flux profiling of *Escherichi coli* mutants in central carbon metabolism using GC-MS," *Eur. J. Biochem.* 270(5) 880-891 (2003).

Fishbein and Bessman, "Purification and properties of an enzyme in human blood and rat liver microsomes catalyzing the formation and hydrolysis of gamma-lactones. I. Tissue localization, stoichiometry, specificity, distinction from esterase," *J. Biol. Chem.* 241(21):4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibra," *J. Biol. Chem.* 241(21):4842-4847 (1966).

Föllner et al., "Analysis of the PHA granule-associate proteins GA20 and GA11 in *Methylobacterium extorquens* and *Methylobacterium rhodesianum*," *J. Basic Microbiol.* 37(1):11-21 (1997).

Fong and Palsson, "Metabolic gene-deletion strains of *Escherichia coli* evolve to computationally predicted growth phenotypes," *Nat. Genet.* 36(10):1056-1058 (2004).

Fong et al., "Description and interpretation of adaptive evolution of *Escherichia coli* K-12 MG1655 by using a genome-scale in silico metabolic model," *J. Bacteriol.* 185(21):6400-6408 (2003).

Fontaine et al., "Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184(3):821-830 (2002).

Ford, et al., "Molecular properties of the lysl+ gene and the regulation of alpha-aminoadipate reductase in *Schizosaccharomyces pombe*," *Curr. Genet.* 28(2):131-137 (1995).

Forster et al., "Genome-scale reconstruction of the *Saccharomyces cerevisiae* metabolic network," *Genome Res.* 13:244-253 (2003).

Friedrich et al., "The complete stereochemistry of the enzymatic dehydration of 4-hydroxybutyryl coenzyme A to crotonyl coenzyme A," *Angew. Chem. Int. Ed. Engl.* 47:3254-3257 (2008).

Fries et al., "Reaction Mechanism of the Heteroameric ($\alpha_2\beta_2$) E1 Component of 2-Oxo Acid Dehydrogenase Multienzyme Complexes," *Biochemistry* 42:6996-7002 (2003).

Fuhrer, et al., "Computational prediction and experimental verification of the gene encoding the NAD+/NADP+-dependent succinate semialdehyde dehydrogenase in *Escherichia coli*," *J. Bacteriol.* 189:8073-8078 (2007).

Fujii et al., "Characterization of L-lysine 6-aminotransferase and its structural gene from *Favobacterium lutescens* IFO3084," *J. Biochem.* 128(3):391-397 (2000).

Fujii et al., "Error-prone rolling circle amplification: the simplest random mutagenesis protocol," *Nat. Protoc.* 1(5):2493-2497 (2006).

Fujii et al., "One-step random mutagenesis by error-prone rolling circle amplification," *Nucleic Acids Res.* 32(19):e145 (2004).

Fujita et al., "Novel Substrate Specificity of designer3-Isopropylmalate Dehydrogenase Derived from thermus thermophilus HB1," *Biosci. Biotechnol. Biochem.* 65(12):2695-2700 (2001).

Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics* 68:144-151 (2000).

Fukuda and Wakagi, "Substrate recognition by 2-oxoacid:ferredoxin oxidoreductase from *Sulfolobus* sp. Strain 7," *Biochim Biophys. Acta* 1597:74-80 (2002).

Fukuda et al., "Role of a highly conserved YPITP motif in 2-oxoacid:ferredoxin oxidoreductase," *Eur. J. Biochem.* 268:5639-5646 (2001).

Gallego et al., "A role for glutamate decarboxylase during tomato ripening: the characterisation of a cDNA encoding a putative glutamate decarboxylase with a calmodulin-binding site," *Plant Mol. Biol.* 27:1143-1151 (1995).

Gay et al., "Cloning Structural Gene sacB, Which codes for Exoenzyme Levansucrase of *Bacillus subtilis*: Epxresion of the Gene in *Escherichia coli*," *J. Bacteriol.* 153:1424-1431 (1983).

Gerhardt et al., "Fermentation of 4-aminobutyrate by *Clostridium aminobutyricum*: cloning of two genes involved in the formation and dehydration of 4-hydroxybutyryl-CoA," *Arch. Microbiol.* 174:189-199 (2000).

Gerngross and Martin, "Enzyme-catalyzed synthesis of poly((R)-(−)-3-hydroxybutyrate): formation of macroscopic granules in vitro," *Proc. Natl. Acad. Sci. U.S.A.* 92:6279-6783 (1995).

Gerngross, et al., "Overexpression and purification of the soluble polyhydroxyalkanoate synthase from *Alcaligenes eutrophus*: evidence for a required posttranslational modification for catalytic activity," *Biochemistry* 33:9311-9320 (1994).

Gibbs et al., "Degenerate oligonucleotide gene shuffling (DOGS): a method for enhancing the frequency of recombination with family shuffling," *Gene.* 271:13-20 (2001).

Giesel and Simon, "On the occurrence of enoate reductase and 2-oxo-carboxylate reductase in *Clostridia* and some observations on the amino acid fermentation by *Peptostreptococcus anaerobius*," *Arch. Microbiol.* 135(1):51-57 (1983).

Girbal, et al., "Regulation of metabolic shifts in *Clostridium acetobutylicum* ATCC 824," *FEMS Microbiol. Rev.* 17:287-297 (1995).

Goda et al., "Cloning, Sequencing, and Expression in *Escherichia coli* of the *Clostridium tetanomorphum* Gene Encoding β-Methylaspartase and Characterization of the Recombinant Protein," *Biochemistry* 31:10747-10756 (1992).

Gong et al., "Effects of transport properites of ion-exchange membranes on desalination of 1,3-propanediol fermentation broth by electrodialysis," *Desalination* 191:193-199 (2006).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

Gonzalez, et al., "Cloning of a yeast gene coding for the glutamate synthase small subunit (GUS2) by complementation of *Saccharomyces cerevisiae* and *Escherichia coli* glutamate auxotrophs," *Mol. Microbiol.* 6:301-308 (1992).

Gonzalez-Pajuelo et al., "Metabolic engineering of *Clostridium acetobutylicum* for the industrial production of 1,3-propanediol from glycerol," *Met. Eng.* 7:329-336 (2005).

Goupil et al., "Imbalance of leucine flux in *Lactoccus lactis* and its use for the isolation of diacetyl-overproducing strains," *Appl. Environ. Microbiol.* 62(7):2636-2640 (1996).

Goupil-Feuillerat et al., "Transcriptional and translational regulation of alpha-acetolactate decarboxylase of *Lactococcus lactis* subsp. Lactis," *J. Bacteriol.* 182(19):5399-5408 (2000).

Green et al., "Catabolism of α-Ketoglutarate by a sucA Mutant of *Bradyrhizobium japonicum*: Evidence for an Alternative Tricarboxylic Acid Cycle," *J. Bacteriol.* 182(10):2838-2844 (2000).

Gregerson, et al., "Molecular characterization of NADH-dependent glutamate synthase from alfalfa nodules," *Plant Cell* 5:215-226 (1993).

Guirard and Snell, "Purification and properties of ornithine decarboxylase from *Lactobacillus* sp. 30a," *J. Biol. Chem.* 255(12):5960-5964 (1980).

Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from *Schizosaccharomyces pombe*," *Yeast* 21(15):1279-1288 (2004).

Guo et al., "Site-directed mutational analysis of the novel catalytic domains of alpha-aminoadipate reductase (Lys2p) from *Candida albicans*," *Mol. Genet. Genomics* 269(2):271-279 (2003).

Guzman, et al., "Tight regulation, modulation and high-level expression by vectors containing the arabinose PBAD promoter," *J. Bacteriol.* 177(14):4121-4130 (1995).

Hadfield et al., "Active site analysis of the potential antimicrobial target aspartate semialdehyde dehydrogenase," *Biochemistry* 40(48):14475-14483 (2001).

Hadfield et al., "Structure of aspartate-beta-semialdehyde dehydrogenase from *Escherichia coli*, a key enzyme in the aspartate family of amino acid biosynthesis," *J. Mol. Biol.* 289(4):991-1002 (1999).

Hammer and Bode, "Purification and characterization of an inducible L-lysine:2-oxoglutarate 6-aminostransferase from *Dandida utilis*," *J. Basic Microbiol.* 32:21-27 (1992).

Hansford, "Control of mitochondrial substrate oxidation," *Curr. Top. Bioenerg.* 10:217-278 (1980).

Hasegawa et al., "Transcriptional regulation of ketone body-utilizing enzyme, acetoacetyl-CoA synthetase, by C/EBPα during adipocyte differentiation," *Biochim Biophys. Acta* 1779:414-419 (2008).

Hashidoko et al., "Cloning of a DNA Fragment Carrying the 4-Hydroxycinnamate Decarboxylase (*pof*K) Gene from *Klebsiella oxtoca*, and Its Constitutive Expression in *Escherichia coli* JM109 Cells," *Biosci. Biotech. Biochem.* 217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80 (1989).

Hasson et al., "The Crystal Structure of Benzoylformate Decarboxylase at 1.6 Å Resolution: Diversity of Catalytic Residues in thiamin Diphosphate-Dependent Enzymes," *Biochemistry* 37:9918-9930 (1998).

Hawes et al., "Mammalian 3-hydroxyisobutyrate dehydrogenase," *Methods Enzymol.* 324:218-228 (2000).

Hayden et al., "Glutamate dehydrogenase of *Halobacterium salinarum*: evidence that the gene sequence currently assigned to the NADP+-dependent enzyme is in fact that of the NAD+-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. U.S.A.* 99(25):15926-15931 (2002).

Hein, et al., "Biosynthesis of poly(4-hydroxybutyric acid) by recombinant strains of *Escherichia coli*," *FEMS Microbiol. Lett.* 153(2):411-418 (1997).

Henne, et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy, et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).

Henning et al., "Identification of Novel enzoylformate Decarboxlyases by Growth Selection," *App. Environ. Microbiol.* 72(12)7510-7517 (2006).

Hermes et al., "Searching sequence space by definably random mutagenesis: Improving the catalytic potency of an enzyme," *Proc. Natl. Acad. Sci. U.S.A.* 87:696-700 (1990).

Herrmann et al., "Energy conservation via electron-transferring flavoprotein in anaerobic bacteria," *J. Bacteriol.* 190(3):784-791 (2007).

Herrmann et al., "Two beta-alanyl-CoA:ammonia lyases in *Clostridium propionicum*," *FEBS J.* 272:813-821 (2005).

Hesslinger et al., "Novel keto acid formate-lyase and propionate kinase enzymes are components of an anaerobic pathway in *Escherichia coli* that degrades L-threonine to propionate," *Mol. Microbiol* 27:477-492 (1998).

Hester et al., "Purification of active E1 alpha 2 beta 2 of *Pseudomonas putida* branched-chain-oxoacid dehydrogenase," *Eur. J. Biochem.* 233(3):828-836 (1995).

Heydari et al., "Highly Stable L-Lysine 6-Dehydrogenase from the Thermophile *Geobacillus stearothemophilus* Isolated from a Japanese Hot Spring: Characterization, gene Cloning and Sequencing, and Expression," *Appl. Environ. Microbiol.* 70:937-942 (2004).

Hezayen et al., "Biochemical and enzymological properties of the polyhydroxybutyrate synthase from the extremely halophilic archaeon strain 56," *Arch. Biochem. Biophys.* 403(2):284-291 (2002).

Hibbert et al. "Directed evolution of biocatalytic processes," *Biomol. Eng.* 22:11-19 (2005).

Hijarrubia et al., "Domain Structure characterization of the Multifunctional α-Aminoadipate Reductase from *Penicillium chrysogenum* by Limited Proteolysis," *J. Biol. Chem.* 278:8250-8256 (2003).

Hillmer and Gottschalk, "Solubilization and partial characterization of particulate dehydrogenases from *Clostridium kluyveri*," *Biochim Biophys. Acta* 334:12-23 (1974).

Hiramitsu, et al., "Production of Poly(3-hydroxybutyrate-co-4-hydroxybutyrate) by *Alcallgenes latus*," *Biotechnol Lett.* 15:461-464 (1993).

Hirano et al., "Purification and Characterization of the alcohol dehydrogenase with a broad substrate specificity originated from 2-phenylethanol-assimilating *Brevibacterium* sp. KU 1390," *J. Biosci. Bioeng.* 100(3):318-322 (2005).

Hiser et al., "ERG10 from *Saccharomyces cerevisiae* encodes acetoacetyl-CoA thiolase," *J. Biol. Chem.* 269:31383-31389 (1994).

Hoffmeister et al., "Mitochondrial trans-2-enoyl-CoA reductase of wax ester fermentation from *Euglena gracilis* defines a new family of enzymes involved in lipid synthesis," *J. Biol. Chem.* 280:4329-4338 (2005).

Hogan et al., "Improved specificity toward substrates with ositively charged side chains by site-directed mutagenesis of the L-lactate dehydrogenase of *Bacillus stearothermophilus*," *Biochemistry* 34(13):4225-4230 (1995).

Hong and Lee, "Enhanced Production of Succinic Acid by Metabolically Engineered *Escherichia coli* with Amplified Activities of Malic Enzyme and Fumarase," *Biotechnol. Bioprocess Eng.* 9:252-255 (2004).

Hong, et al., "The genome sequence of the capnophilic rumen bacterium *Mannheimia succiniciproducens*," *Nat. Biotechnol.* 22(10):1275-1281 (2004).

Huang et al., "Identification and Characterization of a Second Butyrate Kinase from *Clostridium acetobutylicum* ATCC 824," *J. Mol. Microbiol. Biotechnol.* 2(1):33-38 (2000).

Huang et al., "Purification and Characterization of a Ferulic Acid Decarboxylase from *Pseudomonas fluorescens*," *J. Bacteriol.* 176(19):5912-5918 (1994).

Hughes et al., "Evidence for Isofunctional Enzymes in the Degradation of Phenol, *m*- and *p*-Toulate, and *p*-Cresol via Catechol meta-Cleavage Pathways in *Alcaligenes eutrophus*," *J. Bacteriol.* 158:79-83 (1984).

Hugler et al., "Malonyl-coenzyme A reductase from *Chloroflexus aurantiacus*, a key enzyme of the 3-hydroxypropionate cycle for autotrophic Co(2) fixation," *J.Bacteriol.* 184:2404-2410 (2002).

Huh et al., "Global analysis of protein localization in budding yeast," *Nature* 425:686-691 (2003).

Huisman and Lalonde, "Ch. 30: Enzyme Evolution for Chemical Process Applications," In R N. Patel (ed.), Biocatalysis in the pharmaceutical and biotechnology industries, CRC Press, Boca Raton, FL, p. 717-742 (2007).

Huo and Viola, "Substrate specificity and identification of functional groups of homoserine kinase from *Escherichia col*," *Biochemistry* 35(50):16180-16185 (1996).

Ibarra et al., "*Escherichia coli* K-12 undergoes adaptive evolution to achieve in silico predicted optimal growth," *Nature* 420(6912):186-189 (2002).

Iffland et al., "Directed molecular evolution of cytochrome c peroxidase," *Biochemistry* 39(25):10790-10798 (2000).

Ikai and Yamamoto, "Identification and Analysis of a Gene Encoding L-2,4-Diaminobutyrate:2-Ketoglutarate 4-Aminotransferase Invloved in the 1,3-Diaminopropane Production Pathway in *Acinetobacter baumanni*," *J. Bacteriol.* 179(16):5118-5125 (1997).

Imai and Ohno, "Measurement of yeast intracellular pH by image processing and the change it undergoes during growth phase," *J. Biotechnol.* 38:165-172 (1995).

Ingoldsby et al., "The discovery of four distinct glutamate dehydrogenase genes in a strain of *Halobacterium salinarum*," *Gene* 349:237-244 (2005).

Ishida et al., "Efficient production of L-Lactic acid by metabolically engineered *Saccharomyces cerevisiae* with a genome-integrated L-lactate dehydrogenase gene," *Appl. Environ. Microbiol.* 71:1964-1970 (2005).

Ishige et al., "Wax ester production from n-alkanes by *Acinetobacter* sp. strain M-1: ultrastructure of cellular inclusions and role of acyl coenzyme A reductase," *Appl. Environ. Microbiol.* 68(3):1192-1195 (2002).

Ismaiel et al., "Purification and characterization of a primary-secondary alcohol dehydrogenase from two strains of *Clostridium beijerinckii*," *J. Bacteriol.* 175(16):5097-5105 (1993).

Ismail et al., "Functional genomics by NMR spectroscopy Phenylacetate catabolism in *Escherichia coli*," *Eur. J. Biochem.* 270:3047-3054 (2003).

Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Jacobi et al., "The hyp operon gene products are required for the maturation of catalytically active hydrogenase isoenzymes in *Escherichia coli*," *Arch. Microbiol.* 158:444-451 (1992).

Jesudason and Marchessault, "Synthetic Poly[(R,S)-.beta.-hydroxyalkanoates] with Butyl and Hexyl Side Chains," *Macromolecules* 27:2595-2602 (1994).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Johnson et al., "Alteration of a single amino acid changes the substrate specificity of dihydroflavonol 4-reductase," *Plant J.* 25(3):325-333 (2001).

Johnston et al., "Complete nucleotide sequence of *Saccharomyces cerevisiae* chromosome VIII," *Science* 265:2077-2082 (1994).

Jones and Woods, "Acetone-butanol fermentation revisited," *Microbiol. Rev.* 50(4):484-524 (1986).

Jones et al., "Purification and characterization of D-b-hydroxybutyrate dehydrogenase expressed in *Escherichia coli*," *Biochem. Cell Biol.* 71(7-8):406-410 (1993).

Kakimoto et al., "β-Aminoisobutyrate-α-ketoglutarate transaminase in relation to β-aminoisobutyric aciduria," *Biochim Biophys. Acta.* 156(2):374-380 (1968).

Kaneko et al., "Sequence analysis of the genome of the unicellular cyanobacterium *Synechocystis* sp. strain PCC6803, II. Sequence determination of the entire genome and assignment of potential protein-coding regions," *DNA Res.* 3:109-136 (1996).

Kapatral et al., "Genome Sequence and Analysis of the Oral Bacterium *Fusobacterium nucleatum* Strain ATCCF 25586," *J. Bacteriol.* 184(7):2005-2018 (2002).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Kato et al., "Open reading frame 3 of the barotolerant bacterium strain DSS12 is complementary with cydD in *Escherichia coli*: cydD functions are required for cell stability at high pressure," *J. Biochem.* 120:301-305 (1996).

Kato et al., "Production of a novel copolyester of 3-hydroxybutyric acid with a medium-chain-length 3-hydroxyalkanoic acids by *Pseudomonas* sp. 61-3 from sugars," *Appl. Microbiol. Biotechnol.* 45:363-370 (1996).

Kazahaya et al, "Aerobic Dissimilation of Glucose by Heterolactic Bacteria," *J. Gen. Appl. Microbiol.* 18(1):43-55 (1972).

Keng and Viola, "Specificity of Aspartokinase III from *Escherichia coli* and an Examination of Important Catalytic Residues," *Arch. Biochem. Biophys.* 335:73-81 (1996).

Kessler et al., "Pyruvate-formate-lyase-deactivase and acetyl-CoA reductase activities of *Escherichia coli* reside on a polymeric protein particle encoded by adhE," *FEBS.Lett.* 281:59-63 (1991).

Khan et al., "Molecular properties and enhancement of thermostability by random mutagenesis of glutamate ehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al., "Construction of an *Escherichia coli* K-12 Mutant for Homoethanologenic Fermentation of glucose or Xylose without Foreign Genes," *Appl. Environ. Microbiol.* 73:1766-1771 (2007).

Kim et al., "Effect of overexpression of Actinobacillus succinogenes phosphoenolpyruvate carboxykinase on succinate production in *Escherichia coli*," *Appl. Environ. Microbiol.* 70:1238-1241 (2004).

Kim, "Purification and Propertis of a mine α-Ketoglutarate Transaminase from *Escherichia coli*," *J. Biol. Chem.* 239:783-786 (1964).

Kimura et al., "Production of Poly(3-hydroxybutyrate-co-4-hydroxybutyrate) by *Pseudomonas acidovorans*," *Biotechnol. Lett.* 14(6):445-450 (1992).

Kinnaird et al., "The complete nucleotide sequence of the *Neurospora crassa* am (NADP-specific glutamate dehydrogenase) gene," *Gene* 26:253-260 (1983).

Kino et al., "Synthesis of DL-tryptophan by modified broad specificity amino acid racemase from *Pseudomonas putida* IFO 12996," *Appl. Microbiol. Biotechnol.* 73(6):1299-1305 (2007).

Kinoshita, "Purification of two alcohol dehydrogenases from *Zymomonas mobilis* and their properties," *Appl. Microbiol. Biotechnol.* 22:249-254 (1985).

Kirby et al., "Purification and properties of rabbit brain and liver 4-aminobutyrate aminotransferases isolated by monoclonal-antibody Immunoadsorbent chromatography," *Biochem. J.* 230:481-488 (1985).

Kizer et al., "Application of Functional Genomics to Pathway Optimization for Increased Isoprenoid Production," *Appl. Environ. Microbiol.* 74(10):3229-3241 (2008).

Klatt et al., "Comparative genomics provides evidence for the 3-hydroxypropionate autotrophic pathway in filamentous anoxygenic phototrophic bacteria and in hot spring microbial mats," *Environ. Microbiol.* 9(8):2067-2078 (2007).

Klenk et al., "The complete genome sequence of the hyperthermophilic, sulphate-reducing archaeon *Archaeoglobus fulgidus*," *Nature* 390:364-370 (1997).

Knapp et al., "Crystal Structure of the Truncated Cubic Core Component of the *Escherichia coli* 2-Oxoglutarate Dehydrogenase Multienzyme Complex," *J. Mol. Biol.* 289:655-668 (1998).

Knappe and Sawers, "A radical-chemical route to acetyl-CoA: the anaerobically induced pyruvate formate-lyase system of *Escherichia coli*," *FEMS Microbiol. Rev.* 75:383-398 (1990).

Kobayashi et al., "Frementative Production of 1,4-Butanediol from Sugars by *Bacillus* sp.," Agric. Biol. Chem. 51(6):1689-1690 (1987).

Kobayashi et al., "Physiochemical, Catalytic, and Immunochemical Properties of Fumarases Crystallized Separately from Mitochondrial and Cytosolic Fractions of Rat Liver," *J. Biochem.* 89:1923-1931 (1981).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the NADP+-dependent Glutamate Dehydrogenase from *Escherichia coli*," *J. Mol. Biol.* 234:1270-1273 (1993).

Korolev et al., "Autotracing of *Escherichia coli* acetate CoA-transferase α-subunit structure using 3.4 Å MAD and 1.9 Å native data," *Acta. Cryst.* D58:2116-2121 (2002).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kreimeyer et al., "Indentification of the Last Unknown Genes in the fermentation Pathway of Lysine," *J. Biol. Chem.* 282:7191-7197 (2007).

Kretz et al., "Gene site saturation mutagenesis: a comprehensive mutagenesis approach," *Methods Enzymol.* 388:3-11 (2004).

Krieger et al., "Pyruvate decarboxylase from *Kluyveromyces lactis* an enzyme with an extraordinary substrate activation behaviour," *Eur. J. Biochem.* 269:3256-3263 (2002).

Kumamaru et al., "Enhanced degradation of polychlorinated biphenyls by directed evolution of biphenyl dioxgenase," *Nat. Biotechnol.* 16(7)663-666 (1998).
Kunioka et al., "New bacterial copolyesters produced in *Alcaligenes eutrophus* from organic acids," *Polym. Commun.* 29:174-176 (1988).
Kurihara et al., "A Novel Putrescine Utilization Pathway Involves γ-Glutamylated Intermediates of *Escherichia coli* K-12," *J. Biol. Chem.* 280(6) 4602-4608 (2005).
Kuznetsova et al., "Enzyme genomics: Application of general enzymatic screens to discover new enzymes," *FEMS Microbiol. Rev.* 29:263-279 (2005).
Kwok and Hanson, "GFP-labelled Rubisco and aspartate aminotransferase are present in plastid stromules and traffic between plastids," *J. Exp. Bot.* 55:(397)595-604 (2004).
Kwon et al., "Brain 4-aminobutyrate aminotransferase. Isolation and sequence of a cDNA encoding the enzyme," *J. Biol. Chem.* 267:7215-7216 (1992).
Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.* 16(9):1448-1452 (2006).
Lageveen, et al., "Formation of Polyesters by *Pseudomonas oleovorans*: Effect of Substrates on Formation and Composition of Poly-(R)-3-Hydroxyalkanoates and Poly-(R)-3-Hydroxyalkenoates," *Appl. Environ. Microbiol.* 54:2924-2932 (1988).
Lam and Winkler, "Metabolic Relationships between Pyridoxine (vitamin $B_6$) and Serine Biosynthesis in *Escherichia coli* K-12," *J. Bacteriol.* 172(11):6518-6528 (1990).
Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395:147-155 (2006).
Lamed and Zeikus, "Novel NAP-linked alcohol-aldehyde/ketone oxidoreductase in thermophilic ethanologenic bacteria," *Biochem. J.* 195:183-190 (1981).
Lebbink et al., "Engineering activity and stability of *Thermotoga maritima* glutamate dehydrogenase. II: construction of a 16-residue ion-pair network at the subunit interface," *J. Mol. Biol.* 289(2):357-369 (1999).
Lebbink et al., "Engineering activity and stability of *Thermotoga maritima* Glutamate Dydrogenase. I. Introduction of a Six-residue Ion-pair Network in the Hinge Region," *J. Mol. Biol.* 280:287-296 (1998).
Leduc et al., "The Hotdog Thiesterase EntH (YbdB) Plays a Role in Vivo in Optimal Enterobactin biosynthesis by Interacting with the ArCP Domain of EntB," *J. Bacteriol.* 189(19):7112-7126 (2007).
Lee and Cho, "Identification of essential active-site residues in ornithine decarboxylase of *Nicotiana glutinosa* decarboxylating both L-ornithine and L-lysine," *Biochem. J.* 360(Pt 3):657-665 (2001).
Lee et al., "Biosynthesis of enantiopure (s)-3-hydroxybutyric acid in metabolically engineered *Escherichia coli*," *Appl. Microbiol. Biotechnol.* 79(4):633-641 (2008).
Lee et al., "Phylogenetic diversity and the structural basis of substrate specificity in the beta/alpha-barrel fold basic amino acid decarboxylases," *J. Biol. Chem.* 282(37):27115-27125 (2007).
Lee et al., "A new approach to directed gene evolution by recombined extension on truncated templates (Rett)," *J. Molec. Catalysis* 26:119-129 (2003).
Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," *Appl. Microbiol. Biotechnol.* 42: 901-909 (1995).
Lee et al., "Enhanced biosynthesis of P(3HB-3HV) and P(3HB-4HB) by amplification of the cloned PHB biosynthesis genes in *Alcatigenes eutrophus*," *Biotechnol. Lett.* 19:771-774 (1997).
Lemoigne and Rouklehman, "Fermentation b-Hydroxybutyrique," *Annales des Fermentations* 5:527-536 (1925).
Lemonnier and Lane, "Expression of the second lysine decarboxylase gene of *Escherichia coli*," *Microbiology* 144(Pt 3):751-760 (1998).

Lepore et al., "The x-ray crystal structure of lysine-2,3-aminomutase from *Clostridium subterminale*," *Proc. Natl. Acad. Sci. U.S.A.* 102:13819-13824 (2005).
Li and Jordan, "Effecrts of Substitution of Tryptophan 412 in the Substrate Activation Pathway of Yeast Pyruvate Decarboxylase," *Biochemistry* 38:10004-10012 (1999).
Li, Guang-Shan, "Development of a reporter system for the study of gene expression for solvent production in *Clostridium beijerinckii* NRRL B592 and *Clostridium acetobutylicum* ATCC 824," Dissertation, Department of Biochemestry, Virginia Polytechnic Institute and State University (Sep. 1998).
Lian and Whitman, "Sterochemical and Isotopic Labeling Studies of 4-Oxalocrotonate Decarboxylase and Vinylpyruvate Hydratase: Analysis and Mechanistic Implications," *J. Am. Chem. Soc.* 116:10403-10411 (1994).
Liebergesell and Steinbuchel, "Cloning and nucleotide sequences of genes relevant for biosynthesis of poly(3-hydroxybutyric acid) in *Chromatium vinosum* strain D," *Eur. J. Biochem.* 209(1):135-150 (1992).
Lin et al., "Fed-batch culture of a metabolically engineered *Escherichia coli* strain designed for high-level succinate production and yield under aerobic conditions," *Biotechnol. Bioeng.* 90(6):775-779 (2005).
Lin et al., "Functional expression of horseradish peroxidase in *E. coli* by directed evolution," *Biotechnol. Prog.* 15(3):467-471 (1999).
Lingen et al., "Alteration of the Substrate Specificity of Benzoylformate Decarboxylase from *Pseudomonas putida* by Directed Evolution," *Chembiochem* 4:721-726 (2003).
Lingen et al., "Improving the carboligase activity of benzoylformate decarboxylase from *Pseudomonas putida* by a combination of directed evolution and site-directed mutagenesis," *Protein Eng.* 15:585-593 (2002).
Link et al., "Methods for generating precise deletions and insertions in the genome of wild-type *Escherichia coli*: application to open reading frame characterization," *J. Bacteriol.* 179:6228-6237 (1997).
Liu and Steinbuchel, "Exploitation of butyrate kinase and phosphotransbutyrylase from *Clostridium acetobutylicum* for the in vitro biosynthesis of poly (hydroxyalkanoic acid)," *Appl. Microbiol. Biotechnol.* 53(5):545-552 (2000).
Liu et al., "Crystal Structures of Unbound and Aminoxyacetate-Bound *Escherichia coli* Y-Aminobutyrate Aminotransferase," *Biochem.* 43:10896-10905 (2004).
Liu et al., "Kinetic and crystallographic analysis of active site mutants of *Escherichia coli* gamma-aminobutyrate aminotransferase," *Biochemistry* 44:(8):2982-2992 (2005).
Ljungdahl and Andreesen, "Formate dehydrogenase, a selenium—tungsten enzyme from *Clostridium thermoaceticum*," *Methods Enzymol.* 53:360-372 (1978).
Lokanath et al., "Crystal Structure of novel NADP-dependent 3-Hydroxyisobutyrate Dehydrogenase from *Thermus thermophilus* HB8," *J. Mol Biol.* 352:905-917 (2005).
Louie and Chan, "Cloning and characterization of the gamma-glutamyl phosphate reductase gene of *Campylobacter jejuni*," *Mol. Gen. Genet.* 240:29-35 (1993).
Louis et al., "Restricted Distribution of the Butyrate Kinase Pathway among Butyrate-Producing Bacteria from the Human Colon," *J. Bacteriol.* 186(7):2099-2106 (2004).
Low et al., "Mimicking somatic hypermutation: affinity maturation of antibodies displayed on baceriophage using a bacterial mutator strain," *J. Mol. Biol.* 260(3):359-368 (1996).
Lu et al, "Functional analysis and regulation of the divergent spuABCDEFG-spuI operons for polyamine uptake and utilization in *Pseudomonas aeruginosa* PA01," *J. Bacteriol.* 184:3765-3773 (2002).
Lu et al., "Enhanced production of poly(3-hydroxybutyrate-co-3-hydroxyhexanoate) via manipulating the fatty acid beta-oxidation pathway in *E. coli*," *FEMS Microbiol. Lett.* 221(1):97-101 (2003).
Lu et al., "Molecular cloning of polyhydroxyalkanoate synthesis operon from *Aeromonas hydrophila* and its expression in *Escherichia coli*," *Biotechnol. Prog.* 20(5):1332-1336 (2004).
Lutke-Eversloh and Steinbuchel, "Biochemical and molecular characterization of a succinate semialdehyde dehydrogenase involved in the catabolism of 4-hydroxybutyric acid in *Ralstonia eutropha*," *FEMS Microbiol. Lett.* 181:63-71 (1999).

Lutz and Bujard, "Independent and tight regulation of transcriptional units in *Escherichia coli* via the LacR/O, the TetR/O and AraC/I1-I2 regulatory elements," *Nucleic Acids Res.* 25:1203-1210 (1997).

Lutz et al., "Creating multiple-crossover DNA libraries independent of sequence identity," *Proc. Natl. Acad. Sci. U.S.A.* 98(20):11248-11253 (2001).

Lutz et al., "Rapid generation of incremental truncation libraries for protein engineering using α-phosphothioate nucleotides," *Nucleic Acids Res.* 15;29(4):e16 (2001).

Ma et al., "Induced Rebuilding of Aspartase Confromation," *Ann. N.Y. Acad. Sci.* 672:60-65 (1992).

Mack and Buckel, "Conversion of glutaconate CoA-transferase from *Acidaminococcus fermentas* into an acyl-CoA hydrolase by site-directed mutagenesis," *FEBS Lett.* 405:209-212 (1997).

Mack et al., "Location of the two genes encoding glutaconate coenzyme A-transferase at the beginning of the hydroxyglutarate operon in *Acidaminococcus fermentans*," *Eur. J. Biochem.* 226:41-51 (1994).

Mahadevan and Schilling, "The effects of alternate optimal solutions in constraint-based genome-scale metabolic models," *Metab. Eng.* 5(4):264-276 (2003).

Mahadevan et al., "Applications of metabolic modeling to drive bioprocess development for the production of value-added chemicals," *Biotechnol. Bioprocess Eng.* 10(5):408-417 (2005).

Mahan and Csonka, "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.* 156(3):1249-1262 (1983).

Majewski and Domach, "Simple Constrained-Optimization View of Acetate Overflow in *E. coli*," *Biotech. Bioeng.* 35:732-738 (1990).

Majumdar et al., "Functional consequences of substitution in the active site (phosphor) histidine residue of *Escherichia coli* succinyl-CoA synthetase," *Biochim. Biophys. Acta.* 1076:86-90 (1991).

Mandal and Ghosh, "Isolation of a glutamate synthase (GOGAT)-negative, pleiotropically N utilization-defective mutant of *Azospirillum brasilense*: cloning and partial characterization of GOGAT structural gene," *J. Bacteriol.* 175:8024-8029 (1993).

Manning and Pollitt, "Tracer studies of the interconversion of R- and S-methylmalonic semialdehydes in man," *Biochem. J.* 231:481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170(2):991-994 (1988).

Marks et al., "Molecular Cloning and Characterization of (R)-3-Hydroxybutyrate Dehydrogenase from Human Heart," *J. Biol. Chem.* 267:15459-15463 (1992).

Martin et al., "Engineering a mevalonate pathway in *Escherichia coli* for production of terpenoids," *Nat. Biotechnol.* 21:796-802 (2003).

Martinez-Blanco et al., "Purification and Biochemical Characterization of Phenylacetyl-CoA Ligase from *Pseudomonas putida*," *J. Biol. Chem.* 265(12):7084-7090 (1990).

Mat-Jan et al., "Anaerobic growth defects resulting from gene fusions affecting succinyl-CoA synthetase in *Escherichia coli* K12," *Mol. Gen. Genet.* 215:276-280 (1989).

Mattevi et al., "Atomic structure of the cubic core of the pyruvate dehydrogenase multienzyme complex," *Science* 255:1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.* 58(5):1435-1439 (1992).

Mavrovouniotis, "Estimation of standard Gibbs energy changes of biotransformations," *J. Biol. Chem.* 266:14440-14445 (1991).

McKinlay et al., "Prospects for a bio-based succinate industry," *Appl. Microbiol. Biotechnol.* 76(4):727-740 (2007).

McLaggan et al., "Interdependence of K+ and glutamate accumulation during osmotic adaptation of *Escherichia coli*," *J. Biol. Chem.* 269:1911-1917 (1994).

McPherson and Wootton, "Complete nucleotide sequence of the *Escherichia coli* gdhA gene," *Nucleic Acids Res.* 11(15):5257-5266 (1983).

Melchiorsen et al., "The level of pyruvate-formate lyase controls the shift from homolactic to mixed-acid product formation in *Lactoccus lactis*," *Appl. Microbiol. Biotechnol.* 58(3):338-344 (2002).

Meng and Chuang, "Site-Directed Mutagenesis and functional Analysis of the Active-Site Residues of the E2 Component of Bovine Branched-Chain α-Keto Acid Dehydrogenase Complex," *Biochem.* 33:12879-12885 (1994).

Menzel et al., "Enzymatic evidence for an involvement of pyruvate dehydrogenase in the anaerobic glycerol metabolism of *Klebsiella pneumoniae*," *J. Biotechnol.* 56:135-142 (1997).

Menzel et al., "Kinetic, dynamic, and pathway studies of glycerol metabolism by *Klebsiella pneumoniae* in anaerobic continuous culsutre: IV. Enzynmes and fluxes of pyruvate metabolism," *Botechnol. Bioeng.* 60(5):617-626 (1998).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Metz et al., "Purification of a jojoba embryo fatty acyl-coenzyme A reductase and expression of its cDNA in high erucic acid rapeseed," *Plant Physiol.* 122(3):635-644 (2000).

Metzer and Halpern, "In vivo cloning and characterization of the gabCTDP gene cluster of *Escherichia coli* K-12," *J. Bacteriol.* 172:3250-3256 (1990).

Metzer et al., "Isolation and properties of *Escherichia coli* K-12 mutants impaired in the utilization of gamma-aminobutyrate," *J. Bacteriol.* 137(3):1111-1118 (1979).

Miles and Guest, "Molecular genetic aspects of the citric acid cycle of *Escherichia coli*," *Biochem. Soc. Symp.* 54:45-65 (1987).

Miller and Brenchly, "Cloning and characterization of gdhA, the structural gene for glutamate dehydrogenase of *Salmonella typhimurium*," *J. Bacteriol.* 157:171-178 (1984).

Misono and Nagasaki, "Occurrence of L-Lysine ϵ-Dehydrogenase in *Agrobacterium tumefaciens*," *J. Bacteriol.* 150(1):398-401 (1982).

Miyamoto and Katsuki, "Possible physiological roles of aspartase, NAD- and NADP-requiring glutamate dehydrogenases of *Pseudomonas fluorescens*," *J. Biochem.* 112:52-56 (1992).

Miyazaki et al., "α-Aminoadipate aminotransferase from an extremely thermophilic bacterium, *Thermus thermophilus*," *Microbiology* 150:2327-2334 (2004).

Mizobata et al., "Purification and Characterization of a thermostable Class II Fumarase from *Thermus thermophilus*," *Arch. Biochem. Biophys.* 355:49-55 (1998).

Momany et al., "Crystallographic Structures of a PLP-Dependent Ornithine Decarboxylase from *Lactobacillus* 30a to 3.0 Å Resolution," *J. Mol. Biol.* 242:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moore et al., "Expression and Purification of Aspartate β-Semialdehyde Dehydrogenase from Infectious Microorganisms," *Protein Expr. Purif.* 25:189-194 (2002).

Morris et al., "Nucleotide sequence of the LYS2 gene of *Saccharomyces cerevisiae*: homology to *Bacillus brevis* tyrocidine synthetasel," *Gene* 98:141-145 (1991).

Mountain et al., "The *Klebsiella aerogenes* glutamate dehydrogenase (gdnA) gene: cloning, high-level expression and hybrid enzyme formation in *Escherichia coli*," *Mol. Gen. Genet.* 199:141-145 (1985).

Muh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Muh et al., "Mossbauer study of 4-hydroxybutyryl-CoA dehydratase—probing the role of an iron-sulfur cluster in an overall non-redox reaction," *Eur. J. Biochem.* 248:380-384 (1997).

Muller et al., "Nucleotide exchange and excision technology (NExT) DNA shuffling: a robust method for DNA fragmentation and directed evolution," *Nucleic Acids Res.* 33(13):e117 (2005).

Mullins et al., "A specialized citric acid cycle requiring succinyl-coenzyme A (CoA):acetate CoA-transferase (AarC) confers acetic acid resistance on the acidophile *Acetobacter aceti*," *J. Bacteriol.* 190:4933-4940 (2008).

Muratsubaki and Enomoto, "One of the fumarate reductase isoenzymes from *Saccharomyces cerevisiae* is encoded by the OSM1 gene," *Arch. Biochem. Biophys.* 352(2):175-181 (1998).

Musfeldt and Schonheit, "Novel Type of ADP-Forming Acetyl Coenzyme A Synthetase in Hyperthermophilic Archaea: Heterologous Expression and Characterization of Isoenzymes from the Sulfate Reducer *Archaeoglobus fulgidus* and the Methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Nagasu et al., "Nucleotide Sequence of the GDH gene coding for the NADP-specific glutamate dehydrogenase of *Saccharomyces cerevisiae*," *Gene* 37:247-253 (1985).

Naggert et al., "Cloning, Sequencing, and Characterization of *Escherichia coli* thioesteraseII," *J. Biol. Chem.* 266(17):11044-11050 (1991).

Najmudin et al., "Purification, crystallization and preliminary X-ray crystallographic studies on acetolactate decarboxylase," *Acta. Crystallogr. D. Biol. Crystallog.* 59:1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

Namba et al., "Coenzyme A and Nicotinamide Adenine dinucleotide-deptendent Branched Chain α-Keto Acid Dehydrogenase," *J. Biol. Chem.* 244:4437-4447 (1969).

Ness et al., "Synthetic shuffling expands functional protein diversity by allowing amino acids to recombine independently," *Nat. Biotechnol.* 20(12):1251-1255 (2002).

Nexant, "1,4-Butanediol/THF—PERP Program New Report Alert," Nexant ChemSystems PERP Report 02/03-7, p. 1-5 (Jan. 2004).

Niegemann et al., "Molecular organization of the *Escherichia coli* gab cluster: nucleotide sequence of the structural genes gabD and gabP and expression of the GABA permease gene," *Arch. Microbiol.* 160:454-460 (1993).

Nishizawa et al., "Gene expression and characterization of two 2-oxoacid:ferredoxin oxidoreductases from *Aeropyrum pernix* K1," *FEBS. Lett.* 579:2319-2322 (2005).

Niu et al., "Benzene-free synthesis of adipic acid," *Biotechnol. Prog.* 18:201-211 (2002).

Niu, et al., "Benzene-free synthesis of adipic acid," *Biotechnol. Prog.* 18:201-211 (2002).

Nolling et al., "Genome sequence and comparative analysis of the solvent-producing bacterium *Clostridium acetobutylicum*," *J. Bacteriol.* 183(16):4823-4838 (2001).

Nowicki et al., "Recombinant tyrosine aminotransferase from *Trypanosoma cruzi*: structural characterization and site directed mutagenesis of a broad substrate specificity enzyme," *Biochim. Biophys. Acta* 1546(2):268-281 (2001).

Nowrousian et al., "The fungal acl1 and acl2 genes encode two polypeptides with homology to the N- and C-terminal parts of the animal ATP citrate lyase polypeptide," *Curr. Genet.* 37(3):189-193 (2000).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by a *Pseudomonas*, Purification and Properties of a Deacetylase-Thiolesterase utilizing 4-Acetamidobutyrl CoA and Related Compounds," *J. Biol. Chem.* 256:7642-7651 (1981).

Okino et al., "An efficient succinic acid production process in a metabolically engineered *Corynebacterium glutamicum* strain," *Appl. Microbiol. Biotechnol.* 81(3):459-464 (2008).

Oku and Kaneda, "Biosynthesis of Branched-chain Fatty Acids in *Bacillis subtilis*," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism," *Enzyme Protein* 47(3):136-148 (1993).

Oliver et al., "Determination of the nucleotide sequence for the glutamate synthase structural genes of *Escherichia coli* K-12," *Gene* 60:1-11 (1987).

Olivera et al., "Molecular characterization of the phenylacetic acid catabolic pathway in *Pseudomonas putida* U: The phenylacetyl-CoA catabolon," *Proc. Natl. Acad. Sci. U.S.A.* 95:6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from *Bacillus subtilis*," *Microbiology* 140:1023-1025 (1994).

Ostermeier et al., "A combinatorial approach to hybrid enzymes independent of DNA homology," *Nat Biotechnol.* 17(12):1205-1209 (1999).

Ostermeier et al., "Combinatorial protein engineering by incremental truncation," *Proc. Natl. Acad. Sci. U.S.A.* 96(7):3562-3567 (1999).

O'Sullivan, et al., "Purification and characterisation of acetolactate decarboxylase from *Leuconostoc lactis* NCW1," *FEMS Microbiol. Lett.* 194(2):245-249 (2001).

Otten and Quax, "Directed evolution: selecting today's biocatalysts," *Biomol. Eng.* (22):1-9 (2005).

Palosaari and Rogers, "Purification and properties of the inducible coenzyme A-linked butyraldehyde dehydrogenase from *Clostridium acetobutylicum*," *J. Bacteriol.* 170(7):2971-2976 (1988).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and Characterization of a New Enoyl coenzyme A Hydratase involved in biosynthesis of Medium-Chain-Length Polyhdroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng*, 86:681-686 (2004).

Park et al., "Regulation of succinate dehydrogenase (sdhCDAB) operon expression ion *Escherichia coli* in response to carbon supply and anaerobiosis: role of ArcA and Fnr," *Mol. Micriobiol.* 15:473-482 (1995).

Park et al., "Aerobic regulation of the sucABCD genes of *Escherichia coli*, which encode alpha-ketoglutarate dehydrogenase and succinyl coenzyme a synthetase: roles of ArcA, Fnr, and the upstream sdhCDAB promoter," *J. Bacteriol.* 179:4138-4142 (1997).

Park et al., "Isolation and characterization of recombinant mitochondrial 4-aminobutyrate aminotransferase," *J. Biol. Chem.* 268:7636-7639 (1993).

Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene.* 68(2): 275-283 (1988).

Pauwels et al., "The N-acetylglutamate synthase? N-acetylglutamate kinase metabolon of *Saccharomyces cerevisiae* allows cor-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Pelanda et al., "glutamate synthase genes of the diazotroph *Azospirillum brasillense*. Cloning, sequencing, and analysis of functional domains," *J. Biol. Chem.* 268:3099-3106 (1993).

Peoples and Sinskey, "Fine structural analysis of the *Zoogloea ramigera* phhA-phhB locus encoding beta-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino Acid Sequence of Alcohol Dehydrogenase from the *Thermophilic Bacterium Thermoanaerobium brockii*," *Biochem.* 28:6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70(2):420-426 (2005).

Petitdemange et al., "Regulation of the NADH and NADPH-ferredoxin oxidoreductases in *Clostridia* of the butyric group," *Biochim Biophys. Acta.* 421(2):334-337 (1976).

Phalip et al., "Purification and properties of the alpha-acetolactate decarboxylase from *Lactococcus lactis* subsp. *Lactis* NCDO 2118," *FEBS Lett.* 351:95-99 (1994).

Pharkya et al., "Exploring the overproduction of amino acids using the bilevel optimization framework OptKnock," *Biotechnol. Bioeng.* 84(7):887-899 (2003).

Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).

Pohl et al., "Remarkably broad substrate tolerance of malonyl-CoA synthetase, an enzyme capable of intracellular synthesis of polyketide precursors," *J. Am. Chem Soc.* 123(24): 5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Poirier et al., "Polyhydroxybutyrate, a Biodegradable Thermoplastic Produced in Transgenic Plants," *Science* 256:520-523 (1992).

Polovnikova et al., "Structural and Kinetic Analysis of Catalysis by a thiamin diphosphate-Dependent Enzyme, Benzoylformate Decarboxylase," *Biochemistry* 42:1820-1830 (2003).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175:377-385 (1993).

Presecan et al., "The *Bacillus subtillis* genome from gerBC (311 degrees) to licR (334 degrees)," *Microbiology* 143:3313-3328 (1997).

Price et al., "Genome-scale models of microbial cells: evaluating the consequences of constraints," *Nat. Rev. Microbiol.* 2(11):886-897 (2004).

Pritchard et al., "A general model of error-prone PCR," *J. Theor. Biol.* 234:497-509 (2005).

Purnell et al., "Modulation of higher-plant NAD(H)-dependent glutamate dehydrogenase activity in transgenic tobacco via alteration of beta subunit levels," *Planta* 222:167-180 (2005).

Qi et al., "Functional expression of prokaryotic and eukaryotic genes in *Escherichia coli* for conversion of glucose to *p*-hydroxystyrene," *Metab. Eng.* 9:268-276 (2007).

Qiu et al., "Metabolic engineering for the production of copolyesters consisting of 3-hydroxybutyrate and 3-hydroxyhexanoate by *Aeromonas hydrophilia*," *Macromol. Biosci.* 4(3):255-261 (2004).

Radhakrishnan et al., "Applications of metabolic modeling to drive bioprocess development for the production of value-aded chemicals," *Biotechnol. Bioprocess. Eng.* 10:408-417 (2005).

Rajpal et al., "A general method for greatly improving the affinity of antibodies by using combinatorial libraries," *Proc. Natl. Acad. Sci. U.S.A.* 102(24):8466-8471 (2005).

Ramon-Maiques et al., "Structure of Acetylglutamate Kinase, a Key Enzyme for Arginine Biosynthesis and a Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur. J. Biochem.* 149:401-404 (1985).

Rathinasabapathi, "Propionate, a source of β-alanine, is an inhibitor of β-alanine methylation in *Limonium latifolium, Plumbaginaceae*," *J. Plant Physiol.* 159:671-674 (2002).

Recasens et al., "Cysteine Sulfinate Aminotransferase and Aspartate Aminotransferase Isoenzymes of Rat Brain. Purification, Characterization, and Further Evidence for Identity," *Biochemistry* 19:4583-4589 (1980).

Redenbach et al., "A set of ordered cosmids and a detailed genetic and physical map for the 8 Mb *Streptomyces coelicolor* A3(2) chromosome," *Mol. Microbiol.* 21:77-96 (1996).

Reed et al., "An expanded genome-scale model of *Escherichia coli* K-12 (iJR904 GSM/GPR)," *Genome Biol.* 4(9):R54 (2003).

Reetz and Carballeria, "Iterative aturation mutagenesis (ISM) for rapid directed evolution of functional enzymes," *Nat. Protoc.* 2(4):891-903 (2007).

Reetz et al., "Creation of Enantioselective biocatalysts for Organic Chemistry by in Vitro Evolution," *Agnew. Chem. Int. Ed. Engl.* 36:2830-2832 (1997).

Reetz et al., "Directed Evolution of an Enantioselective Enzyme through Combinatorial Multiple-Cassette Mutagenesis," *Agnew. Chem. Int. Ed. Engl.* 40:3589-3591 (2001).

Reetz et al., "Iterative Saturation Mutagenesis on the Basis of B Factors as a Strategy for Increasing Protein Thermostability," *Agnew. Chem. Int. Ed. Engl.* 45:7745-7751 (2006).

Reetz et al., Expanding the range of substrate acceptance of enzymes: combinatorial active-site saturation test, Angew. Chem. Int. Ed. Engl. 44(27):4192-4196 (2005).

Regev-Rudzki et al., "Yeast Aconitase in Two Locations and Two Metabolic Pathways: Seeing Small Amounts Is Believing," *Mol. Biol. Cell* 16:4163-4171 (2005).

Reidhaar-Olson and Sauer, "Combinatorial cassette mutagenesis as a probe of the informational content of protein sequences," *Science* 241(4861):53-57 (1988).

Reidhaar-Olson et al., "Random mutagenesis of protein sequences using oligonucleotide cassettes," *Methods Enzymol.* 208:564-586 (1991).

Reiser and Somerville, "Isolation of mutants of *Acinetobacter calcoaceticus* deficient in wax ester synthesis and complementation of one mutation with a gene encoding a fatty acyl coenzyme a reductase," *J. Bacteriol.* 179(9):2969-2975 (1997).

Reitzer, "Ammonia Assimillation and the Biosynthesis of Glutamine, Glutamate, Aspartate, Asparagine, 1-Alanine, and d-Alanine," In Neidhardt (Ed.), *Escherichia Coli and Salmonella: Cellular and Molecular Biology*, ASM Press: Washington, DC, p. 391-407 (1996).

Repetto and Tzagoloff, "Structure and Regulation of KGD1, the Structural Gene for Yeast α-Ketoglutarate Dehydrogenase," *Mol. Cell.* 9:2695-2705 (1989).

Resnekov et al., "Organization and regulation of the *Bacillus subtilis* odhAB operon, which encodes two of the subenzymes of the 2-oxoglutarate dehydrogenase complex," *Mol. Gen. Genet.* 234(2):285-296 (1992).

Ribeiro et al., "Microbial reduction of α-acetyl-γ-butyrolactone," *Tetrahedron: Asymmetry*, 17(6):984-988 (2006).

Rigden et al., "A cofactor-dependent phosphoglycerate mutase homolog from *Bacillus stearothermophilus* is actually a broad specificity phosphatase," *Protein Sci.* 10:1835-1846 (2001).

Riondet et al., "Measurement of the intracellular pH in *Escherichia coli* with the internally conjugated fluorescent probe 5- (and 6) carboxyfluorescein succinimidyl ester," *Biotechnol. Tech.* 11:735-738 (1997).

Riviere et al., "Acetyl: Succinate CoA-transferase in Procyclic *Trypanosoma brucei*," *J. Biol Chem.* 279(44):45337-45346 (2004).

Robinson et al., "Studies on Rat Brain Acyl-Coenzyme a Hydrolase (Short Chain)," *Biochem. Biophys. Res. Commun.* 71:959-965 (1976).

Roca et al., "Metabolic engineering of ammonium assimilation in xylose-fermenting *Saccharmyces cerevisiae* improves ethanol production," *Appl. Environ. Microbiol.* 69(8):4732-4736 (2003).

Rohdich et al., "Enoate reductases of *Clostridia*. Cloning, sequencing, and expression," *J. Biol. Chem.* 276(8):5779-5787 (2001).

Romero et al., "Partial purification, characterization and nitrogen regulation of the lysine epsilon-aminotransferase of *Streptomyces clavuligerus*," *J. Ind. Microbiol. Biotechnol.* 18(4):241-246 (1997).

Rose and Weaver, "The role of the allosteric B site in the fumarase reaction," *Proc. Natl. Acad. Sci. U.S.A.* 101:3393-3397 (2004).

Rose et al., "Enzymatic phosphorylation of acetate," *J. Biol. Chem.* 211(2):737-756 (1954).

Roy and Dawes, "Cloning and Characterization of the Gene Encoding Lipamide Dehydrogenase in *Saccharomyces cerevisiae*," *J. Gen. Microbiol.* 133:925-933 (1987).

Sabo et al., "Purification and Physical Properties of Inducible *Escherichia coli* Lysine Decarboxylase," *Biochemistry* 13(4):662-670 (1974).

Saito and Doi, "Microbial synthesis and properties of poly(3-hydroxybutyrate-co-4-hydroxybutyrate) in *Comamonas acidovorans*," *Int. J. Biol. Macromol.* 16:99-104 (1994).

Saito et al., "Microbial Synthesis and properties of Poly(3-hydroxybutyrate-co-4-hydroxybutyrate)," *Polym. Int.* 39:169-174 (1996).

Sakakibara et al., "Isolation and characterization of a cDNA that encodes maize glutamate dehydrogenase," *Plant Cell Physiol.* 36:789-797 (1995).

Salmon et al., "Global gene expression profiling in *Escherichia coli* K12: effects of oxygen availability and ArcA," *J. Biol. Chem.* 280(15):15084-15096 (2005).

Samsonova et al., "Molecular cloning and characterization of *Escherichia coli* K12 ygjG gene," *BMC Microbiol.* 3:2 (2003).

Sanchez et al., "Properties and functions of two succinic-semialdehyde dehydrogenases from *Pseudomonas putida*," *Biochim Biophys. Acta*. 953(3):249-257 (1988).

Sanchez et al., "Purification and properties of two succinic semialdehyde dehydrogenases from *Klebsiella pneumoniae*," *Biochim Biophys. Acta*. 990(3):225-231 (1989).

Sariaslani, "Development of a Combined Biological and Chemical Process for Production of Industrial Aromatics from Renewable Resources," *Annu. Rev. Microbiol.* 61:51-69 (2007).

Sato et al., "Poly[(R)-3-Hydroxybutyrate] Formation in *Escherichia coli* from Glucose through an Enoyl-CoA Hydratase-Mediated Pathway," *J. Biosci. Bioeng.* 103(1):38-44 (2007).

Scherf and Buckel, "Purification and properties of 4-hydroxybutyrate coenzyme a transferase from *Clostridium aminobutyricum*," *Appl. Environ. Microbiol.* 57(9):2699-2702 (1991).

Scherf and Buckel, "Purification and properties of an iron-sulfur and FAD-containing 4-hydroxybuturyl-CoA dehydratase/vinylacetyl-CoA Δ3-Δ2-isomerase from *Clostridium aminobutyricum*," *Eur. J. Biochem.* 215:421-429 (1993).

Scherf et al., "Suffinate-ethanol fermentation in *Clostridium kluyveri*: purification and characterisation of 4-hydroxybutyryl-CoA dehydratase/vinylacetyl-CoA delta 3-delta 2-isomerase," *Arch. Microbiol.* 161:239-245 (1994).

Schilling et al., "Toward Metabolic Phenomics: Analysis of Genomic Data Using Flux Balances," *Biotechnol. Prog.* 15:288-295 (1999).

Schilling et al., "Combining Pathway Analysis with Flux Balance Analysis for the Comprehensive Study of Metabolic Systems," *Biotechnol. Bioeng.* 71(4):286-306 (2000-2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schneider et al., "The *Escherichia coli* gabDTPC operon: specific gamma-aminobutyrate catabolism and nonspecific induction," *J. Bacteriol.* 184:6976-6986 (2002).

Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.* 56:1-6 (1990).

Scott and Jakoby, "Soluble γ-Aminobutyric-Glutamic Transaminase from *Pseudomonas fluorescens*," *J. Biol. Chem.* 234:932-936 (1959).

Selifonova et al., "Rapid evolution of novel traits in microorganisms," *Appl. Environ. Microbiol.* 67(8):3645-3649 (2001).

Sen et al., "Developments in directed evolution for improving enzyme functions," *Appl. Biochem. Biotechnol.* 143(3):212-223 (2007).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen rregulation and the glycolysis pathway in *Eschericiha coli* under microaerobic growth conditions," *Biotechnol. Bioeng.* 92(2):147-159 (2005).

Shames et al., "Interaction of aspartate and aspartate-derived antimetabolites with the enzymes of the threonine biosynthetic pathway of *Escherichia ecoli*," *J. Biol. Chem.* 259(24):15331-15339 (1984).

Shao et al., "Random-priming in vitro recombination: an effective tool for directed evolution," *Nucleic Acids Res.* 26(2):681-683 (1998).

Shi et al., "The structure of L-aspartate ammonia-lyase from *Escherichia coli*," *Biochem.* 36(30):9136-9144 (1997).

Shigeoka and Nakano, "Characterization and molecular properties of 2-oxoglutarate decarboxylase from *Euglena gracilis*," *Arch. Biochem. Biophys*. 288:22-28 (1991).

Shigeoka and Nakano, "The effect of thiamin on the activation of thiamin pyrophosphate-dependent 2-oxoglutarate decarboxylase in *Euglena gracilis*," *Biochem. J.* 292:463-467 (1993).

Shigeoka et al., "Effect of L-glutamate on 2-oxoglutarate decarboxylase in *Euglena gracilis*," *Biochem. J.* 282:319-323 (1992).

Shimomura et al., "3-Hydroxyisobutyryl-CoA Hydrolase," *Meth. Enzymol.* 324:229-240 (2000).

Shimomura et al., "Purification and Partial Characterization of 3-Hydroxyisobutyryl-coenzyme A Hydrolase of Rat Liver," *J. Biol. Chem.* 269:14248-14253 (1994).

Shingler et al., "Nucleotide Sequence and Functional Analysis of the Complete Phenol/3,4-Dimethylphenol Catabolic Pathway of *Pseudomonas* sp. Strain CF600," *J. Bacteriol.* 174(3):711-724 (1992).

Shiraki et al., "Fermentative production of (R)-(–)-(3) hydroxybutyrate using 3-hydroxybutyrate dehydrogenase null mutant of *Ralstonia eutropha* and recombinant *Escherichia coli*," *J. Biosci. Bioeng.* 102(6):529-534 (2006).

Shukla et al., "Production of D(–)-lactate from sucrose and molasses," *Biotechnol. Lett.* 26(9):689-693 (2004).

Sieber et al., "Libraries of hybrid proteins from distantly related sequences," *Nat. Biotechnol.* 19(5):456-460 (2001).

Siegert et al., "Exchanging the substrate specificities of pyruvate decarboxylase from *Zymomonas mobilis* and benzoylase from *Pseudomonas puada*," *Protein Eng. Des. Sel.* 18:345-357 (2005).

Simonov et al.,"Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Sinclair et al, "Purification and characterization of the branched chain α-ketoacid dehydrogenase complex from *Saccharomyces cerevisiae*," *Biochem. Mol. Biol. Int.* 31(5):911-922 (1993).

Sjostrom et al., "Purfication and characterisation of a plasminogen-binding protein from *Haemophilus influenzae*. Sequence determination reveals identity with aspartase," *Biochim Biophys. Acta*. 1324:182-190 (1997).

Skarstedt and Silverstein, "*Escherichia coli* Acetate Kinase Mechanism Studied by Net Initial Rate, Equilibriu, and Independent Isotopic Exchange Kinetics," *J. Biol. Chem.* 251:6775-6783 (1976).

Skinner and Cooper, "An *Escherichia coli* mutant defective in the NAD-dependent succinate semialdehyde dehydrogenase," *Arch. Microbiol.* 132(3):270-275 (1982).

Smit et al., "Identification, Cloning, and Characterization of a *Lactococcus lactis* Branched-Chain α-Keto Acid Decarboxylase Involved in Flavor Formation," *Appl. Environ. Microbiol.* 71:303-311 (2005).

Smith et al., "Fumarate metabolism and the microaerophily of *Campylobacter* species," *Int. J. Biochem. Cell Biol.* 31:961-975 (1999).

Smith et al., "Purification and characteristics of a gamma-glutamyl kinase involved in *Escherichia coli* proline biosynthesis," *J.Bacteriol.* 157:545-551 (1984).

Smith et al., "Complete genome sequence of *Methanobacterium thermoautotrophicum* deltaH: functional analysis and comparative genomics," *J. Bacteriol.* 179:7135-7155 (1997).

Snedecor et al., "Selection, expression, and nucleotide sequencing of the glutamate dehydrogenase gene of *Peptostreptococcus asaccharolyticus*," *J. Bacteriol.* 173:6162-6167 (1991).

Soda and Misono, "L-Lysine:alpha-ketoglutarate aminotransferase. II. Purification, crystallization, and properties," *Biochemistry* 7(11):4110-4119 (1968).

Sohling and Gottschalk, "Molecular analysis of the anaerobic succinate degradation pathway in *Clostridium kluyveri.*," *J. Bacteriol.* 178(3):871-880 (1996).

Sohling and Gottschalk, "Purification and characterization of a coenzyme-A-dependent succinate-semialdehyde dehydrogenase from *Clostridium kluyveri*," *Eur. J. Biochem.* 212:121-127 (1993).

Sohling et al., "Molecular analysis of the anaerobic succinate degradation pathway in *Clostridium kluyveri*," *J. Bacteriol.* 178(3):871-880 (1996).

Sokatch et al., "Purification of a Branched-Chain Keto Acid Dehydrogenase from *Pseudomonas putida*," *J. Bacteriol.* 647-652 (1981).

Song et al., "Structure, Function, and Mechanism of the Phenylacetate Pathway Hot Dog-fold Thioesterase PaaI," *J. Biol. Chem.* 281(16):11028-11038 (2006).

Song et al., "Construction of recombinant *Escherichia coli* strains producing poly (4-hydroxybutyric acid) homopolyester from glucose," *Wei Sheng Wu Xue Bao*, 45(3):382-386 (2005). (In Chinese, includes English abstract).

Spencer and Guest, "Transcription analysis of the sucAB, aceEF and 1pd genes of *Escherichia coli*," *Mol. Gen. Genetics* 200:145-154 (1985).

Spencer et al., "Nucleotide sequence of the sucB gene encoding the dihydrolipoamide succinyltransferase of *Escherichia coli* K12 and homology with the corresponding acetyltransferase," *Eur. J. Biochem.* 141(2):361-374 (1984).

Stadtman, "The enzymatic synthesis of β-alanyl coenzyme A," *J. Am. Chem. Soc.* 77:5765-5766 (1955).

Stanley et al., "Expression and Sterochemical and Isotope Effect Studies of Active 4-Oxalocrotonate Decarboxylase," *Biochem.* 39:(4):718-726 (2000).

Steinbüchel and Schlegel, "NAD-linked L(+)-lactate dehydrogenase from the strict aerobe *Alcaligenes eutrophus*. 2. Kinetic properties and inhibition by oxaloacetate," *Eur. J. Biochem.* 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem.* 141:555-564 (1984).

Steinbuchel and Schlegel, "Physiology and molecular genetics of poly(beta-hydroxy-alkanoic acid) synthesis in *Alcaligenes eutrophus*," *Mol. Microbiol.* 5(3):535-542 (1991).

Steinbuchel and Valentin, "Diversity of bacterial polyhydroxyalkanoic acids," *FEMS Microbiol. Lett.* 128:219-228 (1995).

Steinbuchel et al., "A *Pseudomonas* strain accumulating polyesters of 3-hydroxybutyric acid and medium-chain-length 3-hydroxyalkanoic acids," *Appl. Microbiol. Biotechnol.* 37:691-697 (1992).

Stemmer, "DNA Shuffling by random fragmentation and reassembly: in vitro recombination for molecular evolution," *Proc. Natl. Acad. Sci. U.S.A.* 91(22):10747-10751 (1994).

Stemmer, "Rapid evolution of a protein in vitro by DNA shuffling," *Nature* 370:389-391 (1994).

Stokell et al., "Probing the roles of key residues in the unique regulatory NADH binding site of type II citrate synthase of *Escherichia coli*," *J. Biol. Chem.* 278(37):35435-35443 (2003).

Stols et al., "New vectors for co-expression of proteins: Structure of *Bacillus subtilis* ScoAB obtained by high-throughput protocols," *Protein Expr. Purif.* 53:396-403 (2007).

Stoyan et al., "Cloning, sequencing and overexpression of the leucine dehydrogenase gene from *Bacillus cereus*," *J. Biotechnol.* 54:77-80 (1997).

Strauss and Fuchs, "Enzymes of a novel autotrophic CO2 fixation pathway in the phototrophic bacterium *Chloroflexus aurantiacus*, the 3-hydroxypropionate cycle," *Eur. J. Biochem.* 215:633-643 (1993).

Suda et al., "Purification and properties of alpha-keoadipate reductase, a newly discovered enzyme from human placenta," *Arch. Biochem. Biophys.* 176(2):610-620 (1976).

Suda et al., "Subcellular Localization and tissue Distribution of α-Ketodaipate Reduction and Oxidation in the Rat," *Biochem. Biophys. Res. Commun.* 77:586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E.coli* alcohol dehydrogenase YqhD: evidence of a covalently modified NADP coenzyme," *J. Mol. Biol.* 342(2):489-502 (2004).

Suthers et al., "Metabolic flux elucidation for large-scale models using 13C labeled isotopes," *Metab. Eng.* 9(5-6):387-405 (2007).

Suzuki et al., "GriC and GriD Constitute a carboxylic acid reductase involved in grixazone biosynthesis in *Streptomyces griseus*," *J. Antibiot.* 60(6):380-387 (2007).

Suzuki, "Phosphotransacetylase of *Escherichia coli* B, activation by pyruvate and inhibition by NADH and certain nucleotides," *Biochim Biophys. Acta* 191(3):559-569 (1969).

Syntichaki et al., "The amino-acid sequence similarity of plant glutamate dehydrogenase to the extremophilic archaeal enzyme conforms to its stress-related function," *Gene.* 168:87-92 (1996).

Takagi and Kisumi, "Isolation of a Versatile *Serratia marcescens* Mutant as a Host and Molecular Cloning of the Aspartase Gene," *J. Bacteriol.* 161(1):1-6 (1985).

Takagi et al., "Purfication, Crystallization, and Molecular Properties of Aspartase from *Pseudomonas fluorescens*," *J. Biochem.* 96:545-552 (1984).

Takahashi et al., "Metabolic Pathways for Cytoxic End Product Formation from Glutamate- and Aspartate-Containing Peptides by *Porphyromonas gingivalis*," *J. Bacteriol.* 182(17):4704-4710 (2000).

Takahashi-Abbe et al., "Biochemical and functional properties of a pyruvate formate-lyase (PFL)-activating system in *Streptococcus mutans*," *Oral Microbiol. Immunol.* 18(5)293-297 (2003).

Takanashi et al., "Characterization of a novel 3-hydroxybutyrate dehydrogenase from *Ralstonia pickettii* T1," *Antonie van Leeuwnhoek* 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182(23):6732-6741 (2000).

Takatsuka et al., "Identification of the amino acid residues conferring substrate specificity upon *Selenomonas ruminantium* lysine decarboxylase," *Biosci. Biotechnol. Biochem.* 63(10):1843-1846 (1999).

Takigawa et al., "Probabilistic path ranking based on adjacent pairwise coexpression for metabolic transcripts analysis," *Bioinformatics* 24(2):250-257 (2008).

Tallant and Krzycki, "Methylthiol:coenzyme M methyltransferase from *Methanosarcina barkeri*, an enzyme of methanogenesis from dimethylsulfide and methylmercaptopropionate," *J. Bacteriol.* 179:6902-6911 (1997).

Tallant et al., "The MtsA subunit of the methylthiol:coenzyme M methyltransferase of *Methanosarcina barkeri* catalyses both half-reactions of corrinoid-dependent dimethylsulfide: coenzyme M methyl transfer," *J. Biol. Chem.* 276:4485-4493 (2001).

Tamaki et al., "Purification, Properties, and Sequencing of Aminisobutyrate Aminotransferases from Rat Liver," *Meth. Enzymol.* 324:376-389 (2000).

Tanaka et al., "Cloning and characterization of a human orthologue of testis-specific succinyl CoA:3-oxo acid CoA transferase (Scot-t) cDNA," *Mol. Hum. Reprod.* 8:16-23 (2001.).

Tanaka et al., "Lysine decarboxylase of *Vibrio parahaemolyticus*: kinetics of transcription and role in acid resistance," *J. Appl. Microbiol.* 104(5):1283-1293 (2007).

Tani et al., "Thermostable NADP(+)-dependent medium-chain alcohol dehydrogenase from *Acinetobacter* sp strain M-1: Purification and characterization and gene expression in *Escherichia coli*," *Appl. Environ. Microbiol.* 66:5231-5235 (2000).

Teller et al., "The glutamate dehydrogenase gene of *Clostridium symbiosum*, Cloning by polymerase chain reaction sequence analysis and over-expression in *Escherichia coli*," *Eur. J. Biochem.* 206:151-159 (1992).

ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.* 64(4):1303-1307 (1998).

Thakur et al., "Changes in the Electroencephalographic and .gamma.-Aminobutyric Acid Transaminsase and Succinic Semialdehyde Dehydrogenase in the Allergen Induced Rat Brain," *Biochem. Int.* 16:235-243 (1998).

Tian et al., "Variant tricarboxylic acid cycle in *Mycobacterium tuberculosis*: identification of alpha-ketoglutarate decarboxylase," *Proc. Natl. Acad. Sci. U.S.A.* 102(30):10670-10675 (2005).

Tobin et al., "Localization of the lysine epsilon-aminotransferase (lat) and delta-(L-alpha-aminoadipyl)-L-cysteinyl-D-Valine synthetase (pcbAB) genes from *Streptomyces clavuligerus* and production of lysine epsilon-aminotransferase activity in *Escherichia coli*," *J. Bacteriol.* 173(19):6223-6229 (1991).

Tomb et al., "The complete genome sequence of the gastric pathogen *Helicobacter pylori*," *Nature* 388:539 (1997).

Toth et al., "The ald gene, encoding a coenzyme A-acylating aldehyde dehydrogenase, distinguishes *Clostridium beijerinckii* and two other solvent-producing clostridia from *Clostridium acetobutylicum*," *Appl. Environ. Microbiol.* 65(11):4973-4980 (1999).

Tretter and Adam-Vizi, "Alpha-ketoglutarate dehydrogenase: a target and generator of oxidative stress," *Philos. Trans. R. Soc. Lond B. Biol. Sci.* 360:2335-2345 (2005).

Tseng et al., "Metabolic engineering of *Escherichia coli* for enhanced production of (R)- and (S)-3-hydroxybutyrate," *Appl. Environ. Microbiol.* 75(10):3137-3145 (2009).

Tucci and Martin, "A novel prokaryotic trans-2-enoyl-CoA reductase from the spirochete *Treponema denticola*," *FEBS Lett.* 581:1561-1566 (2007).

Twarog and Wolfe, "Role of Buyryl Phosphate in the Energy Metabolism of *Clostridium Tetanomorphum*," *J. Bacteriol.* 86:112-117 (1963).

Tzimagiorgis et al., "Molecular cloning, structure and expression analysis of a full-length mouse brain glutamate dehydrogenase cDNA," *Biochem. Biophys. Acta.* 1089:250-253 (1991).

Tzimagiorgis et al., "Structure and expression analysis of a member of the human glutamate dehydrogenase (GLUD) gene gamily mapped to chromosome 10p11.2," *Hum. Genet.* 91:433-438 (1993).

Umeda et al., "Cloning and sequence analysis of the poly(3-hydroxyalkanoic acid)-synthesis genes of *Pseudomonas acidophila*," *Appl. Biochem. Biotechnol*, 70-72:341-352 (1998).

Uttaro and Opperdoes, "Purification and characterisation of a novel iso-propanol dehydrogenase from *Phytomonas* sp," *Mol. Biochem. Parasitol.* 85:213-219 (1997).

Valentin et al., "Indentication of 4-hydroxyhexanoic acid as a new constituent of biosynthetic polyhydroxyalkanoic acids from bacteria," *Appl. Microbiol. Biotechnol.* 40:710-716 (1994).

Valentin et al., "Identification of 4-hydroxyvaleric acid as a constituent of biosynthetic polyhydroxyalkanoic acids from bacteria," *Appl. Microbiol. Biotechnol.* 36:507-514 (1992).

Valentin et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.* 46:261-267 (1996).

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227:43-60 (1995).

Valentin et al., "Poly(3-hydroxybutyrate-co-4-hydroxybutyrate) formation from gamma-aminobutyrate and glutamate," *Biotechnol Bioeng.* 67(3):291-299 (2000).

Valentin et al., "Production of poly(3-hydroxybutyrate-co-4-hydroxybutyrate) in recombinant *Escherichia coli* grown on glucose," *J. Biotechnol.* 58:33-38 (1997).

Valentine and Wolfe, "Purification and role of phosphotransbutyrylase," *J. Biol. Chem.* 235:1948-1952 (1960).

Valle et al., "Complete nucleotide sequence of the glutamate dehydrogenase gene from *Escherichia coli* K-12," *Gene* 27:193-199 (1984).

Valle et al., "Nucleotide sequence of the promotor and amino-terminal coding region of the glutamate dehydrogenase structural gene of *Escherichia coli*," *Gene* 23:199-209 (1983).

Vamecq et al., "The microsomal dicarboxylyl-CoA synthetase," *Biochem. J.* 230:683-693 (1985).

van der Rest et al., "Functions of the membrane-associated and cytoplasmic malate dehydrogenases in the citric acid cycle of *Escherichia coli*," *J. Bacteriol.* 182(24):6892-6899 (2000).

van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

van Vliet et al., "The iron-induced ferredoxin FdxA of *Campylobacter jejuni* is involved in aerotolerance," *FEMS Microbiol. Lett.* 196:189-193 (2001).

Vanderwinkel et al., "Growth of *Escherichia coli* on Fatty Acids: Requirement for Coenzyme a Transferase Activity," *Biochem. Biophys. Res. Commun.* 33:902-908 (1968).

Vanrolleghem et al., "Validation of a Metabolic Network for *Saccharomyces cerevisiae* Using Mixed Substrate Studies," *Biotechnol. Prog.* 12(4):434-448 (1996).

Varma and Palsson, "Metabolic Flux balancing: Basic concepts, Scientific and Practical Use," *Biotechnol.* 12:994-998 (1994).

Varma and Palsson, "Stoichiometric flux balance models quantitatively predict growth and metabolic by-product secretion in wild-type *Escherichia coli* W3110," *Appl. Environ. Microbiol.* 60:3724-3731 (1994).

Vazquez et al., "Phosphotransbutyrylase Expression in *Bacillus megaterium*," *Curr. Microbiol.* 42:345-349 (2001).

Venkitasubramanian et al. Biocatalysis in the Pharmaceutical and Biotechnology Industries, ed. R.N. Patel, Chapter 15, pp. 425-440, CRC Press LLC, Boca Raton, Fl. 2007.

Venkitasubramanian et al., "Reduction of Carboxylic Acids by *Nocardia* Aldehyde Oxidoreductase Requires a Phosphopantetheinylated Enzyme," *J. Biol Chem.* 282:478-485 (2007).

Vernal et al., "Cloning and heterologous expression of a broad specificity aminotransferase of *Leishmania mexicana* promastigotes1," *FEMS Microbiol. Lett.* 229(2):217-222 (2003).

Vernal et al., "Isolation and partial characterization of a broad specificity aminotransferase from *Leishmania mexicana* promastigotes," *Mol. Biochem. Parasitol.* 96(1-2):83-92 (1998).

Vey et al., "Structural basis for glycyl radical formation by pyruvate formate-lyase activating enzyme," *Proc. Natl. Acad. Sci. U.S.A.* 105(42):16137-16141 (2008).

Viola, "L-aspartase: new tricks from an old enzyme," *Adv. Enzymol. Relat. Areas. Mol. Biol.* 74:295-341 (2000).

Vita et al., "Disulfide bond-dependent mechanism of protection against oxidative stress in pyruvate-ferredoxin oxidoreductase of anaerobic *Desulfovibrio* bacteria," *Biochemistry* 47(3):957-964 (2008).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27(18):e18 (1999).

Wakil et al., "Studies on the Fatty Acid Oxidizing System of Animal Tissues," *J. Biol. Chem.* 207:631-638 (1954).

Walter et al., "Sequence and arrangement of two genes of the butyrate-synthesis pathway of *Clostridium acetobutylicum* ATCC 824," *Gene* 134:107-111 (1993).

Walter et al., "Molecular characterization of two *Clostridium acetobutylicum* ATCC 824 butanol dehydrogenase isozyme genes," *J. Bacteriol.* 174(22):7149-7158 (1992).

Wang et al., "Molecular cloning and functional identification of a novel phenylacetyl-CoA ligase gene from *Penicillium chrysogenum*," *Biochem. Biophys. Res. Commun.* 360(2):453-458 (2007).

Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).

Wang et al., "Isolation of poly-3-hydroxybutyrate metabolism genes from complex microbial communities by phenotypic complementation of bacterial mutants," *Appl. Environ. Microbiol.* 72(1):384-391 (2006).

Wang et al., "Screening microorganisms for utilization of furfural and possible intermediates in its degradative pathway," *Biotechnol. Lett.* 16(9):977-982 (1994).

Ward et al., "Molecular analysis of the role of two aromatic aminotransferases and a broad-specificity aspartate aminotransferase in the aromatic amino acid metabolism of *Pyrococcus furiosus*," *Archaea.* 1:133-141 (2002).

Weaver, "Structure of free fumarase C from *Escherichia coli*," *Acta. Crystallog. D. Biol. Crystallogr.* 61:1395-1401 (2005).

Weidner and Sawers, "Molecular Characterization of the Genes Encoding Pyruvate Formate-Lyase and Its Activating Enzyme of *Clostridium pasteurianum*," *J. Bacteriol.* 178(8):2440-2444 (1996).

Welch et al., "Purification and characterization of the NADH-dependent butanol dehydrogenase from *Clostridium acetobutylicum* (ATCC 824)," *Arch. Biochem. Biophys.* 273(2):309-318 (1989).

Werpy et al., "Top Value Added Chemicals from Biomass. vol. I—Results of Screening for Potential Candidates from Sugars and Synthesis Gas," DOE Report (2004).

Westin et al., "The Identification of Succinyl-CoA Thioesterase Suggests a Novel Pathway for Succinate Production in Peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbiol.* 7:1917-1926 (2005).

Whalen and Berg, "Analysis of an *avtA*::Mu *d*1(Ap lac) Mutant: Metabolic role of Transaminase C," *J. Bacteriol.* 150(2):739-746 (1982).

Whalen and Berg, "Gratuitous Repression of *avtA* in *Escherichia coli* and *Salmonella typhimurium*," *J. Bacteriol.* 158(2):571-574 (1984).

Wiesenborn et al., "Coenzyme A Transferase from *Clostridium acetobutylicum* ATC 824 and Its Role in the Uptake of Acids," *Appl. Environ. Microbiol.* 55:323-329 (1989).

Wilkie and Warren, "Recombinant Expression, Purification, and Characterization of Three Isoenzymes of Aspartate Aminotrannsferase from *Arabidopsis thaliana*," *Protein Expr. Purif.* 12:381-389 (1998).

Wilks et al., "A specific, highly active malate dehydrogenase by redesign of a lactate dehydrogenase framework," *Science* 242(4885):1541-1544 (1988).

Wilks et al., "Design for a broad substrate specificity keto acid dehydrogenase," *Biochemistry* 29(37)8587-8591 (1990).

Wilks et al., "Design of a specific phenyllactate dehydrogenase by peptide loop exchange on the *Bacillus stearothermophilus* lactate dehydrogenase framework," *Biochemistry* 31(34):7802-7806 (1992).

Willadsen and Buckel, "Assay of 4-hydroxybutyryl-CoA dehydrasate from *Clostridium aminobutyricum*," *FEMS Microbiol. Lett.* 70:187-191 (1990).

Williams et al., "Biodegradable plastics from plants," *CHEMTECH* 26:38-44 (1996).

Willke and Vorlop, "Biotechnological production of itaconic acid," *Appl. Microbiol. Biotechnol.* 56:289-295 (2001).

Winzer et al., "Differential regulation of two thiolase genes from *Clostridium acetobutylicum* DSM 792," *J. Mol. Microbiol. Biotechnol.* 2:531-541 (2000).

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wolff et al., "Dehydrogenases involved in the conversion of succinate to 4-hydroxybutanoate by *Clostridium kluyven*," *Appl. Environ. Microbio.* 59:1876-1882 (1993).

Wong et al., "Sequence satruation mutagenesis with tunable mutation frequencies," *Anal. Biochem.* 341:187-189 (2005).

Wong et al., "Sequence saturation mutagenesis (SeSaM): a novel method for directed evolution," *Nucleic Acids Res.* 32(3):e26 (2004).

Wynn et al., "Chaperonins GroEL and GroES Promote Assembly of Heterotramers (α2β2) of Mammalian Mitochondrial Branched-chain α-Keto Acid Decarboxylase in *Escherichia coli*," *J. Biol. Chem.* 267(18):12400-12403 (1992).

Wynn et al., "Cloning and Expression in *Escherichia coli* of a Mature E1β Subunit of Bovine Mitochondrial Branched-chain α-Keto Acid Dehydrogenase Complex," *J. Biol Chem.* 267(3):1881-1887 (1992).

Yagi et al., "Aspartate: 2-Oxoglutarate Aminotransferase from Bakers' Yeast: Crystallization and Charactierization," *J. Biochem.* 92:35-43 (1982).

Yagi et al., "Crystallization and Properties of Aspartate Aminotransferase from *Escherichi coli* B," *FEBS Lett.* 100(1)81-84 (1979).

Yagi et al., "Glutamate-Aspartate Transaminase from Microorganisms," *Meth. Enzymol.* 113:83-89 (1985).

Yakunin and Hallenbeck, "Purification and characterization of pyruvate oxidoreductase from the photosynthetic bacterium *Rhodobacter capsulatus*," *Biochim Biophys. Acta.* 1409(1):39-49 (1998).

Yamamoto et al., "Carboxylation reaction catalyzed by 2-oxoglutarate:ferredoxin oxidoreductases from *Hydrogenobacter thermophilus*," *Extremophiles* 14:79-85 (2010).

Yang et al, "Nucleotide Sequence of the *fadA* Gene. Primary structure of 3-ketoacyl-coenzyme A thiolase from *Escherichia coli* and the structural organization of the *fadAB* operon," *J. Biol. Chem* 265(18):10424-10429 (1990) with correction in *J. Biol. Chem* 266(24):16255 (1991).

Yang et al., "Aspartate Dehydrogenase, a Novel Enszyme Idnetified from Structural and Functional Studies of TM16343," *J. Biol. Chem.* 278:8804-8808 (2003).

Yang et al., "Continuous cultivation of *Lactobacillus rhamnosus* with cell recycling using an acoustic cell settler," *Biotechnol. Bioprocess. Eng.* 7(6):357-361 (2002).

Yang et al., "Nucleotide Sequence of the fadA Gene," *J. Biol. Chem.* 265(18):10424-10429 (1990).

Yang et al., "Nucleotide sequence of the promoter and fadB gene of the fadBA operon and primary structure of the multifunctional fatty acid oxidation protein from *Escherichia coli*," *Biochemistry* 30(27):6788-6795 (1991).

Yano et al., "Directed evolution of an aspartate aminotransferase with new substrate specificities," *Proc. Natl. Acad. Sci. U.S.A.* 95:5511-5515 (1998).

Yarlett et al., "*Trichomonas vaginalis*: characterization of ornithine decarboxylase," *Biochem. J.* 293:487-493 (1993).

Yee et al., "Isolation and characterization of a NADP-dependent glutamate dehydrogenase gene from the primitive eucaryote *Giardia lamblia*," *J. Biol. Chem.* 267:7539-7544 (1992).

Yoshida et al., "the structures of L-rhamnose isomerase from *Pseudomonas stutzeri* in complexs with L-rhamnose and D-allose provide insights into broad substrate specificity," *J. Mol. Biol.* 365(5):1505-1516 (2007).

Youngleson et al., "Homology between hydroxybutyryl and hydroxyacyl coenzyme A dehydrogenase enzymes from *Clostridium acetobutylicum* fermentation and vertebrate fatty acid beta-oxidation pathways," *J. Bacteriol.* 171(12):6800-6807 (1989).

Yu et al., "sucAB and sucCD are mutually essential genes in *Escherichia coli*," *FEMS Microbiol. Lett.* 254(2):245-250 (2006).

Yun et al., "The genes for anabolic 2-oxoglutarate: ferredoxin oxidoreductse from *Hydrogenobacter thermophilus* TK-6," *Biochem. Biophys. Res. Commun.* 282(2):589-594 (2001).

Yun et al., "Omega-Amino acid:pyruvate transaminase from *Alcaligenes denitrificans* Y2k-2: a new catalyst for kinetic resolution of beta-amino acids and amines," *Appl. Environ. Microbiol.* 70(4):2529-2534 (2004).

Zeiher and Randall, "Identification and Characterization of Mitochondrial Acetyl-Coenzyme A Hydrolase from *Pisum sativum* L. Seedlings," *Plant Physiol.* 94:20-27 (1990).

Zhang et al., "2-Oxoacid: Ferredoxin Oxidoreductase from the Thermoacidophilic Archaeon, *Sulfolobus* sp. Strain 7," *J. Biochem.* 120:587-599 (1996).

Zhang et al., "Directed evolution of a fucosidase from a galactosidase by DNA shuffling and screening," *Proc. Natl. Acad. Sci. U.S.A.* 94:4504-4509 (1997).

Zhang et al., "Isolation and Properties of a levo-lactonase from *Fusarium proliferatum* ECD2002: a robust biocatalyst for production of chiral lactones," *App. Microbiol. Biotechnol.* 75(5):1087-1094 (2007).

Zhang, et al., "Kinetic and mechanistic characterization of the polyhydroxybutyrate synthase from *Ralstonia eutropha*," *Biomacromolecules* 1(2):244-251 (2000).

Zhao et al., "Molecular evolution by staggered extension process (StEP) in vitro recombination," *Nat Biotechnol.* 16(3):258-261 (1998).

Zhou et al., "The remarkable structural and functional organization of the eukaryotic pyruvate dehydrogenase complexes," *Proc. Natl. Acad. Sci. USA* 98:14802-14807 (2001).

Zhou et al., "Functional replacement of the *Escherichia coli* D-(−)-lactate dehydrogenase gene (ldhA) with the L-(+)-lactate dehydrogenase gene (ldhL) from *Pediococcus acidilactici*," *Appl. Environ. Micro.* 69:2237-2244 (2003).

Zhuang et al., "The YbgC protein encoded by the ybgC gene of the tol-pal gene cluster of *Haemophilus influenzae* catalyzes acyl-coenzyme A thioester hydrolysis," *FEBS Lett.* 516:161-163 (2002).

URL expressys.de/. (Printed Dec. 21, 2009).

URL openwetware.org/wiki/Synthetic_Biology:BioBricks, Synthetic Biology:BioBricks, portal for information relating to the Registry of Standard Biological Parts (Printed Dec. 21, 2009).

Url shigen.nig.ac.jp/ecoli/pec/genes.List.DetailAction.do (Printed Dec. 21, 2009).

URL_www.genome.jp/dbget-bin/www_bget?cdf:CD2966 (Printed Dec. 21, 2009).

URL_www.genome.jp/dbget-bin/www_bget?cpe:CPE2531 (Printed Dec. 21, 2009).

URL_www.genome.jp/dbget-bin/www_bget?ctc:CTC01366 (Printed Dec. 21, 2009).

URL_www.genome.jp/dbget-bin/www_bget?cth:Cthe_0423 (Printed Mar. 4, 2010).

Genbank Accession No. NP_414549.1; GI:16128002 (May 1, 2007); with corresponding KEGG Database printout of b0008 (May 11, 2010).

Genbank Accession No. NP_414658.1; GI:16128109 (May 1, 2007); with corresponding KEGG Database printout of b0116 (May 10, 2010).

Genbank Accession No. NP_414776.1; GI:16128227 (May 1, 2007); with corresponding KEGG Database printout of b0241 (May 10, 2010).

Genbank Accession No. NP_414777.1; GI:16128228 (May 1, 2007); with corresponding KEGG Database printout of b0242 (May 10, 2010).

Genbank Accession No. NP_414778.1; GI:16128229 (May 1, 2007); with corresponding KEGG Database printout of b0243 (May 10, 2010).

Genbank Accession No. NP_414857.1; GI:16128308 (May 1, 2007); with corresponding KEGG Database printout of b0323 (May 10, 2010).

Genbank Accession No. NP_414867.1; GI:16128318 (May 1, 2007); with corresponding KEGG Database printout of b0333 (May 11, 2010).

Genbank Accession No. NP_414885.1; GI:16128336 (May 1, 2007); with corresponding KEGG Database printout of b0351 (May 10, 2010).

Genbank Accession No. NP_414890.1; GI:16128341 (May 1, 2007); with corresponding KEGG Database printout of b0356 (May 10, 2010).

Genbank Accession No. NP_415010.1; GI:16128461 (May 1, 2007); with corresponding KEGG Database printout of b0477 (May 11, 2010).

Genbank Accession No. NP_415054.1; GI:16128505 (May 1, 2007); with corresponding KEGG Database printout of b0521 (May 10, 2010).

Genbank Accession No. NP_415062.1; GI:16128513 (May 1, 2007); with corresponding KEGG Database printout of b0529 (May 10, 2010).

Genbank Accession No. NP_415249.1; GI:16128696 (May 1, 2007); with corresponding KEGG Database printout of b0721 (May 10, 2010).

Genbank Accession No. NP_415250.1; GI:16128697 (May 1, 2007); with corresponding KEGG Database printout of b0722 (May 10, 2010).

Genbank Accession No. NP_415251.1; GI:16128698 (May 1, 2007); with corresponding KEGG Database printout of b0723 (May 10, 2010).

Genbank Accession No. NP_415252.1; GI:16128699 (May 1, 2007); with corresponding KEGG Database printout of b0724 (May 10, 2010).

Genbank Accession No. NP_415254.1; GI:16128701 (May 1, 2007); with corresponding KEGG Database printout of b0726 (May 10, 2010).

Genbank Accession No. NP_415255.1; GI:16128702 (May 1, 2007); with corresponding KEGG Database printout of b0727 (May 10, 2010).

Genbank Accession No. NP_415256.1; GI:16128703 (May 1, 2007); with corresponding KEGG Database printout of b0728 (May 10, 2010).

Genbank Accession No. NP_415257.1; GI:16128704 (May 1, 2007); with corresponding KEGG Database printout of b0729 (May 10, 2010).

Genbank Accession No. NP_415276.1; GI:16128723 (May 1, 2007); with corresponding KEGG Database printout of b0755 (May 10, 2010).

Genbank Accession No. NP_415284.1; GI:16128731 (May 1, 2007); with corresponding KEGG Database printout of b0763 (May 11, 2010).

Genbank Accession No. NP_415285.1; GI:16128732 (May 1, 2007); with corresponding KEGG Database printout of b0764 (May 11, 2010).

Genbank Accession No. NP_415286.1; GI:16128733 (May 1, 2007); with corresponding KEGG Database printout of b0765 (May 11, 2010).

Genbank Accession No. NP_415288.1; GI:16128735 (May 1, 2007); with corresponding KEGG Database printout of b0767 (May 10, 2010).

Genbank Accession No. NP_415422.1; GI:16128869 (May 1, 2007); with corresponding KEGG Database printout of b0902 (May 10, 2010).

Genbank Accession No. NP_415423.1; GI:16128870 (May 1, 2007); with corresponding KEGG Database printout of b0903 (May 10, 2010).

Genbank Accession No. NP_415449.1; GI:16128896 (May 1, 2007); with corresponding KEGG Database printout of b0929 (May 10, 2010).

Genbank Accession No. NP_415534.1; GI:16128980 (May 1, 2007); with corresponding KEGG Database printout of b1014 (May 10, 2010).

Genbank Accession No. NP_415551.2; GI:90111205 (May 1, 2007); with corresponding KEGG Database printout of b1033 (May 11, 2010).

Genbank Accession No. NP_415619.1; GI:16129064 (May 1, 2007); with corresponding KEGG Database printout of b1101 (May 10, 2010).

Genbank Accession No. NP_415627.1; GI:16129072 (May 1, 2007); with corresponding KEGG Database printout of b1109 (May 10, 2010).

Genbank Accession No. NP_415716.3; GI:145698246 (May 1, 2007); with corresponding KEGG Database printout of b1198 (May 11, 2010).

Genbank Accession No. NP_415717.1; GI:16129162 (May 1, 2007); with corresponding KEGG Database printout of b1199 (May 11, 2010).

Genbank Accession No. NP_415718.4; GI:90111233 (May 1, 2007); with corresponding KEGG Database printout of b1200 (May 11, 2010).

Genbank Accession No. NP_415748.1; GI:16129193 (May 1, 2007); with corresponding KEGG Database printout of b1232 (May 10, 2010).
Genbank Accession No. NP_415757.1; GI:16129202 (May 1, 2007); with corresponding KEGG Database printout of b1241 (May 10, 2010).
Genbank Accession No. NP_415895.1; GI:16129338 (May 1, 2007); with corresponding KEGG Database printout of b1377 (May 10, 2010).
Genbank Accession No. NP_415898.1; GI:16129341 (May 1, 2007); with corresponding KEGG Database printout of b1380 (May 10, 2010).
Genbank Accession No. NP_415938.1; GI:16129380 (May 1, 2007); with corresponding KEGG Database printout of b1421 (May 11, 2010).
Genbank Accession No. NP_415991.1 GI:16129433 (May 1, 2007); with corresponding KEGG Database printout of b1474 (May 10, 2010).
Genbank Accession No. NP_415992.1; GI:16129434 (May 1, 2007); with corresponding KEGG Database printout of b1475 (May 10, 2010).
Genbank Accession No. NP_415993.1; GI:16129435 (May 1, 2007); with corresponding KEGG Database printout of b1476 (May 10, 2010).
Genbank Accession No. NP_415995.4; GI:90111280 (May 1, 2007); with corresponding KEGG Database printout of b1478 (May 10, 2010).
Genbank Accession No. NP_415996.2; GI:90111281 (May 1, 2007); with corresponding KEGG Database printout of b1479 (May 11, 2010).
Genbank Accession No. NP_416119.1; GI:16129560 (May 1, 2007); with corresponding KEGG Database printout of b1602 (May 11, 2010).
Genbank Accession No. NP_416120.1; GI:16129561 (May 1, 2007); with corresponding KEGG Database printout of b1603 (May 11, 2010).
Genbank Accession No. NP_416128.1; GI:16129569 (May 1, 2007); with corresponding KEGG Database printout of b1611 (May 10, 2010).
Genbank Accession No. NP_416129.1; GI:16129570 (May 1, 2007); with corresponding KEGG Database printout of b1612 (May 10, 2010).
Genbank Accession No. NP_416138.1; GI:16129579 (May 1, 2007); with corresponding KEGG Database printout of b1621 (May 10, 2010).
Genbank Accession No. NP_416191.1; GI:16129632 (May 1, 2007); with corresponding KEGG Database printout of b1676 (May 10, 2010).
Genbank Accession No. NP_416237.3; GI:49176138 (May 1, 2007); with corresponding KEGG Database printout of b1723 (May 10, 2010).
Genbank Accession No. NP_416275.1; GI:16129715 (May 1, 2007); with corresponding KEGG Database printout of b1761 (May 10, 2010).
Genbank Accession No. NP_416287.1; GI:16129727 (May 1, 2007); with corresponding KEGG Database printout of b1773 (May 10, 2010).
Genbank Accession No. NP_416331.1; GI:16129771 (May 1, 2007); with corresponding KEGG Database printout of b1817 (May 10, 2010).
Genbank Accession No. NP_416332.1; GI:16129772 (May 1, 2007); with corresponding KEGG Database printout of b1818 (May 10, 2010).
Genbank Accession No. NP_416333.3; GI:49176154 (May 1, 2007); with corresponding KEGG Database printout of b1819 (May 10, 2010).
Genbank Accession No. NP_416363.1; GI:16129802 (May 1, 2007); with corresponding KEGG Database printout of b1849 (May 10, 2010).
Genbank Accession No. NP_416364.1; GI:16129803 (May 1, 2007); with corresponding KEGG Database printout of b1850 (May 10, 2010).
Genbank Accession No. NP_416365.1; GI:16129804 (May 1, 2007); with corresponding KEGG Database printout of b1851 (May 11, 2010).
Genbank Accession No. NP_416366.1; GI:16129805 (May 1, 2007); with corresponding KEGG Database printout of b1852 (May 10, 2010).
Genbank Accession No. NP_416368.1; GI:16129807 (May 1, 2007); with corresponding KEGG Database printout of b1854 (May 10, 2010).
Genbank Accession No. NP_416533.1; GI:16129970 (May 1, 2007); with corresponding KEGG Database printout of b2029 (May 10, 2010).
Genbank Accession No. NP_416600.4; GI:90111385 (May 1, 2007); with corresponding KEGG Database printout of b2097 (May 10, 2010).
Genbank Accession No. NP_416637.1; GI:16130071 (May 1, 2007); with corresponding KEGG Database printout of b2133 (May 10, 2010).
Genbank Accession No. NP_416719.1; GI:16130152 (May 1, 2007); with corresponding KEGG Database printout of b2215 (May 10, 2010).
Genbank Accession No. NP_416779.2; GI:145698289 (May 1, 2007); with corresponding KEGG Database printout of b2276 (May 10, 2010).
Genbank Accession No. NP_416780.1; GI:16130212 (May 1, 2007); with corresponding KEGG Database printout of b2277 (May 10, 2010).
Genbank Accession No. NP_416781.1; GI:16130213 (May 1, 2007); with corresponding KEGG Database printout of b2278 (May 10, 2010).
Genbank Accession No. NP_416782.1; GI:16130214 (May 1, 2007); with corresponding KEGG Database printout of b2279 (May 10, 2010).
Genbank Accession No. NP_416783.1; GI:16130215 (May 1, 2007); with corresponding KEGG Database printout of b2280 (May 10, 2010).
Genbank Accession No. NP_416784.1; GI:16130216 (May 1, 2007); with corresponding KEGG Database printout of b2281 (May 10, 2010).
Genbank Accession No. NP_416785.1; GI:16130217 (May 1, 2007); with corresponding KEGG Database printout of b2282 (May 10, 2010).
Genbank Accession No. NP_416786.4; GI:145698290 (May 1, 2007); with corresponding KEGG Database printout of b2283 (May 10, 2010).
Genbank Accession No. NP_416787.1; GI:16130219 (May 1, 2007); with corresponding KEGG Database printout of b2284 (May 10, 2010).
Genbank Accession No. NP_416788.1; GI:16130220 (May 1, 2007); with corresponding KEGG Database printout of b2285 (May 10, 2010).
Genbank Accession No. NP_416789.2; GI:145698291 (May 1, 2007); with corresponding KEGG Database printout of b2286 (May 10, 2010).
Genbank Accession No. NP_416790.1; GI:16130222 (May 1, 2007); with corresponding KEGG Database printout of b2287 (May 10, 2010).
Genbank Accession No. NP_416791.3; GI:49176207 (May 1, 2007); with corresponding KEGG Database printout of b2288 (May 10, 2010).
Genbank Accession No. NP_416799.1; GI:16130231 (May 1, 2007); with corresponding KEGG Database printout of b2296 (May 10, 2010).
Genbank Accession No. NP_416889.1; GI:16130320 (May 1, 2007); with corresponding KEGG Database printout of b2388 (May 10, 2010).
Genbank Accession No. NP_416910.1; GI:16130341 (May 1, 2007); with corresponding KEGG Database printout of b2415 (May 10, 2010).
Genbank Accession No. NP_416911.1; GI:16130342 (May 1, 2007); with corresponding KEGG Database printout of b2416 (May 10, 2010).

Genbank Accession No. NP_416912.1; GI:16130343 (May 1, 2007); with corresponding KEGG Database printout of b2417 (May 10, 2010).
Genbank Accession No. NP_416917.1; GI:16130348 (May 1, 2007); with corresponding KEGG Database printout of b2422 (May 11, 2010).
Genbank Accession No. NP_416919.1; GI:16130349 (May 1, 2007); with corresponding KEGG Database printout of b2424 (May 10, 2010).
Genbank Accession No. NP_416920.1; GI:16130350 (May 1, 2007); with corresponding KEGG Database printout of b2425 (May 10, 2010).
Genbank Accession No. NP_416958.1; GI:16130388 (May 1, 2007); with corresponding KEGG Database printout of b2463 (May 10, 2010).
Genbank Accession No. NP_416959.1; GI:16130389 (May 1, 2007); with corresponding KEGG Database printout of b2464 (May 11, 2010).
Genbank Accession No. NP_417074.1; GI:16130504 (May 1, 2007); with corresponding KEGG Database printout of b2579 (May 10, 2010).
Genbank Accession No. NP_417259.1; GI:16130686 (May 1, 2007); with corresponding KEGG Database printout of b2779 (May 10, 2010).
Genbank Accession No. NP_417350.1; GI:16130776 (May 1, 2007); with corresponding KEGG Database printout of b2874 (May 10, 2010).
Genbank Accession No. NP_417379.1; GI:16130805 (May 1, 2007); with corresponding KEGG Database printout of b2903 (May 10, 2010).
Genbank Accession No. NP_417380.1; GI:16130806 (May 1, 2007); with corresponding KEGG Database printout of b2904 (May 10, 2010).
Genbank Accession No. NP_417381.1; GI:16130807 (May 1, 2007); with corresponding KEGG Database printout of b2905 (May 10, 2010).
Genbank Accession No. NP_417400.1; GI:16130826 (May 1, 2007); with corresponding KEGG Database printout of b2925 (May 10, 2010).
Genbank Accession No. NP_417450.1; GI:16130876 (May 1, 2007); with corresponding KEGG Database printout of b2976 (May 10, 2010).
Genbank Accession No. NP_417585.2; GI:145698313 (May 1, 2007); with corresponding KEGG Database printout of b3115 (May 10, 2010).
Genbank Accession No. NP_417703.1; GI:16131126 (May 1, 2007); with corresponding KEGG Database printout of b3236 (May 10, 2010).
Genbank Accession No. NP_417845.1; GI:16131264 (May 1, 2007); with corresponding KEGG Database printout of b3386 (May 10, 2010).
Genbank Accession No. NP_417862.1; GI:16131280 (May 1, 2007); with corresponding KEGG Database printout of b3403 (May 10, 2010).
Genbank Accession No. NP_418009.2; GI:90111614 (May 1, 2007); with corresponding KEGG Database printout of b3553 (May 11, 2010).
Genbank Accession No. NP_418069.1; GI:16131483 (May 1, 2007); with corresponding KEGG Database printout of b3612 (May 10, 2010).
Genbank Accession No. NP_418187.1; GI:16131599 (May 1, 2007); with corresponding KEGG Database printout of b3731 (May 12, 2010).
Genbank Accession No. NP_418188.1; GI:16131600 (May 1, 2007); with corresponding KEGG Database printout of b3732 (May 10, 2010).
Genbank Accession No. NP_418189.1; GI:16131601 (May 1, 2007); with corresponding KEGG Database printout of b3733 (May 10, 2010).
Genbank Accession No. NP_418190.1; GI:16131602 (May 1, 2007); with corresponding KEGG Database printout of b3734 (May 10, 2010).
Genbank Accession No. NP_418191.1; GI:16131603 (May 1, 2007); with corresponding KEGG Database printout of b3735 (May 10, 2010).
Genbank Accession No. NP_418192.1; GI:16131604 (May 1, 2007); with corresponding KEGG Database printout of b3736 (May 10, 2010).
Genbank Accession No. NP_418193.1; GI:16131605 (May 1, 2007); with corresponding KEGG Database printout of b3737 (May 10, 2010).
Genbank Accession No. NP_418194.1; GI:16131606 (May 1, 2007); with corresponding KEGG Database printout of b3738 (May 10, 2010).
Genbank Accession No. NP_418195.2; GI:90111645 (May 1, 2007); with corresponding KEGG Database printout of b3739 (May 10, 2010).
Genbank Accession No. NP_418200.1; GI:16131612 (May 1, 2007); with corresponding KEGG Database printout of b3744 (May 10, 2010).
Genbank Accession No. NP_418328.1; GI:16131732 (May 1, 2007); with corresponding KEGG Database printout of b3892 (May 10, 2010).
Genbank Accession No. NP_418329.1; GI:16131733 (May 1, 2007); with corresponding KEGG Database printout of b3893 (May 10, 2010).
Genbank Accession No. NP_418330.1; GI:16131734 (May 1, 2007); with corresponding KEGG Database printout of b3894 (May 10, 2010).
Genbank Accession No. NP_418351.1 GI:16131754 (May 1, 2007); with corresponding KEGG Database printout of b3916 (May 10, 2010).
Genbank Accession No. NP_418352.1; GI:16131755 (May 1, 2007); with corresponding KEGG Database printout of b3917 (May 11, 2010).
Genbank Accession No. NP_418354.1; GI:16131757 (May 1, 2007); with corresponding KEGG Database printout of b3919 (May 10, 2010).
Genbank Accession No. NP_418360.1; GI:16131763 (May 1, 2007); with corresponding KEGG Database printout of b3925 (May 10, 2010).
Genbank Accession No. NP_418386.1; GI:16131789 (May 1, 2007); with corresponding KEGG Database printout of b3951 (May 10, 2010).
Genbank Accession No. NP_418387.3; GI:49176447 (May 1, 2007); with corresponding KEGG Database printout of b3952 (May 10, 2010).
Genbank Accession No. NP_418391.1; GI:16131794 (May 1, 2007); with corresponding KEGG Database printout of b3956 (May 10, 2010).
Genbank Accession No. NP_418397.2; GI:90111670 (May 1, 2007); with corresponding KEGG Database printout of b3962 (May 11, 2010).
Genbank Accession No. NP_418438.1; GI:16131840 (May 1, 2007); with corresponding KEGG Database printout of b4014 (May 10, 2010).
Genbank Accession No. NP_418439.1; GI:16131841 (May 1, 2007); with corresponding KEGG Database printout of b4015 (May 10, 2010).
Genbank Accession No. NP_418449.1; GI:16131851 (May 1, 2007); with corresponding KEGG Database printout of b4025 (May 10, 2010).
Genbank Accession No. NP_418493.1; GI:16131895 (May 1, 2007); with corresponding KEGG Database printout of b4069 (May 10, 2010).
Genbank Accession No. NP_418546.1; GI:16131948 (May 1, 2007); with corresponding KEGG Database printout of b4122 (May 10, 2010).
Genbank Accession No. NP_418562.4; GI:90111690 (May 1, 2007); with corresponding KEGG Database printout of b4139 (May 10, 2010).
Genbank Accession No. NP_418575.1; GI:16131976 (May 1, 2007); with corresponding KEGG Database printout of b4151 (May 10, 2010).

Genbank Accession No. NP_418576.1; GI:16131977 (May 1, 2007); with corresponding KEGG Database printout of b4152 (May 10, 2010).

Genbank Accession No. NP_418577.1; GI:16131978 (May 1, 2007); with corresponding KEGG Database printout of b4153 (May 10, 2010).

Genbank Accession No. NP_418578.1; GI:16131979 (01-May-2007); with corresponding KEGG Database printout of b4154 (May 10, 2010).

Genbank Accession No. NP_418653.1; GI:16132054 (May 1, 2007); with corresponding KEGG Database printout of b4232 (May 10, 2010).

Genbank Accession No. NP_418721.1; GI:16132122 (May 1, 2007); with corresponding KEGG Database printout of b4301 (May 10, 2010).

Genbank Accession No. NP_418798.1; GI:16132198 (May 1, 2007); with corresponding KEGG Database printout of b4381 (May 11, 2010).

Genbank Accession No. NP_418812.1; GI:16132212 (May 1, 2007); with corresponding KEGG Database printout of b4395 (May 10, 2010).

Genbank Accession No. YP_026168.2; GI:90111430 (May 1, 2007); with corresponding KEGG Database printout of b2423 (May 11, 2010).

Genbank Accession No. YP_026205.1; GI:49176316 (May 1, 2007); with corresponding KEGG Database printout of b3114 (May 10, 2010).

Arps et al., "Genetics of Serine Pathway Enzymes in *Methylobacterium extorquens* AM1: Phosphoenolpyruvate Carboxylase and Malyl Coenzyme A Lyase," *J. Bacteriol.* 175(12):3776-3783 (1993).

Branden et al., "Introduction to Protein Structure," *Garland Publishing Inc.*, New York, p. 247 (1991).

Fontaine et al, "A New Type of Glucose Fermentation by *Clostridium thermoaceticum* N.sp.," *J. Bacteriol.* 43:701-715 (1942).

Laivenieks et al., "Cloning sequencing, and overexpression of the *Anaerobiospirillum succinicproducens* phosphoenolpyruvate carboxykinase (pckA) gene," *Appl. Environ. Microbiol.* 63:2273-2280 (1997).

Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).

Seffernick et al., "Melamine deaminase and atrazine chlorohydrolase: 98 percent identical but functionally different," *J. Bacteriol.* 183(3):2405-2410 (2001).

Stanley et al., "Expression and stereochemical and isotope effect studies of active 4-oxalocrotonate decarboxylase," *Biochemistry* 39(12):3514 (2000).

Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiology* 151(Pt 11):3793-3801 (2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Valdes-Hevia and Gancedo, "Isolation and characterization of the gene encoding phosphoenolpyruvate carboxykinase from *Saccharomyces cerevisiae*," *FEBS Lett.* 258(2):313-316 (1989).

Witkowski et al., "Conversion of a beta-ketoacyl synthase to a malonyl decarboxylase by replacement of the active-site cysteine with glutamine," Biochemistry 38(36):11643-11650 (1999).

Yamamoto et al., "Purification and properties of NADP-dependent formate dehydrogenase from *Clostridium thermoaceticum*, a tungsten-selenium-iron protein," *J. Biol. Chem.* 258(3):1826-1832 (1983).

\* cited by examiner

US 8,470,582 B2

METHODS AND ORGANISMS FOR THE GROWTH-COUPLED PRODUCTION OF 1,4-BUTANEDIOL

This application is a continuation of application Ser. No. 11/891,602, filed Aug. 10, 2007, now U.S. Pat. No. 7,947,483, the entire contents of which are incorporated herein by reference.

BACKGROUND OF THE INVENTION

The present invention relates generally to in silico design of organisms, and more specifically to organisms having 1,4-butanediol biosynthetic capability.

1,4-Butanediol (BDO) is a four carbon dialcohol that currently is manufactured exclusively through various petrochemical routes. BDO is part of a large volume family of solvents and polymer intermediates that includes gamma-butyrolactone (GBL), tetrahydrofuran (THF), pyrrolidone, N-methylpyrrolidone (NMP), and N-vinyl-pyrrolidone. The overall market opportunity for this family exceeds $4.0 B.

Approximately 2.5B lb BDO is produced globally per year with 4-5% annual growth and a recent selling price ranging from $1.00-1.20/lb. The demand for BDO stems largely from its use as an intermediate for polybutylene terephthalate (PBT) plastic resins, polyurethane thermoplastics and co-polyester ethers. BDO also serves as a primary precursor to THF, which is employed as an intermediate for poly(tetramethylene glycol) PTMEG copolymers required for lycra and spandex production. Approximately 0.7 B lb of THF is produced globally per year with an annual growth rate over 6%. A significant percentage of growth (>30%) for both BDO and THF is occurring in Asia (China and India). GBL currently is a smaller volume (0.4 B lb/year) product which has numerous applications as a solvent, as an additive for inks, paints, and dyes, as well as the primary precursor to pyrrolidone derivatives such as NMP.

Conventional processes for the synthesis of BDO use petrochemical feedstocks for their starting materials. For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. It has been estimated that 90% of the acetylene produced in the U.S. is consumed for butanediol production. Alternatively, it can be formed by esterification and catalytic hydrogenation of maleic anhydride, which is derived from butane. Downstream, butanediol can be further transformed; for example, by oxidation to γ-butyrolactone, which can be further converted to pyrrolidone and N-methylpyrrolidone, or hydrogenolysis to tetrahydrofuran (FIG. 1). These compounds have varied uses as polymer intermediates, solvents, and additives, and have a combined market of nearly 2 billion lb/year.

The conventional hydrocarbon feedstock-based approach utilizes methane to produce formaldehyde. Thus, a large percentage of the commercial production of BDO relies on methane as a starting material. The production of acetylene also relies on petroleum-based starting material (see FIG. 1). Therefore, the costs of BDO production fluctuate with the price of petroleum and natural gas.

It is desirable to develop a method for production of these chemicals by alternative means that not only substitute renewable for petroleum-based feedstocks, and also use less energy- and capital-intensive processes. The Department of Energy has proposed 1,4-diacids, and particularly succinic acid, as key biologically-produced intermediates for the manufacture of the butanediol family of products (DOE Report, "Top Value-Added Chemicals from Biomass", 2004). However, succinic acid is costly to isolate and purify and requires high temperatures and pressures for catalytic reduction to butanediol.

Thus, there exists a need for alternative means for effectively producing commercial quantities of 1,4-butanediol and its chemical precursors. The present invention satisfies this need and provides related advantages as well.

SUMMARY OF INVENTION

The invention provides a non-naturally occurring microorganism comprising one or more gene disruptions, the one or more gene disruptions occurring in genes encoding an enzyme obligatory to coupling 1,4-butanediol production to growth of the microorganism when the gene disruption reduces an activity of the enzyme, whereby theone or more gene disruptions confers stable growth-coupled production of 1,4-butanediol onto the non-naturally occurring microorganism. The microorganism can further comprise a gene encoding an enzyme in a 1,4-butanediol (BDO) biosynthetic pathway. The invention additionally relates to methods of using microorganisms to produce BDO.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
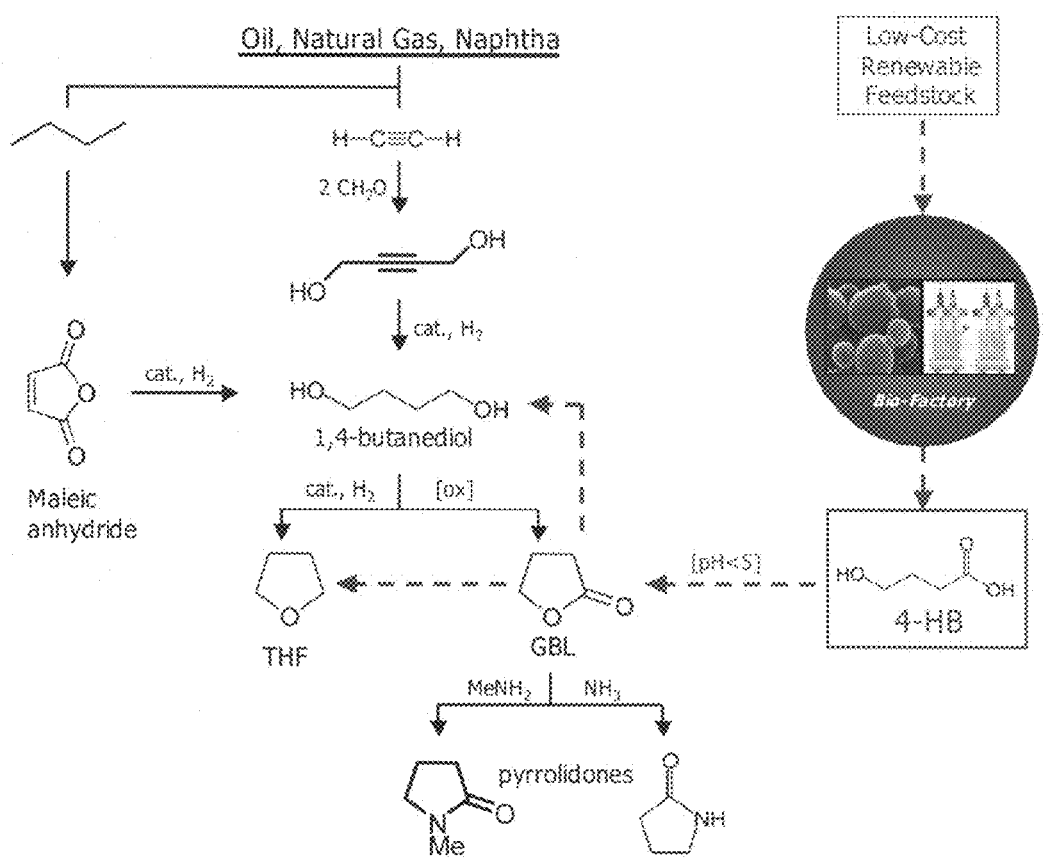
FIG. 1 is a schematic diagram showing an entry point of 4-hydroxybutanoic acid (4-HB) into the product pipeline of the 1,4-butanediol (BDO) family of chemicals, and comparison with chemical synthesis routes from petrochemical feedstocks. Solid black arrows show chemical synthesis routes; dashed blue arrows show a biosynthetic route to 4-HB and subsequent conversion steps to BDO family chemicals.

This invention is directed to the design and production of cells and organisms having biosynthetic production capabilities for 4-hydroxybutanoic acid (4-HB), γ-butyrolactone and 1,4-butanediol. In one embodiment, the invention utilizes in silico stoichiometric models of *Escherichia coli* metabolism that identify metabolic designs for biosynthetic production of 4-hydroxybutanoic acid (4-HB) and 1,4-butanediol (BDO). The results described herein indicate that metabolic pathways can be designed and recombinantly engineered to achieve the biosynthesis of 4-HB and downstream products such as 1,4-butanediol in *Escherichia coli* and other cells or organisms. Biosynthetic production of 4-HB, for example, for the in silico designs can be confirmed by construction of strains having the designed metabolic genotype. These metabolically engineered cells or organisms also can be subjected to adaptive evolution to further augment 4-HB biosynthesis, including under conditions approaching theoretical maximum growth.

The invention is further directed to metabolic engineering strategies for attaining high yields of 1,4-butanediol (BDO) in *Escherichia coli* (see Examples V-VII). As disclosed herein, a genome-scale stoichiometric model of *E. coli* metabolism was employed using the bilevel optimization framework OptKnock to identify in silico strategies with multiple knockouts. The deletions are placed such that the redundancy in the network is reduced with the ultimate effect of coupling growth to the production of BDO in the network. The growth-coupled BDO production characteristic of the designed strains make them genetically stable and amenable to continuous bioprocesses. Strain design strategies were identified assuming the addition of non-native reaction capabilities into *E. coli* leading to a metabolic pathway from succinate semialdehyde to BDO. Out of the hundreds of strategies identified by OptKnock, one design emerged as satisfying multiple criteria. This design, utilizing the removal of adhE, ldhA, mdh, aspA, and pflAB, 1) led to a high predicted BDO yield at maximum growth, 2) required a reasonable number of knockouts, 3) had no detrimental effect on the maximum theoretical BDO yield, 4) brought about a tight coupling of BDO production with cell growth, and 5) was robust with respect to the assumed irreversibility or reversibility of PEP carboxykinase. Also disclosed herein are methods for the experimental testing of the strain designs and their evolution towards the theoretical maximum growth.

In certain embodiments, the 4-HB biosynthesis characteristics of the designed strains make them genetically stable and particularly useful in continuous bioprocesses. Separate strain design strategies were identified with incorporation of different non-native or heterologous reaction capabilities into *E. coli* leading to 4-HB and 1,4-butanediol producing metabolic pathways from either CoA-independent succinic semialdehyde dehydrogenase, succinyl-CoA synthetase and CoA-dependent succinic semialdehyde dehydrogenase, or glutamate: succinic semialdehyde transaminase. In silico metabolic designs were identified that resulted in the biosynthesis of 4-HB in both *E. coli* and yeast species from each of these metabolic pathways. The 1,4-butanediol intermediate γ-butyrolactone can be generated in culture by spontaneous cyclization under conditions at pH<7.5, particularly under acidic conditions, such as below pH 5.5, for example, pH<7, pH<6.5, pH<6, and particularly at pH<5.5 or lower.

Strains identified via the computational component of the platform can be put into actual production by genetically engineering any of the predicted metabolic alterations which lead to the biosynthetic production of 4-HB, 1,4-butanediol or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modification include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a 4-HB biosynthetic pathway and enzymes within a biosynthetic pathway for a BDO family of compounds.

A metabolic modification refers to a biochemical reaction that is altered from its naturally occurring state. Therefore, non-naturally occurring microorganisms having genetic modifications to nucleic acids encoding metabolic polypeptides or, functional fragments thereof. Exemplary metabolic modifications are described further below for both *E. coli* and yeast microbial organisms.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "4-hydroxybutanoic acid" is intended to mean a 4-hydroxy derivative of butyric acid having the chemical formula $C_4H_8O_3$ and a molecular mass of 104.11 g/mol (126.09 g/mol for its sodium salt). The chemical compound 4-hydroxybutanoic acid also is known in the art as 4-HB, 4-hydroxybutyrate, gamma-hydroxybutyric acid or GHB. The term as it is used herein is intended to include any of the compound's various salt forms and include, for example, 4-hydroxybutanoate and 4-hydroxybutyrate. Specific examples of salt forms for 4-HB include sodium 4-HB and potassium 4-HB. Therefore, the terms 4-hydroxybutanoic acid, 4-HB, 4-hydroxybutyrate, 4-hydroxybutanoate, gamma-hydroxybutyric acid and GHB as well as other art recognized names are used synonymously herein.

As used herein, the term "monomeric" when used in reference to 4-HB is intended to mean 4-HB in a non-polymeric or underivatized form. Specific examples of polymeric 4-HB include poly-4-hydroxybutanoic acid and copolymers of, for example, 4-HB and 3-HB. A specific example of a derivatized form of 4-HB is 4-HB-CoA. Other polymeric 4-HB forms and other derivatized forms of 4-HB also are known in the art.

As used herein, the term "γ-butyrolactone" is intended to mean a lactone having the chemical formula $C_4H_6O_2$ and a molecular mass of 86.089 g/mol. The chemical compound γ-butyrolactone also is know in the art as GBL, butyrolactone, 1,4-lactone, 4-butyrolactone, 4-hydroxybutyric acid lactone, and gamma-hydroxybutyric acid lactone. The term as it is used herein is intended to include any of the compound's various salt forms.

As used herein, the term "1-4 butanediol" is intended to mean an alcohol derivative of the alkane butane, carrying two hydroxyl groups which has the chemical formula $C_4H_{10}O_2$ and a molecular mass of 90.12 g/mol. The chemical compound 1-4 butanediol also is known in the art as BDO and is a chemical intermediate or precursor for a family of compounds referred to herein as BDO family of compounds, some of which are exemplified in FIG. 1.

As used herein, the term "tetrahydrofuran" is intended to mean a heterocyclic organic compound corresponding to the fully hydrogenated analog of the aromatic compound furan which has the chemical formula $C_4H_8O$ and a molecular mass of 72.11 g/mol. The chemical compound tetrahydrofuran also is known in the art as THF, tetrahydrofuran, 1,4-epoxybutane, butylene oxide, cyclotetramethylene oxide, oxacyclopentane, diethylene oxide, oxolane, furanidine, hydrofuran, tetra-methylene oxide. The term as it is used herein is intended to include any of the compound's various salt forms.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modificatios will be greater than 50 generations, including indefinitely.

Those skilled in the art will understand that the genetic alterations, including metabolic modifications exemplified herein are described with reference to *E. coli* and yeast genes and their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or non-orthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms of the invention having 4-HB, GBL and/or BDO biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The invention provides a non-naturally occurring microbial biocatalyst including a microbial organism having a 4-hydroxybutanoic acid (4-HB) biosynthetic pathway that includes at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate: succinic semialdehyde transaminase or glutamate decarboxylase, wherein the exogenous nucleic acid is expressed in sufficient amounts to produce monomeric 4-hydroxybutanoic acid (4-HB). Succinyl-CoA synthetase is also referred to as succinyl-CoA synthase or succinyl CoA ligase.

The non-naturally occurring microbial biocatalysts of the invention include microbial organisms that employ combinations of metabolic reactions for biosynthetically producing the compounds of the invention. Exemplary compounds produced by the non-naturally occurring microorganisms include, for example, 4-hydroxybutanoic acid, 1,4-butanediol and γ-butyrolactone. The relationships of these exemplary compounds with respect to chemical synthesis or biosynthesis are exemplified in FIG. 1.

Figure 2:
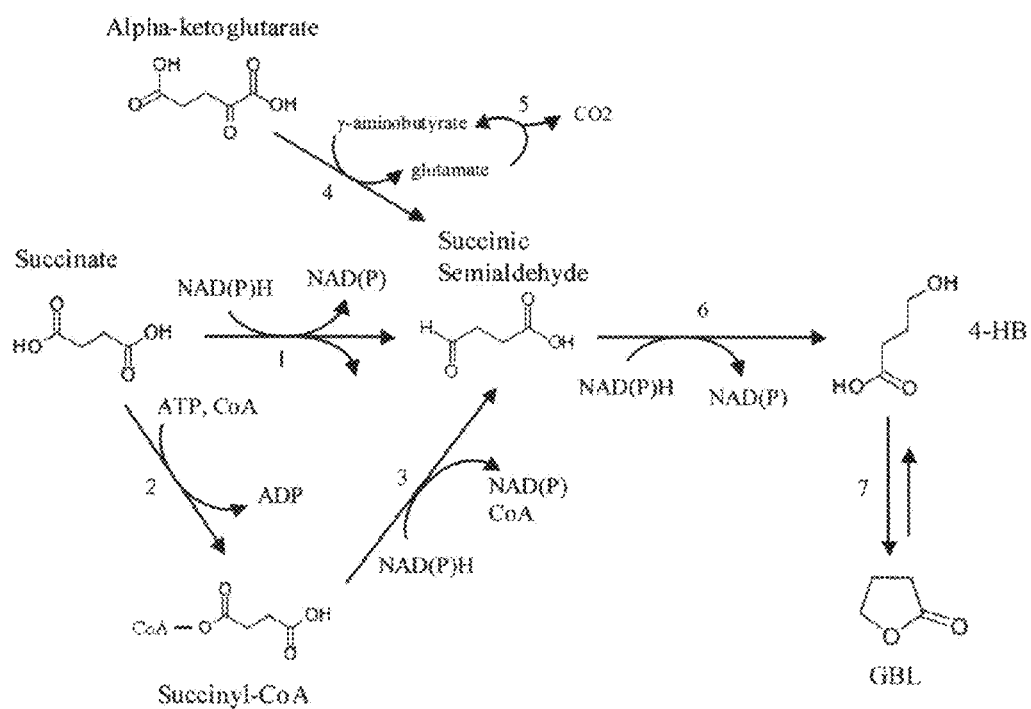
FIG. 2 is a schematic diagram showing biochemical pathways to 4-hydroxybutyurate (4-HB) and γ-butyrolactone (GBL) production. Enzymes catalyzing the 4-HB biosynthetic reactions are: (1) CoA-independent succinic semialdehyde dehydrogenase; (2) succinyl-CoA synthetase; (3) CoA-dependent succinic semialdehyde dehydrogenase; (4) glutamate:succinic semialdehyde transaminase; (5) glutamate decarboxylase; (6) 4-hydroxybutanoate dehydrogenase. Conversion (7) corresponds to a spontaneous, non-enzymatic reaction which converts 4-HB to GBL.

In one embodiment, a non-naturally occurring microbial organism is engineered to produce 4-HB. This compound is one useful entry point into the 1,4-butanediol family of compounds. The biochemical reactions for formation of 4-HB from succinate, from succinate through succinyl-CoA or from α-ketoglutarate are shown in FIG. 2.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The production of 4-HB via biosynthetic modes using the microbial organisms of the invention is particularly useful because it results in monomeric 4-HB. The non-naturally occurring microbial organisms of the invention and their biosynthesis of 4-HB and BDO family compounds also is particularly useful because the 4-HB product (1) is secreted; (2) is devoid of any derivatizations such as Coenzyme A; (3) avoids thermodynamic changes during biosynthesis, and (4) allows for the spontaneous chemical conversion of 4-HB to γ-butyrolactone (GBL) in acidic pH medium. This latter characteristic is exemplified as step 7 in FIG. 2 and also is particularly useful for efficient chemical synthesis or biosynthesis of BDO family compounds such as 1,4-butanediol and/or tetrahydrofuran (THF), for example.

Microbial organisms generally lack the capacity to synthesize 4-HB and therefore, any of the compounds shown in FIG. 1 are known to be within the 1,4-butanediol family of compounds or known by those in the art to be within the 1,4-butanediol family of compounds. Moreover, organisms having all of the requisite metabolic enzymatic capabilities are not known to produce 4-HB from the enzymes described and biochemical pathways exemplified herein. Rather, with the possible exception of a few anaerobic microorganisms described further below, the microorganisms having the enzymatic capability use 4-HB as a substrate to produce, for example, succinate. In contrast, the non-naturally occurring microbial organisms of the invention generate 4-HB as a product. As described above, the biosynthesis of 4-HB in its monomeric form is not only particularly useful in chemical synthesis of BDO family of compounds, it also allows for the further biosynthesis of BDO family compounds and avoids altogether chemical synthesis procedures.

The non-naturally occurring microbial organisms of the invention that can produce monomeric 4-HB are produced by ensuring that a host microbial organism includes functional capabilities for the complete biochemical synthesis of at least one 4-HB biosynthetic pathway of the invention. Ensuring at least one requisite 4-HB biosynthetic pathway confers 4-HB biosynthesis capability onto the host microbial organism.

Three requisite 4-HB biosynthetic pathways are exemplified herein and shown for purposes of illustration in FIG. 2. One requisite 4-HB biosynthetic pathway includes the biosynthesis of 4-HB from succinate. The enzymes participating in this 4-HB pathway include CoA-independent succinic semialdehyde dehydrogenase and 4-hydroxybutanoate dehydrogenase. Another requisite 4-HB biosynthetic pathway includes the biosynthesis from succinate through succinyl-CoA. The enzymes participating in this 4-HB pathway include succinyl-CoA synthetase, CoA-dependent succinic semialdehyde dehydrogenase and 4-hydroxybutanoate dehydrogenase. A third requisite 4-HB biosynthetic pathway includes the biosynthesis of 4-HB from α-ketoglutarate. The enzymes participating in this 4-HB biosynthetic pathway include glutamate: succinic semialdehyde transaminase, glutamate decarboxylase and 4-hydroxybutanoate dehydrogenase. Each of these 4-HB biosynthetic pathways, their substrates, reactants and products are described further below in the Examples.

The non-naturally occurring microbial organisms of the invention can be produced by introducing expressible nucleic acids encoding one or more of the enzymes participating in one or more 4-HB biosynthetic pathways. Depending on the host microbial organism chosen for biosynthesis, nucleic acids for some or all of a particular 4-HB biosynthetic pathway can be expressed. For example, if a chosen host is deficient in both enzymes in the succinate to 4-HB pathway (the succinate pathway) and this pathway is selected for 4-HB biosynthesis, then expressible nucleic acids for both CoA-independent succinic semialdehyde dehydrogenase and 4-hydroxybutanoate dehydrogenase are introduced into the host for subsequent exogenous expression. Alternatively, if the chosen host is deficient in 4-hydroxybutanoate dehydrogenase then an encoding nucleic acid is needed for this enzyme to achieve 4-HB biosynthesis.

In like fashion, where 4-HB biosynthesis is selected to occur through the succinate to succinyl-CoA pathway (the succinyl-CoA pathway), encoding nucleic acids for host deficiencies in the enzymes succinyl-CoA synthetase, CoA-dependent succinic semialdehyde dehydrogenase and/or 4-hydroxybutanoate dehydrogenase are to be exogenously expressed in the recipient host. Selection of 4-HB biosynthesis through the α-ketoglutarate to succinic semialdehyde pathway (the α-ketoglutarate pathway) will utilize exogenous expression for host deficiencies in one or more of the enzymes for glutamate:succinic semialdehyde transaminase, glutamate decarboxylase and/or 4-hydroxybutanoate dehydrogenase.

Depending on the 4-HB biosynthetic pathway constituents of a selected host microbial organism, the non-naturally occurring microbial 4-HB biocatalysts of the invention will include at least one exogenously expressed 4-HB pathway-encoding nucleic acid and up to all six 4-HB pathway encoding nucleic acids. For example, 4-HB biosynthesis can be established from all three pathways in a host deficient in 4-hydroxybutanoate dehydrogenase through exogenous expression of a 4-hydroxybutanoate dehydrogenase encoding nucleic acid. In contrast, 4-HB biosynthesis can be established from all three pathways in a host deficient in all six enzymes through exogenous expression of all six of CoA-independent succinic semialdehyde dehydrogenase, succinyl-CoA synthetase, CoA-dependent succinic semialdehyde dehydrogenase, glutamate: succinic semialdehyde transaminase, glutamate decarboxylase and 4-hydroxybutanoate dehydrogenase.

Given the teachings and guidance provided herein, those skilled in the art will understand that the number of encoding nucleic acids to introduce in an expressible form will parallel the 4-HB pathway deficiencies of the selected host microbial organism. Therefore, a non-naturally occurring microbial organism of the invention can have one, two, three, four, five or six encoding nucleic acids encoding the above enzymes constituting the 4-HB biosynthetic pathways. In some embodiments, the non-naturally occurring microbial organisms also can include other genetic modifications that facilitate or optimize 4-HB biosynthesis or that confer other useful functions onto the host microbial organism. One such other functionality can include, for example, augmentation of the synthesis of one or more of the 4-HB pathway precursors such as succinate, succinyl-CoA and/or α-ketoglutarate.

In some embodiments, a non-naturally occurring microbial organism of the invention is generated from a host that contains the enzymatic capability to synthesize 4-HB. In this specific embodiment it can be useful to increase the synthesis or accumulation of a 4-HB pathway product to, for example, drive 4-HB pathway reactions toward 4-HB production. Increased synthesis or accumulation can be accomplished by, for example, overexpression of nucleic acids encoding one or more of the above-described 4-HB pathway enzymes. Over expression of the 4-HB pathway enzyme or enzymes can occur, for example, through exogenous expression of the endogenous gene or genes, or through exogenous expression of the heterologous gene or genes. Therefore, naturally occurring organisms can be readily generated to be non-naturally 4-HB producing microbial organisms of the invention through overexpression of one, two, three, four, five or all six nucleic acids encoding 4-HB biosynthetic pathway enzymes. In addition, a non-naturally occurring organism can be generated by mutagenesis of an endogenous gene that results in an increase in activity of an enzyme in the 4-HB biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism (see Example II).

"Exogenous" as it is used herein is intended to mean that the referenced molecule or the referenced activity is introduced into the host microbial organism. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acids that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

Sources of encoding nucleic acids for a 4-HB pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. For example, the microbial organisms having 4-HB biosynthetic production are exemplified herein with reference to *E. coli* and yeast hosts. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 4-HB biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 4-HB and other compounds of the invention described herein with reference to a particular organism such as *E. coli* or yeast can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 4-HB biosynthetic pathway exists in an unrelated species, 4-HB biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual genes usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize monomeric 4-HB.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *E. coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

Methods for constructing and testing the expression levels of a non-naturally occurring 4-HB-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). 4-HB and GBL can be separated by, for example, HPLC using a Spherisorb 5 ODS1 column and a mobile phase of 70% 10 mM phosphate buffer (pH=7) and 30% methanol, and detected using a UV detector at 215 nm (Hennessy et al. *J. Forensic Sci.* 46(6):1-9 (2004)). BDO is detected by gas chromatography or by HPLC and refractive index detector using an Aminex HPX-87H column and a mobile phase of 0.5 mM sulfuric acid (Gonzalez-Pajuelo et al., *Met. Eng.* 7:329-336 (2005)).

The non-naturally occurring microbial organisms of the invention are constructed using methods well known in the art as exemplified above to exogenously express at least one nucleic acid encoding a 4-HB pathway enzyme in sufficient amounts to produce monomeric 4-HB. Exemplary levels of expression for 4-HB enzymes in each pathway are described further below in the Examples. Following the teachings and guidance provided herein, the non-naturally occurring microbial organisms of the invention can achieve biosynthesis of monomeric 4-HB resulting in intracellular concentrations between about 0.1-25 mM or more. Generally, the intracellular concentration of monomeric 4-HB is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention.

As described further below, one exemplary growth condition for achieving biosynthesis of 4-HB includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The invention also provides a non-naturally occurring microbial biocatalyst including a microbial organism having 4-hydroxybutanoic acid (4-HB) and 1,4-butanediol (BDO) biosynthetic pathways that include at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate: succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO).

Figure 3:
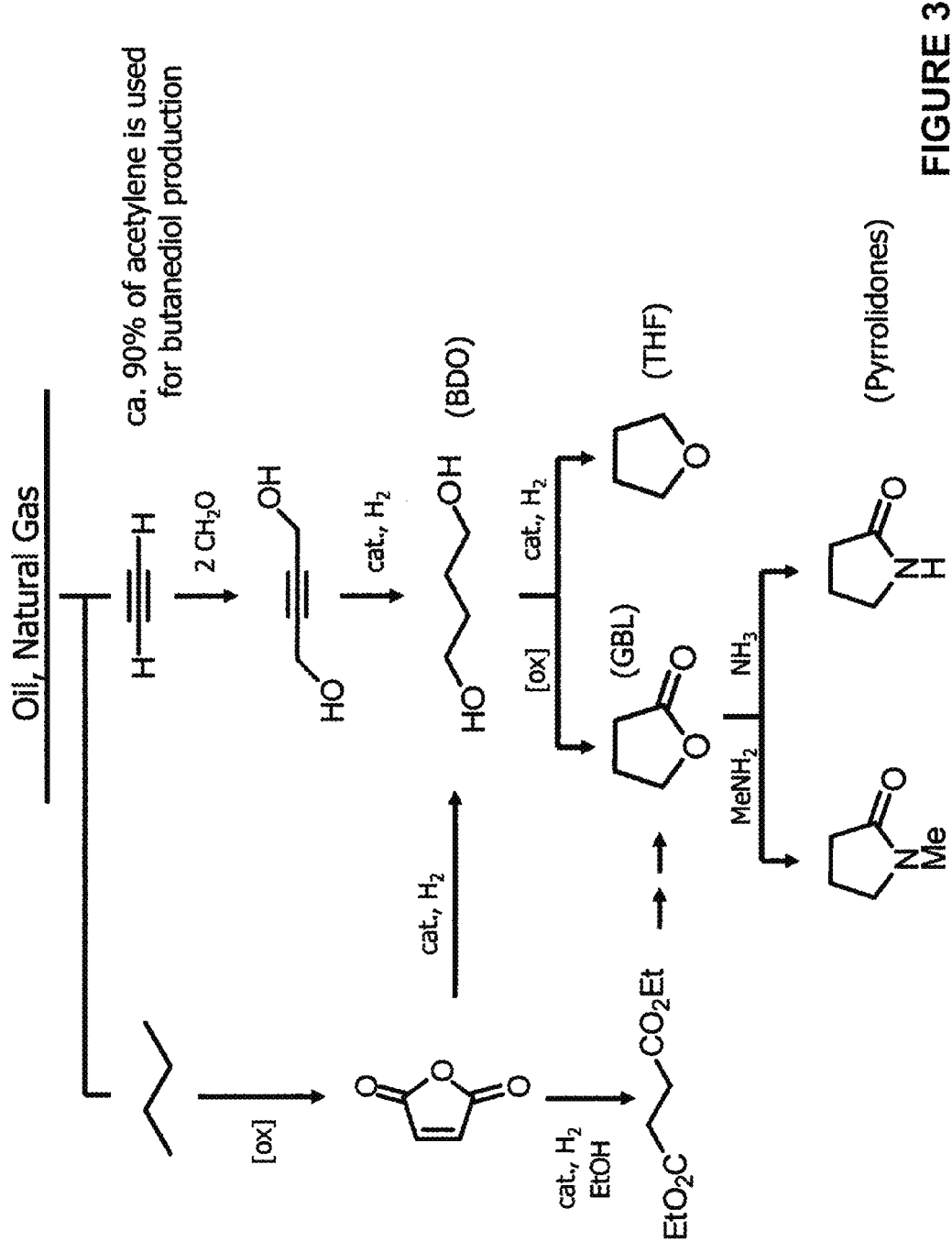
FIG. 3 is a schematic diagram showing the chemical synthesis of 1,4-butanediol (BDO) and downstream products γ-butyrolactone (GBL), tetrahydrofuran (THF) and several pyrrolidones.

Non-naturally occurring microbial organisms also can be generated which biosynthesize BDO. Following the teachings and guidance provided previously for the construction of microbial organisms that synthesize 4-HB, additional BDO pathways can be incorporated into the 4-HB producing microbial organisms to generate organisms that also synthesize BDO and other BDO family compounds. The chemical synthesis of BDO and its downstream products are illustrated in FIG. 3. The non-naturally occurring microbial organisms of the invention capable of BDO biosynthesis circumvent these chemical synthesis using 4-HB as an entry point as illustrated in FIG. 2. As described further below, the 4-HB producers can be used to chemically convert 4-HB to GBL and then to BDO or THF, for example. Alternatively, the 4-HB producers can be further modified to include biosynthetic capabilities for conversion of 4-HB and/or GBL to BDO.

The additional BDO pathways to introduce into 4-HB producers include, for example, the exogenous expression in a host deficient background or the overexpression of a CoA-independent aldehyde dehydrogenase, CoA-dependent aldehyde dehydrogenase or an alcohol dehydrogenase. In the absence of endogenous acyl-CoA synthetase capable of modifying 4-HB, the non-naturally occurring BDO producing microbial organisms can further include an exogenous acyl-CoA synthetase selective for 4-HB. Exemplary alcohol and aldehyde dehydrogenases that can be used for these in vivo conversions from 4-HB to BDO are listed below in Table 1.

TABLE 1

Alcohol and Aldehyde Dehydrogenases for Conversion of 4-HB to BDO.

| ALCOHOL DEHYDROGENASES | |
| --- | --- |
| ec:1.1.1.1 | alcohol dehydrogenase |
| ec:1.1.1.2 | alcohol dehydrogenase (NADP+) |
| ec:1.1.1.4 | (R,R)-butanediol dehydrogenase |
| ec:1.1.1.5 | acetoin dehydrogenase |
| ec:1.1.1.6 | glycerol dehydrogenase |
| ec:1.1.1.7 | propanediol-phosphate dehydrogenase |
| ec:1.1.1.8 | glycerol-3-phosphate dehydrogenase (NAD+) |
| ec:1.1.1.11 | D-arabinitol 4-dehydrogenase |
| ec:1.1.1.12 | L-arabinitol 4-dehydrogenase |
| ec:1.1.1.13 | L-arabinitol 2-dehydrogenase |
| ec:1.1.1.14 | L-iditol 2-dehydrogenase |
| ec:1.1.1.15 | D-iditol 2-dehydrogenase |
| ec:1.1.1.16 | galactitol 2-dehydrogenase |
| ec:1.1.1.17 | mannitol-1-phosphate 5-dehydrogenase |
| ec:1.1.1.18 | inositol 2-dehydrogenase |
| ec:1.1.1.21 | aldehyde reductase |
| ec:1.1.1.23 | histidinol dehydrogenase |
| ec:1.1.1.26 | glyoxylate reductase |
| ec:1.1.1.27 | L-lactate dehydrogenase |
| ec:1.1.1.28 | D-lactate dehydrogenase |
| ec:1.1.1.29 | glycerate dehydrogenase |
| ec:1.1.1.30 | 3-hydroxybutyrate dehydrogenase |
| ec:1.1.1.31 | 3-hydroxyisobutyrate dehydrogenase |
| ec:1.1.1.35 | 3-hydroxyacyl-CoA dehydrogenase |
| ec:1.1.1.36 | acetoacetyl-CoA reductase |
| ec:1.1.1.37 | malate dehydrogenase |
| ec:1.1.1.38 | malate dehydrogenase (oxaloacetate-decarboxylating) |
| ec:1.1.1.39 | malate dehydrogenase (decarboxylating) |
| ec:1.1.1.40 | malate dehydrogenase (oxaloacetate-decarboxylating) (NADP+) |
| ec:1.1.1.41 | isocitrate dehydrogenase (NAD+) |
| ec:1.1.1.42 | isocitrate dehydrogenase (NADP+) |
| ec:1.1.1.54 | allyl-alcohol dehydrogenase |
| ec:1.1.1.55 | lactaldehyde reductase (NADPH) |
| ec:1.1.1.56 | ribitol 2-dehydrogenase |
| ec:1.1.1.59 | 3-hydroxypropionate dehydrogenase |
| ec:1.1.1.60 | 2-hydroxy-3-oxopropionate reductase |
| ec:1.1.1.61 | 4-hydroxybutyrate dehydrogenase |
| ec:1.1.1.66 | omega-hydroxydecanoate dehydrogenase |
| ec:1.1.1.67 | mannitol 2-dehydrogenase |
| ec:1.1.1.71 | alcohol dehydrogenase [NAD(P)+] |
| ec:1.1.1.72 | glycerol dehydrogenase (NADP+) |
| ec:1.1.1.73 | octanol dehydrogenase |
| ec:1.1.1.75 | (R)-aminopropanol dehydrogenase |

TABLE 1-continued

Alcohol and Aldehyde Dehydrogenases for Conversion of 4-HB to BDO.

| EC Number | Enzyme Name |
|---|---|
| ec:1.1.1.76 | (S,S)-butanediol dehydrogenase |
| ec:1.1.1.77 | lactaldehyde reductase |
| ec:1.1.1.78 | methylglyoxal reductase (NADH-dependent) |
| ec:1.1.1.79 | glyoxylate reductase (NADP+) |
| ec:1.1.1.80 | isopropanol dehydrogenase (NADP+) |
| ec:1.1.1.81 | hydroxypyruvate reductase |
| ec:1.1.1.82 | malate dehydrogenase (NADP+) |
| ec:1.1.1.83 | D-malate dehydrogenase (decarboxylating) |
| ec:1.1.1.84 | dimethylmalate dehydrogenase |
| ec:1.1.1.85 | 3-isopropylmalate dehydrogenase |
| ec:1.1.1.86 | ketol-acid reductoisomerase |
| ec:1.1.1.87 | homoisocitrate dehydrogenase |
| ec:1.1.1.88 | hydroxymethylglutaryl-CoA reductase |
| ec:1.1.1.90 | aryl-alcohol dehydrogenase |
| ec:1.1.1.91 | aryl-alcohol dehydrogenase (NADP+) |
| ec:1.1.1.92 | oxaloglycolate reductase (decarboxylating) |
| ec:1.1.1.94 | glycerol-3-phosphate dehydrogenase [NAD(P)+] |
| ec:1.1.1.95 | phosphoglycerate dehydrogenase |
| ec:1.1.1.97 | 3-hydroxybenzyl-alcohol dehydrogenase |
| ec:1.1.1.101 | acylglycerone-phosphate reductase |
| ec:1.1.1.103 | L-threonine 3-dehydrogenase |
| ec:1.1.1.104 | 4-oxoproline reductase |
| ec:1.1.1.105 | retinol dehydrogenase |
| ec:1.1.1.110 | indolelactate dehydrogenase |
| ec:1.1.1.112 | indanol dehydrogenase |
| ec:1.1.1.113 | L-xylose 1-dehydrogenase |
| ec:1.1.1.129 | L-threonate 3-dehydrogenase |
| ec:1.1.1.137 | ribitol-5-phosphate 2-dehydrogenase |
| ec:1.1.1.138 | mannitol 2-dehydrogenase (NADP+) |
| ec:1.1.1.140 | sorbitol-6-phosphate 2-dehydrogenase |
| ec:1.1.1.142 | D-pinitol dehydrogenase |
| ec:1.1.1.143 | sequoyitol dehydrogenase |
| ec:1.1.1.144 | perillyl-alcohol dehydrogenase |
| ec:1.1.1.156 | glycerol 2-dehydrogenase (NADP+) |
| ec:1.1.1.157 | 3-hydroxybutyryl-CoA dehydrogenase |
| ec:1.1.1.163 | cyclopentanol dehydrogenase |
| ec:1.1.1.164 | hexadecanol dehydrogenase |
| ec:1.1.1.165 | 2-alkyn-1-ol dehydrogenase |
| ec:1.1.1.166 | hydroxycyclohexanecarboxylate dehydrogenase |
| ec:1.1.1.167 | hydroxymalonate dehydrogenase |
| ec:1.1.1.174 | cyclohexane-1,2-diol dehydrogenase |
| ec:1.1.1.177 | glycerol-3-phosphate 1-dehydrogenase (NADP+) |
| ec:1.1.1.178 | 3-hydroxy-2-methylbutyryl-CoA dehydrogenase |
| ec:1.1.1.185 | L-glycol dehydrogenase |
| ec:1.1.1.190 | indole-3-acetaldehyde reductase (NADH) |
| ec:1.1.1.191 | indole-3-acetaldehyde reductase (NADPH) |
| ec:1.1.1.192 | long-chain-alcohol dehydrogenase |
| ec:1.1.1.194 | coniferyl-alcohol dehydrogenase |
| ec:1.1.1.195 | cinnamyl-alcohol dehydrogenase |
| ec:1.1.1.198 | (+)-borneol dehydrogenase |
| ec:1.1.1.202 | 1,3-propanediol dehydrogenase |
| ec:1.1.1.207 | (−)-menthol dehydrogenase |
| ec:1.1.1.208 | (+)-neomenthol dehydrogenase |
| ec:1.1.1.216 | farnesol dehydrogenase |
| ec:1.1.1.217 | benzyl-2-methyl-hydroxybutyrate dehydrogenase |
| ec:1.1.1.222 | (R)-4-hydroxyphenyllactate dehydrogenase |
| ec:1.1.1.223 | isopiperitenol dehydrogenase |
| ec:1.1.1.226 | 4-hydroxycyclohexanecarboxylate dehydrogenase |
| ec:1.1.1.229 | diethyl 2-methyl-3-oxosuccinate reductase |
| ec:1.1.1.237 | hydroxyphenylpyruvate reductase |
| ec:1.1.1.244 | methanol dehydrogenase |
| ec:1.1.1.245 | cyclohexanol dehydrogenase |
| ec:1.1.1.250 | D-arabinitol 2-dehydrogenase |
| ec:1.1.1.251 | galactitol 1-phosphate 5-dehydrogenase |
| ec:1.1.1.255 | mannitol dehydrogenase |
| ec:1.1.1.256 | fluoren-9-ol dehydrogenase |
| ec:1.1.1.257 | 4-(hydroxymethyl)benzenesulfonate dehydrogenase |
| ec:1.1.1.258 | 6-hydroxyhexanoate dehydrogenase |
| ec:1.1.1.259 | 3-hydroxypimeloyl-CoA dehydrogenase |
| ec:1.1.1.261 | glycerol-1-phosphate dehydrogenase [NAD(P)+] |
| ec:1.1.1.265 | 3-methylbutanal reductase |
| ec:1.1.1.283 | methylglyoxal reductase (NADPH-dependent) |
| ec:1.1.1.286 | isocitrate-homoisocitrate dehydrogenase |
| ec:1.1.1.287 | D-arabinitol dehydrogenase (NADP+) |
| | butanol dehydrogenase |

ALDEHYDE DEHYDROGENASES

| EC Number | Enzyme Name |
|---|---|
| ec:1.2.1.2 | formate dehydrogenase |
| ec:1.2.1.3 | aldehyde dehydrogenase (NAD+) |
| ec:1.2.1.4 | aldehyde dehydrogenase (NADP+) |
| ec:1.2.1.5 | aldehyde dehydrogenase [NAD(P)+] |
| ec:1.2.1.7 | benzaldehyde dehydrogenase (NADP+) |
| ec:1.2.1.8 | betaine-aldehyde dehydrogenase |
| ec:1.2.1.9 | glyceraldehyde-3-phosphate dehydrogenase (NADP+) |
| ec:1.2.1.10 | acetaldehyde dehydrogenase (acetylating) |
| ec:1.2.1.11 | aspartate-semialdehyde dehydrogenase |
| ec:1.2.1.12 | glyceraldehyde-3-phosphate dehydrogenase (phosphorylating) |
| ec:1.2.1.13 | glyceraldehyde-3-phosphate dehydrogenase (NADP+) (phosphorylating) |
| ec:1.2.1.15 | malonate-semialdehyde dehydrogenase |
| ec:1.2.1.16 | succinate-semialdehyde dehydrogenase [NAD(P)+] |
| ec:1.2.1.17 | glyoxylate dehydrogenase (acylating) |
| ec:1.2.1.18 | malonate-semialdehyde dehydrogenase (acetylating) |
| ec:1.2.1.19 | aminobutyraldehyde dehydrogenase |
| ec:1.2.1.20 | glutarate-semialdehyde dehydrogenase |
| ec:1.2.1.21 | glycolaldehyde dehydrogenase |
| ec:1.2.1.22 | lactaldehyde dehydrogenase |
| ec:1.2.1.23 | 2-oxoaldehyde dehydrogenase (NAD+) |
| ec:1.2.1.24 | succinate-semialdehyde dehydrogenase |
| ec:1.2.1.25 | 2-oxoisovalerate dehydrogenase (acylating) |
| ec:1.2.1.26 | 2,5-dioxovalerate dehydrogenase |
| ec:1.2.1.27 | methylmalonate-semialdehyde dehydrogenase (acylating) |
| ec:1.2.1.28 | benzaldehyde dehydrogenase (NAD+) |
| ec:1.2.1.29 | aryl-aldehyde dehydrogenase |
| ec:1.2.1.30 | aryl-aldehyde dehydrogenase (NADP+) |
| ec:1.2.1.31 | L-aminoadipate-semialdehyde dehydrogenase |
| ec:1.2.1.32 | aminomuconate-semialdehyde dehydrogenase |
| ec:1.2.1.36 | retinal dehydrogenase |
| ec:1.2.1.39 | phenylacetaldehyde dehydrogenase |
| ec:1.2.1.41 | glutamate-5-semialdehyde dehydrogenase |

TABLE 1-continued

Alcohol and Aldehyde Dehydrogenases for Conversion of 4-HB to BDO.

| | |
|---|---|
| ec:1.2.1.42 | hexadecanal dehydrogenase (acylating) |
| ec:1.2.1.43 | formate dehydrogenase (NADP+) |
| ec:1.2.1.45 | 4-carboxy-2-hydroxymuconate-6-semialdehyde dehydrogenase |
| ec:1.2.1.46 | formaldehyde dehydrogenase |
| ec:1.2.1.47 | 4-trimethylammoniobutyraldehyde dehydrogenase |
| ec:1.2.1.48 | long-chain-aldehyde dehydrogenase |
| ec:1.2.1.49 | 2-oxoaldehyde dehydrogenase (NADP+) |
| ec:1.2.1.51 | pyruvate dehydrogenase (NADP+) |
| ec:1.2.1.52 | oxoglutarate dehydrogenase (NADP+) |
| ec:1.2.1.53 | 4-hydroxyphenylacetaldehyde dehydrogenase |
| ec:1.2.1.57 | butanal dehydrogenase |
| ec:1.2.1.58 | phenylglyoxylate dehydrogenase (acylating) |
| ec:1.2.1.59 | glyceraldehyde-3-phosphate dehydrogenase (NAD(P)+) (phosphorylating) |
| ec:1.2.1.62 | 4-formylbenzenesulfonate dehydrogenase |
| ec:1.2.1.63 | 6-oxohexanoate dehydrogenase |
| ec:1.2.1.64 | 4-hydroxybenzaldehyde dehydrogenase |
| ec:1.2.1.65 | salicylaldehyde dehydrogenase |
| ec:1.2.1.66 | mycothiol-dependent formaldehyde dehydrogenase |
| ec:1.2.1.67 | vanillin dehydrogenase |
| ec:1.2.1.68 | coniferyl-aldehyde dehydrogenase |
| ec:1.2.1.69 | fluoroacetaldehyde dehydrogenase |
| ec:1.2.1.71 | succinylglutamate-semialdehyde dehydrogenase |

Therefore, in addition to any of the various modifications exemplified previously for establishing 4-HB biosynthesis in a selected host, the BDO producing microbial organisms can include any of the previous combinations and permutations of 4-HB pathway metabolic modifications as well as any combination of expression for CoA-independent aldehyde dehydrogenase, CoA-dependent aldehyde dehydrogenase or an alcohol dehydrogenase to generate biosynthetic pathways for BDO. Therefore, the BDO producers of the invention can have exogenous expression of, for example, one, two, three, four, five, six, seven, eight, nine or all 10 enzymes corresponding to any of the six 4-HB pathway and/or any of the 4 BDO pathway enzymes.

Design and construction of the genetically modified microbial organisms is carried out using methods well known in the art to achieve sufficient amounts of expression to produce BDO. In particular, the non-naturally occurring microbial organisms of the invention can achieve biosynthesis of BDO resulting in intracellular concentrations between about 0.1-25 mM or more. Generally, the intracellular concentration of BDO is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention. As with the 4-HB producers, the BDO producers also can be sustained, cultured or fermented under anaerobic conditions.

The invention further provides a method for the production of 4-HB. The method includes culturing a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate: succinic semialdehyde transaminase or glutamate decarboxylase under substantially anaerobic conditions for a sufficient period of time to produce monomeric 4-hydroxybutanoic acid (4-HB). The method can additionally include chemical conversion of 4-HB to GBL and to BDO or THF, for example.

It is understood that, in methods of the invention, any of the one or more exogenous nucleic acids can be combined in a non-naturally occurring microbial organism of the invention so long as the desired product is produced, for example, 4-HB, BDO, THF or GBL. For example, a non-naturally occurring microbial organism having a 4-HB biosynthetic pathway can comprise at least two exogenous nucleic acids encoding desired enzymes, such as the combination of 4-hydroxybutanoate dehydrogenase and CoA-independent succinic semialdehyde dehydrogenase; 4-hydroxybutanoate dehydrogenase and CoA-dependent succinic semialdehyde dehydrogenase; CoA-dependent succinic semialdehyde dehydrogenase and succinyl-CoA synthetase; succinyl-CoA synthetase and glutamate decarboxylase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, CoA-independent succinic semialdehyde dehydrogenase and succinyl-CoA synthetase; 4-hydroxybutanoate dehydrogenase, CoA-dependent succinic semialdehyde dehydrogenase and glutamate: succinic semialdehyde transaminase, and so forth, as desired, so long as the combination of enzymes of the desired biosynthetic pathway results in production of the corresponding desired product.

Any of the non-naturally occurring microbial organisms described previously can be cultured to produce the biosynthetic products of the invention. For example, the 4-HB producers can be cultured for the biosynthetic production of 4-HB. The 4-HB can be isolated or be treated as described below to generate GBL, THF and/or BDO. Similarly, the BDO producers can be cultured for the biosynthetic production of BDO. The BDO can be isolated or subjected to further treatments for the chemical synthesis of BDO family compounds such as those downstream compounds exemplified in FIG. 3.

In some embodiments, culture conditions include anaerobic or substantially anaerobic growth or maintenance conditions. Exemplary anaerobic conditions have been described previously and are well known in the art. Exemplary anaerobic conditions for fermentation processes are described below in the Examples. Any of these conditions can be employed with the non-naturally occurring microbial organisms as well as other anaerobic conditions well known in the art. Under such anaerobic conditions, the 4-HB and BDO producers can synthesize monomeric 4-HB and BDO, respectively, at intracellular concentrations of 5-10 mM or more as well as all other concentrations exemplified previously.

A number of downstream compounds also can be generated for the 4-HB and BDO producing non-naturally occurring microbial organisms of the invention. With respect to the 4-HB producing microbial organisms of the invention, monomeric 4-HB and GBL exist in equilibrium in the culture medium. The conversion of 4-HB to GBL can be efficiently accomplished by, for example, culturing the microbial organisms in acid pH medium. A pH less than or equal to 7.5, in particular at or below pH 5.5, spontaneously converts 4-HB to GBL as illustrated in FIG. 1.

The resultant GBL can be separated from 4-HB and other components in the culture using a variety of methods well known in the art. Such separation methods include, for example, the extraction procedures exemplified in the Examples as well as methods which include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art. Separated GBL can be further purified by, for example, distillation.

Another down stream compound that can be produced from the 4-HB producing non-naturally occurring microbial organisms of the invention includes, for example, BDO. This compound can be synthesized by, for example, chemical hydrogenation of GBL. Chemical hydrogenation reactions are well known in the art. One exemplary procedure includes the chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce 1,4-butanediol.

Other procedures well known in the art are equally applicable for the above chemical reaction and include, for example, WO No. 82/03854 (Bradley, et al.), which describes the hydrogenolysis of gamma-butyrolactone in the vapor phase over a copper oxide and zinc oxide catalyst. British Pat. No. 1,230,276, which describes the hydrogenation of gamma-butyrolactone using a copper oxide-chromium oxide catalyst. The hydrogenation is carried out in the liquid phase. Batch reactions also are exemplified having high total reactor pressures. Reactant and product partial pressures in the reactors are well above the respective dew points. British Pat. No. 1,314,126, which describes the hydrogenation of gamma-butyrolactone in the liquid phase over a nickel-cobalt-thorium oxide catalyst. Batch reactions are exemplified as having high total pressures and component partial pressures well above respective component dew points. British Pat. No. 1,344,557, which describes the hydrogenation of gamma-butyrolactone in the liquid phase over a copper oxide-chromium oxide catalyst. A vapor phase or vapor-containing mixed phase is indicated as suitable in some instances. A continuous flow tubular reactor is exemplified using high total reactor pressures. British Pat. No. 1,512,751, which describes the hydrogenation of gamma-butyrolactone to 1,4-butanediol in the liquid phase over a copper oxide-chromium oxide catalyst. Batch reactions are exemplified with high total reactor pressures and, where determinable, reactant and product partial pressures well above the respective dew points. U.S. Pat. No. 4,301,077, which describes the hydrogenation to 1,4-butanediol of gamma-butyrolactone over a Ru—Ni—Co—Zn catalyst. The reaction can be conducted in the liquid or gas phase or in a mixed liquid-gas phase. Exemplified are continuous flow liquid phase reactions at high total reactor pressures and relatively low reactor productivities. U.S. Pat. No. 4,048,196, which describes the production of 1,4-butanediol by the liquid phase hydrogenation of gamma-butyrolactone over a copper oxide-zinc oxide catalyst. Further exemplified is a continuous flow tubular reactor operating at high total reactor pressures and high reactant and product partial pressures. And U.S. Pat. No. 4,652,685, which describes the hydrogenation of lactones to glycols.

A further downstream compound that can be produced form the 4-HB producing microbial organisms of the invention includes, for example, THF. This compound can be synthesized by, for example, chemical hydrogenation of GBL. One exemplary procedure well known in the art applicable for the conversion of GBL to THF includes, for example, chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce tetrahydrofuran. Other procedures well know in the art are equally applicable for the above chemical reaction and include, for example, U.S. Pat. No. 6,686,310, which describes high surface area sol-gel route prepared hydrogenation catalysts. Processes for the reduction of gamma butyrolactone to tetrahydrofuran and 1,4-butanediol also are described.

The culture conditions can include, for example, liquid culture procedures as well as fermentation and other large scale culture procedures. As described further below in the Examples, particularly useful yields of the biosynthetic products of the invention can be obtained under anaerobic or substantially anaerobic culture conditions.

The invention further provides a method of manufacturing 4-HB. The method includes fermenting a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase or glutamate decarboxylase under substantially anaerobic conditions for a sufficient period of time to produce monomeric 4-hydroxybutanoic acid (4-HB), the process comprising fed-batch fermentation and batch separation; fed-batch fermentation and continuous separation, or continuous fermentation and continuous separation.

The culture and chemical hydrogenations described above also can be scaled up and grown continuously for manufacturing of 4-HB, GBL, BDO and/or THF. Exemplary growth procedures include, for example, fed-batch fermentation and batch separation; fed-batch fermentation and continuous separation, or continuous fermentation and continuous separation. All of these processes are well known in the art. Employing the 4-HB producers allows for simultaneous 4-HB biosynthesis and chemical conversion to GBL, BDO and/or THF by employing the above hydrogenation procedures simultaneous with continuous cultures methods such as fermentation. Other hydrogenation procedures also are well known in the art and can be equally applied to the methods of the invention.

Fermentation procedures are particularly useful for the biosynthetic production of commercial quantities of 4-HB and/or BDO. Generally, and as with non-continuous culture procedures, the continuous and/or near-continuous production of 4-HB or BDO will include culturing a non-naturally occurring 4-HB or BDO producing organism of the invention in sufficient neutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods.

Fermentation procedures are well known in the art. Briefly, fermentation for the biosynthetic production of 4-HB, BDO or other 4-HB derived products of the invention can be utilized in, for example, fed-batch fermentation and batch separation; fed-batch fermentation and continuous separation, or continuous fermentation and continuous separation. Examples of batch and continuous fermentation procedures well known in the art are exemplified further below in the Examples.

In addition, to the above fermentation procedures using the 4-HB or BDO producers of the invention for continuous production of substantial quantities of monomeric 4-HB and BDO, respectively, the 4-HB producers also can be, for example, simultaneously subjected to chemical synthesis procedures as described previously for the chemical conversion of monomeric 4-HB to, for example, GBL, BDO and/or THF. The BDO producers can similarly be, for example, simultaneously subjected to chemical synthesis procedures as described previously for the chemical conversion of BDO to, for example, THF, GBL, pyrrolidones and/or other BDO family compounds. In addition, the products of the 4-HB and BDO producers can be separated from the fermentation culture and sequentially subjected to chemical conversion, as disclosed herein.

Briefly, hydrogenation of GBL in the fermentation broth can be performed as described by Frost et al., *Biotechnology Progress* 18: 201-211 (2002). Another procedure for hydrogenation during fermentation include, for example, the methods described in, for example, U.S. Pat. No. 5,478,952. This method is further exemplified in the Examples below.

Therefore, the invention additionally provides a method of manufacturing γ-butyrolactone (GBL), tetrahydrofuran (THF) or 1,4-butanediol (BDO). The method includes fermenting a non-naturally occurring microbial organism having 4-hydroxybutanoic acid (4-HB) and 1,4-butanediol (BDO) biosynthetic pathways, the pathways comprise at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate:succinic semialdehyde transaminase, glutamate decarboxylase, CoA-independent 1,4-butanediol semialdehyde dehydrogenase, CoA-dependent 1,4-butanediol semialdehyde dehydrogenase, 1,4-butanediol alcohol dehydrogenase, either CoA-dependent or independent, under substantially anaerobic conditions for a sufficient period of time to produce 1,4-butanediol (BDO), GBL or THF, the fermenting comprising fed-batch fermentation and batch separation; fed-batch fermentation and continuous separation, or continuous fermentation and continuous separation.

In addition to the biosynthesis of 4-HB, BDO and other products of the invention as described herein, the non-naturally occurring microbial organisms and methods of the invention also can be utilized in various combinations with each other and with other microbial organisms and methods well known in the art to achieve product biosynthesis by other routes. For example, one alternative to produce BDO other than use of the 4-HB producers and chemical steps or other than use of the BDO producer directly is through addition of another microbial organism capable of converting 4-HB or a 4-HB product exemplified herein to BDO.

One such procedure includes, for example, the fermentation of a 4-HB producing microbial organism of the invention to produce 4-HB, as described above and below. The 4-HB can then be used as a substrate for a second microbial organism that converts 4-HB to, for example, BDO, GBL and/or THF. The 4-HB can be added directly to another culture of the second organism or the original culture of 4-HB producers can be depleted of these microbial organisms by, for example, cell separation, and then subsequent addition of the second organism to the fermentation broth can utilized to produce the final product without intermediate purification steps. One exemplary second organism having the capacity to biochemically utilize 4-HB as a substrate for conversion to BDO, for example, is *Clostridium acetobutylicum* (see, for example, Jewell et al., *Current Microbiology*, 13:215-19 (1986)).

In other embodiments, the non-naturally occurring microbial organisms and methods of the invention can be assembled in a wide variety of subpathways to achieve biosynthesis of, for example, 4-HB and/or BDO as described. In these embodiments, biosynthetic pathways for a desired product of the invention can be segregated into different microbial organisms and the different microbial organisms can be co-cultured to produce the final product. In such a biosynthetic scheme, the product of one microbial organism is the substrate for a second microbial organism until the final product is synthesized. For example, the biosynthesis of BDO can be accomplished as described previously by constructing a microbial organism that contains biosynthetic pathways for conversion of a substrate such as endogenous succinate through 4-HB to the final product BDO. Alternatively, BDO also can be biosynthetically produced from microbial organisms through co-culture or co-fermentation using two organisms in the same vessel. A first microbial organism being a 4-HB producer with genes to produce 4-HB from succinic acid, and a second microbial organism being a BDO producer with genes to convert 4-HB to BDO.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 4-HB, BDO, GBL and THF products of the invention.

One computational method for identifying and designing metabolic alterations favoring biosynthesis of a product is the OptKnock computational framework, Burgard et al., *Biotechnol Bioeng*, 84: 647-57 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of 4-HB and/or BDO or used in connection with the non-naturally occurring microbial organisms for further optimization of 4-HB and/or BDO biosynthesis.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic alterations favoring biosynthetic production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities. As described in the Examples below, this computation methodology was used to identify and analyze the feasible as well as the optimal 4-HB biosynthetic pathways in 4-HB non-producing microbial organisms.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *E. coli* on a variety of single-carbon sources as well as the metabolism of *H. influenzae* as described in Edwards and Palsson, *Proc. Natl. Acad. Sci. USA* 97:5528-5533 (2000), Edwards and Palsson, *J. Biol. Chem.* 274:17410-17416 (1999) and Edwards et al., *Nature Biotech.* 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of 4-HB, BDO, GBL, THF and other BDO family compounds in host microbial organisms other than *E. coli* and yeast. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to biosynthetically produce a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. The production of a desired biochemical generally is in direct competition with biomass formation for intracellular resources. Under these circumstances, enhanced rates of biochemical production will necessarily result in sub-maximal growth rates. The knockouts suggested by the above metabolic modeling and simulation programs such as OptKnock are designed to restrict the allowable solution boundaries forcing a change in metabolic behavior from the wild-type strain. Although the actual solution boundaries for a given strain will expand or contract as the substrate uptake rate(s) increase or decrease, each experimental point will lie within its calculated solution boundary. Plots such as these enable accurate predictions of how close the designed strains are to their performance limits which also indicates how much room is available for improvement.

The OptKnock mathematical framework is exemplified herein for pinpointing gene deletions leading to product biosynthesis and, particularly, growth-coupled product biosynthesis. The procedure builds upon constraint-based metabolic modeling which narrows the range of possible phenotypes that a cellular system can display through the successive imposition of governing physico-chemical constraints, Price et al., *Nat. Rev. Microbiol.*, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows:

$$\text{maximize } v_{cellular\ objective}$$
$$\text{subject to } \sum_{j=1}^{M} S_{ij} v_j = 0, \quad \forall\, i \in N$$
$$v_{substrate} = v_{substrate\_uptake}\ \text{mmol/gDW·hr}$$
$$\forall\, i \in \{\text{limiting substrate}(s)\}$$
$$v_{atp} \geq v_{atp\_main}\ \text{mmol/gDW·hr}$$
$$v_j \geq 0, \quad \forall\, j \in \{irrev.\ \text{reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., *Escherichia coli and Salmonella: Cellular and Molecular Biology*, 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol. Bioeng.*, 74: 364-375 (2001), Burgard et al., *Biotechnol. Prog.*, 17: 791-797 (2001). These binary variables, $$y_j = \begin{cases} 1, & \text{if reaction flux } v_j \text{ is active} \\ 0, & \text{if reaction flux } v_j \text{ is not active} \end{cases}, \forall\, j \in M$$

assume a value of 1 if reaction j is active and a value of 0 if it is inactive. The following constraint, $$v_j^{min} \cdot y_j \leq v_j \leq v_j^{max} \cdot y_j, \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab. Eng.*, 5: 264-76 (2003).

Optimal gene/reaction knockouts are identified by solving a bilevel optimization problem that chooses the set of active reactions ($y_j=1$) such that an optimal growth solution for the resulting network overproduces the chemical of interest. Mathematically, this bilevel optimization problem is expressed as the following bilevel mixed-integer optimization problem:

$$\text{maximize } v_{chemical} \quad \text{(OptKnock)}$$
$$y_j$$
$$\begin{pmatrix} \text{subject to maximize } v_{biomass} \\ v_j \\ \text{subject to } \sum_{j=1}^{M} S_{ij} v_j = 0, \quad \forall\, i \in N \\ v_{substrate} = v_{substrate\_uptake} \\ \forall\, i \in \{\text{limiting substrate}(s)\} \\ v_{atp} \geq v_{atp\_main} \end{pmatrix}$$
$$v_{biomass} \geq v_{biomass}^{target}$$
$$v_j^{min} \cdot y_j \leq v_j \leq v_j^{max} \cdot y_j, \quad \forall\, j \in M$$
$$\sum_{j \in M^{forward}} (1 - y_j) = K$$
$$y_j \in \{0, 1\}, \quad \forall\, j \in M$$

where $v_{chemical}$ is the production of the desired target product, for example succinate or other biochemical product, and K is the number of allowable knockouts. Note that setting K equal to zero returns the maximum biomass solution of the complete network, while setting K equal to one identifies the single gene/reaction knockout ($y_j=0$) such that the resulting network involves the maximum overproduction given its maximum biomass yield. The final constraint ensures that the resulting network meets a minimum biomass yield. Burgard et al., *Biotechnol. Bioeng.*, 84: 647-57 (2003), provide a more detailed description of the model formulation and solution procedure. Problems containing hundreds of binary variables can be solved in the order of minutes to hours using CPLEX 8.0, *GAMS: The Solver Manuals*. 2003: GAMS Development Corporation, accessed via the GAMS, Brooke et al., *GAMS Development Corporation* (1998), modeling environment on an IBM RS6000-270 workstation. The OptKnock framework has already been able to identify promising gene deletion strategies for biochemical overproduction, Burgard et al., *Biotechnol. Bioeng.*, 84: 647-57 (2003), Pharkya et al., *Biotechnol. Bioeng.*, 84: 887-899 (2003), and establishes a systematic framework that will naturally encompass future improvements in metabolic and regulatory modeling frameworks.

Any solution of the above described bilevel OptKnock problem will provide one set of metabolic reactions to disrupt. Elimination of each reaction within the set or metabolic modification can result in 4-HB or BDO as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve 4-HB or BDO production are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the succinate coupling are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of 4-HB or other biochemical product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatory couples product biosynthesis to growth. For example, if a previously identified growth-coupled metabolic modification specifies reactions 1, 2, and 3 for disruption, then the following constraint prevents the same reactions from being simultaneously considered in subsequent solutions: $y_1+y_2+y_3 \geq 1$. The integer cut method is well known in the art and can be found described in, for example, reference, Burgard et al., *Biotechnol. Prog.*, 17: 791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to biosynthetic production of a product, a modification of the integer cut method can be employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single knockouts are considered and the two parameter sets, objstore$_{iter}$ and ystore$_{iter,j}$, are introduced to store the objective function ($v_{chemical}$) and reaction on-off information ($y_j$), respectively, at each iteration, iter. The following constraints are then successively added to the OptKnock formulation at each iteration.

$$v_{chemical} \geq \text{objstore}_{iter} + \epsilon - M \cdot \Sigma_{j \in ystore_{iter,j}=0} y_j$$

In the above equation, $\epsilon$ and M are a small and a large numbers, respectively. In general, $\epsilon$ can be set at about 0.01 and M can be set at about 1000. However, numbers smaller and/or larger then these numbers also can be used. M ensures that the constraint can be binding only for previously identified knockout strategies, while $\epsilon$ ensures that adding knockouts to a previously identified strategy must lead to an increase of at least $\epsilon$ in biochemical production at optimal growth. The approach moves onto double deletions whenever a single deletion strategy fails to improve upon the wild-type strain. Triple deletions are then considered when no double deletion strategy improves upon the wild-type strain, and so on. The end result is a ranked list, represented as desired biochemical production at optimal growth, of distinct deletion strategies that differ from each other by at least one knockout. This optimization procedure as well as the identification of a wide variety of reaction sets that, when disrupted, lead to the biosynthesis, including growth-coupled production, of a biochemical product. Given the teachings and guidance provided herein, those skilled in the art will understand that the methods and metabolic engineering designs exemplified herein are equally applicable to identify new biosynthetic pathways and/or to the obligatory coupling of cell or microorganism growth to any biochemical product.

The methods exemplified above and further illustrated in the Examples below enable the construction of cells and organisms that biosynthetically produce, including obligatory couple production of a target biochemical product to growth of the cell or organism engineered to harbor the identified genetic alterations. In this regard, metabolic alterations have been identified that result in the biosynthesis of 4-HB and 1,4-butanediol. Microorganism strains constructed with the identified metabolic alterations produce elevated levels of 4-HB or BDO compared to unmodified microbial organisms. These strains can be beneficially used for the commercial production of 4-HB, BDO, THF and GBL, for example, in continuous fermentation process without being subjected to the negative selective pressures.

Therefore, the computational methods described herein enable the identification and implementation of metabolic modifications that are identified by an in silico method selected from OptKnock or SimPheny. The set of metabolic modifications can include, for example, addition of one or more biosynthetic pathway enzymes and/or functional disruption of one or more metabolic reactions including, for example, disruption by gene deletion.

Application of the OptKock method to identify pathways suitable for growth-coupled production of 1,4-butanediol (BDO) is described in Examples V-VII. As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al. *Biotechnol. Bioeng.* 84:647-657 (2003)).

Figure 5:
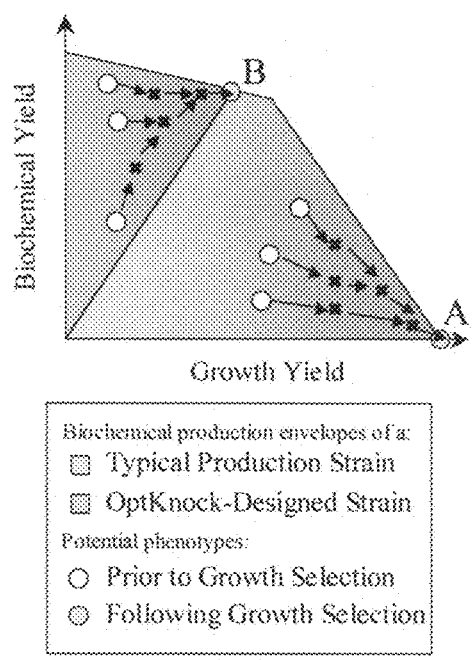
FIG. 5 shows the hypothetical production envelopes of an OptKnock-designed strain contrasted against a typical non-growth-coupled production strain. Note that the potential evolutionary trajectories of the OptKnock strain are fundamentally different in that they lead to a high producing phenotype.

Growth-coupled biochemical production can be visualized in the context of the biochemical production limits of a typical metabolic network. These limits are obtained from an in silico metabolic model by fixing the uptake rate(s) of the limiting substrate(s) to their experimentally measured value(s) and calculating the maximum and minimum rates of biochemical production at each attainable level of growth. The production envelopes essentially bracket what is possible by encompassing all potential biological phenotypes available to a given strain. Although exceptions exist, typically the production of a desired biochemical is in direct competition with biomass formation for intracellular resources (see FIG. 5, gray region). Thus increased biochemical yields will necessarily result in sub-maximal growth. Furthermore, the application of growth selective pressures may drive the performance of a non-growth-coupled production strain towards a low producing phenotype (point A, FIG. 5), regardless of its initial starting point. The knockouts suggested by OptKnock are designed to restrict the allowable solution boundary, forcing a change in metabolic behavior as depicted in FIG. 5 (cyan region). Evolutionary engineering approaches can thus be applied to drive the performance of an OptKnock designed strain to the rightmost boundary. This will result in a high producing strain that should be inherently stable to further growth selective pressures (point B, FIG. 5).

An in silico stoichiometric model of *E. coli* metabolism was employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework was applied to pinpoint gene deletions leading to the growth-coupled production of BDO (see Examples V-VII). The strategies were initially determined by employing a reduced model of the *E. coli* metabolic network. This "small" model captures the key metabolic functionalities in the network, thus eliminating the redundancy associated with the genome-scale metabolic networks. Care was taken to ensure that the model was not reduced to the point where potentially active pathways possessing viable targets were neglected. Overall, the reduced model contained 262 reactions and its implementation reduced OptKnock CPU times approximately ten-fold when compared to the application of OptKnock to the genome-scale *E. coli* model (Reed et al., *Genome Biol.* 4:R54 (2003)).

Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

Figure 6:
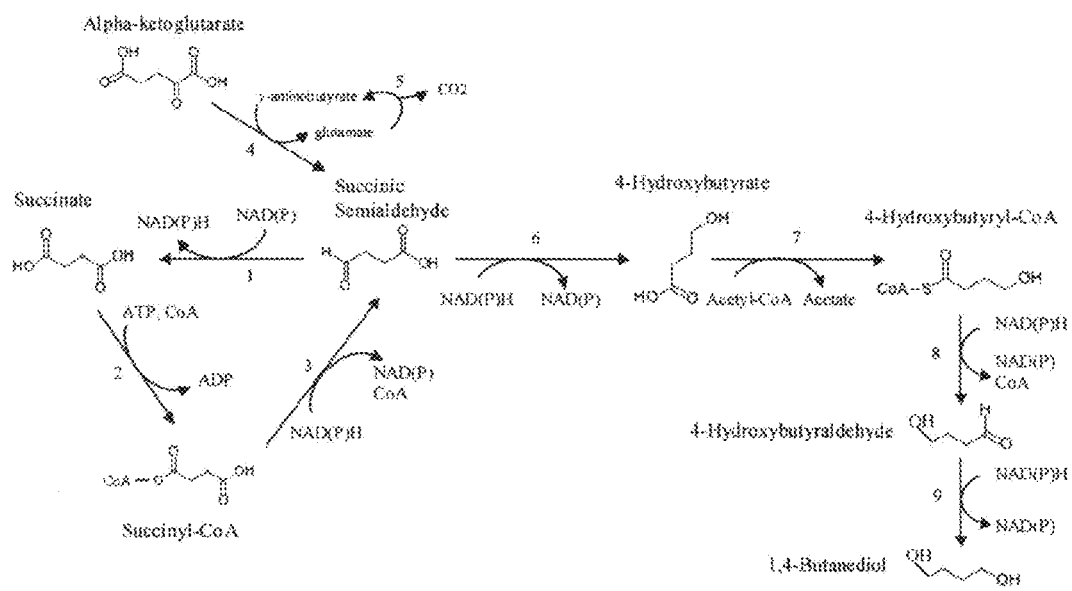
FIG. 6 shows biochemical pathways to 1,4-butanediol. 1) CoA-independent succinic semialdehyde dehydrogenase; 2) succinyl-CoA synthetase; 3) CoA-dependent succinic semialdehyde dehydrogenase; 4) glutamate:succinate semialdehyde transaminase; 5) glutamate decarboxylase; 6) 4-hydroxybutanoate dehydrogenase; 7) 4-hydroxybutyryl CoA:acetyl-CoA transferase; 8) aldehyde dehydrogenase; 9) alcohol dehydrogenase.

For biochemical pathways to 1,4-butanediol, the conversion of glucose to BDO in *E. coli* is expected to derive from a total of three intracellular reduction steps from succinate semialdehyde (see FIG. 6). Succinate semialdehyde is natively produced by *E. coli* through the TCA cycle intermediate, alpha-ketoglutarate, via the action of two enzymes, glutamate: succinic semialdehyde transaminase and glutamate decarboxylase. An alternative pathway, used by the obligate anaerobe *Clostridium kluyveri* to degrade succinate, activates succinate to succinyl-CoA, and then converts succinyl-CoA to succinic semialdehyde using a CoA-dependant succinic semialdehyde dehydrogenase (Sohling and Gottschalk, *Eur. J. Biochem.* 212:121-127 (1993)). The conversion of succinate semialdehyde to BDO first requires the activity of 4-hydroxybutanoate (4-HB) dehydrogenase, an enzyme which is not native to *E. coli* or yeast but is found in various bacteria such as *C. kluyveri* and *Ralstonia eutropha* (Lutke-Eversloh and Steinbuchel, *FEMS Microbiol. Lett.* 181:63-71 (1999); Sohling and Gottschalk, *J. Bacteriol.* 178: 871-880 (1996); Valentin et al., *Eur. J. Biochem.* 227:43-60 (1995); Wolff and Kenealy, *Protein Expr. Purif.* 6:206-212 (1995)). Precedent for the 4-HB to BDO conversion has been demonstrated in the strict anaerobe, *Clostridium acetobutylicum*, which when fed 4-HB, was shown to quantitatively produce BDO (Jewell et al., *Current Microbiology* 13:215-219 (1986)). The required biotransformations from 4-HB to BDO are assumed to be similar to those of the butyric acid to butanol conversion common to Clostridia species which proceeds via a CoA-derivative (Girbal et al., *FEMS Microbiology Reviews* 17:287-297 (1995)).

In an additional embodiment, the invention provides a non-naturally occurring microorganism comprising one or more gene disruptions, the one or more gene disruptions occurring in genes encoding an enzyme obligatory to coupling 1,4-butanediol production to growth of the microorganism when the gene disruption reduces an activity of the enzyme, whereby the one or more gene disruptions confers stable growth-coupled production of 1,4-butanediol onto the non-naturally occurring microorganism. The one or more gene disruptions can be, for example, those disclosed in Table 6 or 7. The one or more gene disruptions can comprise a deletion of the one or more genes, such as those genes disclosed in Table 6 or 7.

As disclosed herein, the non-naturally occurring microorganism can be a bacterium, yeast or fungus. For example, the non-naturally occurring microorganism can be a bacterium such as *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. The non-naturally occurring microorganism can also be a yeast such as *Saccharomyces cerevisiae, Schizosaccharomyces pombe, Kluyveromyces lactis, Kluyveromyces marxianus, Aspergillus terreus, Aspergillus niger*, and *Pichia pastoris*.

A non-naturally occurring microorganism of the invention can comprise a set of metabolic modifications obligatory coupling 1,4-butanediol production to growth of the microorganism, the set of metabolic modifications comprising disruption of one or more genes selected from the set of genes comprising adhE, ldhA, pflAB; adhE, ldhA, pflAB, mdh; adhE, ldhA, pflAB, mdh, mqo; adhE, ldhA, pflAB, mdh, aspA; adhE, mdh, ldhA, pflAB, sfcA; adhE, mdh, ldhA, pflAB, maeB; adhE, mdh, ldhA, pflAB, sfcA, maeB; adhE, ldhA, pflAB, mdh, pntAB; adhE, ldhA, pflAB, mdh, gdhA; adhE, ldhA, pflAB, mdh, pykA, pykF, dhaKLM, deoC, edd, yiaE, ycdW; and adhE, ldhA, pflAB, mdh, pykA, pykF, dhaKLM, deoC, edd, yiaE, ycdW, prpC, gsk, or an ortholog thereof, wherein the microorganism exhibits stable growth-coupled production of 1,4-butanediol.

In one embodiment, the invention provides a non-naturally occurring microorganism comprising a set of metabolic modifications obligatory to coupling 1,4-butanediol production to growth of the microorganism, the set of metabolic modifications comprising disruption of one or more genes, or an ortholog thereof, wherein the set of metabolic modifications comprises disruption of adhE and ldhA, wherein the microorganism exhibits stable growth-coupled production of 1,4-butanediol. In an additional embodiment, the set of metabolic modifications can further comprise disruption of mdh. In another embodiment, the set of metabolic modifications can further comprise disruption of one or more genes selected from the set of genes comprising mqo, aspA, sfcA, maeB, pntAB, and gdhA and can include, for example, disruption of sfcA and maeB. In still another embodiment, the set of metabolic modifications can further comprise disruption of one or more genes selected from the set of genes comprising pykA, pykF, dhaKLM, deoC, edd, yiaE, ycdW, prpC, and gsk, including disruption of all of pykA, pykF, dhaKLM, deoC, edd, yiaE and ycdW, and can further comprise disruption of prpC and gsk. Any of the above-described set of metabolic modifications can further comprise disruption of pflAB. In a particular embodiment, the set of metabolic modifications comprise disruption of one or more genes selected from the set of genes comprising adhE, ldhA, pflAB, mdh, and aspA, including up to all of genes adhE, ldhA, pflAB, mdh, and aspA.

A non-naturally occurring microorganism of the invention can further comprise a 1,4-butanediol (BDO) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate: succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO), as disclosed herein.

The invention additionally provides a method of producing a non-naturally occurring microorganism having stable growth-coupled production of 1,4-butanediol by identifying in silico a set of metabolic modifications requiring 1,4-butanediol production during exponential growth under a defined set of conditions, and genetically modifying a microorganism to contain the set of metabolic modifications requiring 1,4-butanediol production. Such methods can additionally include the addition of exogenous genes expressing desired enzyme activities to a microorganism. Such a set of metabolic modifications can be identified by an in silico method selected from OptKnock or SimPheny (see above and Examples V-VII).

The invention additionally provides a microorganism produced by the methods disclosed herein. Furthermore, the invention provides a method of producing 1,4-butanediol coupled to the growth of a microorganism. The method can include the steps of culturing under exponential growth phase in a sufficient amount of nutrients and media a non-naturally occurring microorganism comprising a set of metabolic modifications obligatorily coupling 1,4-butanediol production to growth of the microorganism, wherein the microorganism exhibits stable growth-coupled production of 1,4-butanediol, and isolating 1,4-butanediol produced from the non-naturally occurring microorganism. The set of metabolic modifications comprising disruption of one or more genes can be selected from the set of genes comprising adhE, ldhA, pflAB; adhE, ldhA, pflAB, mdh; adhE, ldhA, pflAB, mdh, mqo; adhE, ldhA, pflAB, mdh, aspA; adhE, ldhA, pflAB, sfcA; adhE, mdh, ldhA, pflAB, maeB; adhE, mdh, ldhA, pflAB, sfcA, maeB; adhE, ldhA, pflAB, mdh, pntAB; adhE, ldhA, pflAB, mdh, gdhA; adhE, ldhA, pflAB, mdh, pykA, pykF, dhaKLM, deoC, edd, yiaE, ycdW; and adhE, ldhA, pflAB, mdh, pykA, pykF, dhaKLM, deoC, edd, yiaE, ycdW, prpC, gsk, or an ortholog thereof.

In one embodiment, the invention provides a method of producing 1,4-butanediol coupled to the growth of a microorganism. The method can include the steps of culturing under exponential growth phase in a sufficient amount of nutrients and media a non-naturally occurring microorganism comprising a set of metabolic modifications obligatorily coupling 1,4-butanediol production to growth of the microorganism, the set of metabolic modifications comprising disruption of one or more genes, or an ortholog thereof, wherein the set of metabolic modifications comprises disruption of adhE and ldhA, wherein the microorganism exhibits stable growth-coupled production of 1,4-butanediol; and isolating 1,4-butanediol produced from the non-naturally occurring microorganism. In an additional embodiment, the set of metabolic modifications can further comprise disruption of mdh. In another embodiment, the set of metabolic modifications can further comprise disruption of one or more genes selected from the set of genes comprising mqo, aspA, sfcA, maeB, pntAB, and gdhA and can include, for example, disruption of sfcA and maeB. In still another embodiment, the set of metabolic modifications can further comprise disruption of one or more genes selected from the set of genes comprising pykA, pykF, dhaKLM, deoC, edd, yiaE, ycdW, prpC, and gsk, including disruption of all of pykA, pykF, dhaKLM, deoC, edd, yiaE and ycdW, and can further comprise disruption of prpC and gsk. Any of the above-described set of metabolic modifications can further comprise disruption of pflAB.

In a method of producing BDO, the non-naturally occurring microorganism can further comprise a 1,4-butanediol (BDO) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate: succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO).

It is understood that modifications which do not substantially affect the activity of the various embodiments of this invention are also included within the definition of the invention provided herein. Accordingly, the following examples are intended to illustrate but not limit the present invention.

Example I

Biosynthesis of 4-Hydroxybutanoic Acid

This Example describes the biochemical pathways for 4-HB production.

Previous reports of 4-HB synthesis in microbes have focused on this compound as an intermediate in production of the biodegradable plastic poly-hydroxyalkanoate (PHA) (U.S. Pat. No. 6,117,658). The use of 4-HB/3-HB copolymers can be advantageous over the more traditional poly-3-hydroxybutyrate polymer (PHB) because the resulting plastic is less brittle (Saito and Doi, *Intl. J. Biol. Macromol.* 16:99-104 (1994)). The production of monomeric 4-HB described herein is a fundamentally different process for several reasons: 1). The product is secreted, as opposed to PHA which is produced intracellularly and remains in the cell; 2) for organisms that produce hydroxybutanoate polymers, free 4-HB is not produced, but rather the Coenzyme A derivative is used by the polyhydroxyalkanoate synthase; 3) in the case of the polymer, formation of the granular product changes thermodynamics; and 4) extracellular pH is not an issue for production of the polymer, whereas it will affect whether 4-HB is present in the free acid or conjugate base state, and also the equilibrium between 4-HB and GBL.

4-HB can be produced in two enzymatic reduction steps from succinate, a central metabolite of the TCA cycle, with succinic semialdehyde as the intermediate (FIG. 2). The first of these enzymes, succinic semialdehyde dehydrogenase, is native to many organisms including *E. coli*, in which both NADH- and NADPH-dependent enzymes have been found (Donnelly and Cooper, *Eur. J. Biochem.* 113:555-561 (1981); Donnelly and Cooper, *J. Bacteriol.* 145:1425-1427 (1981); Marek and Henson, *J. Bacteriol.* 170:991-994 (1988)). There is also evidence supporting succinic semialdehyde dehydrogenase activity in *S. cerevisiae* (Ramos et al., *Eur. J. Biochem.* 149:401-404 (1985)), and a putative gene has been identified by sequence homology. However, most reports indicate that this enzyme proceeds in the direction of succinate synthesis, opposite to that shown in FIG. 2 (Donnelly and Cooper, supra; Lutke-Eversloh and Steinbuchel, *FEMS Microbiol. Lett.* 181: 63-71 (1999)), participating in the degradation pathway of 4-HB and gamma-aminobutyrate. An alternative pathway, used by the obligate anaerobe *Clostridium kluyveri* to degrade succinate, activates succinate to succinyl-CoA, then converts succinyl-CoA to succinic semialdehyde using an alternative succinic semialdehyde dehydrogenase which is known to function in this direction (Sohling and Gottschalk, *Eur. J. Biochem.* 212:121-127 (1993)). However, this route has the energetic cost of ATP required to convert succinate to succinyl-CoA.

The second enzyme of the pathway, 4-hydroxybutanoate dehydrogenase, is not native to *E. coli* or yeast but is found in various bacteria such as *C. kluyveri* and *Ralstonia eutropha* (Lutke-Eversloh and Steinbuchel, supra; Sohling and Gottschalk, *J. Bacteriol.* 178:871-880 (1996); Valentin et al., *Eur. J. Biochem.* 227:43-60 (1995); Wolff and Kenealy, *Protein Expr. Purif.* 6:206-212 (1995)). These enzymes are known to be NADH-dependent, though NADPH-dependent forms can exist. An additional pathway to 4-HB from alpha-ketoglutarate was demonstrated in *E. coli* resulting in the accumulation of poly(4-hydroxybutyric acid) (Song et al., *Wei Sheng Wu Xue. Bao.* 45:382-386 (2005)). The recombinant strain required the overexpression of three heterologous genes, PHA synthase (*R. eutropha*), 4-hydroxybutyrate dehydrogenase (*R. eutropha*) and 4-hydroxybutyrate:CoA transferase (*C. kluyveri*), along with two native *E. coli* genes: glutamate:succinic semialdehyde transaminase and glutamate decarboxylase. Steps 4 and 5 in FIG. 2 can alternatively be carried out by an alpha-ketoglutarate decarboxylase such as the one identified in *Euglena gracilis* (Shigeoka et al., *Biochem. J.* 282(Pt2):319-323 (1992); Shigeoka and Nakano, *Arch. Biochem. Biophys.* 288:22-28 (1991); Shigeoka and Nakano, *Biochem J.* 292(Pt 2):463-467 (1993)). However, this enzyme has not yet been applied to impact the production of 4-HB or related polymers in any organism.

The reported directionality of succinic semialdehyde dehydrogenase led to the investigation of the thermodynamics of 4-HB metabolism. Specifically, this study investigated whether or not the reactions involved in the conversion of succinate or succinyl-CoA to 4-HB are thermodynamically favorable (i.e., $\Delta G_r < 0$) under the typical physiological conditions present in *E. coli* and *S. cerevisiae*. All oxidation/reduction reactions were assumed to utilize NADH, although the results for assuming NADPH utilization would be similar. Standard Gibbs free energies of formation ($\Delta G_f^\circ$) were calculated for each compound in FIG. 2 based on the group contribution method (Mavrovouniotis, M. L., *J. Biol. Chem.* 266:14440-14445 (1991)). Each standard Gibbs energy of formation was then transformed in order to obtain a criterion of spontaneous change at specified pressure, temperature, pH, and ionic strength (Alberty, R. A., *Biochem. Biophys. Acta* 1207:1-11 (1994)) (equation 1).

$$\Delta G'_f(I, \text{pH}) = \Delta G_f^\circ(I=0) + N_H RT\ln(10^{pH}) - 2.915\sqrt{I}\frac{z^2 - N_H}{1+B\sqrt{I}} \quad (1)$$

Where $\Delta G_f^\circ$ is the standard Gibbs energy of formation, $N_H$ is the number of hydrogen atoms in the compound, R is the universal gas constant, T is constant at 298K, z is the charge of the molecule at the pH of interest, I is the ionic strength in M, and B is a constant equal to $1.6 \text{ L}^{0.5}/\text{mol}^{0.5}$.

Equation 1 reveals that both intracellular pH and ionic strength play a role in determining thermodynamic feasibility. Normally, intracellular pH of cells is very well regulated, even when there are large variations in the culture pH. The intracellular pH of *E. coli* and *S. cerevisiae* have both been reported in the literature. *E. coli* maintains an intracellular pH of 7.4-7.7 during typical growth conditions in neutral buffers, but can drop to 7.2 in pH 6 medium, and even go as low as 6.9 for external pH of 5 (Riondet et al., *Biotechnology Tech.* 11:735-738 (1997)). However, growth of *E. coli* is severely inhibited at external pH below 6. Yeast pH exhibits more variation. During exponential growth phase, *S. cerevisiae* internal pH has been measured to be in the range of 6.7-7.0 with external pH controlled at 5.0 (Dombek and Ingram, *Appl. Environ. Microbiol.* 53:1286-1291 (1987)). On the other hand, in resting cells the internal pH drops to below 6 when the external pH is 6 or less (Imai and Ohno, *J. Biotechnol.* 38:165-172 (1995)). This analysis assumes an intracellular pH of 7.4 for *E. coli* and 6.8 for *S. cerevisiae*. An ionic strength of 0.15 also was assumed (Valenti et al., supra).

Transformed Gibbs energies of formation were calculated at the standard state (pH=7.0, I=0) and at physiological states of *E. coli* (pH=7.4, I=0.15) and *S. cerevisiae* (pH=6.8, I=0.15). Transformed Gibbs energies of reaction ($\Delta G_r'$) were then calculated by taking the difference in $\Delta G_f'$ between the products and reactants. The transformed Gibbs energies of the reactions necessary to convert succinate or succinyl-CoA to 4-HB are provided in Table 2. Note that the standard error, $U_{f,est}$, on $\Delta G_f$ calculated by the group contribution theory is 4 kcal/mol. The uncertainty in $\Delta G_r$, $U_{r,est}$, can be calculated as the Euclidean norm of the uncertainty for $\Delta G_f$ of each compound (Equation).

$$U_{r,est} = \sqrt{\sum_{i=1}^{m} n_i^2 * U_{f,est}^2} = \sqrt{\sum_{i=1}^{m} 16 n_i^2} \quad (2)$$

Where n is the stoichiometric coefficient and i is the compound. For the examined reactions, this uncertainty is on the order of 8 kcal/mol.

Table 2.

Gibbs free energy of reaction (kcal/mole) at different pH and ionic strength values. The first column is under standard conditions, while the others are adjusted according to equation 1. Temperature is constant at 298 K. Error bars for these values are on the order of 8 kcal/mol, as calculated by equation 2. Abbreviations: suc, succinate; sucsa, succinic semialdehyde; succoa, succinyl-CoA; Pi, inorganic phosphate.

| Reaction | $\Delta G_r^{\circ'}$ pH = 7.0 IS = 0 | $\Delta G_r'$ pH = 7.4 IS = 0.15M | $\Delta G_r'$ pH = 6.8 IS = 0.15M |
|---|---|---|---|
| succ + NADH + 2 H+ → sucsa + NAD + h2o | 12.0 | 14.4 | 12.8 |
| succ + coa + ATP → succoa + ADP + Pi | 0.30 | −0.03 | −0.03 |
| succoa + NADH + H+ → sucsa + NAD + coa | 4.4 | 7.0 | 6.2 |
| sucsa + NADH + H+ → 4hb + NAD | −5.0 | −3.8 | −4.6 |

Table 2 reveals that the reaction most likely to encounter a thermodynamic barrier after considering potential uncertainty in our calculations is succinic semialdehyde dehydrogenase (step 1 in FIG. 2). Whether this reaction can be driven closer to thermodynamic feasibility by varying the assumed concentrations of the participating metabolites also was studied. For example, the standard Gibbs energies assume concentrations of 1 M for all participating compounds (except water). In an anaerobic environment, NADH will be present at a several-fold higher concentration than NAD. Assuming [NADH]=5×[NAD], we calculated the effect on $\Delta G_r'$ using the equation $$\Delta G_f' = \Delta G_f^{0\prime} + RT \ln \frac{\prod [prod]}{\prod [react]} \quad (3)$$

This change results in a difference of only about 1 kcal/mol in the delta G values for succinic semialdehyde dehydrogenase. Equation 3 was also used to calculate other effects on $\Delta G_r$, such as high succinate concentration to drive the reactions. A 1000-fold difference in the concentrations of succinate and succinic semialdehyde will contribute about 5 kcal/mol to delta G. Taken together with an assumed uncertainty of 8 kcal/mol, the possibility that succinic semialdehyde dehydrogenase will operate in the direction towards succinic semialdehyde under some set of physiological conditions cannot be eliminated. Thus we still consider the direct route from succinate to 4-HB in our subsequent theoretical analysis.

The microbial production capabilities of 4-hydroxybutyrate were explored in two microbes, *Escherichia coli* and *Saccharomyces cerevisiae*, using in silico metabolic models of each organism. Potential pathways to 4-HB proceed via a succinate, succinyl-CoA, or alpha-ketoglutarate intermediate as shown in FIG. 2.

The first step in the 4-HB production pathway from succinate involves the conversion of succinate to succinic semialdehyde via an NADH- or NADPH-dependant succinic semialdehyde dehydrogenase. In *E. coli*, gabD is an NADP-dependant succinic semialdehyde dehydrogenase and is part of a gene cluster involved in 4-aminobutyrate uptake and degradation (Niegemann et al., *Arch. Microbiol.* 160:454-460 (1993); Schneider et al., *J. Bacteriol.* 184:6976-6986 (2002)). sad is believed to encode the enzyme for NAD-dependant succinic semialdehyde dehydrogenase activity (Marek and Henson, supra). *S. cerevisiae* contains only the NADPH-dependant succinic semialdehyde dehydrogenase, putatively assigned to UGA2, which localizes to the cytosol (Huh et al., *Nature* 425:686-691 (2003)). The maximum yield calculations assuming the succinate pathway to 4-HB in both *E. coli* and *S. cerevisiae* require only the assumption that a non-native 4-HB dehydrogenase has been added to their metabolic networks.

The pathway from succinyl-CoA to 4-hydroxybutyrate was described in U.S. Pat. No. 6,117,658 as part of a process for making polyhydroxyalkanoates comprising 4-hydroxybutyrate monomer units. *Clostridium kluyveri* is one example organism known to possess CoA-dependant succinic semialdehyde dehydrogenase activity (Sohling and Gottschalk, supra; Sohling and Gottschalk, supra). In this study, it is assumed that this enzyme, from *C. kluyveri* or another organism, is expressed in *E. coli* or *S. cerevisiae* along with a non-native or heterologous 4-HB dehydrogenase to complete the pathway from succinyl-CoA to 4-HB. The pathway from alpha-ketoglutarate to 4-HB was demonstrated in *E. coli* resulting in the accumulation of poly(4-hydroxybutyric acid) to 30% of dry cell weight (Song et al., supra). As *E. coli* and *S. cerevisiae* natively or endogenously possess both glutamate:succinic semialdehyde transaminase and glutamate decarboxylase (Coleman et al., *J. Biol. Chem.* 276: 244-250 (2001)), the pathway from AKG to 4-HB can be completed in both organisms by assuming only that a non-native 4-HB dehydrogenase is present.

Example II

Production of 4-Hydroxybutanoic Acid in *E. coli*

This Example describes the biosynthetic yields for 4-hydroxybutanoic acid resulting from each biochemical pathway.

In this section, the maximum theoretical yields of 4-HB from glucose are calculated assuming that each of the three metabolic pathways depicted in FIG. 2 are functional in *E. coli*. A genome-scale metabolic model of *E. coli*, similar to the one described in Reed et al., *Genome Biol.* 4:R54 (2003), was used as the basis for the analysis. The energetic gain, in terms of ATP molecules produced, of each maximum yielding pathway is calculated assuming anaerobic conditions, unless otherwise stated. 4-Hydroxybutyrate is assumed to exit in *E. coli* via proton symport, as is the case with most organic acids. It is also possible that GBL is secreted by simple diffusion, and in this case the energetics would be more favorable than in the case considered here. The impact of cofactor specificity (i.e., NADH or NADPH-dependence) of the participating enzymes on the maximum yield and energetics of each pathway also was investigated.

The results from the analysis are shown in Tables 3 A-C. From an energetic and yield standpoint, the succinate to 4-HB pathway is the most promising provided that the thermodynamic concerns raised in Example I can be overcome. Specifically, the calculations reveal that the maximum theoretical yield of 4-HB from glucose is 1.33 mol/mol (0.77 g/g; 0.89 Cmol/Cmol) assuming the succinate to 4-HB pathway is functional. In addition, the anaerobic production of 4-HB via succinate would result in the net production of either 1.8, 1.5, or 1.1 mol of ATP per glucose depending upon the assumed cofactor specificity of the participating enzymes. These energetic yields are comparable to the 2.0 ATP per glucose that can be obtained via substrate level phosphorylation by the production of ethanol or lactate suggesting the potential for anaerobic homo-4-HB production in *E. coli*.

The succinyl-CoA route to 4-HB is the second most promising pathway when considering maximum yield and energetics. A 1.33 mol/mol yield of 4-HB is achievable in *E. coli* if at least one of the pathway steps is assumed NADH-dependant. However, because this pathway requires the formation of succinyl-CoA, its energetic yield is considerably lower than that of the succinate pathway. An oxygen requirement is anticipated at high 4-HB yields if both the CoA-dependant succinic semialdehyde dehydrogenase and 4-HB dehydrogenase steps are assumed NADPH-dependant. In this case, the production of 4-HB at the maximum yield would result in no net ATP gain and could not support the energetic maintenance demands needed for *E. coli* survival. Thus, some energy would have to originate from oxidative phosphorylation to enable homo-fermentative 4-HB production. The alpha-ketoglutarate pathway toward 4-HB is the least favorable of the three potential routes with a maximum achievable yield of 1.0 mol 4-HB per mol of glucose. In addition to the lower maximum yield, this pathway requires the utilization of 1.5 moles of oxygen per mol of glucose converted to 4-HB. The energetics of this pathway are unaffected by the assumed cofactor specificity of 4-HB dehydrogenase.

TABLE 3

The overall substrate conversion stoichiometry to 4-HB assuming the A) succinate, B) succinyl-CoA, or C) alpha-ketoglutarate production routes are functional in *E. coli*. Glucose and oxygen are taken up while all other molecules are produced.

A) Succinate Pathway

| Cofactor Specificity | 2 NADH steps | 1 NADH step 1 NADPH step | 2 NADPH steps |
|---|---|---|---|
| Glucose | −1.000 | −1.000 | −1.000 |
| Oxygen | 0.000 | 0.000 | 0.000 |
| Protons | 1.333 | 1.333 | 1.333 |
| 4HB | 1.333 | 1.333 | 1.333 |
| CO2 | 0.667 | 0.667 | 0.667 |
| H2O | 0.667 | 0.667 | 0.667 |
| ATP | 1.800 | 1.510 | 1.097 |

B) Succinyl-CoA Pathway

| Cofactor Specificity | 2 NADH steps | 1 NADH step 1 NADPH step | 2 NADPH steps | 2 NADPH steps |
|---|---|---|---|---|
| Glucose | −1.000 | −1.000 | −1.000 | −1.000 |
| Oxygen | 0.000 | 0.000 | −0.036 | 0.000 |
| Protons | 1.333 | 1.333 | 1.325 | 1.294 |
| 4HB | 1.333 | 1.333 | 1.325 | 1.294 |
| CO2 | 0.667 | 0.667 | 0.698 | 0.082 |
| H2O | 0.667 | 0.667 | 0.698 | 0.470 |
| ATP | 0.467 | 0.177 | 0.000 | 0.000 |

C) Alpha-ketoglutarate Pathway

| Cofactor Specificity | 1 NADH step | 1 NADPH step |
|---|---|---|
| Glucose | −1.000 | −1.000 |
| Oxygen | −1.500 | −1.500 |
| Protons | 1.000 | 1.000 |
| 4HB | 1.000 | 1.000 |
| CO2 | 2.000 | 2.000 |
| H2O | 2.000 | 2.000 |
| ATP | 5.500 | 5.500 |

In order to corroborate the computational predictions proposed in this report, the strains expressing a complete pathway to 4-HB can be constructed and tested. Corroboration is performed with both *E. coli* (Example II) and *S. cerevisiae* (Example III). In *E. coli*, the relevant genes are expressed in a synthetic operon behind an inducible promoter on a medium- or high-copy plasmid; for example the $P_{BAD}$ promoter which is induced by arabinose, on a plasmid of the pBAD series (Guzman et al., *J. Bacteriol.* 177:4121-4130 (1995)). In *S. cerevisiae*, genes are integrated into the chromosome behind the PDC1 promoter, replacing the native pyruvate carboxylase gene. It has been reported that this results in higher expression of foreign genes than from a plasmid (Ishida et al., *Appl. Environ. Microbiol.* 71:1964-1970 (2005)), and will also ensure expression during anaerobic conditions.

Cells containing the relevant constructs are grown in minimal media containing glucose, with addition of arabinose in the case of *E. coli* containing genes expressed under the $P_{BAD}$ promoter. Periodic samples are taken for both gene expression and enzyme activity analysis. Enzyme activity assays are performed on crude cell extracts using procedures well known in the art. Alternatively, assays based on the oxidation of NAD(P)H, which is produced in all dehydrogenase reaction steps and detectable by spectrophotometry can be utilized. In addition, antibodies can be used to detect the level of particular enzymes. In lieu of or in addition to enzyme activity measurements, RNA can be isolated from parallel samples and transcript of the gene of interest measured by reverse transcriptase PCR. Any constructs lacking detectable transcript expression are reanalyzed to ensure the encoding nucleic acids are harbored in an expressible form. Where transcripts are detected, this result indicates either a lack of translation or production of inactive enzyme. A variety of methods well known in the art can additionally be employed, such as codon optimization, engineering a strong ribosome binding site, use of a gene from a different species, and prevention of N-glycosylation (for expression of bacterial enzymes in yeast) by conversion of Asn residues to Asp. Once all required enzyme activities are detected, the next step is to measure the production of 4-HP in vivo. Triplicate shake flask cultures are grown either anaerobically or microaerobically, depending on the conditions required (see above), and periodic samples taken. Organic acids present in the culture supernatants are analyzed by HPLC using the Aminex AH-87X column. The elution time of 4-HB will be determined using a standard purchased from a chemical supplier.

The CoA-independent pathway can be implemented and tested for corroboration. In this case, the genes overexpressed are the native succinic semialdehyde dehydrogenase from each organism, and the 4-hydroxybutanoate dehydrogenase from *Ralstonia eutropha*. Once both enzyme activities are detected as discussed above, the strains are tested for 4-HB production. Corroboration also can be obtained from implementing the CoA-dependent pathway. The CoA-dependent succinic semialdehyde dehydrogenase and the 4-hydroxybutanoate dehydrogenase from *Clostridium kluyveri* are expressed as described above. In addition, overexpression of the native succinyl-CoA synthetase also can be performed, to funnel more succinate into the heterologous pathway. Finally, if 4-HB production is unfavorable, different culture conditions can be tested, such as a change in oxygenation status which can manipulate the NAD(P)H/NAD(P) ratio.

Example III

Production of 4-Hydroxybutanoic Acid in Yeast

This Example describes the biosynthetic yields for 4-hydroxybutanoic acid resulting from each biochemical pathway in *S. cerevisiae*.

In this section, the maximum theoretical yields of 4-HB from glucose are calculated assuming that each of the three metabolic pathways depicted in FIG. 2 are functional in *S. cerevisiae*. A genome-scale metabolic model of *S. cerevisiae*, similar to the one described in Forster et al. (*Genome Res.* 13:244-253 (2003)) was used as the basis for the analysis. The energetic gain of each maximum yielding pathway is calculated assuming anaerobic conditions unless otherwise stated. 4-hydroxybutyrate is assumed to exit *S. cerevisiae* via proton symport, as is the case with most organic acids. The impact of cofactor specificity (i.e., NADH or NADPH-dependence) of the participating enzymes on the maximum yield and energetics of each pathway was also investigated.

The results from the analysis are shown in Tables 4 A-C. As with *E. coli*, the succinate to 4-HB pathway is the most promising provided that the thermodynamic concerns raised in Example I can be overcome. The calculations reveal that the maximum theoretical yield of 4-HB from glucose is 1.33 mol/mol (0.77 g/g; 0.89 Cmol/Cmol) in *S. cerevisiae*. In addition, the anaerobic production of 4-HB via succinate would result in the net production of either 1.4, 1.1, or 0.5 mol of ATP per glucose depending upon the assumed cofactor specificity of the participating enzymes.

The succinyl-CoA route to 4-HB is the second most favorable pathway. A maximum yield of 1.33 mol 4-HB/mol glucose is achievable in S. cerevisiae regardless of cofactor specificity. However, net energy generation at the maximum theoretical yield is possible only if both the CoA-dependant succinic semialdehyde dehydrogenase and 4-HB dehydrogenase steps are assumed to be NADH-dependant. If either step is NADPH-dependant, no net ATP will be gained from anaerobic 4-HB production and an alternate energy source (e.g., oxidative phosphorylation) would be required to support cell growth and maintenance. The alpha-ketoglutarate route toward 4-HB is the least favorable of the three potential pathways in S. cerevisiae although the maximum yield of 1.1-1.2 mol 4-HB per mol glucose is slightly higher than was found in E. coli. Nevertheless, this pathway requires an oxygen uptake of 0.8-0.9 mol oxygen per mol glucose to become energetically neutral.

TABLE 4

The overall substrate conversion stoichiometry to 4-HB in S. cerevisiae., assuming the A) succinate, B) succinyl-CoA, or C) alpha-ketoglutarate production routes are functional in S. cerevisiae. Glucose and oxygen are taken up while all other molecules are produced.

| Cofactor Specificity | 2 NADH steps | 1 NADH step 1 NADPH step | 2 NADPH steps |
|---|---|---|---|
| A) Succinate Pathway | | | |
| Glucose | −1.000 | −1.000 | −1.000 |
| Oxygen | 0.000 | 0.000 | 0.000 |
| Protons | 1.333 | 1.333 | 1.333 |
| 4HB | 1.333 | 1.333 | 1.333 |
| CO2 | 0.667 | 0.667 | 0.667 |
| H2O | 0.667 | 0.667 | 0.667 |
| ATP | 1.444 | 1.067 | 0.533 |
| B) Succinyl-CoA Pathway | | | |
| Glucose | −1.000 | −1.000 | −1.000 |
| Oxygen | 0.000 | 0.000 | 0.000 |
| Protons | 1.333 | 1.333 | 1.333 |
| 4HB | 1.333 | 1.333 | 1.333 |
| CO2 | 0.667 | 0.667 | 0.667 |
| H2O | 0.667 | 0.667 | 0.667 |
| ATP | 0.533 | 0.000 | 0.000 |

C) Alpha-ketoglutarate Pathway

| Cofactor Specificity | 1 NADH step | 1 NADPH step |
|---|---|---|
| Glucose | −1.000 | −1.000 |
| Oxygen | −0.785 | −0.879 |
| Protons | 1.159 | 1.138 |
| 4HB | 1.159 | 1.138 |
| CO2 | 1.364 | 1.448 |
| H2O | 1.364 | 1.448 |
| ATP | 0.000 | 0.000 |

Example IV

Biosynthesis of 4-Hydroxybutanoic Acid, γ-Butyrolactone and 1,4-Butanediol

This Example describes the biosynthetic production of 4-hydroxybutanoic acid, γ-butyrolactone and 1,4-butanediol using fermentation and other bioprocesses.

Figure 4:
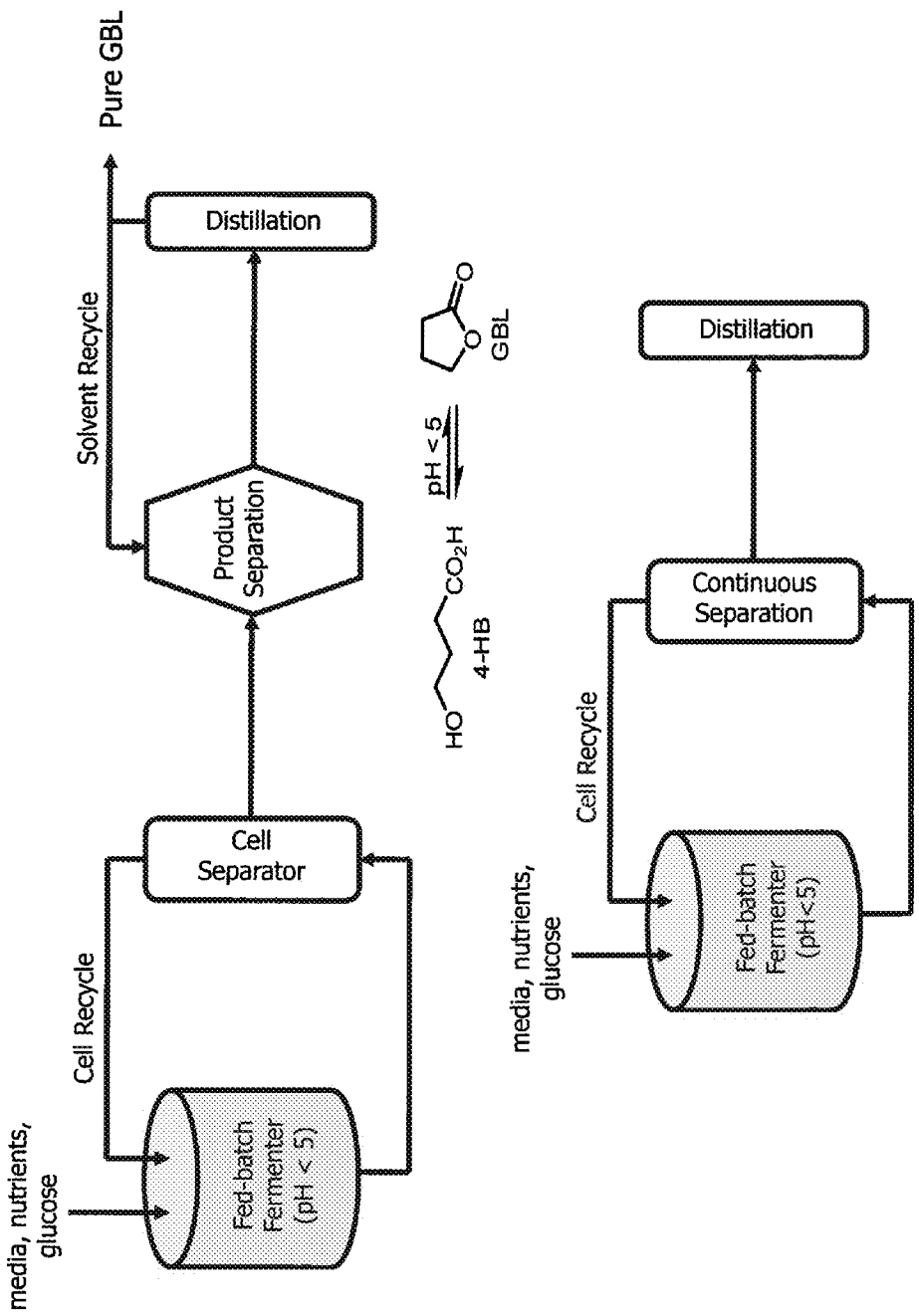
FIG. 4 is a schematic process flow diagram of bioprocesses for the production of γ-butyrolactone. Panel (a) illustrates fed-batch fermentation with batch separation and panel (b) illustrates fed-batch fermentation with continuous separation.

Methods for the integration of the 4-HB fermentation step into a complete process for the production of purified GBL, 1,4-butanediol (BDO) and tetrahydrofuran (THF) are described below. Since 4-HB and GBL are in Equilibrium, the fermentation broth will contain both compounds. At low pH this equilibrium is shifted to favor GBL. Therefore, the fermentation can operate at pH 7.5 or less. After removal of biomass, the product stream enters into a separation step in which GBL is removed and the remaining stream enriched in 4-HB is recycled. Finally, GBL is distilled to remove any impurities. The process operates in one of three ways: 1) fed-batch fermentation and batch separation; 2) fed-batch fermentation and continuous separation; 3) continuous fermentation and continuous separation. The first two of these modes are shown schematically in FIG. 4. The integrated fermentation procedures described below also are used for the BDO producing cells of the invention for biosynthesis of BDO and subsequent BDO family products.

Fermentation Protocol to Produce 4-HB/GBL (Batch):

The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a product separations unit. Isolation of 4-HB and/or GBL would take place by standard separations procedures employed in the art to separate organic products from dilute aqueous solutions, such as liquid-liquid extraction using a water immiscible organic solvent (e.g., toluene) to provide an organic solution of 4-HB/GBL. The resulting solution is then subjected to standard distillation methods to remove and recycle the organic solvent and to provide GBL (boiling point 204-205° C.) which is isolated as a purified liquid.

Fermentation Protocol to Produce 4-HB/GBL (Fully Continuous):

The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of 4-HB/GBL. The resulting solution is subsequently subjected to standard continuous distillation methods to remove and recycle the organic solvent and to provide GBL (boiling point 204-205° C.) which is isolated as a purified liquid.

GBL Reduction Protocol:

Once GBL is isolated and purified as described above, it will then be subjected to reduction protocols such as those well known in the art (references cited) to produce 1,4-butanediol or tetrahydrofuran (THF) or a mixture thereof. Heterogeneous or homogeneous hydrogenation catalysts combined with GBL under hydrogen pressure are well known to provide the products 1,4-butanediol or tetrahydrofuran (THF) or a mixture thereof. It is important to note that the 4-HB/GBL product mixture that is separated from the fermentation broth, as described above, may be subjected directly, prior to GBL isolation and purification, to these same reduction protocols to provide the products 1,4-butanediol or tetrahydrofuran or a mixture thereof. The resulting products, 1,4-butanediol and THF are then isolated and purified by procedures well known in the art.

Fermentation and Hydrogenation Protocol to Produce BDO or THF Directly (Batch):

Cells are grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a reduction unit (e.g., hydrogenation vessel), where the mixture 4-HB/GBL is directly reduced to either 1,4-butanediol or THF or a mixture thereof. Following completion of the reduction procedure, the reactor contents are transferred to a product separations unit. Isolation of 1,4-butanediol and/or THF would take place by standard separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard distillation methods to remove and recycle the organic solvent and to provide 1,4-butanediol and/or THF which are isolated as a purified liquids.

Fermentation and Hydrogenation Protocol to Produce BDO or THF Directly (Fully Continuous):

The cells are first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then passed through a cell separation unit (e.g., centrifuge) to remove cells and cell debris, and the fermentation broth is transferred to a continuous reduction unit (e.g., hydrogenation vessel), where the mixture 4-HB/GBL is directly reduced to either 1,4-butanediol or THF or a mixture thereof. Following completion of the reduction procedure, the reactor contents are transferred to a continuous product separations unit. Isolation of 1,4-butanediol and/or THF would take place by standard continuous separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard continuous distillation methods to remove and recycle the organic solvent and to provide 1,4-butanediol and/or THF which are isolated as a purified liquids.

Fermentation Protocol to Produce BDO Directly (Batch):

The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until BDO reaches a concentration of between 20-200 g/L, with the cell density generally being between 5 and 10 g/L. Upon completion of the cultivation period, the fermenter contents are passed through a cell separation unit (e.g., centrifuge) to remove cells and cell debris, and the fermentation broth is transferred to a product separations unit. Isolation of BDO would take place by standard separations procedures employed in the art to separate organic products from dilute aqueous solutions, such as liquid-liquid extraction using a water immiscible organic solvent (e.g., toluene) to provide an organic solution of BDO. The resulting solution is then subjected to standard distillation methods to remove and recycle the organic solvent and to provide BDO (boiling point 228-229° C.) which is isolated as a purified liquid.

Fermentation Protocol to Produce BDO Directly (Fully Continuous):

The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The BDO concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of BDO concentration. In continuous mode, fermenter contents are constantly removed as new feed medium is supplied. The exit stream, containing cells, medium, and the product BDO, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of BDO. The resulting solution is subsequently subjected to standard continuous distillation methods to remove and recycle the organic solvent and to provide BDO (boiling point 228-229° C.) which is isolated as a purified liquid (mpt 20° C.).

Example V

In Silico Derived Knockout Strategies for Growth-Coupled Production of 1,4-Butanediol in *Escherichia coli*

This example describes the in silico design of knockout strategies to generate growth-coupled production of 1,4-butanediol in *E. coli*.

The strategy for generating growth-coupled production of BDO first involves the demonstration of a functional pathway which is subsequently optimized through adaptive evolution and targeted gene insertions, deletions, and overexpression. Described below in more detail are strain-engineering strategies identified via OptKnock for generating growth-coupled BDO production strains of *Escherichia coli*. All implementations of OptKnock assume that sufficient activities of all enzymes outlined in FIG. 6 are available to *E. coli* under all conditions. In addition, all reduction steps in this pathway are assumed to be NADH-dependent although many of the designs are expected to be applicable regardless of cofactor specificity.

The BDO yield potential of the biochemical pathways to 1,4-butanediol in *E. coli* is detailed below. Three conditions were used, anaerobic, anaerobic+nitrate addition, and aerobic. The maximum theoretical yields for each scenario assuming that the production of BDO must be energetically neutral are shown in Table 5. Table 5 shows the maximum theoretical yields of 1,4-butanediol (BDO) for five sets of environmental conditions: 1) aerobic respiration, 2) anaerobic fermentation with acetate co-production, 3) anaerobic fermentation with ethanol co-production, 4) nitrate respiration leading to nitrite formation, and 5) nitrate respiration leading to ammonia formation. Negative values indicate metabolites taken up; positive values indicate metabolites secreted. Molar units are assumed along with pathway energetic neutrality. The maximum theoretical yield without assuming energetic neutrality is 1.091 mol/mol (0.545 g/g) glucose for all cases. The highest yield is obtained under aerobic conditions where enough ATP to render the pathway energetically neutral can be generated with minimal loss of carbon through respiration. In the anaerobic case, the yield drops as ATP is made via substrate level phosphorylation and either acetate or ethanol is made as a byproduct. Controlled nitrate addition can provide nearly the same yield as oxygen, the exact amount depending upon whether further reduction of nitrite to ammonia occurs.

If phosphoenolpyruvate (PEP) carboxykinase is assumed to operate in the direction of phosphoenolpyruvate to oxaloacetate, BDO production becomes an energy-generating endeavor and the maximum theoretical yield for all scenarios becomes 0.545 g/g with $CO_2$ as the only byproduct. PEP carboxykinase is known to produce oxaloacetate from PEP in rumen bacteria such as *Mannheimia succiniciproducens* (Hong et al., *Nat. Biotechnol.* 22:1275-1281 (2004)). However, the role of PEP carboxykinase in producing oxaloacetate in *E. coli* is believed to be minor as compared to PEP carboxylase possibly due to the higher Km for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of K-12 (Kwon et al., *J. Microbiol. Biotechnol.* 16:1448-1452 (2006)).

In more detail, the designs identified for increasing BDO production in *E. coli* are described below. A non-growth associated energetic maintenance requirement of 7.6 mmol/gDW/hr was assumed along with a maximum specific glucose uptake rate of 20 mmol/gDW/hr. BDO was assumed to be exported via diffusion. Knockout strategies were identified assuming that 1) PEP carboxykinase is irreversible and functions only to convert oxaloacetate to PEP and 2) PEP carboxykinase is reversible. For both cases, the OptKnock code described in Burgard et al. (*Biotechnol. Bioeng.* 84:647-657 (2003)) was modified to allow for limited, unlimited or no nitrate respiration. Adding the possibility of nitrate respiration serves to increase the maximum theoretical yield of BDO when PEP carboxykinase is assumed irreversible and also, in some cases, enables the selection of knockout strategies that otherwise would not be selected under anaerobic conditions due to unfavorable energetics. Specifically, six nitrate uptake reactions were added to the *E. coli* network with lower bounds of 0, −2, −5, −10, −20, or −1000 mmol/gDW/hr (the negative values signify metabolite uptake in the stoichiometric model). The dual constraints of OptKnock were adjusted accordingly and an additional constraint was added that allowed only one nitrate uptake reaction to be active at a time. OptKnock selects the optimum amount of nitrate respiration for each identified knockout strategy. Finally, all simulations assume that the reaction catalyzed by adhE in *E. coli* (that is, acetyl-CoA+NADH→ethanol+NAD) has been removed. Because acetyl-CoA is a necessary intermediate for BDO production, nearly all OptKnock designs would include this deletion anyway to prevent ethanol production from competing with BDO production. Including this deletion a priori was done to lower the CPU time of the computational procedure.

The knockout strategies derived by OptKnock are given in Tables 6 and 7 assuming PEP carboxykinase to be irreversible and reversible, respectively. In this description, the knockout strategies are listed by reaction abbreviations in all capital letters for simplicity. The corresponding genes that would have to be knocked out to prevent a particular reaction from occurring in *E. coli* are provided in Table 8 along with the reaction stoichiometry. The metabolite names corresponding to Table 8 are listed in Table 9.

TABLE 5

Maximum theoretical yields of 1,4-butanediol (BDO) for five sets of environmental conditions.

| | | Anerobic | | | |
|---|---|---|---|---|---|
| | Aerobic | Acetate Coproduction | Ethanol Coproduction | Nitrate to Nitrite | Nitrate to Ammonia |
| Glucose | −1.000 | −1.000 | −1.000 | −1.000 | −1.000 |
| Oxygen | −0.068 | | | | |
| Nitrate | | | | −0.147 | −0.092 |
| H+ | | 0.144 | | | −0.184 |
| $H_2O$ | 0.607 | 0.519 | 0.498 | 0.612 | 0.621 |
| $CO_2$ | 1.686 | 1.558 | 1.668 | 1.690 | 1.770 |
| Nitrite | | | | 0.147 | |
| Ammonia | | | | | 0.092 |
| Acetate | | 0.144 | | | |
| Ethanol | | | 0.173 | | |
| BDO | 1.079 | 1.039 | 0.997 | 1.078 | 1.058 |

TABLE 6

Knockout strategies derived by OptKnock, assuming PEP carboxykinase to be irreversible.

| # | Metabolic Transformations Targeted for Removal †, ‡, # | BDO | BIO | AC | ALA | CO2 | FOR | GLC | GLY | H+ | H2O | LAC | NH4 | NO3 | PI | PYR | SO4 | SUC | VAL |
|---|---|---|---|---|---|---|---|---|---|---|---|---|---|---|---|---|---|---|---|
| 1 | ADHEr | 5.67 | 0.57 | 25.42 | 0.00 | -5.74 | 28.42 | -20.00 | 0.00 | 57.91 | -0.90 | 0.00 | -4.96 | 0.00 | -0.61 | 0.00 | -0.10 | 0.00 | 0.00 |
| 2 | ADHEr, PFLi | 9.95 | 0.50 | 22.31 | 0.00 | 14.90 | 0.00 | -20.00 | 0.00 | 25.85 | 14.07 | 0.00 | -4.31 | 0.00 | -0.53 | 0.00 | -0.09 | 0.00 | 0.00 |
| 3 | ADHEr, NADH6 | 6.92 | 0.52 | 25.03 | 0.00 | -0.07 | 20.82 | -20.00 | 0.00 | 49.54 | 2.51 | 0.00 | -4.48 | 0.00 | -0.55 | 0.00 | -0.09 | 0.00 | 0.00 |
| 4 | ADHEr, THD2 | 6.55 | 0.56 | 23.75 | 0.00 | -3.54 | 26.67 | -20.00 | 0.00 | 54.38 | 0.13 | 0.00 | -4.83 | 0.00 | -0.60 | 0.00 | -0.10 | 0.00 | 0.00 |
| 5 | ADHEr, PGI | 6.21 | 0.30 | 28.99 | 0.00 | -5.98 | 30.57 | -20.00 | 0.00 | 61.72 | -6.65 | 0.00 | -2.62 | 0.00 | -0.32 | 0.00 | -0.05 | 0.00 | 0.00 |
| 6 | ADHEr, PFK | 6.13 | 0.31 | 29.10 | 0.00 | -6.17 | 30.70 | -20.00 | 0.00 | 61.98 | -6.68 | 0.00 | -2.66 | 0.00 | -0.33 | 0.00 | -0.05 | 0.00 | 0.00 |
| 7 | ADHEr, FBA | 6.13 | 0.31 | 29.10 | 0.00 | -6.17 | 30.70 | -20.00 | 0.00 | 61.98 | -6.68 | 0.00 | -2.66 | 0.00 | -0.33 | 0.00 | -0.05 | 0.00 | 0.00 |
| 8 | ADHEr, ATPS4r | 6.15 | 0.61 | 23.38 | 0.00 | -3.10 | 26.55 | -20.00 | 0.00 | 54.24 | 1.88 | 0.00 | -5.25 | -2.00 | -0.65 | 0.00 | -0.11 | 0.00 | 0.00 |
| 9 | ADHEr, TPI | 6.13 | 0.31 | 29.10 | 0.00 | -6.17 | 30.70 | -20.00 | 0.00 | 61.98 | -6.68 | 0.00 | -2.66 | 0.00 | -0.33 | 0.00 | -0.05 | 0.00 | 0.00 |
| 10 | ADHEr, SUCD4 | 5.85 | 0.47 | 26.89 | 0.00 | -5.92 | 29.33 | -20.00 | 0.00 | 59.54 | -3.22 | 0.00 | -4.04 | 0.00 | -0.50 | 0.00 | -0.08 | 0.00 | 0.00 |
| 11 | ADHEr, RPE | 5.78 | 0.57 | 25.20 | 0.00 | -5.45 | 28.19 | -20.00 | 0.00 | 57.44 | -0.76 | 0.00 | -4.95 | 0.00 | -0.61 | 0.00 | -0.10 | 0.00 | 0.00 |
| 12 | ADHEr, GLCpts | 5.78 | 0.51 | 26.33 | 0.00 | -5.85 | 28.99 | -20.00 | 0.00 | 58.92 | -2.34 | 0.00 | -4.39 | 0.00 | -0.54 | 0.00 | -0.09 | 0.00 | 0.00 |
| 13 | ADHEr, GLUDy | 5.77 | 0.52 | 26.20 | 0.00 | -5.84 | 28.90 | -20.00 | 0.00 | 58.78 | -2.13 | 0.00 | -4.47 | 0.00 | -0.55 | 0.00 | -0.09 | 0.00 | 0.00 |
| 14 | ADHEr, TAL | 5.73 | 0.57 | 25.30 | 0.00 | -5.59 | 28.30 | -20.00 | 0.00 | 57.67 | -0.83 | 0.00 | -4.95 | 0.00 | -0.61 | 0.00 | -0.10 | 0.00 | 0.00 |
| 15 | ADHEr, MDH | 5.73 | 0.54 | 25.90 | 0.00 | -5.80 | 28.72 | -20.00 | 0.00 | 58.44 | -1.66 | 0.00 | -4.66 | 0.00 | -0.58 | 0.00 | -0.09 | 0.00 | 0.00 |
| 16 | ADHEr, FUM | 5.73 | 0.54 | 25.90 | 0.00 | -5.80 | 28.72 | -20.00 | 0.00 | 58.44 | -1.66 | 0.00 | -4.66 | 0.00 | -0.58 | 0.00 | -0.09 | 0.00 | 0.00 |
| 17 | ADHEr, CBMK2 | 5.68 | 0.57 | 25.48 | 0.00 | -5.75 | 28.46 | -20.00 | 0.00 | 57.99 | -1.01 | 0.00 | -4.92 | 0.00 | -0.61 | 0.00 | -0.10 | 0.00 | 0.00 |
| 18 | ADHEr, HEX1, PGI | 11.82 | 0.22 | 18.07 | 0.00 | 8.10 | 19.23 | -20.00 | 0.00 | 38.88 | 0.36 | 0.00 | -1.93 | 0.00 | -0.24 | 0.00 | -0.04 | 0.00 | 0.00 |
| 19 | ADHEr, EDA, PGI | 11.82 | 0.22 | 18.05 | 0.00 | 8.10 | 19.22 | -20.00 | 0.00 | 38.86 | 0.38 | 0.00 | -1.94 | 0.00 | -0.24 | 0.00 | -0.04 | 0.00 | 0.00 |
| 20 | ADHEr, PFLi, PGI | 10.87 | 0.20 | 25.96 | 0.00 | 16.29 | 0.00 | -20.00 | 0.00 | 27.38 | 9.09 | 0.00 | -1.73 | 0.00 | -0.21 | 0.00 | -0.03 | 0.00 | 0.00 |
| 21 | ADHEr, FBA, PFLi | 10.83 | 0.20 | 26.02 | 0.00 | 16.23 | 0.00 | -20.00 | 0.00 | 27.46 | 9.11 | 0.00 | -1.75 | 0.00 | -0.22 | 0.00 | -0.04 | 0.00 | 0.00 |

TABLE 6-continued

Knockout strategies derived by OptKnock, assuming PEP carboxykinase to be irreversible.

| # | Knockouts | | | | | | | | | | | | | | | |
|---|---|---|---|---|---|---|---|---|---|---|---|---|---|---|---|---|
| 22 | ADHEr, PFLi, TPI | 10.83 | 0.20 | 26.02 | 0.00 | 16.23 | 0.00 | −20.00 | 0.00 | 27.46 | 9.11 | 0.00 | −1.75 | 0.00 | −0.04 | 0.00 |
| 23 | ADHEr, PFK, PFLi | 10.83 | 0.20 | 26.02 | 0.00 | 16.23 | 0.00 | −20.00 | 0.00 | 27.46 | 9.11 | 0.00 | −1.75 | 0.00 | −0.04 | 0.00 |
| 24 | ADHEr, PFLi, THD2 | 10.49 | 0.49 | 21.02 | 0.00 | 15.71 | 0.00 | −20.00 | 0.00 | 24.49 | 14.16 | 0.00 | −4.23 | 0.00 | −0.09 | 0.00 |
| 25 | ADHEr, GLCpts, PFLi | 10.15 | 0.43 | 23.16 | 0.00 | 15.20 | 0.00 | −20.00 | 0.00 | 26.22 | 12.93 | 0.00 | −3.72 | 0.00 | −0.08 | 0.00 |
| 26 | ADHEr, GLUDy, PFLi | 10.10 | 0.45 | 22.94 | 0.00 | 15.12 | 0.00 | −20.00 | 0.00 | 26.12 | 13.23 | 0.00 | −3.87 | 0.00 | −0.08 | 0.00 |
| 27 | ADHEr, PFLi, RPE | 10.02 | 0.50 | 22.14 | 0.00 | 15.00 | 0.00 | −20.00 | 0.00 | 25.67 | 14.08 | 0.00 | −4.30 | 0.00 | −0.09 | 0.00 |
| 28 | ADHEr, PFLi, TAL | 9.99 | 0.50 | 22.22 | 0.00 | 14.95 | 0.00 | −20.00 | 0.00 | 25.76 | 14.07 | 0.00 | −4.30 | 0.00 | −0.09 | 0.00 |
| 29 | ADHEr, CBMK2, PFLi | 9.96 | 0.49 | 22.36 | 0.00 | 14.92 | 0.00 | −20.00 | 0.00 | 25.87 | 13.99 | 0.00 | −4.27 | 0.00 | −0.09 | 0.00 |
| 30 | ADHEr, ATPS4r, PGI | 8.97 | 0.26 | 23.60 | 0.00 | 0.95 | 24.98 | −20.00 | 0.00 | 50.46 | −3.19 | 0.00 | −2.28 | 0.00 | −0.05 | 0.00 |
| 31 | ADHEr, ATPS4r, NADH6 | 8.62 | 0.48 | 23.04 | 0.00 | 6.28 | 13.23 | −20.00 | 0.00 | 39.68 | 6.46 | 0.00 | −4.15 | 0.00 | −0.08 | 0.00 |
| 32 | ADHEr, ATPS4r, TPI | 8.26 | 0.26 | 27.70 | 0.00 | 3.99 | 16.78 | −20.00 | 0.00 | 46.33 | 0.48 | 0.00 | −2.25 | 0.00 | −0.05 | 0.00 |
| 33 | ADHEr, ATPS4r, FUM | 8.26 | 0.26 | 27.70 | 0.00 | 3.99 | 16.78 | −20.00 | 0.00 | 46.33 | 0.48 | 0.00 | −2.25 | 0.00 | −0.05 | 0.00 |
| 34 | ADHEr, ATPS4r, PFK | 8.26 | 0.26 | 27.70 | 0.00 | 3.99 | 16.78 | −20.00 | 0.00 | 46.33 | 0.48 | 0.00 | −2.25 | 0.00 | −0.05 | 0.00 |
| 35 | ADHEr, ATPS4r, FBA | 7.88 | 0.50 | 23.49 | 0.00 | 2.67 | 18.21 | −20.00 | 0.00 | 45.24 | 3.90 | 0.00 | −4.30 | 0.00 | −0.09 | 0.00 |
| 36 | ADHEr, NADH6, THD2 | 7.86 | 0.49 | 22.44 | 0.00 | 0.04 | 23.43 | −20.00 | 0.00 | 49.33 | 1.11 | 0.00 | −4.22 | 0.00 | −0.09 | 0.00 |
| 37 | ADHEr, ATPS4r, MDH | 7.86 | 0.49 | 22.44 | 0.00 | 0.04 | 23.43 | −20.00 | 0.00 | 49.33 | 1.11 | 0.00 | −4.22 | 0.00 | −0.09 | 0.00 |
| 38 | ADHEr, NADH6, PGI | 7.58 | 0.23 | 28.71 | 0.00 | 0.18 | 22.36 | −20.00 | 0.00 | 52.73 | −3.12 | 0.00 | −2.02 | 0.00 | −0.04 | 0.00 |
| 39 | ADHEr, FUM, THD2 | 7.55 | 0.49 | 22.66 | 0.00 | −1.33 | 25.25 | −20.00 | 0.00 | 51.43 | 0.18 | 0.00 | −4.28 | 0.00 | −0.09 | 0.00 |

TABLE 6-continued

Knockout strategies derived by OptKnock, assuming PEP carboxykinase to be irreversible.

| | | | | | | | | | | | | | | | |
|---|---|---|---|---|---|---|---|---|---|---|---|---|---|---|---|
| 40 | ADHEr, MDH, THD2 | 7.55 | 0.49 | 22.66 | 0.00 | −1.33 | 25.25 | −20.00 | 0.00 | 51.43 | 0.18 | 0.00 | −4.28 | 0.00 | −0.53 | 0.00 | −0.09 | 0.00 |
| 41 | ADHEr, NADH6, PFK | 7.50 | 0.24 | 28.80 | 0.00 | −0.03 | 22.54 | −20.00 | 0.00 | 53.03 | −3.17 | 0.00 | −2.06 | 0.00 | −0.25 | 0.00 | −0.04 | 0.00 |
| 42 | ADHEr, FBA, NADH6 | 7.50 | 0.24 | 28.80 | 0.00 | −0.03 | 22.54 | −20.00 | 0.00 | 53.03 | −3.17 | 0.00 | −2.06 | 0.00 | −0.25 | 0.00 | −0.04 | 0.00 |
| 43 | ADHEr, NADH6, TPI | 7.50 | 0.24 | 28.80 | 0.00 | −0.03 | 22.54 | −20.00 | 0.00 | 53.03 | −3.17 | 0.00 | −2.06 | 0.00 | −0.25 | 0.00 | −0.04 | 0.00 |
| 44 | ADHEr, GLCpts, NADH6 | 7.06 | 0.45 | 25.94 | 0.00 | −0.06 | 21.24 | −20.00 | 0.00 | 50.38 | 1.14 | 0.00 | −3.90 | 0.00 | −0.48 | 0.00 | −0.08 | 0.00 |
| 45 | ADHEr, NADH6, RPE | 7.05 | 0.52 | 24.82 | 0.00 | 0.30 | 20.47 | −20.00 | 0.00 | 48.96 | 2.70 | 0.00 | −4.46 | 0.00 | −0.55 | 0.00 | −0.09 | 0.00 |
| 46 | ADHEr, GLUDy, NADH6 | 7.02 | 0.47 | 25.73 | 0.00 | −0.06 | 21.14 | −20.00 | 0.00 | 50.18 | 1.46 | 0.00 | −4.03 | 0.00 | −0.50 | 0.00 | −0.08 | 0.00 |
| 47 | ADHEr, FUM, NADH6 | 7.01 | 0.47 | 25.63 | 0.00 | −0.06 | 21.10 | −20.00 | 0.00 | 50.09 | 1.61 | 0.00 | −4.10 | 0.00 | −0.51 | 0.00 | −0.08 | 0.00 |
| 48 | ADHEr, MDH, NADH6 | 7.01 | 0.47 | 25.63 | 0.00 | −0.06 | 21.10 | −20.00 | 0.00 | 50.09 | 1.61 | 0.00 | −4.10 | 0.00 | −0.51 | 0.00 | −0.08 | 0.00 |
| 49 | ADHEr, NADH6, TAL | 6.98 | 0.52 | 24.92 | 0.00 | 0.12 | 20.64 | −20.00 | 0.00 | 49.23 | 2.61 | 0.00 | −4.47 | 0.00 | −0.55 | 0.00 | −0.09 | 0.00 |
| 50 | ADHEr, GLCpts, THD2 | 6.56 | 0.49 | 24.86 | 0.00 | −3.91 | 27.44 | −20.00 | 0.00 | 55.80 | −1.43 | 0.00 | −4.27 | 0.00 | −0.53 | 0.00 | −0.09 | 0.00 |
| 51 | ADHEr, GLUDy, THD2 | 6.56 | 0.50 | 24.67 | 0.00 | −3.84 | 27.31 | −20.00 | 0.00 | 55.57 | −1.17 | 0.00 | −4.36 | 0.00 | −0.54 | 0.00 | −0.09 | 0.00 |
| 52 | ADHEr, PGI, SUCD4 | 6.33 | 0.22 | 30.11 | 0.00 | −6.16 | 31.28 | −20.00 | 0.00 | 62.99 | −8.37 | 0.00 | −1.95 | 0.00 | −0.24 | 0.00 | −0.04 | 0.00 |
| 53 | ADHEr, GLCpts, PGI | 6.28 | 0.26 | 29.59 | 0.00 | −6.08 | 30.96 | −20.00 | 0.00 | 62.41 | −7.58 | 0.00 | −2.25 | 0.00 | −0.28 | 0.00 | −0.05 | 0.00 |
| 54 | ADHEr, HEX1, PFK | 6.28 | 0.22 | 30.24 | 0.00 | −6.31 | 31.41 | −20.00 | 0.00 | 63.24 | −8.47 | 0.00 | −1.94 | 0.00 | −0.24 | 0.00 | −0.04 | 0.00 |
| 55 | ADHEr, FBA, HEX1 | 6.28 | 0.22 | 30.24 | 0.00 | −6.31 | 31.41 | −20.00 | 0.00 | 63.24 | −8.47 | 0.00 | −1.94 | 0.00 | −0.24 | 0.00 | −0.04 | 0.00 |
| 56 | ADHEr, HEX1, TPI | 6.28 | 0.22 | 30.24 | 0.00 | −6.31 | 31.41 | −20.00 | 0.00 | 63.24 | −8.47 | 0.00 | −1.94 | 0.00 | −0.24 | 0.00 | −0.04 | 0.00 |

TABLE 6-continued

Knockout strategies derived by OptKnock, assuming PEP carboxykinase to be irreversible.

| | | | | | | | | | | | | | | |
|---|---|---|---|---|---|---|---|---|---|---|---|---|---|---|
| 57 | ADHEr, PFK, SUCD4 | 6.27 | 0.23 | 30.17 | 0.00 | −6.30 | 31.37 | −20.00 | 0.00 | 63.17 | −8.37 | 0.00 | −1.98 | 0.00 | −0.25 | 0.00 | −0.04 | 0.00 |
| 58 | ADHEr, FBA, SUCD4 | 6.27 | 0.23 | 30.17 | 0.00 | −6.30 | 31.37 | −20.00 | 0.00 | 63.17 | −8.37 | 0.00 | −1.98 | 0.00 | −0.25 | 0.00 | −0.04 | 0.00 |
| 59 | ADHEr, SUCD4, TPI | 6.27 | 0.23 | 30.17 | 0.00 | −6.30 | 31.37 | −20.00 | 0.00 | 63.17 | −8.37 | 0.00 | −1.98 | 0.00 | −0.25 | 0.00 | −0.04 | 0.00 |
| 60 | ADHEr, GLUDy, PGI | 6.26 | 0.27 | 29.44 | 0.00 | −6.06 | 30.86 | −20.00 | 0.00 | 62.23 | −7.35 | 0.00 | −2.35 | 0.00 | −0.29 | 0.00 | −0.05 | 0.00 |
| 61 | ADHEr, GLCpts, TPI | 6.21 | 0.26 | 29.69 | 0.00 | −6.24 | 31.07 | −20.00 | 0.00 | 62.64 | −7.61 | 0.00 | −2.29 | 0.00 | −0.28 | 0.00 | −0.05 | 0.00 |
| 62 | ADHEr, GLCpts, PFK | 6.21 | 0.26 | 29.69 | 0.00 | −6.24 | 31.07 | −20.00 | 0.00 | 62.64 | −7.61 | 0.00 | −2.29 | 0.00 | −0.28 | 0.00 | −0.05 | 0.00 |
| 63 | ADHEr, FBA, GLCpts | 6.21 | 0.26 | 29.69 | 0.00 | −6.24 | 31.07 | −20.00 | 0.00 | 62.64 | −7.61 | 0.00 | −2.29 | 0.00 | −0.28 | 0.00 | −0.05 | 0.00 |
| 64 | ADHEr, PFK, RPE | 6.20 | 0.30 | 29.01 | 0.00 | −6.02 | 30.60 | −20.00 | 0.00 | 61.77 | −6.66 | 0.00 | −2.63 | 0.00 | −0.32 | 0.00 | −0.05 | 0.00 |
| 65 | ADHEr, FBA, RPE | 6.20 | 0.30 | 29.01 | 0.00 | −6.02 | 30.60 | −20.00 | 0.00 | 61.77 | −6.66 | 0.00 | −2.63 | 0.00 | −0.32 | 0.00 | −0.05 | 0.00 |
| 66 | ADHEr, RPE, TPI | 6.20 | 0.30 | 29.01 | 0.00 | −6.02 | 30.60 | −20.00 | 0.00 | 61.77 | −6.66 | 0.00 | −2.63 | 0.00 | −0.32 | 0.00 | −0.05 | 0.00 |
| 67 | ADHEr, GLUDy, TPI | 6.19 | 0.27 | 29.54 | 0.00 | −6.23 | 30.98 | −20.00 | 0.00 | 62.47 | −7.38 | 0.00 | −2.38 | 0.00 | −0.29 | 0.00 | −0.05 | 0.00 |
| 68 | ADHEr, FBA, GLUDy | 6.19 | 0.27 | 29.54 | 0.00 | −6.23 | 30.98 | −20.00 | 0.00 | 62.47 | −7.38 | 0.00 | −2.38 | 0.00 | −0.29 | 0.00 | −0.05 | 0.00 |
| 69 | ADHEr, GLUDy, PFK | 6.19 | 0.27 | 29.54 | 0.00 | −6.23 | 30.98 | −20.00 | 0.00 | 62.47 | −7.38 | 0.00 | −2.38 | 0.00 | −0.29 | 0.00 | −0.05 | 0.00 |
| 70 | ADHEr, TAL, TPI | 6.17 | 0.31 | 29.05 | 0.00 | −6.09 | 30.65 | −20.00 | 0.00 | 61.87 | −6.67 | 0.00 | −2.64 | 0.00 | −0.33 | 0.00 | −0.05 | 0.00 |
| 71 | ADHEr, PFK, TAL | 6.17 | 0.31 | 29.05 | 0.00 | −6.09 | 30.65 | −20.00 | 0.00 | 61.87 | −6.67 | 0.00 | −2.64 | 0.00 | −0.33 | 0.00 | −0.05 | 0.00 |
| 72 | ADHEr, FBA, TAL | 6.17 | 0.31 | 29.05 | 0.00 | −6.09 | 30.65 | −20.00 | 0.00 | 61.87 | −6.67 | 0.00 | −2.64 | 0.00 | −0.33 | 0.00 | −0.05 | 0.00 |
| 73 | ADHEr, ATPS4r, GLUDy | 6.17 | 0.55 | 24.36 | 0.00 | −3.40 | 27.23 | −20.00 | 0.00 | 55.50 | 0.48 | 0.00 | −4.75 | −2.00 | −0.59 | 0.00 | −0.10 | 0.00 |
| 74 | ADHEr, PYK, SUCD4 | 6.00 | 0.38 | 28.04 | 0.00 | −6.05 | 30.04 | −20.00 | 0.00 | 60.81 | −5.01 | 0.00 | −3.32 | 0.00 | −0.41 | 0.00 | −0.07 | 0.00 |
| 75 | ADHEr, GLCpts, SUCD4 | 5.97 | 0.40 | 27.84 | 0.00 | −6.03 | 29.92 | −20.00 | 0.00 | 60.59 | −4.70 | 0.00 | −3.45 | 0.00 | −0.43 | 0.00 | −0.07 | 0.00 |

TABLE 6-continued

Knockout strategies derived by OptKnock, assuming PEP carboxykinase to be irreversible.

| # | Knockouts | | | | | | | | | | | | | |
|---|---|---|---|---|---|---|---|---|---|---|---|---|---|---|
| 76 | ADHEr, RPE, SUCD4 | 5.95 | 0.46 | 26.74 | 0.00 | −5.68 | 29.16 | −20.00 | 0.00 | 59.19 | −3.14 | 0.00 | −4.01 | 0.00 | −0.08 | 0.00 |
| 77 | ADHEr, FUM, GLUDy | 5.94 | 0.42 | 27.58 | 0.00 | −6.00 | 29.76 | −20.00 | 0.00 | 60.30 | −4.29 | 0.00 | −3.61 | 0.00 | −0.07 | 0.00 |
| 78 | ADHEr, GLUDy, MDH | 5.94 | 0.42 | 27.58 | 0.00 | −6.00 | 29.76 | −20.00 | 0.00 | 60.30 | −4.29 | 0.00 | −3.61 | 0.00 | −0.07 | 0.00 |
| 79 | ADHEr, GLUDy, SUCD4 | 5.94 | 0.42 | 27.54 | 0.00 | −5.99 | 29.74 | −20.00 | 0.00 | 60.27 | −4.24 | 0.00 | −3.63 | 0.00 | −0.07 | 0.00 |
| 80 | ADHEr, SUCD4, TAL | 5.90 | 0.46 | 26.81 | 0.00 | −5.79 | 29.24 | −20.00 | 0.00 | 59.36 | −3.18 | 0.00 | −4.02 | 0.00 | −0.08 | 0.00 |
| 81 | ADHEr, GLCpts, RPE | 5.89 | 0.51 | 26.14 | 0.00 | −5.59 | 28.78 | −20.00 | 0.00 | 58.51 | −2.22 | 0.00 | −4.37 | 0.00 | −0.09 | 0.00 |
| 82 | ADHEr, GLCpts, GLUDy | 5.87 | 0.46 | 27.02 | 0.00 | −5.93 | 29.42 | −20.00 | 0.00 | 59.69 | −3.42 | 0.00 | −3.96 | 0.00 | −0.08 | 0.00 |
| 83 | ADHEr, GLCpts, MDH | 5.85 | 0.47 | 26.83 | 0.00 | −5.91 | 29.29 | −20.00 | 0.00 | 59.47 | −3.12 | 0.00 | −4.08 | 0.00 | −0.08 | 0.00 |
| 84 | ADHEr, FUM, GLCpts | 5.85 | 0.47 | 26.83 | 0.00 | −5.91 | 29.29 | −20.00 | 0.00 | 59.47 | −3.12 | 0.00 | −4.08 | 0.00 | −0.08 | 0.00 |
| 85 | ADHEr, GLUDy, RPE | 5.87 | 0.52 | 26.00 | 0.00 | −5.57 | 28.69 | −20.00 | 0.00 | 58.35 | −2.00 | 0.00 | −4.46 | 0.00 | −0.09 | 0.00 |
| 86 | ADHEr, GLCpts, TAL | 5.84 | 0.51 | 26.23 | 0.00 | −5.72 | 28.88 | −20.00 | 0.00 | 58.71 | −2.28 | 0.00 | −4.38 | 0.00 | −0.09 | 0.00 |
| 87 | ADHEr, FUM, RPE | 5.84 | 0.54 | 25.70 | 0.00 | −5.53 | 28.50 | −20.00 | 0.00 | 58.02 | −1.54 | 0.00 | −4.64 | 0.00 | −0.09 | 0.00 |
| 88 | ADHEr, MDH, RPE | 5.84 | 0.54 | 25.70 | 0.00 | −5.53 | 28.50 | −20.00 | 0.00 | 58.02 | −1.54 | 0.00 | −4.64 | 0.00 | −0.09 | 0.00 |
| 89 | ADHEr, MDH, PYK | 5.82 | 0.47 | 26.84 | 0.00 | −5.98 | 29.28 | −20.00 | 0.00 | 59.61 | −3.17 | 0.00 | −4.03 | 0.00 | −0.08 | 0.00 |
| 90 | ADHEr, FUM, PYK | 5.82 | 0.47 | 26.84 | 0.00 | −5.98 | 29.28 | −20.00 | 0.00 | 59.61 | −3.17 | 0.00 | −4.03 | 0.00 | −0.08 | 0.09 |
| 91 | ADHEr, MDH, TAL | 5.79 | 0.54 | 25.79 | 0.00 | −5.66 | 28.61 | −20.00 | 0.00 | 58.22 | −1.60 | 0.00 | −4.65 | 0.00 | −0.09 | 0.00 |
| 92 | ADHEr, FUM, TAL | 5.79 | 0.54 | 25.79 | 0.00 | −5.66 | 28.61 | −20.00 | 0.00 | 58.22 | −1.60 | 0.00 | −4.65 | 0.00 | −0.09 | 0.00 |
| 93 | ADHEr, GLUDy, TAL | 5.82 | 0.52 | 26.09 | 0.00 | −5.70 | 28.79 | −20.00 | 0.00 | 58.55 | −2.06 | 0.00 | −4.47 | 0.00 | −0.09 | 0.00 |

TABLE 6-continued

Knockout strategies derived by OptKnock, assuming PEP carboxykinase to be irreversible.

| # | Strategy | | | | | | | | | | | | | | | | | | |
|---|---|---|---|---|---|---|---|---|---|---|---|---|---|---|---|---|---|---|---|
| 94 | ADHEr, CBMK2, GLU5K | 5.68 | 0.57 | 25.51 | 0.00 | −5.76 | 28.48 | −20.00 | 0.00 | 58.02 | −1.05 | 0.00 | −4.90 | 0.00 | −0.61 | 0.00 | −0.10 | 0.00 | 0.00 |
| 95 | ADHEr, CBMK2, G5SD | 5.68 | 0.57 | 25.51 | 0.00 | −5.76 | 28.48 | −20.00 | 0.00 | 58.02 | −1.05 | 0.00 | −4.90 | 0.00 | −0.61 | 0.00 | −0.10 | 0.00 | 0.00 |
| 96 | ADHEr, ASNS2, CBMK2 | 5.68 | 0.57 | 25.51 | 0.00 | −5.76 | 28.48 | −20.00 | 0.00 | 58.02 | −1.05 | 0.00 | −4.90 | 0.00 | −0.61 | 0.00 | −0.10 | 0.00 | 0.00 |
| 97 | ADHEr, CBMK2, SO4t2 | 5.68 | 0.57 | 25.50 | 0.00 | −5.75 | 28.47 | −20.00 | 0.00 | 58.00 | −1.03 | 0.00 | −4.91 | 0.00 | −0.61 | 0.00 | −0.10 | 0.00 | 0.00 |
| 98 | ADHEr, CBMK2, HEX1 | 5.68 | 0.57 | 25.48 | 0.00 | −5.75 | 28.46 | −20.00 | 0.00 | 57.99 | −1.01 | 0.00 | −4.92 | 0.00 | −0.61 | 0.00 | −0.10 | 0.00 | 0.00 |
| 99 | ADHEr, EDA, PFLi, PGI | 14.76 | 0.16 | 16.11 | 0.00 | 22.13 | 0.00 | −20.00 | 0.00 | 17.24 | 10.28 | 0.00 | −1.38 | 0.00 | −0.17 | 0.00 | −0.03 | 0.00 | 0.00 |
| 100 | ADHEr, EDA, NADH6, PGI | 14.39 | 0.13 | 16.96 | 0.00 | 21.96 | 1.24 | −20.00 | 0.00 | 19.11 | 9.91 | 0.00 | −1.11 | −2.00 | −0.14 | 0.00 | −0.02 | 0.00 | 0.00 |
| 101 | ADHEr, FRD2, GLUDy, LDH_D | 12.91 | 0.12 | 12.29 | 0.00 | −0.02 | 38.75 | −20.00 | 0.00 | 51.90 | −10.70 | 0.00 | −1.05 | 0.00 | −0.13 | 0.00 | −0.02 | 0.00 | 0.00 |
| 102 | ADHEr, FRD2, LDH_D, THD2 | 12.89 | 0.13 | 12.25 | 0.00 | −0.02 | 38.70 | −20.00 | 0.00 | 51.85 | −10.60 | 0.00 | −1.09 | 0.00 | −0.13 | 0.00 | −0.02 | 0.00 | 0.00 |
| 103 | ADHEr, ACKr, ACS, PPC | 12.62 | 0.11 | 12.68 | 0.00 | 0.33 | 39.20 | −20.00 | 0.00 | 52.67 | −10.25 | 0.00 | −0.96 | −2.00 | −0.12 | 0.00 | −0.02 | 0.00 | 0.00 |
| 104 | ADHEr, GLUDy, LDH_D, PPC | 12.60 | 0.16 | 11.81 | 0.00 | 0.47 | 38.84 | −20.00 | 0.00 | 51.79 | −9.20 | 0.00 | −1.38 | −2.00 | −0.17 | 0.00 | −0.03 | 0.00 | 0.00 |
| 105 | ADHEr, LDH_D, PPC, THD2 | 12.60 | 0.16 | 11.72 | 0.00 | 0.49 | 38.81 | −20.00 | 0.00 | 51.71 | −9.09 | 0.00 | −1.43 | −2.00 | −0.18 | 0.00 | −0.03 | 0.00 | 0.00 |
| 106 | ADHEr, ATPS4r, EDA, PGI | 11.95 | 0.15 | 19.06 | 0.00 | 8.00 | 19.85 | −20.00 | 0.00 | 39.98 | −1.21 | 0.00 | −1.30 | 0.00 | −0.16 | 0.00 | −0.03 | 0.00 | 0.00 |
| 107 | ADHEr, EDA, GLCpts, PGI | 11.95 | 0.15 | 19.03 | 0.00 | 8.00 | 19.83 | −20.00 | 0.00 | 39.94 | −1.16 | 0.00 | −1.32 | 0.00 | −0.16 | 0.00 | −0.03 | 0.00 | 0.00 |

TABLE 6-continued

Knockout strategies derived by OptKnock, assuming PEP carboxykinase to be irreversible.

| | | | | | | | | | | | | | | | | | | | |
|---|---|---|---|---|---|---|---|---|---|---|---|---|---|---|---|---|---|---|---|
| 108 | ADHEr, EDA, GLUDy, PGI | 11.86 | 0.20 | 18.37 | 0.00 | 8.07 | 19.42 | −20.00 | 0.00 | 39.21 | −0.12 | 0.00 | −1.73 | 0.00 | −0.21 | 0.00 | −0.04 | 0.00 | 0.00 |
| 109 | ADHEr, GLUDy, HEX1, PGI | 11.85 | 0.20 | 18.38 | 0.00 | 8.05 | 19.43 | −20.00 | 0.00 | 39.24 | −0.13 | 0.00 | −1.74 | 0.00 | −0.21 | 0.00 | −0.04 | 0.00 | 0.00 |
| 110 | ADHEr, ATPS4r, FRD2, LDH_D | 11.72 | 0.28 | 7.78 | 0.00 | 9.70 | 25.16 | −20.00 | 0.00 | 37.14 | 5.32 | 0.00 | −4.64 | −5.00 | −0.30 | 0.00 | −0.05 | 0.00 | 2.22 |
| 111 | ADHEr, ACKr, NADH6, PYK | 11.48 | 0.56 | 11.79 | 0.00 | 27.19 | 0.00 | −20.00 | 0.00 | 15.78 | 25.99 | 0.00 | −4.86 | −20.00 | −0.60 | 0.00 | −0.10 | 0.00 | 0.00 |
| 112 | ADHEr, ACKr, LDH_D, NADH6 | 11.02 | 0.64 | 11.37 | 0.00 | 26.49 | 0.00 | −20.00 | 0.00 | 15.94 | 27.24 | 0.00 | −5.56 | −20.00 | −0.69 | 0.00 | −0.11 | 0.00 | 0.00 |
| 113 | ADHEr, GLCpts, PFLi, PGI | 10.95 | 0.17 | 26.34 | 0.00 | 16.41 | 0.00 | −20.00 | 0.00 | 27.55 | 8.60 | 0.00 | −1.48 | 0.00 | −0.18 | 0.00 | −0.03 | 0.00 | 0.00 |
| 114 | ADHEr, GLUDy, PFLi, PGI | 10.93 | 0.18 | 26.24 | 0.00 | 16.38 | 0.00 | −20.00 | 0.00 | 27.51 | 8.73 | 0.00 | −1.55 | 0.00 | −0.19 | 0.00 | −0.03 | 0.00 | 0.00 |
| 115 | ADHEr, FBA, GLCpts, PFLi | 10.91 | 0.17 | 26.39 | 0.00 | 16.36 | 0.00 | −20.00 | 0.00 | 27.62 | 8.62 | 0.00 | −1.50 | 0.00 | −0.19 | 0.00 | −0.03 | 0.00 | 0.00 |
| 116 | ADHEr, GLCpts, PFK, PFLi | 10.91 | 0.17 | 26.39 | 0.00 | 16.36 | 0.00 | −20.00 | 0.00 | 27.62 | 8.62 | 0.00 | −1.50 | 0.00 | −0.19 | 0.00 | −0.03 | 0.00 | 0.00 |
| 117 | ADHEr, GLCpts, TPI | 10.91 | 0.17 | 26.39 | 0.00 | 16.36 | 0.00 | −20.00 | 0.00 | 27.62 | 8.62 | 0.00 | −1.50 | 0.00 | −0.19 | 0.00 | −0.03 | 0.00 | 0.00 |
| 118 | ADHEr, FBA, GLUDy, PFLi | 10.89 | 0.18 | 26.30 | 0.00 | 16.33 | 0.00 | −20.00 | 0.00 | 27.58 | 8.75 | 0.00 | −1.56 | 0.00 | −0.19 | 0.00 | −0.03 | 0.00 | 0.00 |
| 119 | ADHEr, GLUDy, PFK, PFLi | 10.89 | 0.18 | 26.30 | 0.00 | 16.33 | 0.00 | −20.00 | 0.00 | 27.58 | 8.75 | 0.00 | −1.56 | 0.00 | −0.19 | 0.00 | −0.03 | 0.00 | 0.00 |
| 120 | ADHEr, GLUDy, TPI | 10.89 | 0.18 | 26.30 | 0.00 | 16.33 | 0.00 | −20.00 | 0.00 | 27.58 | 8.75 | 0.00 | −1.56 | 0.00 | −0.19 | 0.00 | −0.03 | 0.00 | 0.00 |
| 121 | ADHEr, FBA, PFLi, RPE | 10.86 | 0.20 | 25.97 | 0.00 | 16.28 | 0.00 | −20.00 | 0.00 | 27.40 | 9.09 | 0.00 | −1.74 | 0.00 | −0.21 | 0.00 | −0.04 | 0.00 | 0.00 |
| 122 | ADHEr, PFLi, RPE, TPI | 10.86 | 0.20 | 25.97 | 0.00 | 16.28 | 0.00 | −20.00 | 0.00 | 27.40 | 9.09 | 0.00 | −1.74 | 0.00 | −0.21 | 0.00 | −0.04 | 0.00 | 0.00 |

TABLE 6-continued

Knockout strategies derived by OptKnock, assuming PEP carboxykinase to be irreversible.

| | | | | | | | | | | | | |
|---|---|---|---|---|---|---|---|---|---|---|---|---|
| 123 | ADHEr, PFK, PFLi, RPE | 10.86 | 0.20 | 25.97 | 0.00 | 16.28 | 0.00 | −20.00 | 0.00 | 27.40 | 9.09 | 0.00 | −1.74 | 0.00 | −0.21 | 0.00 | −0.04 | 0.00 |
| 124 | ADHEr, PFK, PFLi, TAL | 10.85 | 0.20 | 26.00 | 0.00 | 16.25 | 0.00 | −20.00 | 0.00 | 27.43 | 9.10 | 0.00 | −1.74 | 0.00 | −0.22 | 0.00 | −0.04 | 0.00 |
| 125 | ADHEr, PFLi, TAL, TPI | 10.85 | 0.20 | 26.00 | 0.00 | 16.25 | 0.00 | −20.00 | 0.00 | 27.43 | 9.10 | 0.00 | −1.74 | 0.00 | −0.22 | 0.00 | −0.04 | 0.00 |
| 126 | ADHEr, FBA, PFLi, TAL | 10.85 | 0.20 | 26.00 | 0.00 | 16.25 | 0.00 | −20.00 | 0.00 | 27.43 | 9.10 | 0.00 | −1.74 | 0.00 | −0.22 | 0.00 | −0.04 | 0.00 |
| 127 | ADHEr, ATPS4r, NADH6, PGI | 10.64 | 0.17 | 23.71 | 0.00 | 8.96 | 13.97 | −20.00 | 0.00 | 38.90 | 1.46 | 0.00 | −1.48 | 0.00 | −0.18 | 0.00 | −0.03 | 0.00 |
| 128 | ADHEr, GLCpts, PFLi, THD2 | 10.62 | 0.42 | 22.05 | 0.00 | 15.90 | 0.00 | −20.00 | 0.00 | 25.05 | 13.01 | 0.00 | −3.65 | 0.00 | −0.45 | 0.00 | −0.07 | 0.00 |
| 129 | ADHEr, GLUDy, PFLi, THD2 | 10.59 | 0.44 | 21.77 | 0.00 | 15.85 | 0.00 | −20.00 | 0.00 | 24.89 | 13.33 | 0.00 | −3.81 | 0.00 | −0.47 | 0.00 | −0.08 | 0.00 |
| 130 | ADHEr, LDH_D, PFLi, SUCD4 | 10.53 | 0.30 | 24.78 | 0.00 | 15.78 | 0.00 | −20.00 | 0.00 | 26.92 | 10.77 | 0.00 | −2.61 | 0.00 | −0.32 | 0.00 | −0.05 | 0.00 |
| 131 | ADHEr, LDH_D, NADH6, PFLi | 10.31 | 0.38 | 23.85 | 0.00 | 15.45 | 0.00 | −20.00 | 0.00 | 26.52 | 12.01 | 0.00 | −3.25 | 0.00 | −0.40 | 0.00 | −0.07 | 0.00 |
| 132 | ADHEr, ATPS4r, LDH_D, SUCD4 | 10.30 | 0.35 | 21.88 | 0.00 | 12.39 | 8.06 | −20.00 | 0.00 | 32.44 | 8.53 | 0.00 | −3.04 | −2.00 | −0.38 | 0.00 | −0.06 | 0.00 |
| 133 | ADHEr, FUM, PFLi, PYK | 10.29 | 0.38 | 23.75 | 0.00 | 15.41 | 0.00 | −20.00 | 0.00 | 26.47 | 12.15 | 0.00 | −3.32 | 0.00 | −0.41 | 0.00 | −0.07 | 0.00 |
| 134 | ADHEr, MDH, PFLi, PYK | 10.29 | 0.38 | 23.75 | 0.00 | 15.41 | 0.00 | −20.00 | 0.00 | 26.47 | 12.15 | 0.00 | −3.32 | 0.00 | −0.41 | 0.00 | −0.07 | 0.00 |
| 135 | ADHEr, GLCpts, GLUDy, PFLi | 10.28 | 0.39 | 23.71 | 0.00 | 15.40 | 0.00 | −20.00 | 0.00 | 26.46 | 12.20 | 0.00 | −3.35 | 0.00 | −0.41 | 0.00 | −0.07 | 0.00 |
| 136 | ADHEr, GLCpts, PFLi, RPE | 10.21 | 0.43 | 23.02 | 0.00 | 15.29 | 0.00 | −20.00 | 0.00 | 26.07 | 12.94 | 0.00 | −3.71 | 0.00 | −0.46 | 0.00 | −0.08 | 0.00 |

TABLE 6-continued

Knockout strategies derived by OptKnock, assuming PEP carboxykinase to be irreversible.

| # | Knockouts | | | | | | | | | | | | | | | | | | |
|---|---|---|---|---|---|---|---|---|---|---|---|---|---|---|---|---|---|---|---|
| 137 | ADHEr, GLCpts, PFLi, TAL | 10.18 | 0.43 | 23.09 | 0.00 | 15.25 | 0.00 | −20.00 | 0.00 | 26.14 | 12.93 | 0.00 | −3.72 | 0.00 | −0.46 | 0.00 | −0.08 | 0.00 | 0.00 |
| 138 | ADHEr, GLUDy, PFLi, RPE | 10.16 | 0.45 | 22.79 | 0.00 | 15.22 | 0.00 | −20.00 | 0.00 | 25.96 | 13.24 | 0.00 | −3.87 | 0.00 | −0.48 | 0.00 | −0.08 | 0.00 | 0.00 |
| 139 | ADHEr, CBMK2, GLCpts, PFLi | 10.16 | 0.43 | 23.21 | 0.00 | 15.22 | 0.00 | −20.00 | 0.00 | 26.24 | 12.87 | 0.00 | −3.69 | 0.00 | −0.46 | 0.00 | −0.07 | 0.00 | 0.00 |
| 140 | ADHEr, LDH_D, MDH, PFLi | 10.15 | 0.43 | 23.14 | 0.00 | 15.19 | 0.00 | −20.00 | 0.00 | 26.21 | 12.95 | 0.00 | −3.73 | 0.00 | −0.46 | 0.00 | −0.08 | 0.00 | 0.00 |
| 141 | ADHEr, FUM, LDH_D, PFLi | 10.15 | 0.43 | 23.14 | 0.00 | 15.19 | 0.00 | −20.00 | 0.00 | 26.21 | 12.95 | 0.00 | −3.73 | 0.00 | −0.46 | 0.00 | −0.08 | 0.00 | 0.00 |
| 142 | ADHEr, GLUDy, PFLi, TAL | 10.13 | 0.45 | 22.86 | 0.00 | 15.17 | 0.00 | −20.00 | 0.00 | 26.04 | 13.23 | 0.00 | −3.87 | 0.00 | −0.48 | 0.00 | −0.08 | 0.00 | 0.00 |
| 143 | ADHEr, CBMK2, GLUDy, PFLi | 10.11 | 0.44 | 22.98 | 0.00 | 15.14 | 0.00 | −20.00 | 0.00 | 26.14 | 13.17 | 0.00 | −3.84 | 0.00 | −0.48 | 0.00 | −0.08 | 0.00 | 0.00 |
| 144 | ADHEr, ASNS2, G5SD, PFLi | 10.04 | 0.49 | 22.20 | 0.00 | 15.02 | 0.00 | −20.00 | 0.00 | 25.69 | 14.01 | 0.00 | −4.26 | 0.00 | −0.53 | 0.00 | −0.09 | 0.00 | 0.00 |
| 145 | ADHEr, CBMK2, PFLi, RPE | 10.00 | 0.49 | 22.28 | 0.00 | 14.97 | 0.00 | −20.00 | 0.00 | 25.78 | 14.00 | 0.00 | −4.26 | 0.00 | −0.53 | 0.00 | −0.09 | 0.00 | 0.00 |
| 146 | ADHEr, CBMK2, PFLi, TAL | 9.96 | 0.49 | 22.35 | 0.00 | 14.91 | 0.00 | −20.00 | 0.00 | 25.87 | 14.01 | 0.00 | −4.28 | 0.00 | −0.53 | 0.00 | −0.09 | 0.00 | 0.00 |
| 147 | ADHEr, ASNS2, GLU5K, PFLi | 9.96 | 0.49 | 22.35 | 0.00 | 14.91 | 0.00 | −20.00 | 0.00 | 25.87 | 14.01 | 0.00 | −4.28 | 0.00 | −0.53 | 0.00 | −0.09 | 0.00 | 0.00 |
| 148 | ADHEr, ATPS4r, GLCpts, MDH | 9.96 | 0.37 | 21.98 | 0.00 | 9.04 | 11.74 | −20.00 | 0.00 | 36.36 | 5.89 | 0.00 | −3.22 | 0.00 | −0.40 | 0.00 | −0.07 | 0.00 | 0.00 |
| 149 | ADHEr, ATPS4r, FUM, GLCpts | 9.96 | 0.37 | 21.98 | 0.00 | 9.04 | 11.74 | −20.00 | 0.00 | 36.36 | 5.89 | 0.00 | −3.22 | 0.00 | −0.40 | 0.00 | −0.07 | 0.00 | 0.00 |
| 150 | ADHEr, ATPS4r, FBA, NADH6 | 9.87 | 0.17 | 27.44 | 0.00 | 11.15 | 7.29 | −20.00 | 0.00 | 35.96 | 4.45 | 0.00 | −1.50 | 0.00 | −0.19 | 0.00 | −0.03 | 0.00 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 151 | ADHEr, ATPS4r, NADH6, TPI | 9.87 | 0.17 | 27.44 | 0.00 | 11.15 | 7.29 | −20.00 | 0.00 | 35.96 | 4.45 | 0.00 | −1.50 | 0.00 | −0.19 | 0.00 | −0.03 | 0.00 |
| 152 | ADHEr, ATPS4r, NADH6, PFK | 9.87 | 0.17 | 27.44 | 0.00 | 11.15 | 7.29 | −20.00 | 0.00 | 35.96 | 4.45 | 0.00 | −1.50 | 0.00 | −0.19 | 0.00 | −0.03 | 0.00 |
| 153 | ADHEr, ATPS4r, FUM, PGL | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 154 | ADHEr, ATPS4r, MDH, PGDH | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 155 | ADHEr, ATPS4r, FUM, G6PDHy | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 156 | ADHEr, ATPS4r, FUM, PGDH | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 157 | ADHEr, ATPS4r, MDH, PGL | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 158 | ADHEr, ATPS4r, G6PDHy, MDH | 9.82 | 0.44 | 23.35 | 0.00 | 13.64 | 2.12 | −20.00 | 0.00 | 28.60 | 11.87 | 0.00 | −3.80 | 0.00 | −0.47 | 0.00 | −0.08 | 0.00 |
| 159 | ADHEr, ATPS4r, LDH_D, PPC | 9.81 | 0.44 | 12.15 | 0.00 | 1.32 | 36.78 | −20.00 | 0.00 | 52.07 | −0.41 | 0.00 | −3.83 | −10.00 | −0.47 | 0.00 | −0.08 | 0.02 |
| 160 | ADHEr, ATPS4r, FUM, TAL | 9.77 | 0.44 | 23.32 | 0.00 | 13.29 | 2.67 | −20.00 | 0.00 | 29.13 | 11.60 | 0.00 | −3.81 | 0.00 | −0.47 | 0.00 | −0.08 | 0.00 |
| 161 | ADHEr, ATPS4r, MDH, TAL | 9.77 | 0.44 | 23.32 | 0.00 | 13.29 | 2.67 | −20.00 | 0.00 | 29.13 | 11.60 | 0.00 | −3.81 | 0.00 | −0.47 | 0.00 | −0.08 | 0.00 |
| 162 | ADHEr, ATPS4r, GLCpts, NADH6 | 9.76 | 0.42 | 22.90 | 0.00 | 13.62 | 4.00 | −20.00 | 0.00 | 29.90 | 11.59 | 0.00 | −3.65 | −2.00 | −0.45 | 0.00 | −0.07 | 0.00 |
| 163 | ADHEr, ATPS4r, MDH, RPE | 9.72 | 0.44 | 23.30 | 0.00 | 12.97 | 3.18 | −20.00 | 0.00 | 29.62 | 11.34 | 0.00 | −3.82 | 0.00 | −0.47 | 0.00 | −0.08 | 0.00 |

TABLE 6-continued

Knockout strategies derived by OptKnock, assuming PEP carboxykinase to be irreversible.

| # | Knockouts | | | | | | | | | | | | | | | | |
|---|---|---|---|---|---|---|---|---|---|---|---|---|---|---|---|---|---|
| 164 | ADHEr, ATPS4r, FUM, RPE | 9.72 | 23.30 | 0.00 | 12.97 | 3.18 | −20.00 | 0.00 | 29.62 | 11.34 | 0.00 | −3.82 | 0.00 | −0.47 | 0.00 | −0.08 | 0.00 |
| 165 | ADHEr, ATPS4r, NADH6, PGDH | 9.39 | 23.42 | 0.00 | 11.71 | 4.69 | −20.00 | 0.00 | 31.40 | 10.80 | 0.00 | −4.00 | 0.00 | −0.50 | 0.00 | −0.08 | 0.00 |
| 166 | ADHEr, ATPS4r, NADH6, PGL | 9.39 | 23.42 | 0.00 | 11.71 | 4.69 | −20.00 | 0.00 | 31.40 | 10.80 | 0.00 | −4.00 | 0.00 | −0.50 | 0.00 | −0.08 | 0.00 |
| 167 | ADHEr, ATPS4r, G6PDHy, NADH6 | 9.39 | 23.42 | 0.00 | 11.71 | 4.69 | −20.00 | 0.00 | 31.40 | 10.80 | 0.00 | −4.00 | 0.00 | −0.50 | 0.00 | −0.08 | 0.00 |
| 168 | ADHEr, ATPS4r, NADH6, TAL | 9.34 | 23.40 | 0.00 | 11.35 | 5.25 | −20.00 | 0.00 | 31.94 | 10.51 | 0.00 | −4.01 | 0.00 | −0.50 | 0.00 | −0.08 | 0.00 |
| 169 | ADHEr, ATPS4r, NADH6, RPE | 9.29 | 23.37 | 0.00 | 11.02 | 5.76 | −20.00 | 0.00 | 32.44 | 10.25 | 0.00 | −4.02 | 0.00 | −0.50 | 0.00 | −0.08 | 0.00 |
| 170 | ADHEr, G6PDHy, ME2, THD2 | 9.08 | 19.50 | 0.00 | 0.35 | 26.49 | −20.00 | 0.00 | 49.05 | −0.86 | 0.00 | −3.72 | 0.00 | −0.46 | 0.00 | −0.08 | 0.00 |
| 171 | ADHEr, ME2, PGL, THD2 | 9.08 | 19.50 | 0.00 | 0.35 | 26.49 | −20.00 | 0.00 | 49.05 | −0.86 | 0.00 | −3.72 | 0.00 | −0.46 | 0.00 | −0.08 | 0.00 |
| 172 | ADHEr, G6PDHy, PPC, THD2 | 8.99 | 0.47 | 0.00 | 6.58 | 33.74 | −20.00 | 0.00 | 45.14 | 6.22 | 8.06 | −4.07 | −20.00 | −0.50 | 0.00 | −0.08 | 0.00 |
| 173 | ADHEr, PGL, PPC, THD2 | 8.99 | 0.47 | 0.00 | 6.58 | 33.74 | −20.00 | 0.00 | 45.14 | 6.22 | 8.06 | −4.07 | −20.00 | −0.50 | 0.00 | −0.08 | 0.00 |
| 174 | ADHEr, ATPS4r, GLUDy, NADH6 | 8.65 | 0.43 | 23.82 | 6.11 | 13.67 | −20.00 | 0.00 | 40.57 | 5.40 | 0.00 | −3.75 | 0.00 | −0.46 | 0.00 | −0.08 | 0.00 |
| 175 | ADHEr, ACKr, FRD2, LDH_D | 8.46 | 0.64 | 8.81 | 9.05 | 20.63 | −20.00 | 0.00 | 37.61 | 15.97 | 0.00 | −6.24 | −15.00 | −0.69 | 2.92 | −0.11 | 0.68 |
| 176 | ADHEr, ATPS4r, FBA, RPE | 8.29 | 0.26 | 27.65 | 3.98 | 16.88 | −20.00 | 0.00 | 46.36 | 0.40 | 0.00 | −2.23 | 0.00 | −0.28 | 0.00 | −0.05 | 0.00 |
| 177 | ADHEr, ATPS4r, RPE, TPI | 8.29 | 0.26 | 27.65 | 3.98 | 16.88 | −20.00 | 0.00 | 46.36 | 0.40 | 0.00 | −2.23 | 0.00 | −0.28 | 0.00 | −0.05 | 0.00 |

TABLE 6-continued

Knockout strategies derived by OptKnock, assuming PEP carboxykinase to be irreversible.

| # | Knockouts | | | | | | | | | | | | | | | | |
|---|---|---|---|---|---|---|---|---|---|---|---|---|---|---|---|---|---|
| 178 | ADHEr, ATPS4r, PFK, RPE | 8.29 | 0.26 | 27.65 | 0.00 | 3.98 | 16.88 | −20.00 | 0.00 | 46.36 | 0.40 | 0.00 | −2.23 | 0.00 | −0.05 | 0.00 | 0.00 |
| 179 | ADHEr, ATPS4r, GLUDy, PFK | 8.28 | 0.23 | 28.10 | 0.00 | 3.79 | 17.22 | −20.00 | 0.00 | 46.98 | −0.22 | 0.00 | −2.02 | 0.00 | −0.04 | 0.00 | 0.00 |
| 180 | ADHEr, ATPS4r, GLUDy, TPI | 8.28 | 0.23 | 28.10 | 0.00 | 3.79 | 17.22 | −20.00 | 0.00 | 46.98 | −0.22 | 0.00 | −2.02 | 0.00 | −0.04 | 0.00 | 0.00 |
| 181 | ADHEr, ATPS4r, FBA, GLUDy | 8.28 | 0.23 | 28.10 | 0.00 | 3.79 | 17.22 | −20.00 | 0.00 | 46.98 | −0.22 | 0.00 | −2.02 | 0.00 | −0.04 | 0.00 | 0.00 |
| 182 | ADHEr, ATPS4r, PFK, TAL | 8.28 | 0.26 | 27.67 | 0.00 | 3.98 | 16.83 | −20.00 | 0.00 | 46.35 | 0.44 | 0.00 | −2.24 | 0.00 | −0.05 | 0.00 | 0.00 |
| 183 | ADHEr, ATPS4r, TAL, TPI | 8.28 | 0.26 | 27.67 | 0.00 | 3.98 | 16.83 | −20.00 | 0.00 | 46.35 | 0.44 | 0.00 | −2.24 | 0.00 | −0.05 | 0.00 | 0.00 |
| 184 | ADHEr, ATPS4r, FBA, TAL | 8.28 | 0.26 | 27.67 | 0.00 | 3.98 | 16.83 | −20.00 | 0.00 | 46.35 | 0.44 | 0.00 | −2.24 | 0.00 | −0.05 | 0.00 | 0.00 |
| 185 | ADHEr, ASPT, MDH, PYK | 8.16 | 0.28 | 23.57 | 0.00 | −4.24 | 32.94 | −20.00 | 0.00 | 58.48 | −7.34 | 0.00 | −2.39 | 0.00 | −0.05 | 0.00 | 0.00 |
| 186 | ADHEr, MDH, PGL, THD2 | 8.00 | 0.71 | 13.36 | 0.00 | 7.12 | 24.68 | −20.00 | 0.00 | 43.08 | 12.12 | 0.00 | −6.14 | −15.00 | −0.12 | 0.00 | 0.00 |
| 187 | ADHEr, G6PDHy, MDH, THD2 | 8.00 | 0.71 | 13.36 | 0.00 | 7.12 | 24.68 | −20.00 | 0.00 | 43.08 | 12.12 | 0.00 | −6.14 | −15.00 | −0.12 | 0.00 | 0.00 |
| 188 | ADHEr, GLCpts, NADH6, THD2 | 7.89 | 0.43 | 24.60 | 0.00 | 2.33 | 18.97 | −20.00 | 0.00 | 46.64 | 2.35 | 0.00 | −3.74 | 0.00 | −0.08 | 0.00 | 0.00 |
| 189 | ADHEr, GLUDy, NADH6, THD2 | 7.89 | 0.45 | 24.31 | 0.00 | 2.42 | 18.77 | −20.00 | 0.00 | 46.27 | 2.75 | 0.00 | −3.88 | 0.00 | −0.08 | 0.00 | 0.00 |
| 190 | ADHEr, ASPT, LDH_D, MDH | 7.71 | 0.45 | 21.65 | 0.00 | −4.12 | 31.31 | −20.00 | 0.00 | 56.15 | −3.60 | 0.00 | −3.89 | 0.00 | −0.08 | 0.00 | 0.00 |

TABLE 6-continued

Knockout strategies derived by OptKnock, assuming PEP carboxykinase to be irreversible.

| | | | | | | | | | | | | | | | | | | |
|---|---|---|---|---|---|---|---|---|---|---|---|---|---|---|---|---|---|---|
| 191 | ADHEr, GLCpts, NADH6, PGI | 7.65 | 0.19 | 29.27 | 0.00 | 0.15 | 22.63 | −20.00 | 0.00 | 53.28 | −3.94 | 0.00 | −1.68 | 0.00 | −0.21 | 0.00 | −0.03 | 0.00 |
| 192 | ADHEr, LDH_D, SUCD4, THD2 | 7.64 | 0.40 | 24.07 | 0.00 | −1.65 | 26.18 | −20.00 | 0.00 | 53.11 | −1.90 | 0.00 | −3.49 | 0.00 | −0.43 | 0.00 | −0.07 | 0.00 |
| 193 | ADHEr, GLUDy, NADH6, PGI | 7.62 | 0.21 | 29.06 | 0.00 | 0.16 | 22.53 | −20.00 | 0.00 | 53.08 | −3.63 | 0.00 | −1.81 | 0.00 | −0.22 | 0.00 | −0.04 | 0.00 |
| 194 | ADHEr, ACKr, FUM, LDH_D | 7.62 | 0.32 | 7.79 | 0.00 | −2.23 | 9.47 | −20.00 | 0.00 | 37.34 | 13.82 | 0.00 | −2.77 | 0.00 | −0.34 | 17.80 | −0.06 | 0.00 |
| 195 | ADHEr, FBA, GLCpts, NADH6 | 7.59 | 0.20 | 29.34 | 0.00 | −0.03 | 22.79 | −20.00 | 0.00 | 53.53 | −3.99 | 0.00 | −1.71 | 0.00 | −0.21 | 0.00 | −0.03 | 0.00 |
| 196 | ADHEr, GLCpts, NADH6, TPI | 7.59 | 0.20 | 29.34 | 0.00 | −0.03 | 22.79 | −20.00 | 0.00 | 53.53 | −3.99 | 0.00 | −1.71 | 0.00 | −0.21 | 0.00 | −0.03 | 0.00 |
| 197 | ADHEr, ACKr, LDH_D, MDH | 7.62 | 0.32 | 7.79 | 0.00 | −2.23 | 9.47 | −20.00 | 0.00 | 37.34 | 13.82 | 0.00 | −2.77 | 0.00 | −0.34 | 17.80 | −0.06 | 0.00 |
| 198 | ADHEr, GLCpts, NADH6, PFK | 7.59 | 0.20 | 29.34 | 0.00 | −0.03 | 22.79 | −20.00 | 0.00 | 53.53 | −3.99 | 0.00 | −1.71 | 0.00 | −0.21 | 0.00 | −0.03 | 0.00 |
| 199 | ADHEr, GLCpts, MDH, THD2 | 7.58 | 0.43 | 23.76 | 0.00 | −1.67 | 26.01 | −20.00 | 0.00 | 52.82 | −1.38 | 0.00 | −3.71 | 0.00 | −0.46 | 0.00 | −0.08 | 0.00 |
| 200 | ADHEr, FUM, GLCpts, THD2 | 7.58 | 0.43 | 23.76 | 0.00 | −1.67 | 26.01 | −20.00 | 0.00 | 52.82 | −1.38 | 0.00 | −3.71 | 0.00 | −0.46 | 0.00 | −0.08 | 0.00 |
| 201 | ADHEr, NADH6, PFK, RPE | 7.57 | 0.23 | 28.73 | 0.00 | 0.14 | 22.39 | −20.00 | 0.00 | 52.79 | −3.13 | 0.00 | −2.03 | 0.00 | −0.25 | 0.00 | −0.04 | 0.00 |
| 202 | ADHEr, FBA, NADH6, RPE | 7.57 | 0.23 | 28.73 | 0.00 | 0.14 | 22.39 | −20.00 | 0.00 | 52.79 | −3.13 | 0.00 | −2.03 | 0.00 | −0.25 | 0.00 | −0.04 | 0.00 |
| 203 | ADHEr, NADH6, RPE, TPI | 7.57 | 0.23 | 28.73 | 0.00 | 0.14 | 22.39 | −20.00 | 0.00 | 52.79 | −3.13 | 0.00 | −2.03 | 0.00 | −0.25 | 0.00 | −0.04 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 204 | ADHEr, GLUDy, NADH6, TPI | 7.56 | 0.21 | 29.14 | 0.00 | −0.03 | 22.70 | −20.00 | 0.00 | 53.35 | −3.69 | 0.00 | −1.84 | 0.00 | −0.23 | 0.00 | −0.04 | 0.00 |
| 205 | ADHEr, GLUDy, NADH6, PFK | 7.56 | 0.21 | 29.14 | 0.00 | −0.03 | 22.70 | −20.00 | 0.00 | 53.35 | −3.69 | 0.00 | −1.84 | 0.00 | −0.23 | 0.00 | −0.04 | 0.00 |
| 206 | ADHEr, FBA, GLUDy, NADH6 | 7.56 | 0.21 | 29.14 | 0.00 | −0.03 | 22.70 | −20.00 | 0.00 | 53.35 | −3.69 | 0.00 | −1.84 | 0.00 | −0.23 | 0.00 | −0.04 | 0.00 |
| 207 | ADHEr, NADH6, PFK, TAL | 7.54 | 0.24 | 28.76 | 0.00 | 0.06 | 22.46 | −20.00 | 0.00 | 52.90 | −3.15 | 0.00 | −2.04 | 0.00 | −0.25 | 0.00 | −0.04 | 0.00 |
| 208 | ADHEr, FBA, NADH6, TAL | 7.54 | 0.24 | 28.76 | 0.00 | 0.06 | 22.46 | −20.00 | 0.00 | 52.90 | −3.15 | 0.00 | −2.04 | 0.00 | −0.25 | 0.00 | −0.04 | 0.00 |
| 209 | ADHEr, NADH6, TAL, TPI | 7.54 | 0.24 | 28.76 | 0.00 | 0.06 | 22.46 | −20.00 | 0.00 | 52.90 | −3.15 | 0.00 | −2.04 | 0.00 | −0.25 | 0.00 | −0.04 | 0.00 |
| 210 | ADHEr, ACKr, AKGD, ATPS4r | 7.24 | 0.58 | 7.55 | 0.00 | 52.00 | 0.00 | −20.00 | 0.00 | 11.65 | 55.34 | 0.00 | −4.99 | −82.37 | −0.62 | 0.00 | −0.10 | 0.00 |
| 211 | ADHEr, GLCpts, NADH6, RPE | 7.17 | 0.45 | 25.76 | 0.00 | 0.26 | 20.93 | −20.00 | 0.00 | 49.87 | 1.30 | 0.00 | −3.88 | 0.00 | −0.48 | 0.00 | −0.08 | 0.00 |
| 212 | ADHEr, FUM, GLCpts, NADH6 | 7.15 | 0.40 | 26.55 | 0.00 | −0.06 | 21.52 | −20.00 | 0.00 | 50.95 | 0.21 | 0.00 | −3.50 | 0.00 | −0.43 | 0.00 | −0.07 | 0.00 |
| 213 | ADHEr, GLCpts, MDH, NADH6 | 7.15 | 0.40 | 26.55 | 0.00 | −0.06 | 21.52 | −20.00 | 0.00 | 50.95 | 0.21 | 0.00 | −3.50 | 0.00 | −0.43 | 0.00 | −0.07 | 0.00 |
| 214 | ADHEr, GLCpts, GLUDy, NADH6 | 7.15 | 0.41 | 26.54 | 0.00 | −0.06 | 21.51 | −20.00 | 0.00 | 50.94 | 0.22 | 0.00 | −3.51 | 0.00 | −0.43 | 0.00 | −0.07 | 0.00 |
| 215 | ADHEr, FUM, NADH6, PYK | 7.15 | 0.41 | 26.54 | 0.00 | −0.06 | 21.51 | −20.00 | 0.00 | 50.94 | 0.23 | 0.00 | −3.51 | 0.00 | −0.43 | 0.00 | −0.07 | 0.00 |
| 216 | ADHEr, MDH, NADH6, PYK | 7.15 | 0.41 | 26.54 | 0.00 | −0.06 | 21.51 | −20.00 | 0.00 | 50.94 | 0.23 | 0.00 | −3.51 | 0.00 | −0.43 | 0.00 | −0.07 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 217 | ADHEr, ACKr, ATPS4r, SUCOAS | 7.14 | 0.58 | 7.46 | 0.00 | 16.55 | 35.80 | −20.00 | 0.00 | 47.39 | 20.07 | 0.00 | −5.03 | −47.55 | 0.00 | −0.10 | 0.00 | 0.00 |
| 218 | ADHEr, GLUDy, NADH6, RPE | 7.14 | 0.46 | 25.54 | 0.00 | 0.27 | 20.82 | −20.00 | 0.00 | 49.66 | 1.63 | 0.00 | −4.01 | 0.00 | −0.50 | −0.08 | 0.00 | 0.00 |
| 219 | ADHEr, MDH, NADH6, RPE | 7.13 | 0.47 | 25.45 | 0.00 | 0.27 | 20.78 | −20.00 | 0.00 | 49.57 | 1.76 | 0.00 | −4.07 | 0.00 | −0.50 | −0.08 | 0.00 | 0.00 |
| 220 | ADHEr, FUM, NADH6, RPE | 7.13 | 0.47 | 25.45 | 0.00 | 0.27 | 20.78 | −20.00 | 0.00 | 49.57 | 1.76 | 0.00 | −4.07 | 0.00 | −0.50 | −0.08 | 0.00 | 0.00 |
| 221 | ADHEr, GLCpts, NADH6, TAL | 7.12 | 0.45 | 25.84 | 0.00 | 0.11 | 21.08 | −20.00 | 0.00 | 50.11 | 1.23 | 0.00 | −3.89 | 0.00 | −0.48 | −0.08 | 0.00 | 0.00 |
| 222 | ADHEr, GLUDy, NADH6, TAL | 7.09 | 0.46 | 25.63 | 0.00 | 0.11 | 20.98 | −20.00 | 0.00 | 49.91 | 1.55 | 0.00 | −4.02 | 0.00 | −0.50 | −0.08 | 0.00 | 0.00 |
| 223 | ADHEr, FUM, NADH6, TAL | 7.07 | 0.47 | 25.53 | 0.00 | 0.11 | 20.93 | −20.00 | 0.00 | 49.82 | 1.69 | 0.00 | −4.08 | 0.00 | −0.51 | −0.08 | 0.00 | 0.00 |
| 224 | ADHEr, MDH, NADH6, TAL | 7.07 | 0.47 | 25.53 | 0.00 | 0.11 | 20.93 | −20.00 | 0.00 | 49.82 | 1.69 | 0.00 | −4.08 | 0.00 | −0.51 | −0.08 | 0.00 | 0.00 |
| 225 | ADHEr, CBMK2, GLU5K, NADH6 | 6.93 | 0.51 | 25.11 | 0.00 | −0.07 | 20.86 | −20.00 | 0.00 | 49.62 | 2.38 | 0.00 | −4.43 | 0.00 | −0.55 | −0.09 | 0.00 | 0.00 |
| 226 | ADHEr, CBMK2, G5SD, NADH6 | 6.93 | 0.51 | 25.11 | 0.00 | −0.07 | 20.86 | −20.00 | 0.00 | 49.62 | 2.38 | 0.00 | −4.43 | 0.00 | −0.55 | −0.09 | 0.00 | 0.00 |
| 227 | ADHEr, CBMK2, NADH6, SO42 | 6.93 | 0.51 | 25.10 | 0.00 | −0.07 | 20.86 | −20.00 | 0.00 | 49.60 | 2.40 | 0.00 | −4.44 | 0.00 | −0.55 | −0.09 | 0.00 | 0.00 |
| 228 | ADHEr, ASNS2, CBMK2, NADH6 | 6.93 | 0.51 | 25.11 | 0.00 | −0.07 | 20.86 | −20.00 | 0.00 | 49.61 | 2.38 | 0.00 | −4.43 | 0.00 | −0.55 | −0.09 | 0.00 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 229 | ADHEr, ATPS4r, PYK, SUCD4 | 6.69 | 0.36 | 19.85 | 0.00 | 7.01 | 7.99 | −20.00 | 0.00 | 38.27 | 6.92 | 7.87 | −3.12 | −2.00 | −0.39 | 0.00 | −0.06 | 0.00 | 0.00 |
| 230 | ADHEr, GLCpts, PGI, SUCD4 | 6.40 | 0.18 | 30.74 | 0.00 | −6.26 | 31.69 | −20.00 | 0.00 | 63.71 | −9.35 | 0.00 | −1.56 | 0.00 | −0.19 | 0.00 | −0.03 | 0.00 | 0.00 |
| 231 | ADHEr, FUM, GLUDy, PGI | 6.38 | 0.19 | 30.56 | 0.00 | −6.23 | 31.57 | −20.00 | 0.00 | 63.51 | −9.07 | 0.00 | −1.67 | 0.00 | −0.21 | 0.00 | −0.03 | 0.00 | 0.00 |
| 232 | ADHEr, GLUDy, MDH, PGI | 6.38 | 0.19 | 30.56 | 0.00 | −6.23 | 31.57 | −20.00 | 0.00 | 63.51 | −9.07 | 0.00 | −1.67 | 0.00 | −0.21 | 0.00 | −0.03 | 0.00 | 0.00 |
| 233 | ADHEr, GLUDy, PGI, SUCD4 | 6.37 | 0.20 | 30.45 | 0.00 | −6.21 | 31.50 | −20.00 | 0.00 | 63.38 | −8.89 | 0.00 | −1.74 | 0.00 | −0.22 | 0.00 | −0.04 | 0.00 | 0.00 |
| 234 | ADHEr, GLCpts, SUCD4, TPI | 6.35 | 0.18 | 30.80 | 0.00 | −6.37 | 31.76 | −20.00 | 0.00 | 63.86 | −9.35 | 0.00 | −1.59 | 0.00 | −0.20 | 0.00 | −0.03 | 0.00 | 0.00 |
| 235 | ADHEr, GLCpts, PFK, SUCD4 | 6.35 | 0.18 | 30.80 | 0.00 | −6.37 | 31.76 | −20.00 | 0.00 | 63.86 | −9.35 | 0.00 | −1.59 | 0.00 | −0.20 | 0.00 | −0.03 | 0.00 | 0.00 |
| 236 | ADHEr, FBA, GLCpts, SUCD4 | 6.35 | 0.18 | 30.80 | 0.00 | −6.37 | 31.76 | −20.00 | 0.00 | 63.86 | −9.35 | 0.00 | −1.59 | 0.00 | −0.20 | 0.00 | −0.03 | 0.00 | 0.00 |
| 237 | ADHEr, HEX1, RPE, TPI | 6.32 | 0.22 | 30.18 | 0.00 | −6.20 | 31.34 | −20.00 | 0.00 | 63.09 | −8.46 | 0.00 | −1.92 | 0.00 | −0.24 | 0.00 | −0.04 | 0.00 | 0.00 |
| 238 | ADHEr, FBA, HEX1, RPE | 6.32 | 0.22 | 30.18 | 0.00 | −6.20 | 31.34 | −20.00 | 0.00 | 63.09 | −8.46 | 0.00 | −1.92 | 0.00 | −0.24 | 0.00 | −0.04 | 0.00 | 0.00 |
| 239 | ADHEr, HEX1, PFK, RPE | 6.32 | 0.22 | 30.18 | 0.00 | −6.20 | 31.34 | −20.00 | 0.00 | 63.09 | −8.46 | 0.00 | −1.92 | 0.00 | −0.24 | 0.00 | −0.04 | 0.00 | 0.00 |
| 240 | ADHEr, FUM, GLUDy, TPI | 6.32 | 0.20 | 30.62 | 0.00 | −6.35 | 31.65 | −20.00 | 0.00 | 63.67 | −9.08 | 0.00 | −1.70 | 0.00 | −0.21 | 0.00 | −0.04 | 0.00 | 0.00 |
| 241 | ADHEr, FBA, GLUDy, MDH | 6.32 | 0.20 | 30.62 | 0.00 | −6.35 | 31.65 | −20.00 | 0.00 | 63.67 | −9.08 | 0.00 | −1.70 | 0.00 | −0.21 | 0.00 | −0.03 | 0.00 | 0.00 |
| 242 | ADHEr, FUM, | 6.32 | 0.20 | 30.62 | 0.00 | −6.35 | 31.65 | −20.00 | 0.00 | 63.67 | −9.08 | 0.00 | −1.70 | 0.00 | −0.21 | 0.00 | −0.03 | 0.00 | 0.00 |

TABLE 6-continued

Knockout strategies derived by OptKnock, assuming PEP carboxykinase to be irreversible.

| # | Knockouts | | | | | | | | | | | | | | | | | |
|---|---|---|---|---|---|---|---|---|---|---|---|---|---|---|---|---|---|---|
| 243 | GLUDy, PFK | 6.32 | 0.20 | 30.62 | 0.00 | -6.35 | 31.65 | -20.00 | 0.00 | 63.67 | -9.08 | 0.00 | -1.70 | 0.00 | -0.21 | 0.00 | -0.03 | 0.00 |
| 244 | ADHEr, GLUDy, MDH, PFK | 6.32 | 0.20 | 30.62 | 0.00 | -6.35 | 31.65 | -20.00 | 0.00 | 63.67 | -9.08 | 0.00 | -1.70 | 0.00 | -0.21 | 0.00 | -0.03 | 0.00 |
| 245 | ADHEr, GLUDy, MDH, TPI | 6.32 | 0.20 | 30.62 | 0.00 | -6.35 | 31.65 | -20.00 | 0.00 | 63.67 | -9.08 | 0.00 | -1.70 | 0.00 | -0.21 | 0.00 | -0.03 | 0.00 |
| 246 | ADHEr, FBA, FUM, GLUDy | 6.32 | 0.23 | 29.99 | 0.00 | -6.14 | 31.21 | -20.00 | 0.00 | 62.85 | -8.19 | 0.00 | -2.02 | 0.00 | -0.25 | 0.00 | -0.04 | 0.00 |
| 247 | ADHEr, GLCpts, GLUDy, PGI | 6.32 | 0.23 | 30.12 | 0.00 | -6.19 | 31.30 | -20.00 | 0.00 | 63.02 | -8.37 | 0.00 | -1.95 | 0.00 | -0.24 | 0.00 | -0.04 | 0.00 |
| 248 | ADHEr, RPE, SUCD4, TPI | 6.32 | 0.23 | 30.12 | 0.00 | -6.19 | 31.30 | -20.00 | 0.00 | 63.02 | -8.37 | 0.00 | -1.95 | 0.00 | -0.24 | 0.00 | -0.04 | 0.00 |
| 249 | ADHEr, FBA, RPE, SUCD4 | 6.32 | 0.23 | 30.12 | 0.00 | -6.19 | 31.30 | -20.00 | 0.00 | 63.02 | -8.37 | 0.00 | -1.95 | 0.00 | -0.24 | 0.00 | -0.04 | 0.00 |
| 250 | ADHEr, PFK, RPE, SUCD4 | 6.31 | 0.20 | 30.55 | 0.00 | -6.34 | 31.60 | -20.00 | 0.00 | 63.59 | -8.96 | 0.00 | -1.75 | 0.00 | -0.22 | 0.00 | -0.04 | 0.00 |
| 251 | ADHEr, GLUDy, HEX1, PFK | 6.31 | 0.20 | 30.55 | 0.00 | -6.34 | 31.60 | -20.00 | 0.00 | 63.59 | -8.96 | 0.00 | -1.75 | 0.00 | -0.22 | 0.00 | -0.04 | 0.00 |
| 252 | ADHEr, GLUDy, HEX1, TPI | 6.31 | 0.20 | 30.55 | 0.00 | -6.34 | 31.60 | -20.00 | 0.00 | 63.59 | -8.96 | 0.00 | -1.75 | 0.00 | -0.22 | 0.00 | -0.04 | 0.00 |
| 253 | ADHEr, FBA, GLUDy, HEX1 | 6.31 | 0.20 | 30.51 | 0.00 | -6.34 | 31.58 | -20.00 | 0.00 | 63.55 | -8.90 | 0.00 | -1.77 | 0.00 | -0.22 | 0.00 | -0.04 | 0.00 |
| 254 | ADHEr, FBA, GLUDy, SUCD4 | 6.31 | 0.20 | 30.51 | 0.00 | -6.34 | 31.58 | -20.00 | 0.00 | 63.55 | -8.90 | 0.00 | -1.77 | 0.00 | -0.22 | 0.00 | -0.04 | 0.00 |
| 255 | ADHEr, GLUDy, PFK, SUCD4 | 6.31 | 0.20 | 30.51 | 0.00 | -6.34 | 31.58 | -20.00 | 0.00 | 63.55 | -8.90 | 0.00 | -1.77 | 0.00 | -0.22 | 0.00 | -0.04 | 0.00 |
| 256 | ADHEr, FBA, | 6.30 | 0.22 | 30.21 | 0.00 | -6.25 | 31.37 | -20.00 | 0.00 | 63.16 | -8.47 | 0.00 | -1.93 | 0.00 | -0.24 | 0.00 | -0.04 | 0.00 |

TABLE 6-continued

Knockout strategies derived by OptKnock, assuming PEP carboxykinase to be irreversible.

| # | Knockouts | | | | | | | | | | | | | | | | | |
|---|---|---|---|---|---|---|---|---|---|---|---|---|---|---|---|---|---|---|
| 257 | ADHEr, HEX1, TAL | 6.30 | 0.22 | 30.21 | 0.00 | -6.25 | 31.37 | -20.00 | 0.00 | 63.16 | -8.47 | 0.00 | -1.93 | 0.00 | -0.24 | 0.00 | -0.04 | 0.00 |
| 258 | ADHEr, HEX1, PFK, TAL | 6.30 | 0.22 | 30.21 | 0.00 | -6.25 | 31.37 | -20.00 | 0.00 | 63.16 | -8.47 | 0.00 | -1.93 | 0.00 | -0.24 | 0.00 | -0.04 | 0.00 |
| 259 | ADHEr, HEX1, TAL, TPI | 6.29 | 0.23 | 30.14 | 0.00 | -6.24 | 31.33 | -20.00 | 0.00 | 63.09 | -8.37 | 0.00 | -1.97 | 0.00 | -0.24 | 0.00 | -0.04 | 0.00 |
| 260 | ADHEr, PFK, SUCD4, TAL | 6.29 | 0.23 | 30.14 | 0.00 | -6.24 | 31.33 | -20.00 | 0.00 | 63.09 | -8.37 | 0.00 | -1.97 | 0.00 | -0.24 | 0.00 | -0.04 | 0.00 |
| 261 | ADHEr, SUCD4, TAL, TPI | 6.29 | 0.23 | 30.14 | 0.00 | -6.24 | 31.33 | -20.00 | 0.00 | 63.09 | -8.37 | 0.00 | -1.97 | 0.00 | -0.24 | 0.00 | -0.04 | 0.00 |
| 262 | ADHEr, FBA, SUCD4, TAL | 6.28 | 0.22 | 6.40 | 0.00 | -6.31 | 7.56 | -20.00 | 0.00 | 39.41 | 15.34 | 0.00 | -1.92 | 0.00 | -0.24 | 23.88 | -0.04 | 0.00 |
| 263 | ADHEr, ACKr, LDH_D, SUCD4 | 6.26 | 0.26 | 29.61 | 0.00 | -6.11 | 30.98 | -20.00 | 0.00 | 62.45 | -7.59 | 0.00 | -2.26 | 0.00 | -0.28 | 0.00 | -0.05 | 0.00 |
| 264 | ADHEr, GLCpts, RPE, TPI | 6.26 | 0.26 | 29.61 | 0.00 | -6.11 | 30.98 | -20.00 | 0.00 | 62.45 | -7.59 | 0.00 | -2.26 | 0.00 | -0.28 | 0.00 | -0.05 | 0.00 |
| 265 | ADHEr, GLCpts, PFK, RPE | 6.26 | 0.26 | 29.61 | 0.00 | -6.11 | 30.98 | -20.00 | 0.00 | 62.45 | -7.59 | 0.00 | -2.26 | 0.00 | -0.28 | 0.00 | -0.05 | 0.00 |
| 266 | ADHEr, FBA, GLCpts, RPE | 6.26 | 0.23 | 0.00 | 0.00 | -6.29 | 1.22 | -20.00 | 0.00 | 32.99 | 21.84 | 0.00 | -2.02 | 0.00 | -0.25 | 30.11 | -0.04 | 0.00 |
| 267 | ADHEr, ACt6, LDH_D, MDH | 6.26 | 0.24 | 30.08 | 0.00 | -6.29 | 31.31 | -20.00 | 0.00 | 63.07 | -8.22 | 0.00 | -2.04 | 0.00 | -0.25 | 0.00 | -0.04 | 0.00 |
| 268 | ADHEr, GLCpts, GLUDy, TPI | 6.26 | 0.23 | 0.00 | 0.00 | -6.29 | 1.22 | -20.00 | 0.00 | 32.99 | 21.84 | 0.00 | -2.02 | 0.00 | -0.25 | 30.11 | -0.04 | 0.00 |
| 269 | ADHEr, ACt6, FUM, LDH_D | 6.26 | 0.24 | 30.08 | 0.00 | -6.29 | 31.31 | -20.00 | 0.00 | 63.07 | -8.22 | 0.00 | -2.04 | 0.00 | -0.25 | 0.00 | -0.04 | 0.00 |
| 270 | ADHEr, FBA, GLCpts, GLUDy | 6.26 | 0.24 | 30.08 | 0.00 | -6.29 | 31.31 | -20.00 | 0.00 | 63.07 | -8.22 | 0.00 | -2.04 | 0.00 | -0.25 | 0.00 | -0.04 | 0.00 |

TABLE 6-continued

Knockout strategies derived by OptKnock, assuming PEP carboxykinase to be irreversible.

| | | | | | | | | | | | |
|---|---|---|---|---|---|---|---|---|---|---|---|
| 271 | ADHEr, GLUDy, PFK | 6.25 | 0.27 | 29.46 | 0.00 | −6.09 | 30.88 | −20.00 | 0.00 | 62.28 | −7.35 | 0.00 | −2.35 | 0.00 | −0.29 | 0.00 | −0.05 | 0.00 |
| 272 | ADHEr, GLUDy, RPE, TPI | 6.25 | 0.27 | 29.46 | 0.00 | −6.09 | 30.88 | −20.00 | 0.00 | 62.28 | −7.35 | 0.00 | −2.35 | 0.00 | −0.29 | 0.00 | −0.05 | 0.00 |
| 273 | ADHEr, FBA, GLUDy, RPE | 6.25 | 0.27 | 29.46 | 0.00 | −6.09 | 30.88 | −20.00 | 0.00 | 62.28 | −7.35 | 0.00 | −2.35 | 0.00 | −0.29 | 0.00 | −0.05 | 0.00 |
| 274 | ADHEr, GLUDy, PFK, RPE | 6.24 | 0.26 | 29.65 | 0.00 | −6.17 | 31.02 | −20.00 | 0.00 | 62.54 | −7.60 | 0.00 | −2.27 | 0.00 | −0.28 | 0.00 | −0.05 | 0.00 |
| 275 | ADHEr, GLCpts, TAL, TPI | 6.24 | 0.26 | 29.65 | 0.00 | −6.17 | 31.02 | −20.00 | 0.00 | 62.54 | −7.60 | 0.00 | −2.27 | 0.00 | −0.28 | 0.00 | −0.05 | 0.00 |
| 276 | ADHEr, FBA, GLCpts, TAL | 6.24 | 0.26 | 29.65 | 0.00 | −6.17 | 31.02 | −20.00 | 0.00 | 62.54 | −7.60 | 0.00 | −2.27 | 0.00 | −0.28 | 0.00 | −0.05 | 0.00 |
| 277 | ADHEr, GLCpts, PFK, TAL | 6.22 | 0.27 | 29.50 | 0.00 | −6.15 | 30.93 | −20.00 | 0.00 | 62.37 | −7.36 | 0.00 | −2.36 | 0.00 | −0.29 | 0.00 | −0.05 | 0.00 |
| 278 | ADHEr, GLUDy, PFK, TAL | 6.22 | 0.27 | 29.50 | 0.00 | −6.15 | 30.93 | −20.00 | 0.00 | 62.37 | −7.36 | 0.00 | −2.36 | 0.00 | −0.29 | 0.00 | −0.05 | 0.00 |
| 279 | ADHEr, FBA, GLUDy, TAL | 6.22 | 0.27 | 29.50 | 0.00 | −6.15 | 30.93 | −20.00 | 0.00 | 62.37 | −7.36 | 0.00 | −2.36 | 0.00 | −0.29 | 0.00 | −0.05 | 0.00 |
| 280 | ADHEr, GLUDy, TAL, TPI | 6.09 | 0.33 | 28.74 | 0.00 | −6.13 | 30.48 | −20.00 | 0.00 | 61.59 | −6.12 | 0.00 | −2.88 | 0.00 | −0.36 | 0.00 | −0.06 | 0.00 |
| 281 | ADHEr, FUM, GLUDy, MDH, PYK | 6.09 | 0.33 | 28.74 | 0.00 | −6.13 | 30.48 | −20.00 | 0.00 | 61.59 | −6.12 | 0.00 | −2.88 | 0.00 | −0.36 | 0.00 | −0.06 | 0.00 |
| 282 | ADHEr, PYK, RPE, SUCD4 | 6.08 | 0.38 | 27.93 | 0.00 | −5.86 | 29.92 | −20.00 | 0.00 | 60.54 | −4.99 | 0.00 | −3.28 | 0.00 | −0.41 | 0.00 | −0.07 | 0.00 |
| 283 | ADHEr, GLUDy, PYK, SUCD4 | 6.08 | 0.34 | 28.65 | 0.00 | −6.12 | 30.43 | −20.00 | 0.00 | 61.49 | −5.98 | 0.00 | −2.94 | 0.00 | −0.36 | 0.00 | −0.06 | 0.00 |
| 284 | ADHEr, MDH, PYK, SUCD4 | 6.06 | 0.35 | 28.51 | 0.00 | −6.10 | 30.34 | −20.00 | 0.00 | 61.33 | −5.76 | 0.00 | −3.02 | 0.00 | −0.37 | 0.00 | −0.06 | 0.00 |

TABLE 6-continued

Knockout strategies derived by OptKnock, assuming PEP carboxykinase to be irreversible.

| | | | | | | | | | | | | | | |
|---|---|---|---|---|---|---|---|---|---|---|---|---|---|---|
| 285 | ADHEr, FUM, PYK, SUCD4 | 6.06 | 0.35 | 28.51 | 0.00 | −6.10 | 30.34 | −20.00 | 0.00 | 61.33 | −5.76 | 0.00 | 0.00 | −0.37 | 0.00 | −0.06 | 0.00 |
| 286 | ADHEr, GLCpts, RPE, SUCD4 | 6.06 | 0.40 | 27.70 | 0.00 | −5.83 | 29.77 | −20.00 | 0.00 | 60.29 | −4.64 | 0.00 | −3.02 | −0.42 | 0.00 | −0.07 | 0.00 |
| 287 | ADHEr, GLCpts, GLUDy, MDH | 6.05 | 0.35 | 28.44 | 0.00 | −6.10 | 30.30 | −20.00 | 0.00 | 61.26 | −5.65 | 0.00 | −3.42 | −0.38 | 0.00 | −0.06 | 0.00 |
| 288 | ADHEr, FUM, GLCpts, GLUDy | 6.05 | 0.35 | 28.44 | 0.00 | −6.10 | 30.30 | −20.00 | 0.00 | 61.26 | −5.65 | 0.00 | −3.07 | −0.38 | 0.00 | −0.06 | 0.00 |
| 289 | ADHEr, GLCpts, GLUDy, SUCD4 | 6.04 | 0.36 | 28.39 | 0.00 | −6.09 | 30.27 | −20.00 | 0.00 | 61.21 | −5.58 | 0.00 | −3.07 | −0.38 | 0.00 | −0.06 | 0.00 |
| 290 | ADHEr, PYK, SUCD4, TAL | 6.04 | 0.38 | 27.98 | 0.00 | −5.95 | 29.98 | −20.00 | 0.00 | 60.67 | −5.00 | 0.00 | −3.10 | −0.41 | 0.00 | −0.07 | 0.00 |
| 291 | ADHEr, GLUDy, MDH, RPE | 6.03 | 0.41 | 27.44 | 0.00 | −5.79 | 29.60 | −20.00 | 0.00 | 59.98 | −4.23 | 0.00 | −3.30 | −0.44 | 0.00 | −0.07 | 0.00 |
| 292 | ADHEr, FUM, GLUDy, RPE | 6.03 | 0.41 | 27.44 | 0.00 | −5.79 | 29.60 | −20.00 | 0.00 | 59.98 | −4.23 | 0.00 | −3.58 | −0.44 | 0.00 | −0.07 | 0.00 |
| 293 | ADHEr, GLUDy, RPE, SUCD4 | 6.02 | 0.42 | 27.40 | 0.00 | −5.78 | 29.58 | −20.00 | 0.00 | 59.94 | −4.17 | 0.00 | −3.58 | −0.45 | 0.00 | −0.07 | 0.00 |
| 294 | ADHEr, GLCpts, SUCD4, TAL | 6.02 | 0.40 | 27.77 | 0.00 | −5.92 | 29.84 | −20.00 | 0.00 | 60.43 | −4.67 | 0.00 | −3.60 | −0.42 | 0.00 | −0.07 | 0.00 |
| 295 | ADHEr, GLUDy, MDH, TAL | 5.99 | 0.42 | 27.50 | 0.00 | −5.89 | 29.68 | −20.00 | 0.00 | 60.14 | −4.26 | 0.00 | −3.43 | −0.44 | 0.00 | −0.07 | 0.00 |
| 296 | ADHEr, FUM, GLUDy, TAL | 5.99 | 0.42 | 27.50 | 0.00 | −5.89 | 29.68 | −20.00 | 0.00 | 60.14 | −4.26 | 0.00 | −3.60 | −0.44 | 0.00 | −0.07 | 0.00 |
| 297 | ADHEr, GLUDy, SUCD4, TAL | 5.98 | 0.42 | 27.47 | 0.00 | −5.88 | 29.66 | −20.00 | 0.00 | 60.10 | −4.21 | 0.00 | −3.62 | −0.45 | 0.00 | −0.07 | 0.00 |

TABLE 6-continued

Knockout strategies derived by OptKnock, assuming PEP carboxykinase to be irreversible.

| | | | | | | | | | | | | |
|---|---|---|---|---|---|---|---|---|---|---|---|---|
| 298 | ADHEr, GLCpts, GLUDy, RPE | 5.96 | 0.46 | 26.84 | 0.00 | −5.70 | 29.23 | −20.00 | 0.00 | 59.31 | −3.31 | 0.00 | −3.94 | 0.00 | −0.49 | 0.00 | −0.08 | 0.00 |
| 299 | ADHEr, FUM, GLCpts, RPE | 5.94 | 0.47 | 26.66 | 0.00 | −5.67 | 29.11 | −20.00 | 0.00 | 59.10 | −3.02 | 0.00 | −4.06 | 0.00 | −0.50 | 0.00 | −0.08 | 0.00 |
| 300 | ADHEr, GLCpts, MDH, RPE | 5.94 | 0.47 | 26.66 | 0.00 | −5.67 | 29.11 | −20.00 | 0.00 | 59.10 | −3.02 | 0.00 | −4.06 | 0.00 | −0.50 | 0.00 | −0.08 | 0.00 |
| 301 | ADHEr, FUM, LDH_D, SUCD4 | 5.92 | 0.43 | 27.41 | 0.00 | −5.98 | 29.66 | −20.00 | 0.00 | 60.12 | −4.04 | 0.00 | −3.71 | 0.00 | −0.46 | 0.00 | −0.08 | 0.00 |
| 302 | ADHEr, LDH_D, MDH, SUCD4 | 5.92 | 0.43 | 27.41 | 0.00 | −5.98 | 29.66 | −20.00 | 0.00 | 60.12 | −4.04 | 0.00 | −3.71 | 0.00 | −0.46 | 0.00 | −0.08 | 0.00 |
| 303 | ADHEr, GLCpts, GLUDy, TAL | 5.92 | 0.46 | 26.93 | 0.00 | −5.81 | 29.32 | −20.00 | 0.00 | 59.49 | −3.36 | 0.00 | −3.95 | 0.00 | −0.49 | 0.00 | −0.08 | 0.00 |
| 304 | ADHEr, FUM, GLCpts, TAL | 5.90 | 0.47 | 26.74 | 0.00 | −5.78 | 29.20 | −20.00 | 0.00 | 59.28 | −3.07 | 0.00 | −4.07 | 0.00 | −0.50 | 0.00 | −0.08 | 0.00 |
| 305 | ADHEr, GLCpts, MDH, TAL | 5.90 | 0.47 | 26.74 | 0.00 | −5.78 | 29.20 | −20.00 | 0.00 | 59.28 | −3.07 | 0.00 | −4.07 | 0.00 | −0.50 | 0.00 | −0.08 | 0.00 |
| 306 | ADHEr, CBMK2, GLU5K, SUCD4 | 5.86 | 0.46 | 26.97 | 0.00 | −5.93 | 29.38 | −20.00 | 0.00 | 59.63 | −3.34 | 0.00 | −3.99 | 0.00 | −0.49 | 0.00 | −0.08 | 0.00 |
| 307 | ADHEr, CBMK2, G5SD, SUCD4 | 5.86 | 0.46 | 26.97 | 0.00 | −5.93 | 29.38 | −20.00 | 0.00 | 59.63 | −3.34 | 0.00 | −3.99 | 0.00 | −0.49 | 0.00 | −0.08 | 0.00 |
| 308 | ADHEr, CBMK2, GLU5K, RPE | 5.79 | 0.56 | 25.29 | 0.00 | −5.47 | 28.25 | −20.00 | 0.00 | 57.55 | −0.91 | 0.00 | −4.89 | 0.00 | −0.60 | 0.00 | −0.10 | 0.00 |
| 309 | ADHEr, CBMK2, G5SD, RPE | 5.79 | 0.56 | 25.29 | 0.00 | −5.47 | 28.25 | −20.00 | 0.00 | 57.55 | −0.91 | 0.00 | −4.89 | 0.00 | −0.60 | 0.00 | −0.10 | 0.00 |
| 310 | ADHEr, CBMK2, GLCpts, GLU5K | 5.79 | 0.50 | 26.42 | 0.00 | −5.86 | 29.04 | −20.00 | 0.00 | 59.02 | −2.47 | 0.00 | −4.34 | 0.00 | −0.54 | 0.00 | −0.09 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 311 | ADHEr, ASNS2, CBMK2, RPE | 5.79 | 0.56 | 25.29 | 0.00 | −5.47 | 28.25 | −20.00 | 0.00 | 57.55 | −0.91 | 0.00 | 0.00 | −0.60 | 0.00 | 0.00 | 0.00 |
| 312 | ADHEr, CBMK2, G5SD, GLCpts | 5.79 | 0.50 | 26.42 | 0.00 | −5.86 | 29.04 | −20.00 | 0.00 | 59.02 | −2.47 | 0.00 | −4.89 | −0.54 | 0.00 | −0.09 | 0.00 |
| 313 | ADHEr, ASNS2, CBMK2, GLCpts | 5.79 | 0.50 | 26.42 | 0.00 | −5.86 | 29.04 | −20.00 | 0.00 | 59.02 | −2.47 | 0.00 | −4.34 | −0.54 | 0.00 | −0.09 | 0.00 |
| 314 | ADHEr, ASNS2, CBMK2, GLU5K, TAL | 5.74 | 0.57 | 25.40 | 0.00 | −5.60 | 28.36 | −20.00 | 0.00 | 57.77 | −0.98 | 0.00 | −4.34 | −0.61 | 0.00 | −0.10 | 0.00 |
| 315 | ADHEr, CBMK2, G5SD, TAL | 5.74 | 0.57 | 25.40 | 0.00 | −5.60 | 28.36 | −20.00 | 0.00 | 57.77 | −0.98 | 0.00 | −4.89 | −0.61 | 0.00 | −0.10 | 0.00 |
| 316 | ADHEr, ASNS2, CBMK2, TAL | 5.74 | 0.57 | 25.40 | 0.00 | −5.60 | 28.36 | −20.00 | 0.00 | 57.77 | −0.98 | 0.00 | −4.90 | −0.61 | 0.00 | −0.10 | 0.00 |
| 317 | ADHEr, CBMK2, GLU5K, MDH | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |
| 318 | ADHEr, CBMK2, FUM, G5SD | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |
| 319 | ADHEr, CBMK2, G5SD, MDH | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |
| 320 | ADHEr, CBMK2, FUM, GLU5K | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |
| 321 | ADHEr, ASNS2, CBMK2, MDH | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |
| 322 | ADHEr, ASNS2, CBMK2, FUM | 5.74 | 0.53 | 25.99 | 0.00 | −5.81 | 28.77 | −20.00 | 0.00 | 58.54 | −1.80 | 0.00 | −4.61 | −0.57 | 0.00 | −0.09 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 323 | ADHEr, ASNS2, GLU5K, SO4t2 | 5.68 | 0.57 | 25.48 | 0.00 | −5.75 | 28.46 | −20.00 | 0.00 | 57.99 | −1.01 | 0.00 | −4.92 | 0.00 | −0.61 | 0.00 | −0.10 | 0.00 | 0.00 |
| 324 | ADHEr, ASPT, LDH_D, MDH, PFLi | 14.96 | 0.23 | 14.07 | 0.00 | 22.42 | 0.00 | −20.00 | 0.00 | 15.71 | 11.71 | 0.00 | −2.00 | 0.00 | −0.25 | 0.00 | −0.04 | 0.00 | 0.00 |
| 325 | ADHEr, EDA, GLUDy, PFLi, PGI | 14.81 | 0.14 | 16.32 | 0.00 | 22.21 | 0.00 | −20.00 | 0.00 | 17.33 | 10.00 | 0.00 | −1.23 | 0.00 | −0.15 | 0.00 | −0.02 | 0.00 | 0.00 |
| 326 | ADHEr, ATPS4r, G6PDHy, GLCpts, MDH | 14.63 | 0.18 | 15.95 | 0.00 | 21.94 | 0.00 | −20.00 | 0.00 | 17.25 | 10.67 | 0.00 | −1.59 | 0.00 | −0.20 | 0.00 | −0.03 | 0.00 | 0.00 |
| 327 | ADHEr, ATPS4r, GLCpts, MDH, PGL | 14.63 | 0.18 | 15.95 | 0.00 | 21.94 | 0.00 | −20.00 | 0.00 | 17.25 | 10.67 | 0.00 | −1.59 | 0.00 | −0.20 | 0.00 | −0.03 | 0.00 | 0.00 |
| 328 | ADHEr, EDA, GLUDy, NADH6, PGI | 14.42 | 0.11 | 17.14 | 0.00 | 21.96 | 1.32 | −20.00 | 0.00 | 19.28 | 9.64 | 0.00 | −0.99 | −2.00 | −0.12 | 0.00 | −0.02 | 0.00 | 0.00 |
| 329 | ADHEr, G6PDHy, LDH_D, PPC, THD2 | 13.73 | 0.10 | 9.55 | 0.00 | 1.40 | 40.38 | −20.00 | 0.00 | 50.65 | −10.49 | 0.00 | −0.87 | −2.00 | −0.11 | 0.00 | −0.02 | 0.00 | 0.00 |
| 330 | ADHEr, LDH_D, PGL, PPC, THD2 | 13.73 | 0.10 | 9.55 | 0.00 | 1.40 | 40.38 | −20.00 | 0.00 | 50.65 | −10.49 | 0.00 | −0.87 | −2.00 | −0.11 | 0.00 | −0.02 | 0.00 | 0.00 |
| 331 | ADHEr, ATPS4r, FRD2, LDH_D, NADH6 | 13.37 | 0.17 | 4.27 | 6.42 | 13.23 | 18.61 | −20.00 | 0.00 | 30.48 | 9.33 | 0.00 | −7.86 | −5.00 | −0.18 | 0.00 | −0.03 | 0.00 | 0.00 |
| 332 | ADHEr, EDA, LDH_D, PPC, THD2 | 13.09 | 0.16 | 10.61 | 0.00 | 1.33 | 38.58 | −20.00 | 0.00 | 50.31 | −8.88 | 0.00 | −1.36 | −2.00 | −0.17 | 0.00 | −0.03 | 0.00 | 0.00 |

TABLE 6-continued

Knockout strategies derived by OptKnock, assuming PEP carboxykinase to be irreversible.

| | | | | | | | | | | | | | |
|---|---|---|---|---|---|---|---|---|---|---|---|---|---|
| 333 | ADHEr, FRD2, GLUDy, LDH_D, RPE | 12.96 | 0.12 | 12.19 | 0.00 | 0.07 | 38.74 | −20.00 | 0.00 | 51.78 | −10.71 | 0.00 | −1.03 | 0.00 | −0.13 | 0.00 | −0.02 | 0.00 |
| 334 | ADHEr, FRD2, LDH_D, RPE, THD2 | 12.95 | 0.12 | 12.13 | 0.00 | 0.07 | 38.68 | −20.00 | 0.00 | 51.70 | −10.58 | 0.00 | −1.08 | 0.00 | −0.13 | 0.00 | −0.02 | 0.00 |
| 335 | ADHEr, FRD2, LDH_D, THD2 | 12.94 | 0.11 | 12.36 | 0.00 | −0.02 | 38.83 | −20.00 | 0.00 | 52.00 | −10.88 | 0.00 | −0.98 | 0.00 | −0.12 | 0.00 | −0.02 | 0.00 |
| 336 | ADHEr, FRD2, GLUDy, LDH_D, TAL | 12.94 | 0.12 | 12.24 | 0.00 | 0.03 | 38.74 | −20.00 | 0.00 | 51.84 | −10.71 | 0.00 | −1.04 | 0.00 | −0.13 | 0.00 | −0.02 | 0.00 |
| 337 | ADHEr, FRD2, LDH_D, TAL, THD2 | 12.92 | 0.13 | 12.19 | 0.00 | 0.03 | 38.69 | −20.00 | 0.00 | 51.77 | −10.59 | 0.00 | −1.09 | 0.00 | −0.13 | 0.00 | −0.02 | 0.00 |
| 338 | ADHEr, ATPS4r, LDH_D, NADH6, PPC | 12.83 | 0.28 | 9.13 | 0.00 | 9.66 | 29.15 | −20.00 | 0.00 | 40.26 | 1.95 | −10.00 | −2.42 | 0.00 | −0.30 | 0.00 | −0.05 | 0.00 |
| 339 | ADHEr, ASPT, FUM, GLUDy, LDH_D | 12.77 | 0.13 | 12.57 | 0.00 | −0.13 | 38.55 | −20.00 | 0.00 | 52.04 | −10.53 | 0.00 | −1.12 | 0.00 | −0.14 | 0.00 | −0.02 | 0.00 |
| 340 | ADHEr, ASPT, FUM, LDH_D, THD2 | 12.75 | 0.13 | 12.54 | 0.00 | −0.14 | 38.50 | −20.00 | 0.00 | 51.99 | −10.42 | 0.00 | −1.16 | 0.00 | −0.14 | 0.00 | −0.02 | 0.00 |
| 341 | ADHEr, ME2, PFLi, PGL, THD2 | 12.69 | 0.38 | 17.31 | 0.00 | 19.01 | 0.00 | −20.00 | 0.00 | 19.99 | 13.21 | 0.00 | −3.25 | 0.00 | −0.40 | 0.00 | −0.07 | 0.00 |
| 342 | ADHEr, G6PDHy, ME2, PFLi, THD2 | 12.69 | 0.38 | 17.31 | 0.00 | 19.01 | 0.00 | −20.00 | 0.00 | 19.99 | 13.21 | 0.00 | −3.25 | 0.00 | −0.40 | 0.00 | −0.07 | 0.00 |
| 343 | ADHEr, ACKr, | 12.67 | 0.10 | 12.72 | 0.00 | 0.38 | 39.23 | −20.00 | 0.00 | 52.69 | −10.40 | −2.00 | −0.89 | 0.00 | −0.11 | 0.00 | −0.02 | 0.00 |

TABLE 6-continued

Knockout strategies derived by OptKnock, assuming PEP carboxykinase to be irreversible.

| | | | | | | | | | | | | |
|---|---|---|---|---|---|---|---|---|---|---|---|---|
| 344 | ACS, PPC, RPE | 12.67 | 0.16 | 11.69 | 0.00 | 0.58 | 38.82 | −20.00 | 0.00 | 51.63 | −9.20 | 0.00 | −1.37 | −2.00 | −0.17 | 0.00 | −0.03 | 0.00 |
| 345 | ADHEr, GLUDy, LDH_D, PPC, RPE | 12.67 | 0.16 | 11.57 | 0.00 | 0.60 | 38.78 | −20.00 | 0.00 | 51.52 | −9.06 | 0.00 | −1.42 | −2.00 | −0.18 | 0.00 | −0.03 | 0.00 |
| 346 | ADHEr, LDH_D, PPC, RPE, THD2 | 12.64 | 0.16 | 11.75 | 0.00 | 0.53 | 38.83 | −20.00 | 0.00 | 51.71 | −9.20 | 0.00 | −1.37 | −2.00 | −0.17 | 0.00 | −0.03 | 0.00 |
| 347 | ADHEr, GLUDy, LDH_D, PPC, TAL | 12.63 | 0.16 | 11.65 | 0.00 | 0.55 | 38.79 | −20.00 | 0.00 | 51.61 | −9.08 | 0.00 | −1.42 | −2.00 | −0.18 | 0.00 | −0.03 | 0.00 |
| 348 | ADHEr, LDH_D, PPC, TAL, THD2 | 12.62 | 0.10 | 12.80 | 0.00 | 0.31 | 39.24 | −20.00 | 0.00 | 52.79 | −10.40 | 0.00 | −0.91 | −2.00 | −0.11 | 0.00 | −0.02 | 0.00 |
| 349 | ADHEr, GLCpts, GLUDy, LDH_D, PPC | 12.62 | 0.11 | 12.74 | 0.00 | 0.32 | 39.22 | −20.00 | 0.00 | 52.73 | −10.32 | 0.00 | −0.93 | −2.00 | −0.12 | 0.00 | −0.02 | 0.00 |
| 350 | ADHEr, GLCpts, LDH_D, PPC, THD2 | 12.38 | 0.13 | 12.45 | 0.00 | 9.92 | 10.79 | −20.00 | 0.00 | 30.65 | 6.43 | 0.00 | −1.13 | 0.00 | −0.14 | 6.48 | −0.02 | 0.00 |
| 351 | ADHEr, ACKr, GLUDy, LDH_D, PGI | 12.20 | 0.20 | 10.35 | 0.00 | 18.28 | 0.00 | −20.00 | 0.00 | 19.76 | 9.70 | 8.01 | −1.71 | 0.00 | −0.21 | 0.00 | −0.03 | 0.00 |
| 352 | ADHEr, ASPT, ATPS4r, GLCpts, MDH | 12.11 | 0.25 | 21.60 | 0.00 | 18.15 | 0.00 | −20.00 | 0.00 | 23.35 | 10.54 | 0.00 | −2.12 | 0.00 | −0.26 | 0.00 | −0.04 | 0.00 |
| 353 | ADHEr, LDH_D, PFLi, SUCD4, THD2 | 12.05 | 0.24 | 12.18 | 0.00 | 12.02 | 25.48 | −20.00 | 0.00 | 39.36 | 4.35 | 0.00 | −2.07 | −13.40 | −0.26 | 0.00 | −0.04 | 0.00 |
| 354 | ADHEr, ACKr, AKGD, ATPS4r, PYK | 12.00 | 0.24 | 12.13 | 0.00 | 12.20 | 25.51 | −20.00 | 0.00 | 39.36 | 4.62 | 0.00 | −2.09 | −13.93 | −0.26 | 0.00 | −0.04 | 0.00 |

TABLE 6-continued

Knockout strategies derived by OptKnock, assuming PEP carboxykinase to be irreversible.

| # | Knockouts | | | | | | | | | | | | | | | | |
|---|---|---|---|---|---|---|---|---|---|---|---|---|---|---|---|---|---|
| 355 | ADHEr, ATPS4r, EDA, GLUDy, PGI | 11.98 | 0.13 | 19.29 | 0.00 | 7.97 | 19.98 | −20.00 | 0.00 | 40.22 | −1.56 | 0.00 | −1.15 | 0.00 | −0.02 | 0.00 | 0.00 |
| 356 | ADHEr, EDA, GLCpts, GLUDy, PGI | 11.98 | 0.14 | 19.25 | 0.00 | 7.98 | 19.96 | −20.00 | 0.00 | 40.18 | −1.51 | 0.00 | −1.18 | 0.00 | −0.02 | 0.00 | 0.00 |
| 357 | ADHEr, ACKr, LDH_D, MDH, SUCD4 | 11.91 | 0.20 | 12.01 | 3.31 | 5.46 | 24.78 | −20.00 | 0.00 | 41.50 | 0.47 | 0.00 | −5.01 | 0.00 | −0.21 | 0.00 | 0.00 |
| 358 | ADHEr, ACKr, GLUDy, NADH6, PYK | 11.90 | 0.49 | 12.16 | 0.00 | 27.81 | 0.00 | −20.00 | 0.00 | 15.63 | 24.87 | −20.00 | −4.23 | 0.00 | −0.52 | 0.00 | 0.00 |
| 359 | ADHEr, FUM, LDH_D, PFLi, THD2 | 11.76 | 0.39 | 19.51 | 0.00 | 17.62 | 0.00 | −20.00 | 0.00 | 22.30 | 13.05 | 0.00 | −3.40 | 0.00 | −0.42 | 0.00 | 0.00 |
| 360 | ADHEr, LDH_D, MDH, PFLi, THD2 | 11.76 | 0.39 | 19.51 | 0.00 | 17.62 | 0.00 | −20.00 | 0.00 | 22.30 | 13.05 | 0.00 | −3.40 | 0.00 | −0.42 | 0.00 | 0.00 |
| 361 | ADHEr, ACt6, ATPS4r, LDH_D, PPC | 11.67 | 0.14 | 0.00 | 0.00 | 1.15 | 24.89 | −19.46 | 0.00 | 38.65 | 4.77 | 0.00 | −1.18 | 12.79 | −0.15 | 0.00 | 0.00 |
| 362 | ADHEr, ACKr, LDH_D, PYRi2, SUCD4 | 11.66 | 0.21 | 11.78 | 0.00 | 8.63 | 21.96 | −20.00 | 0.00 | 37.33 | 2.88 | 0.00 | −3.91 | 0.00 | −0.22 | 0.00 | 2.12 |
| 363 | ADHEr, ATPS4r, FUM, LDH_D, SUCD4 | 11.59 | 0.23 | 20.54 | 0.00 | 13.84 | 9.06 | −20.00 | 0.00 | 31.25 | 6.51 | 0.00 | −2.01 | 0.00 | −0.25 | 0.00 | 0.00 |

TABLE 6-continued

Knockout strategies derived by OptKnock, assuming PEP carboxykinase to be irreversible.

| | | | | | | | | | | | | | | | |
|---|---|---|---|---|---|---|---|---|---|---|---|---|---|---|---|
| 364 | ADHEr, ATPS4r, LDH_D, MDH, SUCD4 | 11.59 | 0.23 | 20.54 | 0.00 | 13.84 | 9.06 | −20.00 | 0.00 | 31.25 | 6.51 | 0.00 | −2.01 | −2.00 | −0.25 | 0.00 | −0.04 | 0.00 |
| 365 | ADHEr, ACKr, CBMK2, NADH6, PYK | 11.52 | 0.55 | 11.82 | 0.00 | 27.24 | 0.00 | −20.00 | 0.00 | 15.76 | 25.89 | 0.00 | −4.80 | −20.00 | −0.59 | 0.00 | −0.10 | 0.00 |
| 366 | ADHEr, ACKr, NADH6, PYK, RPE | 11.50 | 0.56 | 11.81 | 0.00 | 27.22 | 0.00 | −20.00 | 0.00 | 15.77 | 25.93 | 0.00 | −4.82 | −20.00 | −0.60 | 0.00 | −0.10 | 0.00 |
| 367 | ADHEr, ACKr, ASNS2, NADH6, PYK | 11.50 | 0.56 | 11.80 | 0.00 | 27.21 | 0.00 | −20.00 | 0.00 | 15.77 | 25.95 | 0.00 | −4.83 | −20.00 | −0.60 | 0.00 | −0.10 | 0.00 |
| 368 | ADHEr, ACKr, NADH6, PYK, TAL | 11.49 | 0.56 | 11.80 | 0.00 | 27.20 | 0.00 | −20.00 | 0.00 | 15.77 | 25.96 | 0.00 | −4.84 | −20.00 | −0.60 | 0.00 | −0.10 | 0.00 |
| 369 | ADHEr, ASPT, ATPS4r, FUM, LDH_D | 11.46 | 0.30 | 8.96 | 0.00 | 8.56 | 25.90 | −20.00 | 0.00 | 38.85 | 4.50 | 0.00 | −4.47 | −5.00 | −0.33 | 0.00 | −0.05 | 1.84 |
| 370 | ADHEr, ASPT, ATPS4r, LDH_D, MDH | 11.43 | 0.34 | 17.13 | 0.00 | 8.27 | 17.71 | −20.00 | 0.00 | 37.24 | 3.02 | 0.00 | −2.92 | 0.00 | −0.36 | 0.00 | −0.06 | 0.00 |
| 371 | ADHEr, MDH, PFLi, PYK, THD2 | 11.38 | 0.38 | 20.90 | 0.00 | 17.05 | 0.00 | −20.00 | 0.00 | 23.58 | 12.56 | 0.00 | −3.25 | 0.00 | −0.40 | 0.00 | −0.07 | 0.00 |
| 372 | ADHEr, FUM, PFLi, PYK, THD2 | 11.38 | 0.38 | 20.90 | 0.00 | 17.05 | 0.00 | −20.00 | 0.00 | 23.58 | 12.56 | 0.00 | −3.25 | 0.00 | −0.40 | 0.00 | −0.07 | 0.00 |
| 373 | ADHEr, ACKr, FUM, LDH_D, NADH6 | 11.25 | 0.53 | 11.54 | 0.00 | 23.26 | 0.00 | −20.00 | 0.00 | 17.50 | 23.94 | 0.00 | −4.61 | −15.00 | −0.57 | 2.16 | −0.09 | 0.00 |

TABLE 6-continued

Knockout strategies derived by OptKnock, assuming PEP carboxykinase to be irreversible.

| | | | | | | | | | | | | | | |
|---|---|---|---|---|---|---|---|---|---|---|---|---|---|---|
| 374 | ADHEr, ATPS4r, G6PDHy, LDH_D, SUCD4 | 11.24 | 0.27 | 20.72 | 0.00 | 13.49 | 8.70 | −20.00 | 0.00 | 31.38 | 7.29 | 0.00 | −2.38 | −2.00 | −0.29 | 0.00 | −0.05 | 0.00 |
| 375 | ADHEr, ATPS4r, LDH_D, PGL, SUCD4 | 11.24 | 0.27 | 20.72 | 0.00 | 13.49 | 8.70 | −20.00 | 0.00 | 31.38 | 7.29 | 0.00 | −2.38 | −2.00 | −0.29 | 0.00 | −0.05 | 0.00 |
| 376 | ADHEr, ATPS4r, LDH_D, PGDH, SUCD4 | 11.24 | 0.27 | 20.72 | 0.00 | 13.49 | 8.70 | −20.00 | 0.00 | 31.38 | 7.29 | 0.00 | −2.38 | −2.00 | −0.29 | 0.00 | −0.05 | 0.00 |
| 377 | ADHEr, GLYCL, PGL, PPC, THD2 | 11.24 | 0.14 | 2.95 | 0.00 | 3.54 | 28.60 | −20.00 | 0.02 | 42.95 | −5.10 | 10.37 | −1.24 | −2.00 | −0.15 | 0.00 | −0.02 | 0.00 |
| 378 | ADHEr, G6PDHy, GLYCL, PPC, THD2 | 11.24 | 0.14 | 2.95 | 0.00 | 3.54 | 28.60 | −20.00 | 0.02 | 42.95 | −5.10 | 10.37 | −1.24 | −2.00 | −0.15 | 0.00 | −0.02 | 0.00 |
| 379 | ADHEr, FTHFD, G6PDHy, PPC, THD2 | 11.22 | 0.14 | 2.94 | 0.00 | 3.54 | 28.55 | −20.00 | 0.00 | 42.92 | −5.08 | 10.43 | −1.22 | −2.00 | −0.15 | 0.00 | −0.02 | 0.00 |
| 380 | ADHEr, FTHFD, PGL, PPC, THD2 | 11.22 | 0.14 | 2.94 | 0.00 | 3.54 | 28.55 | −20.00 | 0.00 | 42.92 | −5.08 | 10.43 | −1.22 | −2.00 | −0.15 | 0.00 | −0.02 | 0.00 |
| 381 | ADHEr, MTHFC, PGL, PPC, THD2 | 11.22 | 0.14 | 2.94 | 0.00 | 3.54 | 28.55 | −20.00 | 0.00 | 42.92 | −5.08 | 10.43 | −1.22 | −2.00 | −0.15 | 0.00 | −0.02 | 0.00 |
| 382 | ADHEr, G6PDHy, MTHFC, PPC, THD2 | 11.22 | 0.14 | 2.94 | 0.00 | 3.54 | 28.55 | −20.00 | 0.00 | 42.92 | −5.08 | 10.43 | −1.22 | −2.00 | −0.15 | 0.00 | −0.02 | 0.00 |
| 383 | ADHEr, ATPS4r, LDH_D, PFLi, SUCD4 | 11.20 | 0.32 | 22.07 | 0.00 | 17.78 | 0.00 | | | 24.34 | 12.44 | 0.00 | −2.76 | −2.00 | −0.34 | 0.00 | −0.06 | 0.00 |

TABLE 6-continued

Knockout strategies derived by OptKnock, assuming PEP carboxykinase to be irreversible.

| | | | | | | | | | | | | | | |
|---|---|---|---|---|---|---|---|---|---|---|---|---|---|---|
| 384 | ADHEr, ATPS4r, LDH_D, SUCD4, TAL | 11.18 | 0.28 | 20.84 | 0.00 | 13.41 | 8.69 | −20.00 | 0.00 | 31.49 | 7.30 | 0.00 | −2.40 | −2.00 | −0.30 | 0.00 | −0.05 | 0.00 |
| 385 | ADHEr, ATPS4r, LDH_D, RPE, SUCD4 | 11.13 | 0.28 | 23.11 | 0.00 | 17.68 | 0.00 | −20.00 | 0.00 | 25.09 | 11.65 | 0.00 | −2.41 | −2.00 | −0.30 | 0.00 | −0.05 | 0.00 |
| 386 | ADHEr, ATPS4r, FUM, GLCpts, NADH6 | 11.13 | 0.27 | 19.49 | 0.00 | 16.68 | 0.00 | −20.00 | 0.00 | 24.27 | 10.51 | 2.86 | −2.34 | 0.00 | −0.29 | 0.00 | −0.05 | 0.00 |
| 387 | ADHEr, ATPS4r, GLCpts, MDH, NADH6 | 11.13 | 0.27 | 19.49 | 0.00 | 16.68 | 0.00 | −20.00 | 0.00 | 24.27 | 10.51 | 2.86 | −2.34 | 0.00 | −0.29 | 0.00 | −0.05 | 0.00 |
| 388 | ADHEr, ATPS4r, LDH_D, NADH6, PFLi | 11.12 | 0.34 | 22.41 | 0.00 | 16.65 | 0.00 | −20.00 | 0.00 | 24.82 | 11.74 | 0.00 | −2.93 | 0.00 | −0.36 | 0.00 | −0.06 | 0.00 |
| 389 | ADHEr, ACKr, MALS, NADH12, NADH6 | 11.06 | 0.63 | 11.41 | 0.00 | 26.56 | 0.00 | −20.00 | 0.00 | 15.92 | 27.12 | 0.00 | −5.49 | −20.00 | −0.68 | 0.00 | −0.11 | 0.00 |
| 390 | ADHEr, ACKr, ICL, NADH12, NADH6 | 11.06 | 0.63 | 11.41 | 0.00 | 26.56 | 0.00 | −20.00 | 0.00 | 15.92 | 27.12 | 0.00 | −5.49 | −20.00 | −0.68 | 0.00 | −0.11 | 0.00 |
| 391 | ADHEr, ACKr, CBMK2, LDH_D, NADH6 | 11.06 | 0.64 | 11.40 | 0.00 | 26.54 | 0.00 | −20.00 | 0.00 | 15.93 | 27.15 | 0.00 | −5.51 | −20.00 | −0.68 | 0.00 | −0.11 | 0.00 |
| 392 | ADHEr, ATPS4r, GLCpts, MDH, PFLi | 11.04 | 0.35 | 22.48 | 0.00 | 16.54 | 0.00 | −20.00 | 0.00 | 24.94 | 11.83 | 0.00 | −2.99 | 0.00 | −0.37 | 0.00 | −0.06 | 0.00 |
| 393 | ADHEr, ATPS4r, FUM, GLCpts, PFLi | 11.04 | 0.35 | 22.48 | 0.00 | 16.54 | 0.00 | −20.00 | 0.00 | 24.94 | 11.83 | 0.00 | −2.99 | 0.00 | −0.37 | 0.00 | −0.06 | 0.00 |

TABLE 6-continued

Knockout strategies derived by OptKnock, assuming PEP carboxykinase to be irreversible.

| | | | | | | | | | | | | |
|---|---|---|---|---|---|---|---|---|---|---|---|---|
| 394 | ADHEr, ACKr, ASNS2, LDH_D, NADH6 | 11.03 | 0.64 | 11.38 | 0.00 | 26.51 | 0.00 | 0.00 | 15.93 | 27.21 | 0.00 | -5.54 | -20.00 | 0.00 | -0.11 | 0.00 |
| 395 | ADHEr, ACKr, ATPS4r, LDH_D, THD2 | 11.00 | 0.38 | 11.21 | 0.00 | 5.04 | 32.88 | -20.00 | 0.00 | 46.77 | 0.94 | 0.00 | -3.26 | -10.00 | 0.00 | -0.07 | 0.00 |
| 396 | ADHEr, GLCpts, GLUDy, PFLi, PGI | 11.00 | 0.15 | 26.58 | 0.00 | 16.49 | 0.00 | -20.00 | 0.00 | 27.66 | 8.29 | 0.00 | -1.32 | 0.00 | -0.16 | 0.00 |
| 397 | ADHEr, GLCpts, GLUDy, PFK, PFLi | 10.97 | 0.15 | 26.63 | 0.00 | 16.45 | 0.00 | -20.00 | 0.00 | 27.73 | 8.31 | 0.00 | -1.34 | 0.00 | -0.17 | 0.00 |
| 398 | ADHEr, FBA, GLCpts, GLUDy, PFLi | 10.97 | 0.15 | 26.63 | 0.00 | 16.45 | 0.00 | -20.00 | 0.00 | 27.73 | 8.31 | 0.00 | -1.34 | 0.00 | -0.17 | 0.00 |
| 399 | ADHEr, GLCpts, GLUDy, PFLi, TPI | 10.97 | 0.15 | 26.63 | 0.00 | 16.45 | 0.00 | -20.00 | 0.00 | 27.73 | 8.31 | 0.00 | -1.34 | 0.00 | -0.17 | 0.00 |
| 400 | ADHEr, ATPS4r, GLCpts, NADH6, PGI | 10.97 | 0.11 | 27.23 | 0.00 | 15.95 | 0.99 | -20.00 | 0.00 | 29.02 | 7.07 | 0.00 | -0.99 | 0.00 | -0.12 | 0.00 |
| 401 | ADHEr, ATPS4r, GLCpts, NADH6, TPI | 10.95 | 0.12 | 27.26 | 0.00 | 15.95 | 0.94 | -20.00 | 0.00 | 29.02 | 7.11 | 0.00 | -1.00 | 0.00 | -0.12 | 0.00 |
| 402 | ADHEr, ATPS4r, GLCpts, NADH6, PFK | 10.95 | 0.12 | 27.26 | 0.00 | 15.95 | 0.94 | -20.00 | 0.00 | 29.02 | 7.11 | 0.00 | -1.00 | 0.00 | -0.12 | 0.00 |
| 403 | ADHEr, ATPS4r, FBA, GLCpts, NADH6 | 10.95 | 0.12 | 27.26 | 0.00 | 15.95 | 0.94 | -20.00 | 0.00 | 29.02 | 7.11 | 0.00 | -1.00 | 0.00 | -0.12 | 0.00 |
| 404 | ADHEr, GLCpts, PFLi, RPE, TPI | 10.94 | 0.17 | 26.35 | 0.00 | 16.40 | 0.00 | -20.00 | 0.00 | 27.57 | 8.61 | 0.00 | -1.49 | 0.00 | -0.18 | 0.00 |

TABLE 6-continued

Knockout strategies derived by OptKnock, assuming PEP carboxykinase to be irreversible.

| # | Knockouts | | | | | | | | | | | | | | | | | |
|---|---|---|---|---|---|---|---|---|---|---|---|---|---|---|---|---|---|---|
| 405 | ADHEr, GLCpts, PFK, PFLi, RPE | 10.94 | 0.17 | 26.35 | 0.00 | 16.40 | 0.00 | -20.00 | 0.00 | 27.57 | 8.61 | 0.00 | -1.49 | 0.00 | -0.18 | 0.00 | -0.03 | 0.00 |
| 406 | ADHEr, FBA, GLCpts, PFLi, RPE | 10.94 | 0.17 | 26.35 | 0.00 | 16.40 | 0.00 | -20.00 | 0.00 | 27.57 | 8.61 | 0.00 | -1.49 | 0.00 | -0.18 | 0.00 | -0.03 | 0.00 |
| 407 | ADHEr, ATPS4r, NADH6, PFLi, PYK | 10.93 | 0.28 | 24.13 | 0.00 | 16.38 | 0.00 | -20.00 | 0.00 | 26.12 | 10.57 | 0.00 | -2.42 | 0.00 | -0.30 | 0.00 | -0.05 | 0.00 |
| 408 | ADHEr, GLCpts, PFK, PFLi, TAL | 10.93 | 0.17 | 26.37 | 0.00 | 16.38 | 0.00 | -20.00 | 0.00 | 27.59 | 8.62 | 0.00 | -1.49 | 0.00 | -0.18 | 0.00 | -0.03 | 0.00 |
| 409 | ADHEr, FBA, GLCpts, PFLi, TAL | 10.93 | 0.17 | 26.37 | 0.00 | 16.38 | 0.00 | -20.00 | 0.00 | 27.59 | 8.62 | 0.00 | -1.49 | 0.00 | -0.18 | 0.00 | -0.03 | 0.00 |
| 410 | ADHEr, GLCpts, PFLi, TAL, TPI | 10.93 | 0.17 | 26.37 | 0.00 | 16.38 | 0.00 | -20.00 | 0.00 | 27.59 | 8.62 | 0.00 | -1.49 | 0.00 | -0.18 | 0.00 | -0.03 | 0.00 |
| 411 | ADHEr, FBA, GLUDy, PFLi, RPE | 10.92 | 0.18 | 26.25 | 0.00 | 16.37 | 0.00 | -20.00 | 0.00 | 27.52 | 8.73 | 0.00 | -1.55 | 0.00 | -0.19 | 0.00 | -0.03 | 0.00 |
| 412 | ADHEr, GLUDy, PFK, PFLi, RPE | 10.92 | 0.18 | 26.25 | 0.00 | 16.37 | 0.00 | -20.00 | 0.00 | 27.52 | 8.73 | 0.00 | -1.55 | 0.00 | -0.19 | 0.00 | -0.03 | 0.00 |
| 413 | ADHEr, GLUDy, PFLi, RPE, TPI | 10.92 | 0.18 | 26.25 | 0.00 | 16.37 | 0.00 | -20.00 | 0.00 | 27.52 | 8.73 | 0.00 | -1.55 | 0.00 | -0.19 | 0.00 | -0.03 | 0.00 |
| 414 | ADHEr, GLUDy, PFLi, TAL, TPI | 10.91 | 0.18 | 26.27 | 0.00 | 16.35 | 0.00 | -20.00 | 0.00 | 27.55 | 8.74 | 0.00 | -1.56 | 0.00 | -0.19 | 0.00 | -0.03 | 0.00 |
| 415 | ADHEr, GLUDy, PFK, PFLi, TAL | 10.91 | 0.18 | 26.27 | 0.00 | 16.35 | 0.00 | -20.00 | 0.00 | 27.55 | 8.74 | 0.00 | -1.56 | 0.00 | -0.19 | 0.00 | -0.03 | 0.00 |
| 416 | ADHEr, FBA, GLUDy, PFLi, TAL | 10.91 | 0.18 | 26.27 | 0.00 | 16.35 | 0.00 | -20.00 | 0.00 | 27.55 | 8.74 | 0.00 | -1.56 | 0.00 | -0.19 | 0.00 | -0.03 | 0.00 |
| 417 | ADHEr, ATPS4r, LDH_D, | 10.79 | 0.32 | 21.77 | 0.00 | 14.53 | 5.29 | -20.00 | 0.00 | 29.37 | 9.67 | 0.00 | -2.81 | -2.00 | -0.35 | 0.00 | -0.06 | 0.00 |

TABLE 6-continued

Knockout strategies derived by OptKnock, assuming PEP carboxykinase to be irreversible.

| | | | | | | | | | | | |
|---|---|---|---|---|---|---|---|---|---|---|---|
| | NADH6, SUCD4 | | | | | | | | | | |
| 418 | ADHEr, FUM, LDH_D, PFLi, SUCD4 | 10.76 | 0.23 | 25.74 | 0.00 | 16.13 | 0.00 | −20.00 | 0.00 | 27.34 | 9.50 | 0.00 | −1.95 | 0.00 | −0.24 | 0.00 | −0.04 | 0.00 |
| 419 | ADHEr, LDH_D, MDH, PFLi, SUCD4 | 10.76 | 0.23 | 25.74 | 0.00 | 16.13 | 0.00 | −20.00 | 0.00 | 27.34 | 9.50 | 0.00 | −1.95 | 0.00 | −0.24 | 0.00 | −0.04 | 0.00 |

TABLE 7

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 1 | ADHEr, NADH6 | 6.44 | 0.72 | 22.08 | 0.00 | 1.90 | 17.19 | 0.00 | −20.00 | 0.00 | 44.88 | 8.96 | 0.00 | 0.00 | −6.26 | −2.00 | 0.00 | −0.78 | −0.13 | 0.23 | 0.00 | 0.00 |
| 2 | ADHEr, ENO | 6.29 | 0.03 | 33.29 | 0.00 | −6.29 | 33.43 | 0.00 | −20.00 | 0.00 | 66.92 | −12.07 | 0.00 | 0.00 | −0.24 | −2.00 | 0.00 | −0.03 | 0.00 | 0.00 | 0.00 | 0.00 |
| 3 | ADHEr, PGM | 6.29 | 0.03 | 33.29 | 0.00 | −6.29 | 33.43 | 0.00 | −20.00 | 0.00 | 66.92 | −12.07 | 0.00 | 0.00 | −0.24 | −2.00 | 0.00 | −0.03 | 0.00 | 0.00 | 0.00 | 0.00 |
| 4 | ADHEr, PPCK | 5.67 | 0.57 | 25.42 | 0.00 | −5.74 | 28.42 | 0.00 | −20.00 | 0.00 | 57.91 | −0.90 | 0.00 | 0.00 | −4.96 | 0.00 | 0.00 | −0.61 | −0.10 | 0.00 | 0.00 | 0.00 |
| 5 | ADHEr, SUCD4 | 5.54 | 0.65 | 24.41 | 0.00 | −5.63 | 27.79 | 0.00 | −20.00 | 0.00 | 56.80 | 0.68 | 0.00 | 0.00 | −5.60 | 0.00 | 0.00 | −0.69 | −0.11 | 0.00 | 0.00 | 0.00 |
| 6 | ADHEr, ATPS4r | 4.41 | 0.82 | 22.86 | 0.00 | −4.52 | 27.15 | 0.00 | −20.00 | 0.00 | 55.83 | 6.08 | 0.00 | 0.00 | −7.09 | −5.00 | 0.00 | −0.88 | −0.14 | 0.00 | 0.00 | 0.00 |
| 7 | ADHEr, PGI | 1.81 | 0.52 | 0.00 | 0.00 | −11.12 | 2.74 | 0.00 | −20.00 | 0.00 | 56.18 | 21.51 | 0.00 | 0.00 | −4.52 | 0.00 | 0.00 | −0.56 | −0.09 | 24.86 | 0.00 | 0.00 |
| 8 | ADHEr, FUM | 1.32 | 0.74 | 14.95 | 0.00 | −13.58 | 18.85 | 0.00 | −20.00 | 0.00 | 63.42 | 10.90 | 0.00 | 0.00 | −6.44 | 0.00 | 0.00 | −0.80 | −0.13 | 12.16 | 0.00 | 0.00 |
| 9 | ADHEr, HEX1 | 0.82 | 0.77 | 13.74 | 0.00 | −14.47 | 17.74 | 0.00 | −20.00 | 0.00 | 64.01 | 12.29 | 0.00 | 0.00 | −6.62 | 0.00 | 0.00 | −0.82 | −0.13 | 13.54 | 0.00 | 0.00 |
| 10 | ADHEr, MDH | 0.72 | 0.67 | 14.49 | 0.00 | −15.13 | 18.02 | 0.00 | −20.00 | 0.00 | 65.94 | 10.81 | 0.00 | 0.00 | −5.83 | 0.00 | 0.00 | −0.72 | −0.12 | 14.32 | 0.00 | 0.00 |
| 11 | ADHEr, TPI | 0.33 | 0.49 | 15.60 | 0.00 | −16.86 | 18.16 | 0.00 | −20.00 | 0.00 | 70.17 | 8.25 | 0.00 | 0.00 | −4.23 | 0.00 | 0.00 | −0.52 | −0.09 | 16.46 | 0.00 | 0.00 |
| 12 | ADHEr, FBA | 0.33 | 0.49 | 15.60 | 0.00 | −16.86 | 18.16 | 0.00 | −20.00 | 0.00 | 70.17 | 8.25 | 0.00 | 0.00 | −4.23 | 0.00 | 0.00 | −0.52 | −0.09 | 16.46 | 0.00 | 0.00 |
| 13 | ADHEr, PFK | 0.33 | 0.49 | 15.60 | 0.00 | −16.86 | 18.16 | 0.00 | −20.00 | 0.00 | 70.17 | 8.25 | 0.00 | 0.00 | −4.23 | 0.00 | 0.00 | −0.52 | −0.09 | 16.46 | 0.00 | 0.00 |
| 14 | ADHEr, HEX1, PGI | 11.52 | 0.39 | 15.75 | 0.00 | 8.35 | 17.80 | 0.00 | −20.00 | 0.00 | 36.34 | 4.02 | 0.00 | 0.00 | −3.39 | 0.00 | 0.00 | −0.42 | −0.07 | 0.00 | 0.00 | 0.00 |
| 15 | ADHEr, PFLi, PPCK | 9.95 | 0.50 | 22.31 | 0.00 | 14.90 | 0.00 | 0.00 | −20.00 | 0.00 | 25.85 | 14.07 | 0.00 | 0.00 | −4.31 | 0.00 | 0.00 | −0.53 | −0.09 | 0.00 | 0.00 | 0.00 |
| 16 | ADHEr, PFLi, SUCD4 | 9.81 | 0.55 | 21.71 | 0.00 | 14.68 | 0.00 | 0.00 | −20.00 | 0.00 | 25.59 | 14.87 | 0.00 | 0.00 | −4.72 | 0.00 | 0.00 | −0.58 | −0.10 | 0.00 | 0.00 | 0.00 |
| 17 | ADHEr, ACKr, NADH6 | 9.81 | 0.86 | 10.27 | 0.00 | 24.66 | 0.00 | 0.00 | −20.00 | 0.00 | 16.36 | 30.54 | 0.00 | 0.00 | −7.41 | −20.00 | 0.00 | −0.92 | −0.15 | 0.00 | 0.00 | 0.00 |
| 18 | ADHEr, NADH6, PFLi | 9.71 | 0.58 | 21.27 | 0.00 | 14.52 | 0.00 | 0.00 | −20.00 | 0.00 | 25.40 | 15.46 | 0.00 | 0.00 | −5.03 | 0.00 | 0.00 | −0.62 | −0.10 | 0.00 | 0.00 | 0.00 |
| 19 | ADHEr, NADH6, PGM | 7.82 | 0.08 | 30.86 | 0.00 | 9.99 | 13.48 | 0.00 | −20.00 | 0.00 | 44.95 | 3.71 | 0.00 | 0.00 | −0.73 | −10.00 | 0.00 | −0.09 | −0.01 | 0.00 | 0.00 | 0.00 |
| 20 | ADHEr, ENO, NADH6 | 7.82 | 0.08 | 30.86 | 0.00 | 9.99 | 13.48 | 0.00 | −20.00 | 0.00 | 44.95 | 3.71 | 0.00 | 0.00 | −0.73 | −10.00 | 0.00 | −0.09 | −0.01 | 0.00 | 0.00 | 0.00 |
| 21 | ADHEr, ASPT, MDH | 7.51 | 0.53 | 20.76 | 0.00 | −4.06 | 30.56 | 0.00 | −20.00 | 0.00 | 55.08 | −1.88 | 0.00 | 0.00 | −4.57 | 0.00 | 0.00 | −0.57 | −0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 22 | ADHEr, NADH6, PGI | 7.36 | 0.35 | 27.02 | 0.00 | 0.27 | 21.51 | 0.00 | −20.00 | 0.00 | 51.05 | −0.60 | 0.00 | 0.00 | −3.07 | 0.00 | 0.00 | −0.38 | −0.06 | 0.00 | 0.00 | 0.00 |
| 23 | ADHEr, NADH6, TPI | 7.25 | 0.36 | 27.17 | 0.00 | −0.05 | 21.80 | 0.00 | −20.00 | 0.00 | 51.52 | −0.71 | 0.00 | 0.00 | −3.11 | 0.00 | 0.00 | −0.38 | −0.06 | 0.00 | 0.00 | 0.00 |
| 24 | ADHEr, FBA, NADH6 | 7.25 | 0.36 | 27.17 | 0.00 | −0.05 | 21.80 | 0.00 | −20.00 | 0.00 | 51.52 | −0.71 | 0.00 | 0.00 | −3.11 | 0.00 | 0.00 | −0.38 | −0.06 | 0.00 | 0.00 | 0.00 |
| 25 | ADHEr, NADH6, PFK | 7.25 | 0.36 | 27.17 | 0.00 | −0.05 | 21.80 | 0.00 | −20.00 | 0.00 | 51.52 | −0.71 | 0.00 | 0.00 | −3.11 | 0.00 | 0.00 | −0.38 | −0.06 | 0.00 | 0.00 | 0.00 |
| 26 | ADHEr, NADH6, PPCK | 6.92 | 0.52 | 25.03 | 0.00 | −0.07 | 20.82 | 0.00 | −20.00 | 0.00 | 49.54 | 2.51 | 0.00 | 0.00 | −4.48 | 0.00 | 0.00 | −0.55 | −0.09 | 0.00 | 0.00 | 0.00 |
| 27 | ADHEr, MDH, NADH6 | 6.76 | 0.59 | 24.04 | 0.00 | −0.08 | 20.37 | 0.00 | −20.00 | 0.00 | 48.62 | 4.00 | 0.00 | 0.00 | −5.12 | 0.00 | 0.00 | −0.63 | −0.10 | 0.00 | 0.00 | 0.00 |
| 28 | ADHEr, FUM, NADH6 | 6.60 | 0.67 | 23.01 | 0.00 | −0.09 | 19.90 | 0.00 | −20.00 | 0.00 | 47.66 | 5.55 | 0.00 | 0.00 | −5.78 | 0.00 | 0.00 | −0.72 | −0.12 | 0.00 | 0.00 | 0.00 |
| 29 | ADHEr, PPCK, THD2 | 6.55 | 0.56 | 23.75 | 0.00 | −3.54 | 26.67 | 0.00 | −20.00 | 0.00 | 54.38 | 0.13 | 0.00 | 0.00 | −4.83 | 0.00 | 0.00 | −0.60 | −0.10 | 0.00 | 0.00 | 0.00 |
| 30 | ADHEr, NADH6, RPE | 6.53 | 0.77 | 21.10 | 0.00 | 5.45 | 13.37 | 0.00 | −20.00 | 0.00 | 40.40 | 13.24 | 0.00 | 0.00 | −6.66 | −5.00 | 0.00 | −0.82 | −0.13 | 0.23 | 0.00 | 0.00 |
| 31 | ADHEr, NADH6, TAL | 6.48 | 0.77 | 21.41 | 0.00 | 5.18 | 13.97 | 0.00 | −20.00 | 0.00 | 40.88 | 12.86 | 0.00 | 0.00 | −6.69 | −5.00 | 0.00 | −0.83 | −0.14 | 0.00 | 0.00 | 0.00 |
| 32 | ADHEr, PGI, PPCK | 6.21 | 0.30 | 28.99 | 0.00 | −5.98 | 30.57 | 0.00 | −20.00 | 0.00 | 61.72 | −6.65 | 0.00 | 0.00 | −2.62 | 0.00 | 0.00 | −0.32 | −0.05 | 0.00 | 0.00 | 0.00 |
| 33 | ADHEr, PGI, SUCD4 | 6.18 | 0.33 | 28.63 | 0.00 | −5.93 | 30.35 | 0.00 | −20.00 | 0.00 | 61.31 | −6.10 | 0.00 | 0.00 | −2.84 | 0.00 | 0.00 | −0.35 | −0.06 | 0.00 | 0.00 | 0.00 |
| 34 | ADHEr, ATPS4r, PPCK | 6.15 | 0.61 | 23.38 | 0.00 | −3.10 | 26.55 | 0.00 | −20.00 | 0.00 | 54.24 | 1.88 | 0.00 | 0.00 | −5.25 | −2.00 | 0.00 | −0.65 | −0.11 | 0.00 | 0.00 | 0.00 |
| 35 | ADHEr, PFK, PPCK | 6.13 | 0.31 | 29.10 | 0.00 | −6.17 | 30.70 | 0.00 | −20.00 | 0.00 | 61.98 | −6.68 | 0.00 | 0.00 | −2.66 | 0.00 | 0.00 | −0.33 | −0.05 | 0.00 | 0.00 | 0.00 |
| 36 | ADHEr, FBA, PPCK | 6.13 | 0.31 | 29.10 | 0.00 | −6.17 | 30.70 | 0.00 | −20.00 | 0.00 | 61.98 | −6.68 | 0.00 | 0.00 | −2.66 | 0.00 | 0.00 | −0.33 | −0.05 | 0.00 | 0.00 | 0.00 |
| 37 | ADHEr, PPCK, TPI | 6.13 | 0.31 | 29.10 | 0.00 | −6.17 | 30.70 | 0.00 | −20.00 | 0.00 | 61.98 | −6.68 | 0.00 | 0.00 | −2.66 | 0.00 | 0.00 | −0.33 | −0.05 | 0.00 | 0.00 | 0.00 |
| 38 | ADHEr, FBA, HEX1 | 6.11 | 0.32 | 28.91 | 0.00 | −6.15 | 30.59 | 0.00 | −20.00 | 0.00 | 61.78 | −6.39 | 0.00 | 0.00 | −2.77 | 0.00 | 0.00 | −0.34 | −0.06 | 0.00 | 0.00 | 0.00 |
| 39 | ADHEr, HEX1, PFK | 6.11 | 0.32 | 28.91 | 0.00 | −6.15 | 30.59 | 0.00 | −20.00 | 0.00 | 61.78 | −6.39 | 0.00 | 0.00 | −2.77 | 0.00 | 0.00 | −0.34 | −0.06 | 0.00 | 0.00 | 0.00 |
| 40 | ADHEr, HEX1, TPI | 6.11 | 0.32 | 28.91 | 0.00 | −6.15 | 30.59 | 0.00 | −20.00 | 0.00 | 61.78 | −6.39 | 0.00 | 0.00 | −2.77 | 0.00 | 0.00 | −0.34 | −0.06 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 41 | ADHEr, MDH, THD2 | 6.10 | 0.62 | 14.90 | 0.00 | −3.07 | 18.16 | 0.00 | −20.00 | 0.00 | 49.89 | 8.45 | 0.00 | 0.00 | −5.39 | 0.00 | 0.00 | −0.67 | −0.11 | 6.20 | 0.00 | 0.00 |
| 42 | ADHEr, SUCD4, TPI | 6.09 | 0.33 | 28.75 | 0.00 | −6.13 | 30.48 | 0.00 | −20.00 | 0.00 | 61.59 | −6.13 | 0.00 | 0.00 | −2.88 | 0.00 | 0.00 | −0.36 | −0.06 | 0.00 | 0.00 | 0.00 |
| 43 | ADHEr, FBA, SUCD4 | 6.09 | 0.33 | 28.75 | 0.00 | −6.13 | 30.48 | 0.00 | −20.00 | 0.00 | 61.59 | −6.13 | 0.00 | 0.00 | −2.88 | 0.00 | 0.00 | −0.36 | −0.06 | 0.00 | 0.00 | 0.00 |
| 44 | ADHEr, PFK, SUCD4 | 6.09 | 0.33 | 28.75 | 0.00 | −6.13 | 30.48 | 0.00 | −20.00 | 0.00 | 61.59 | −6.13 | 0.00 | 0.00 | −2.88 | 0.00 | 0.00 | −0.36 | −0.06 | 0.00 | 0.00 | 0.00 |
| 45 46 | ADHEr, FUM, PFLi ADHEr, PPCK, SUCD4 | 5.96 5.85 | 0.70 0.47 | 15.28 26.89 | 0.00 0.00 | 4.93 −5.92 | 0.00 29.33 | 0.00 0.00 | −20.00 −20.00 | 0.00 0.00 | 36.10 59.54 | 19.66 −3.22 | 0.00 0.00 | 0.00 0.00 | −6.02 −4.04 | 0.00 0.00 | 0.00 0.00 | −0.75 −0.50 | −0.12 −0.08 | 7.94 0.00 | 0.00 0.00 | 0.00 0.00 |
| 47 | ADHEr, PPCK, RPE | 5.78 | 0.57 | 25.20 | 0.00 | −5.45 | 28.19 | 0.00 | −20.00 | 0.00 | 57.44 | −0.76 | 0.00 | 0.00 | −4.95 | 0.00 | 0.00 | −0.61 | −0.10 | 0.00 | 0.00 | 0.00 |
| 48 | ADHEr, GLCpts, PPCK | 5.78 | 0.51 | 26.33 | 0.00 | −5.85 | 28.99 | 0.00 | −20.00 | 0.00 | 58.92 | −2.34 | 0.00 | 0.00 | −4.39 | 0.00 | 0.00 | −0.54 | −0.09 | 0.00 | 0.00 | 0.00 |
| 49 | ADHEr, GLUDy, MDH | 5.78 | 0.51 | 26.30 | 0.00 | −5.85 | 28.97 | 0.00 | −20.00 | 0.00 | 58.89 | −2.29 | 0.00 | 0.00 | −4.41 | 0.00 | 0.00 | −0.55 | −0.09 | 0.00 | 0.00 | 0.00 |
| 50 | ADHEr, GLUDy, PPCK | 5.77 | 0.52 | 26.20 | 0.00 | −5.84 | 28.90 | 0.00 | −20.00 | 0.00 | 58.78 | −2.13 | 0.00 | 0.00 | −4.47 | 0.00 | 0.00 | −0.55 | −0.09 | 0.00 | 0.00 | 0.00 |
| 51 | ADHEr, MDH, SUCD4 | 5.74 | 0.53 | 25.99 | 0.00 | −5.81 | 28.78 | 0.00 | −20.00 | 0.00 | 58.55 | −1.81 | 0.00 | 0.00 | −4.60 | 0.00 | 0.00 | −0.57 | −0.09 | 0.00 | 0.00 | 0.00 |
| 52 53 | ADHEr, PPCK, TAL ADHEr, FUM, PPCK | 5.73 5.73 | 0.57 0.54 | 25.30 25.90 | 0.00 0.00 | −5.59 −5.80 | 28.30 28.72 | 0.00 0.00 | −20.00 −20.00 | 0.00 0.00 | 57.67 58.44 | −0.83 −1.66 | 0.00 0.00 | 0.00 0.00 | −4.95 −4.66 | 0.00 0.00 | 0.00 0.00 | −0.61 −0.58 | −0.10 −0.09 | 0.00 0.00 | 0.00 0.00 | 0.00 0.00 |
| 54 | ADHEr, MDH, PPCK | 5.73 | 0.54 | 25.90 | 0.00 | −5.80 | 28.72 | 0.00 | −20.00 | 0.00 | 58.44 | −1.66 | 0.00 | 0.00 | −4.66 | 0.00 | 0.00 | −0.58 | −0.09 | 0.00 | 0.00 | 0.00 |
| 55 | ADHEr, RPE, SUCD4 | 5.68 | 0.64 | 24.22 | 0.00 | −5.31 | 27.57 | 0.00 | −20.00 | 0.00 | 56.34 | 0.74 | 0.00 | 0.00 | −5.54 | 0.00 | 0.00 | −0.69 | −0.11 | 0.00 | 0.00 | 0.00 |
| 56 | ADHEr, ME2, SUCD4 | 5.68 | 0.57 | 25.49 | 0.00 | −5.75 | 28.46 | 0.00 | −20.00 | 0.00 | 57.99 | −1.01 | 0.00 | 0.00 | −4.92 | 0.00 | 0.00 | −0.61 | −0.10 | 0.00 | 0.00 | 0.00 |
| 57 | ADHEr, FUM, GLUDy | 5.66 | 0.58 | 25.35 | 0.00 | −5.74 | 28.38 | 0.00 | −20.00 | 0.00 | 57.84 | −0.80 | 0.00 | 0.00 | −5.00 | 0.00 | 0.00 | −0.62 | −0.10 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 58 | ADHEr, GLUDy, SUCD4 | 5.66 | 0.58 | 25.34 | 0.00 | −5.74 | 28.37 | 0.00 | −20.00 | 0.00 | 57.83 | −0.78 | 0.00 | 0.00 | −5.01 | 0.00 | 0.00 | −0.62 | −0.10 | 0.00 | 0.00 | 0.00 |
| 59 | ADHEr, GLCpts, SUCD4 | 5.65 | 0.58 | 25.28 | 0.00 | −5.73 | 28.34 | 0.00 | −20.00 | 0.00 | 57.77 | −0.69 | 0.00 | 0.00 | −5.05 | 0.00 | 0.00 | −0.62 | −0.10 | 0.00 | 0.00 | 0.00 |
| 60 | ADHEr, SUCD4, TAL | 5.61 | 0.64 | 24.31 | 0.00 | −5.46 | 27.67 | 0.00 | −20.00 | 0.00 | 56.56 | 0.71 | 0.00 | 0.00 | −5.56 | 0.00 | 0.00 | −0.69 | −0.11 | 0.00 | 0.00 | 0.00 |
| 61 | ADHEr, FUM, SUCD4 | 5.57 | 0.63 | 24.65 | 0.00 | −5.66 | 27.94 | 0.00 | −20.00 | 0.00 | 57.07 | 0.30 | 0.00 | 0.00 | −5.44 | 0.00 | 0.00 | −0.67 | −0.11 | 0.00 | 0.00 | 0.00 |
| 62 | ADHEr, HEX1, SUCD4 | 5.56 | 0.64 | 24.55 | 0.00 | −5.64 | 27.88 | 0.00 | −20.00 | 0.00 | 56.95 | 0.47 | 0.00 | 0.00 | −5.51 | 0.00 | 0.00 | −0.68 | −0.11 | 0.00 | 0.00 | 0.00 |
| 63 | ADHEr, CBMK2, SUCD4 | 5.55 | 0.64 | 24.49 | 0.00 | −5.64 | 27.84 | 0.00 | −20.00 | 0.00 | 56.89 | 0.56 | 0.00 | 0.00 | −5.55 | 0.00 | 0.00 | −0.69 | −0.11 | 0.00 | 0.00 | 0.00 |
| 64 | ADHEr, FUM, HEX1 | 5.44 | 0.70 | 23.61 | 0.00 | −5.53 | 27.29 | 0.00 | −20.00 | 0.00 | 55.91 | 1.94 | 0.00 | 0.00 | −6.10 | 0.00 | 0.00 | −0.75 | −0.12 | 0.00 | 0.00 | 0.00 |
| 65 | ADHEr, HEX1, PFLi | 5.24 | 0.72 | 14.09 | 0.00 | 3.10 | 0.00 | 0.00 | −20.00 | 0.00 | 38.10 | 20.54 | 0.00 | 0.00 | −6.25 | 0.00 | 0.00 | −0.77 | −0.13 | 9.44 | 0.00 | 0.00 |
| 66 | ADHEr, ATPS4r, PGI | 5.06 | 0.52 | 26.72 | 0.00 | −4.66 | 29.44 | 0.00 | −20.00 | 0.00 | 59.85 | −0.22 | 0.00 | 0.00 | −4.49 | −5.00 | 0.00 | −0.56 | −0.09 | 0.00 | 0.00 | 0.00 |
| 67 | ADHEr, ATPS4r, FBA | 4.91 | 0.53 | 26.89 | 0.00 | −4.99 | 29.65 | 0.00 | −20.00 | 0.00 | 60.29 | −0.25 | 0.00 | 0.00 | −4.56 | −5.00 | 0.00 | −0.56 | −0.09 | 0.00 | 0.00 | 0.00 |
| 68 | ADHEr, ATPS4r, PFK | 4.91 | 0.53 | 26.89 | 0.00 | −4.99 | 29.65 | 0.00 | −20.00 | 0.00 | 60.29 | −0.25 | 0.00 | 0.00 | −4.56 | −5.00 | 0.00 | −0.56 | −0.09 | 0.00 | 0.00 | 0.00 |
| 69 | ADHEr, ATPS4r, TPI | 4.91 | 0.53 | 26.89 | 0.00 | −4.99 | 29.65 | 0.00 | −20.00 | 0.00 | 60.29 | −0.25 | 0.00 | 0.00 | −4.56 | −5.00 | 0.00 | −0.56 | −0.09 | 0.00 | 0.00 | 0.00 |
| 70 | ADHEr, PFLi, TPI | 4.88 | 0.44 | 16.04 | 0.00 | 1.18 | 0.00 | 0.00 | −20.00 | 0.00 | 43.62 | 16.61 | 0.00 | 0.00 | −3.82 | 0.00 | 0.00 | −0.47 | −0.08 | 12.23 | 0.00 | 0.00 |
| 71 | ADHEr, PFK, PFLi | 4.88 | 0.44 | 16.04 | 0.00 | 1.18 | 0.00 | 0.00 | −20.00 | 0.00 | 43.62 | 16.61 | 0.00 | 0.00 | −3.82 | 0.00 | 0.00 | −0.47 | −0.08 | 12.23 | 0.00 | 0.00 |
| 72 | ADHEr, FBA, PFLi | 4.88 | 0.44 | 16.04 | 0.00 | 1.18 | 0.00 | 0.00 | −20.00 | 0.00 | 43.62 | 16.61 | 0.00 | 0.00 | −3.82 | 0.00 | 0.00 | −0.47 | −0.08 | 12.23 | 0.00 | 0.00 |
| 73 | ADHEr, HEX1, THD2 | 4.87 | 0.74 | 22.12 | 0.00 | −6.49 | 25.99 | 0.00 | −20.00 | 0.00 | 56.39 | 3.70 | 0.00 | 0.00 | −6.40 | 0.00 | 0.00 | −0.79 | −0.13 | 1.51 | 0.00 | 0.00 |
| 74 | ADHEr, ATPS4r, RPE | 4.59 | 0.81 | 22.69 | 0.00 | −4.12 | 26.91 | 0.00 | −20.00 | 0.00 | 55.33 | 6.06 | 0.00 | 0.00 | −6.97 | −5.00 | 0.00 | −0.86 | −0.14 | 0.00 | 0.00 | 0.00 |
| 75 | ADHEr, ATPS4r, GLUDy | 4.56 | 0.73 | 24.10 | 0.00 | −4.66 | 27.92 | 0.00 | −20.00 | 0.00 | 57.20 | 4.14 | 0.00 | 0.00 | −6.31 | −5.00 | 0.00 | −0.78 | −0.13 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 76 | ADHEr, ATPS4r, TAL | 4.50 | 0.81 | 22.77 | 0.00 | -4.31 | 27.02 | 0.00 | -20.00 | 0.00 | 55.57 | 6.07 | 0.00 | 0.00 | -7.03 | -5.00 | 0.00 | -0.87 | -0.14 | 0.00 | 0.00 | 0.00 |
| 77 | ADHEr, ATPS4r, CBMK2 | 4.42 | 0.81 | 22.97 | 0.00 | -4.53 | 27.22 | 0.00 | -20.00 | 0.00 | 55.95 | 5.91 | 0.00 | 0.00 | -7.02 | -5.00 | 0.00 | -0.87 | -0.14 | 0.00 | 0.00 | 0.00 |
| 78 | ADHEr, EDA, PGI | 4.21 | 0.51 | 0.00 | 0.00 | -5.69 | 2.64 | 0.00 | -20.00 | 0.00 | 48.84 | 20.66 | 0.00 | 0.00 | -4.37 | 0.00 | 0.00 | -0.54 | -0.09 | 21.30 | 0.00 | 0.00 |
| 79 | ADHEr, PFLi, PGI | 2.48 | 0.52 | 0.00 | 0.00 | -8.45 | 0.00 | 0.00 | -20.00 | 0.00 | 52.22 | 22.80 | 0.00 | 0.00 | -4.46 | 0.00 | 0.00 | -0.55 | -0.09 | 24.28 | 0.00 | 0.00 |
| 80 | ADHEr, MDH, PFK | 1.36 | 0.47 | 17.83 | 0.00 | -14.86 | 20.31 | 0.00 | -20.00 | 0.00 | 68.38 | 5.91 | 0.00 | 0.00 | -4.11 | 0.00 | 0.00 | -0.51 | -0.08 | 13.43 | 0.00 | 0.00 |
| 81 | ADHEr, MDH, TPI | 1.36 | 0.47 | 17.83 | 0.00 | -14.86 | 20.31 | 0.00 | -20.00 | 0.00 | 68.38 | 5.91 | 0.00 | 0.00 | -4.11 | 0.00 | 0.00 | -0.51 | -0.08 | 13.43 | 0.00 | 0.00 |
| 82 | ADHEr, FBA, MDH | 1.36 | 0.47 | 17.83 | 0.00 | -14.86 | 20.31 | 0.00 | -20.00 | 0.00 | 68.38 | 5.91 | 0.00 | 0.00 | -4.11 | 0.00 | 0.00 | -0.51 | -0.08 | 13.43 | 0.00 | 0.00 |
| 83 | ADHEr, HEX1, RPE | 1.13 | 0.76 | 13.77 | 0.00 | -13.77 | 17.76 | 0.00 | -20.00 | 0.00 | 63.09 | 12.13 | 0.00 | 0.00 | -6.59 | 0.00 | 0.00 | -0.82 | -0.13 | 13.08 | 0.00 | 0.00 |
| 84 | ADHEr, MDH, RPE | 1.00 | 0.67 | 14.51 | 0.00 | -14.51 | 18.02 | 0.00 | -20.00 | 0.00 | 65.11 | 10.68 | 0.00 | 0.00 | -5.80 | 0.00 | 0.00 | -0.72 | -0.12 | 13.90 | 0.00 | 0.00 |
| 85 | ADHEr, HEX1, TAL | 0.98 | 0.76 | 13.76 | 0.00 | -14.10 | 17.75 | 0.00 | -20.00 | 0.00 | 63.53 | 12.21 | 0.00 | 0.00 | -6.61 | 0.00 | 0.00 | -0.82 | -0.13 | 13.30 | 0.00 | 0.00 |
| 86 | ADHEr, MDH, TAL | 0.86 | 0.67 | 14.50 | 0.00 | -14.81 | 18.02 | 0.00 | -20.00 | 0.00 | 65.51 | 10.74 | 0.00 | 0.00 | -5.81 | 0.00 | 0.00 | -0.72 | -0.12 | 14.10 | 0.00 | 0.00 |
| 87 | ADHEr, RPE, TPI | 0.47 | 0.48 | 15.53 | 0.00 | -16.54 | 18.07 | 0.00 | -20.00 | 0.00 | 69.75 | 8.23 | 0.00 | 0.00 | -4.19 | 0.00 | 0.00 | -0.52 | -0.08 | 16.35 | 0.00 | 0.00 |
| 88 | ADHEr, PFK, RPE | 0.47 | 0.48 | 15.53 | 0.00 | -16.54 | 18.07 | 0.00 | -20.00 | 0.00 | 69.75 | 8.23 | 0.00 | 0.00 | -4.19 | 0.00 | 0.00 | -0.52 | -0.08 | 16.35 | 0.00 | 0.00 |
| 89 | ADHEr, FBA, RPE | 0.47 | 0.48 | 15.53 | 0.00 | -16.54 | 18.07 | 0.00 | -20.00 | 0.00 | 69.75 | 8.23 | 0.00 | 0.00 | -4.19 | 0.00 | 0.00 | -0.52 | -0.08 | 16.35 | 0.00 | 0.00 |
| 90 | ADHEr, PFK, TAL | 0.40 | 0.49 | 15.57 | 0.00 | -16.69 | 18.11 | 0.00 | -20.00 | 0.00 | 69.95 | 8.24 | 0.00 | 0.00 | -4.21 | 0.00 | 0.00 | -0.52 | -0.09 | 16.41 | 0.00 | 0.00 |
| 91 | ADHEr, FBA, TAL | 0.40 | 0.49 | 15.57 | 0.00 | -16.69 | 18.11 | 0.00 | -20.00 | 0.00 | 69.95 | 8.24 | 0.00 | 0.00 | -4.21 | 0.00 | 0.00 | -0.52 | -0.09 | 16.41 | 0.00 | 0.00 |
| 92 | ADHEr, HEX1, PFLi, PGI | 14.20 | 0.34 | 13.81 | 0.00 | 21.29 | 0.00 | 0.00 | -20.00 | 0.00 | 16.25 | 13.38 | 0.00 | 0.00 | -2.97 | 0.00 | 0.00 | -0.37 | -0.06 | 0.00 | 0.00 | 0.00 |
| 93 | ADHEr, HEX1, NADH6, PGI | 14.07 | 0.28 | 14.98 | 0.00 | 19.90 | 2.36 | 0.00 | -20.00 | 0.00 | 19.31 | 10.91 | 0.00 | 0.00 | -2.40 | 0.00 | 0.00 | -0.30 | -0.05 | 0.00 | 0.00 | 0.00 |
| 94 | ADHEr, EDA, NADH6, PGI | 14.00 | 0.31 | 14.58 | 0.00 | 19.89 | 2.18 | 0.00 | -20.00 | 0.00 | 18.94 | 11.52 | 0.00 | 0.00 | -2.66 | 0.00 | 0.00 | -0.33 | -0.05 | 0.00 | 0.00 | 0.00 |
| 95 | ADHEr, ACKr, NADH6, PGI | 13.92 | 0.34 | 14.10 | 0.00 | 21.85 | 0.00 | 0.00 | -20.00 | 0.00 | 16.55 | 14.23 | 0.00 | 0.00 | -2.97 | -2.00 | 0.00 | -0.37 | -0.06 | 0.00 | 0.00 | 0.00 |
| 96 | ADHEr, FRD2, PGI | 13.31 | 0.25 | 5.13 | 0.00 | 13.27 | 19.78 | 0.00 | -20.00 | 0.00 | 28.86 | 6.78 | 2.14 | 0.00 | -4.35 | 0.00 | 0.00 | -0.27 | -0.04 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 97 | ADHEr, ATPS4r, PGI, SUCD4, LDH_D, MDH | 13.14 | 0.27 | 15.98 | 0.00 | 17.23 | 6.93 | 0.00 | −20.00 | 0.00 | 24.84 | 9.08 | 0.00 | 0.00 | −2.36 | −2.00 | 0.00 | −0.29 | −0.05 | 0.00 | 0.00 | 0.00 |
| 98 | ADHEr, ATPS4r, FDH2, NADH6 | 12.33 | 0.49 | 15.46 | 0.00 | 19.46 | 0.00 | 0.00 | −20.00 | 0.00 | 18.94 | 16.09 | 0.00 | 0.00 | −4.23 | −2.00 | 0.00 | −0.52 | −0.09 | 0.00 | 0.00 | 0.00 |
| 99 | ADHEr, ACKr, NADH6, TPI | 12.03 | 0.46 | 12.29 | 0.00 | 28.02 | 0.00 | 0.00 | −20.00 | 0.00 | 15.58 | 24.49 | 0.00 | 0.00 | −4.01 | −20.00 | 0.00 | −0.50 | −0.08 | 0.00 | 0.00 | 0.00 |
| 100 | ADHEr, ACKr, FBA, NADH6 | 12.03 | 0.46 | 12.29 | 0.00 | 28.02 | 0.00 | 0.00 | −20.00 | 0.00 | 15.58 | 24.49 | 0.00 | 0.00 | −4.01 | −20.00 | 0.00 | −0.50 | −0.08 | 0.00 | 0.00 | 0.00 |
| 101 | ADHEr, ACKr, NADH6, PFK | 12.03 | 0.46 | 12.29 | 0.00 | 28.02 | 0.00 | 0.00 | −20.00 | 0.00 | 15.58 | 24.49 | 0.00 | 0.00 | −4.01 | −20.00 | 0.00 | −0.50 | −0.08 | 0.00 | 0.00 | 0.00 |
| 102 | ADHEr, FRD2, LDH_D, ME2 | 11.95 | 0.26 | 4.09 | 0.00 | 7.62 | 17.42 | 4.30 | −20.00 | 0.00 | 33.78 | 10.90 | 1.81 | 0.00 | −4.09 | 0.00 | 0.00 | −0.28 | −0.05 | 0.00 | 0.00 | 0.00 |
| 103 | ADHEr, HEX1, PGI, PPCK | 11.82 | 0.22 | 18.07 | 0.00 | 8.10 | 19.23 | 0.00 | −20.00 | 0.00 | 38.88 | 0.36 | 0.00 | 0.00 | −1.93 | 0.00 | 0.00 | −0.24 | −0.04 | 0.00 | 0.00 | 0.00 |
| 104 | ADHEr, EDA, PGI, PPCK | 11.82 | 0.22 | 18.05 | 0.00 | 8.10 | 19.22 | 0.00 | −20.00 | 0.00 | 38.86 | 0.38 | 0.00 | 0.00 | −1.94 | 0.00 | 0.00 | −0.24 | −0.04 | 0.00 | 0.00 | 0.00 |
| 105 | ADHEr, HEX1, PGI, SUCD4 | 11.77 | 0.25 | 17.66 | 0.00 | 8.15 | 18.98 | 0.00 | −20.00 | 0.00 | 38.43 | 1.01 | 0.00 | 0.00 | −2.19 | 0.00 | 0.00 | −0.27 | −0.04 | 0.00 | 0.00 | 0.00 |
| 106 | ADHEr, EDA, PGI, SUCD4 | 11.76 | 0.26 | 17.62 | 0.00 | 8.15 | 18.95 | 0.00 | −20.00 | 0.00 | 38.39 | 1.07 | 0.00 | 0.00 | −2.21 | 0.00 | 0.00 | −0.27 | −0.04 | 0.00 | 0.00 | 0.00 |
| 107 | ADHEr, ATPS4r, EDA, PGI | 11.62 | 0.34 | 16.52 | 0.00 | 8.27 | 18.28 | 0.00 | −20.00 | 0.00 | 37.18 | 2.80 | 0.00 | 0.00 | −2.91 | 0.00 | 0.00 | −0.36 | −0.06 | 0.00 | 0.00 | 0.00 |
| 108 | ADHEr, GLUDy, HEX1, PGI | 11.59 | 0.35 | 16.29 | 0.00 | 8.29 | 18.13 | 0.00 | −20.00 | 0.00 | 36.93 | 3.17 | 0.00 | 0.00 | −3.05 | 0.00 | 0.00 | −0.38 | −0.06 | 0.00 | 0.00 | 0.00 |
| 109 | ADHEr, MDH, PGL, THD2 | 11.18 | 0.48 | 13.34 | 0.00 | 4.81 | 23.87 | 0.00 | −20.00 | 0.00 | 40.62 | 2.41 | 0.00 | 0.00 | −4.15 | 0.00 | 0.00 | −0.51 | −0.08 | 0.00 | 0.00 | 0.00 |
| 110 | ADHEr, G6PDHy, MDH, THD2 | 11.18 | 0.48 | 13.34 | 0.00 | 4.81 | 23.87 | 0.00 | −20.00 | 0.00 | 40.62 | 2.41 | 0.00 | 0.00 | −4.15 | 0.00 | 0.00 | −0.51 | −0.08 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 111 | ADHEr, PFLi, PGI, PPCK | 10.87 | 0.20 | 25.96 | 0.00 | 16.29 | 0.00 | 0.00 | −20.00 | 0.00 | 27.38 | 9.09 | 0.00 | 0.00 | −1.73 | 0.00 | 0.00 | −0.21 | −0.03 | 0.00 | 0.00 | 0.00 |
| 112 | ADHEr, PFLi, PPCK, TPI | 10.83 | 0.20 | 26.02 | 0.00 | 16.23 | 0.00 | 0.00 | −20.00 | 0.00 | 27.46 | 9.11 | 0.00 | 0.00 | −1.75 | 0.00 | 0.00 | −0.22 | −0.04 | 0.00 | 0.00 | 0.00 |
| 113 | ADHEr, FBA, PFLi, PPCK | 10.83 | 0.20 | 26.02 | 0.00 | 16.23 | 0.00 | 0.00 | −20.00 | 0.00 | 27.46 | 9.11 | 0.00 | 0.00 | −1.75 | 0.00 | 0.00 | −0.22 | −0.04 | 0.00 | 0.00 | 0.00 |
| 114 | ADHEr, PFK, PFLi, PPCK | 10.83 | 0.20 | 26.02 | 0.00 | 16.23 | 0.00 | 0.00 | −20.00 | 0.00 | 27.46 | 9.11 | 0.00 | 0.00 | −1.75 | 0.00 | 0.00 | −0.22 | −0.04 | 0.00 | 0.00 | 0.00 |
| 115 | ADHEr, ACKr, MDH, NADH6 | 10.80 | 0.74 | 11.20 | 0.00 | 23.65 | 0.00 | 0.00 | −20.00 | 0.00 | 16.47 | 26.42 | 0.00 | 0.00 | −6.41 | −15.00 | 0.00 | −0.79 | −0.13 | 0.00 | 0.00 | 0.00 |
| 116 | ADHEr, NADH6, PFLi, PGI | 10.79 | 0.23 | 25.57 | 0.00 | 16.16 | 0.00 | 0.00 | −20.00 | 0.00 | 27.21 | 9.59 | 0.00 | 0.00 | −1.99 | 0.00 | 0.00 | −0.25 | −0.04 | 0.00 | 0.00 | 0.00 |
| 117 | ADHEr, PFLi, PGI, SUCD4 | 10.79 | 0.23 | 25.57 | 0.00 | 16.16 | 0.00 | 0.00 | −20.00 | 0.00 | 27.21 | 9.59 | 0.00 | 0.00 | −1.99 | 0.00 | 0.00 | −0.25 | −0.04 | 0.00 | 0.00 | 0.00 |
| 118 | ADHEr, FBA, PFLi, SUCD4 | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 119 | ADHEr, PFK, PFLi, SUCD4 | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 120 | ADHEr, NADH6, PFK, PFLi | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 121 | ADHEr, FBA, NADH6, PFLi | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 122 | ADHEr, PFLi, SUCD4, TPI | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 123 | ADHEr, NADH6, PFLi, TPI | 10.74 | 0.23 | 25.64 | 0.00 | 16.09 | 0.00 | 0.00 | −20.00 | 0.00 | 27.30 | 9.62 | 0.00 | 0.00 | −2.01 | 0.00 | 0.00 | −0.25 | −0.04 | 0.00 | 0.00 | 0.00 |
| 124 | ADHEr, HEX1, PFK, PFLi | 10.73 | 0.24 | 25.61 | 0.00 | 16.08 | 0.00 | 0.00 | −20.00 | 0.00 | 27.28 | 9.67 | 0.00 | 0.00 | −2.04 | 0.00 | 0.00 | −0.25 | −0.04 | 0.00 | 0.00 | 0.00 |
| 125 | ADHEr, FBA, HEX1, PFLi | 10.73 | 0.24 | 25.61 | 0.00 | 16.08 | 0.00 | 0.00 | −20.00 | 0.00 | 27.28 | 9.67 | 0.00 | 0.00 | −2.04 | 0.00 | 0.00 | −0.25 | −0.04 | 0.00 | 0.00 | 0.00 |
| 126 | ADHEr, HEX1, PFLi, TPI | 10.73 | 0.24 | 25.61 | 0.00 | 16.08 | 0.00 | 0.00 | −20.00 | 0.00 | 27.28 | 9.67 | 0.00 | 0.00 | −2.04 | 0.00 | 0.00 | −0.25 | −0.04 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 127 | ADHEr, PFLi, PPCK, THD2 | 10.49 | 0.49 | 21.02 | 0.00 | 15.71 | 0.00 | 0.00 | −20.00 | 0.00 | 24.49 | 14.16 | 0.00 | 0.00 | −4.23 | 0.00 | 0.00 | −0.52 | −0.09 | 0.00 | 0.00 | 0.00 |
| 128 | ADHEr, ACKr, GLUDy, NADH6 | 10.40 | 0.75 | 10.81 | 0.00 | 25.55 | 0.00 | 0.00 | −20.00 | 0.00 | 16.16 | 28.93 | 0.00 | 0.00 | −6.51 | −20.00 | 0.00 | −0.81 | −0.13 | 0.00 | 0.00 | 0.00 |
| 129 | ADHEr, ACKr, GLCpts, NADH6 | 10.28 | 0.77 | 10.70 | 0.00 | 25.38 | 0.00 | 0.00 | −20.00 | 0.00 | 16.20 | 29.25 | 0.00 | 0.00 | −6.68 | −20.00 | 0.00 | −0.83 | −0.14 | 0.00 | 0.00 | 0.00 |
| 130 | ADHEr, ACKr, AKGD, ATPS4r | 10.24 | 0.58 | 10.55 | 0.00 | 11.67 | 22.30 | 0.00 | −20.00 | 0.00 | 36.95 | 12.00 | 0.00 | 0.00 | −4.99 | −15.00 | 0.00 | −0.62 | −0.10 | 0.00 | 0.00 | 0.00 |
| 131 | ADHEr, ATPS4r, NADH6, PFLi | 10.17 | 0.53 | 19.34 | 0.00 | 15.23 | 0.00 | 0.00 | −20.00 | 0.00 | 24.21 | 14.83 | 0.00 | 0.00 | −4.62 | 0.00 | 0.00 | −0.57 | −0.09 | 0.00 | 0.00 | 0.00 |
| 132 | ADHEr, GLCpts, PFLi, PPCK | 10.15 | 0.43 | 23.16 | 0.00 | 15.20 | 0.00 | 0.00 | −20.00 | 0.00 | 26.22 | 12.93 | 0.00 | 1.08 | −3.72 | 0.00 | 0.00 | −0.46 | −0.08 | 0.00 | 0.00 | 0.00 |
| 133 | ADHEr, ACKr, ATPS4r, SUCOAS | 10.12 | 0.58 | 10.44 | 0.00 | 10.60 | 23.88 | 0.00 | −20.00 | 0.00 | 38.45 | 11.13 | 0.00 | 0.00 | −5.03 | −14.78 | 0.00 | −0.62 | −0.10 | 0.00 | 0.00 | 0.00 |
| 134 | ADHEr, ACKr, ME2, NADH6 | 10.11 | 0.77 | 10.53 | 0.00 | 22.07 | 0.00 | 0.00 | −20.00 | 0.00 | 18.19 | 27.22 | 0.00 | 0.00 | −6.69 | −15.00 | 0.00 | −0.83 | −0.14 | 1.08 | 0.00 | 0.00 |
| 135 | ADHEr, GLUDy, PFLi, PPCK | 10.10 | 0.45 | 22.94 | 0.00 | 15.12 | 0.00 | 0.00 | −20.00 | 0.00 | 26.12 | 13.23 | 0.00 | 0.00 | −3.87 | 0.00 | 0.00 | −0.48 | −0.08 | 0.00 | 0.00 | 0.00 |
| 136 | ADHEr, ME2, PFLi, SUCD4 | 10.05 | 0.47 | 22.71 | 0.00 | 15.04 | 0.00 | 0.00 | −20.00 | 0.00 | 26.02 | 13.54 | 0.00 | 0.00 | −4.03 | 0.00 | 0.00 | −0.50 | −0.08 | 0.00 | 0.00 | 0.00 |
| 137 | ADHEr, MDH, NADH6, PFLi | 10.04 | 0.47 | 22.67 | 0.00 | 15.02 | 0.00 | 0.00 | −20.00 | 0.00 | 26.01 | 13.59 | 0.00 | 0.00 | −4.06 | 0.00 | 0.00 | −0.50 | −0.08 | 0.00 | 0.00 | 0.00 |
| 138 | ADHEr, PFLi, PPCK, RPE | 10.02 | 0.50 | 22.14 | 0.00 | 15.00 | 0.00 | 0.00 | −20.00 | 0.00 | 25.67 | 14.08 | 0.00 | 0.00 | −4.30 | 0.00 | 0.00 | −0.53 | −0.09 | 0.00 | 0.00 | 0.00 |
| 139 | ADHEr, PFLi, PPCK, TAL | 9.99 | 0.50 | 22.22 | 0.00 | 14.95 | 0.00 | 0.00 | −20.00 | 0.00 | 25.76 | 14.07 | 0.00 | 0.00 | −4.30 | 0.00 | 0.00 | −0.53 | −0.09 | 0.00 | 0.00 | 0.00 |
| 140 | ADHEr, PFLi, GLUDy, | 9.98 | 0.49 | 22.45 | 0.00 | 14.95 | 0.00 | 0.00 | −20.00 | 0.00 | 25.91 | 13.88 | 0.00 | 0.00 | −4.21 | 0.00 | 0.00 | −0.52 | −0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 141 | PFLi, SUCD4 | 9.96 | 0.49 | 22.36 | 0.00 | 14.92 | 0.00 | 0.00 | −20.00 | 0.00 | 25.87 | 13.99 | 0.00 | 0.00 | −4.27 | 0.00 | 0.00 | −0.53 | −0.09 | 0.00 | 0.00 | 0.00 |
| 142 | ADHEr, CBMK2, PFLi, PPCK | 9.92 | 0.57 | 20.45 | 0.00 | 15.84 | 0.00 | 0.00 | −20.00 | 0.00 | 24.48 | 16.33 | 0.00 | 0.00 | −4.91 | −2.00 | 0.00 | −0.61 | −0.10 | 0.00 | 0.00 | 0.00 |
| 143 | ADHEr, ATPS4r, LDH_D, SUCD4 | 9.90 | 0.54 | 21.57 | 0.00 | 14.81 | 0.00 | 0.00 | −20.00 | 0.00 | 25.41 | 14.82 | 0.00 | 0.00 | −4.67 | 0.00 | 0.00 | −0.58 | −0.09 | 0.00 | 0.00 | 0.00 |
| 144 | ADHEr, PFLi, RPE, SUCD4 | 9.86 | 0.85 | 10.32 | 0.00 | 24.74 | 0.00 | 0.00 | −20.00 | 0.00 | 16.34 | 30.40 | 0.00 | 0.00 | −7.33 | −20.00 | 0.00 | −0.91 | −0.15 | 0.00 | 0.00 | 0.00 |
| 145 | ADHEr, ACKr, CBMK2, NADH6 | 9.86 | 0.54 | 21.64 | 0.00 | 14.75 | 0.00 | 0.00 | −20.00 | 0.00 | 25.50 | 14.84 | 0.00 | 0.00 | −4.70 | 0.00 | 0.00 | −0.58 | −0.09 | 0.00 | 0.00 | 0.00 |
| 146 | ADHEr, PFLi, SUCD4, TAL | 9.86 | 0.85 | 10.32 | 0.00 | 24.73 | 0.00 | 0.00 | −20.00 | 0.00 | 16.34 | 30.41 | 0.00 | 0.00 | −7.34 | −20.00 | 0.00 | −0.91 | −0.15 | 0.00 | 0.00 | 0.00 |
| 147 | ADHEr, ACKr, NADH6, RPE | 9.84 | 0.85 | 10.30 | 0.00 | 24.70 | 0.00 | 0.00 | −20.00 | 0.00 | 16.35 | 30.45 | 0.00 | 0.00 | −7.36 | −20.00 | 0.00 | −0.91 | −0.15 | 0.00 | 0.00 | 0.00 |
| 148 | ADHEr, ACKr, FUM, NADH6 | 9.83 | 0.85 | 10.30 | 0.00 | 24.70 | 0.00 | 0.00 | −20.00 | 0.00 | 16.35 | 30.47 | 0.00 | 0.00 | −7.37 | −20.00 | 0.00 | −0.91 | −0.15 | 0.00 | 0.00 | 0.00 |
| 149 | ADHEr, ACKr, NADH6, TAL | 9.83 | 0.85 | 10.29 | 0.00 | 24.69 | 0.00 | 0.00 | −20.00 | 0.00 | 16.35 | 30.48 | 0.00 | 0.00 | −7.38 | −20.00 | 0.00 | −0.91 | −0.15 | 0.00 | 0.00 | 0.00 |
| 150 | ADHEr, ASNS2, NADH6 | 9.83 | 0.54 | 21.78 | 0.00 | 14.70 | 0.00 | 0.00 | −20.00 | 0.00 | 25.62 | 14.78 | 0.00 | 0.00 | −4.68 | 0.00 | 0.00 | −0.58 | −0.09 | 0.00 | 0.00 | 0.00 |
| 151 | ADHEr, CBMK2, PFLi, SUCD4 | 9.83 | 0.85 | 10.29 | 0.00 | 24.68 | 0.00 | 0.00 | −20.00 | 0.00 | 16.36 | 30.49 | 0.00 | 0.00 | −7.38 | −20.00 | 0.00 | −0.91 | −0.15 | 0.00 | 0.00 | 0.00 |
| 152 | ADHEr, ACKr, NADH12, NADH6 | 9.82 | 0.85 | 10.28 | 0.00 | 24.67 | 0.00 | 0.00 | −20.00 | 0.00 | 16.36 | 30.51 | 0.00 | 0.00 | −7.39 | −20.00 | 0.00 | −0.91 | −0.15 | 0.00 | 0.00 | 0.00 |
| | ADHEr, ACKr, NADH6, SO4t2 | | | | | | | | | | | | | | | | | | | | | |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 153 | ADHEr, NADH12, NADH6, PFLi | 9.81 | 0.55 | 21.71 | 0.00 | 14.68 | 0.00 | 0.00 | −20.00 | 0.00 | 25.59 | 14.87 | 0.00 | 0.00 | −4.72 | 0.00 | 0.00 | −0.58 | −0.10 | 0.00 | 0.00 | 0.00 |
| 154 | ADHEr, FUM, NADH6, PFLi | 9.80 | 0.55 | 21.69 | 0.00 | 14.67 | 0.00 | 0.00 | −20.00 | 0.00 | 25.58 | 14.89 | 0.00 | 0.00 | −4.73 | 0.00 | 0.00 | −0.59 | −0.10 | 0.00 | 0.00 | 0.00 |
| 155 | ADHEr, ACKr, PGI, SUCD4 | 9.80 | 0.22 | 9.92 | 0.00 | 12.33 | 11.06 | 0.00 | −20.00 | 0.00 | 30.56 | 12.62 | 0.00 | 0.00 | −6.04 | 0.00 | 0.00 | −0.23 | −0.04 | 1.94 | 0.00 | 4.15 |
| 156 | ADHEr, NADH6, PFLi, TAL | 9.75 | 0.58 | 21.19 | 0.00 | 14.60 | 0.00 | 0.00 | −20.00 | 0.00 | 25.30 | 15.43 | 0.00 | 0.00 | −5.00 | 0.00 | 0.00 | −0.62 | −0.10 | 0.00 | 0.00 | 0.00 |
| 157 | ADHEr, CBMK2, NADH6, PFLi | 9.72 | 0.58 | 21.33 | 0.00 | 14.55 | 0.00 | 0.00 | −20.00 | 0.00 | 25.43 | 15.37 | 0.00 | 0.00 | −4.98 | 0.00 | 0.00 | −0.62 | −0.10 | 0.00 | 0.00 | 0.00 |
| 158 | ADHEr, FUM, HEX1, PFLi | 9.55 | 0.63 | 20.62 | 0.00 | 14.29 | 0.00 | 0.00 | −20.00 | 0.00 | 25.11 | 16.32 | 0.00 | 0.00 | −5.47 | 0.00 | 0.00 | −0.68 | −0.11 | 0.00 | 0.00 | 0.00 |
| 159 | ADHEr, MDH, NADH6, THD2 | 9.34 | 0.55 | 19.65 | 0.00 | 7.38 | 13.18 | 0.00 | −20.00 | 0.00 | 36.73 | 8.10 | 0.00 | 0.00 | −4.75 | 0.00 | 0.00 | −0.59 | −0.10 | 0.00 | 0.00 | 0.00 |
| 160 | ADHEr, ATPS4r, MDH, NADH6 | 9.28 | 0.55 | 19.75 | 0.00 | 7.20 | 13.35 | 0.00 | −20.00 | 0.00 | 37.01 | 8.00 | 0.00 | 0.00 | −4.76 | 0.00 | 0.00 | −0.59 | −0.10 | 0.00 | 0.00 | 0.00 |
| 161 | ADHEr, ATPS4r, FUM, NADH6 | 9.03 | 0.63 | 21.22 | 0.00 | 11.62 | 3.77 | 0.00 | −20.00 | 0.00 | 29.45 | 14.08 | 0.00 | 0.00 | −5.43 | 0.00 | 0.00 | −0.67 | −0.11 | 0.00 | 0.00 | 0.00 |
| 162 | ADHEr, ATPS4r, PGI, PPCK | 8.97 | 0.26 | 23.60 | 0.00 | 0.95 | 24.98 | 0.00 | −20.00 | 0.00 | 50.46 | −3.19 | 0.00 | 0.00 | −2.28 | 0.00 | 0.00 | −0.28 | −0.05 | 0.00 | 0.00 | 0.00 |
| 163 | ADHEr, ASPT, MDH, NADH6 | 8.65 | 0.48 | 19.82 | 0.00 | −0.06 | 26.01 | 0.00 | −20.00 | 0.00 | 49.23 | 0.03 | 0.00 | 0.00 | −4.13 | 0.00 | 0.00 | −0.51 | −0.08 | 0.00 | 0.00 | 0.00 |
| 164 | ADHEr, ATPS4r, NADH6, PPCK | 8.62 | 0.48 | 23.04 | 0.00 | 6.28 | 13.23 | 0.00 | −20.00 | 0.00 | 39.68 | 6.46 | 0.00 | 0.00 | −4.15 | 0.00 | 0.00 | −0.51 | −0.08 | 0.00 | 0.00 | 0.00 |
| 165 | ADHEr, ASPT, MDH, THD2 | 8.60 | 0.50 | 18.60 | 0.00 | −1.82 | 29.38 | 0.00 | −20.00 | 0.00 | 51.55 | −1.24 | 0.00 | 0.00 | −4.34 | 0.00 | 0.00 | −0.54 | −0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 166 | ADHEr, ATPS4r, GLCpts, SUCD4 | 8.49 | 0.65 | 21.41 | 0.00 | 14.16 | 2.07 | 0.00 | −20.00 | 0.00 | 28.11 | 17.57 | 0.00 | 0.00 | −5.62 | −5.00 | 0.00 | −0.70 | −0.11 | 0.00 | 0.00 | 0.00 |
| 167 | ADHEr, ASPT, MDH, PGI | 8.36 | 0.23 | 23.87 | 0.00 | −4.10 | 33.24 | 0.00 | −20.00 | 0.00 | 58.77 | −8.18 | 0.00 | 0.00 | −2.02 | 0.00 | 0.00 | −0.25 | −0.04 | 0.00 | 0.00 | 0.00 |
| 168 | ADHEr, ASPT, FBA, MDH | 8.27 | 0.24 | 24.01 | 0.00 | −4.27 | 33.31 | 0.00 | −20.00 | 0.00 | 59.01 | −8.17 | 0.00 | 0.00 | −2.06 | 0.00 | 0.00 | −0.25 | −0.04 | 0.00 | 0.00 | 0.00 |
| 169 | ADHEr, ASPT, MDH, PFK | 8.27 | 0.24 | 24.01 | 0.00 | −4.27 | 33.31 | 0.00 | −20.00 | 0.00 | 59.01 | −8.17 | 0.00 | 0.00 | −2.06 | 0.00 | 0.00 | −0.25 | −0.04 | 0.00 | 0.00 | 0.00 |
| 170 | ADHEr, ASPT, MDH, TPI | 8.27 | 0.24 | 24.01 | 0.00 | −4.27 | 33.31 | 0.00 | −20.00 | 0.00 | 59.01 | −8.17 | 0.00 | 0.00 | −2.06 | 0.00 | 0.00 | −0.25 | −0.04 | 0.00 | 0.00 | 0.00 |
| 171 | ADHEr, ATPS4r, PFK, PPCK | 8.26 | 0.26 | 27.70 | 0.00 | 3.99 | 16.78 | 0.00 | −20.00 | 0.00 | 46.33 | 0.48 | 0.00 | 0.00 | −2.25 | 0.00 | 0.00 | −0.28 | −0.05 | 0.00 | 0.00 | 0.00 |
| 172 | ADHEr, ATPS4r, FBA, PPCK | 8.26 | 0.26 | 27.70 | 0.00 | 3.99 | 16.78 | 0.00 | −20.00 | 0.00 | 46.33 | 0.48 | 0.00 | 0.00 | −2.25 | 0.00 | 0.00 | −0.28 | −0.05 | 0.00 | 0.00 | 0.00 |
| 173 | ADHEr, ATPS4r, PPCK, TPI | 8.26 | 0.26 | 27.70 | 0.00 | 3.99 | 16.78 | 0.00 | −20.00 | 0.00 | 46.33 | 0.48 | 0.00 | 0.00 | −2.25 | 0.00 | 0.00 | −0.28 | −0.05 | 0.00 | 0.00 | 0.00 |
| 174 | ADHEr, ACKr, EDA, PGI | 8.12 | 0.45 | 8.36 | 0.00 | 1.85 | 10.72 | 0.00 | −20.00 | 0.00 | 42.04 | 11.87 | 0.00 | 0.00 | −3.90 | 0.00 | 0.00 | −0.48 | −0.08 | 9.88 | 0.00 | 0.00 |
| 175 | ADHEr, ATPS4r, HEX1, NADH6 | 7.99 | 0.67 | 21.56 | 0.00 | 6.75 | 10.40 | 0.00 | −20.00 | 0.00 | 36.71 | 11.00 | 0.00 | 0.00 | −5.78 | 0.00 | 0.00 | −0.72 | −0.12 | 0.00 | 0.00 | 0.00 |
| 176 | ADHEr, NADH6, PPCK, THD2 | 7.88 | 0.50 | 23.49 | 0.00 | 2.67 | 18.21 | 0.00 | −20.00 | 0.00 | 45.24 | 3.90 | 0.00 | 0.00 | −4.30 | 0.00 | 0.00 | −0.53 | −0.09 | 0.00 | 0.00 | 0.00 |
| 177 | ADHEr, ATPS4r, GLUDy, MDH | 7.87 | 0.46 | 22.87 | 0.00 | −0.07 | 23.70 | 0.00 | −20.00 | 0.00 | 49.84 | 0.51 | 0.00 | 0.00 | −3.99 | 0.00 | 0.00 | −0.49 | −0.08 | 0.00 | 0.00 | 0.00 |
| 178 | ADHEr, ATPS4r, MDH, PPCK | 7.86 | 0.49 | 22.44 | 0.00 | 0.04 | 23.43 | 0.00 | −20.00 | 0.00 | 49.33 | 1.11 | 0.00 | 0.00 | −4.22 | 0.00 | 0.00 | −0.52 | −0.09 | 0.00 | 0.00 | 0.00 |
| 179 | ADHEr, ATPS4r, FUM, PPCK | 7.86 | 0.49 | 22.44 | 0.00 | 0.04 | 23.43 | 0.00 | −20.00 | 0.00 | 49.33 | 1.11 | 0.00 | 0.00 | −4.22 | 0.00 | 0.00 | −0.52 | −0.09 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 180 | ADHEr, ENO, NADH6, RPE | 7.84 | 0.08 | 30.83 | 0.00 | 10.05 | 13.42 | 0.00 | −20.00 | 0.00 | 44.85 | 3.75 | 0.00 | 0.00 | −0.73 | −10.00 | 0.00 | −0.09 | −0.01 | 0.00 | 0.00 | 0.00 |
| 181 | ADHEr, NADH6, PGM, RPE | 7.84 | 0.08 | 30.83 | 0.00 | 10.05 | 13.42 | 0.00 | −20.00 | 0.00 | 44.85 | 3.75 | 0.00 | 0.00 | −0.73 | −10.00 | 0.00 | −0.09 | −0.01 | 0.00 | 0.00 | 0.00 |
| 182 | ADHEr, NADH6, PGM, TAL | 7.83 | 0.08 | 30.84 | 0.00 | 10.02 | 13.45 | 0.00 | −20.00 | 0.00 | 44.90 | 3.73 | 0.00 | 0.00 | −0.73 | −10.00 | 0.00 | −0.09 | −0.01 | 0.00 | 0.00 | 0.00 |
| 183 | ADHEr, ENO, NADH6, TAL | 7.83 | 0.08 | 30.84 | 0.00 | 10.02 | 13.45 | 0.00 | −20.00 | 0.00 | 44.90 | 3.73 | 0.00 | 0.00 | −0.73 | −10.00 | 0.00 | −0.09 | −0.01 | 0.00 | 0.00 | 0.00 |
| 184 | ADHEr, ASPT, GLCpts, MDH | 7.70 | 0.46 | 21.57 | 0.00 | −4.11 | 31.25 | 0.00 | −20.00 | 0.00 | 56.07 | −3.46 | 0.00 | 0.00 | −3.94 | 0.00 | 0.00 | −0.49 | −0.08 | 0.00 | 0.00 | 0.00 |
| 185 | ADHEr, ASPT, MDH, RPE | 7.65 | 0.52 | 20.47 | 0.00 | −3.75 | 30.40 | 0.00 | −20.00 | 0.00 | 54.60 | −1.79 | 0.00 | 0.00 | −4.54 | 0.00 | 0.00 | −0.56 | −0.09 | 0.00 | 0.00 | 0.00 |
| 186 | ADHEr, ASPT, GLUDy, MDH | 7.65 | 0.47 | 21.39 | 0.00 | −4.10 | 31.10 | 0.00 | −20.00 | 0.00 | 55.85 | −3.11 | 0.00 | 0.00 | −4.08 | 0.00 | 0.00 | −0.51 | −0.08 | 0.00 | 0.00 | 0.00 |
| 187 | ADHEr, ME2, NADH6, THD2 | 7.62 | 0.87 | 17.24 | 0.00 | 18.87 | 0.00 | 0.00 | −20.00 | 0.00 | 23.43 | 27.21 | 0.00 | 0.00 | −7.53 | −15.00 | 0.00 | −0.93 | −0.15 | 0.00 | 0.00 | 0.00 |
| 188 | ADHEr, ME2, SUCD4, THD2 | 7.61 | 0.52 | 22.02 | 0.00 | −0.99 | 24.76 | 0.00 | −20.00 | 0.00 | 50.50 | 0.98 | 0.00 | 0.00 | −4.53 | 0.00 | 0.00 | −0.56 | −0.09 | 0.00 | 0.00 | 0.00 |
| 189 | ADHEr, ASPT, MDH, TAL | 7.58 | 0.53 | 20.61 | 0.00 | −3.90 | 30.48 | 0.00 | −20.00 | 0.00 | 54.83 | −1.83 | 0.00 | 0.00 | −4.56 | 0.00 | 0.00 | −0.56 | −0.09 | 0.00 | 0.00 | 0.00 |
| 190 | ADHEr, NADH6, PGI, PPCK | 7.58 | 0.23 | 28.71 | 0.00 | 0.18 | 22.36 | 0.00 | −20.00 | 0.00 | 52.73 | −3.12 | 0.00 | 0.00 | −2.02 | 0.00 | 0.00 | −0.25 | −0.04 | 0.00 | 0.00 | 0.00 |
| 191 | ADHEr, FUM, PPCK, THD2 | 7.55 | 0.49 | 22.66 | 0.00 | −1.33 | 25.25 | 0.00 | −20.00 | 0.00 | 51.43 | 0.18 | 0.00 | 0.00 | −4.28 | 0.00 | 0.00 | −0.53 | −0.09 | 0.00 | 0.00 | 0.00 |
| 192 | ADHEr, MDH, PPCK, THD2 | 7.55 | 0.49 | 22.66 | 0.00 | −1.33 | 25.25 | 0.00 | −20.00 | 0.00 | 51.43 | 0.18 | 0.00 | 0.00 | −4.28 | 0.00 | 0.00 | −0.53 | −0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 193 | ADHEr, GLUDy, MDH, THD2 | 7.56 | 0.47 | 23.10 | 0.00 | −1.46 | 25.55 | 0.00 | −20.00 | 0.00 | 51.99 | −0.44 | 0.00 | 0.00 | −4.05 | 0.00 | 0.00 | −0.50 | −0.08 | 0.00 | 0.00 | 0.00 |
| 194 | ADHEr, ASPT, CBMK2, MDH | 7.52 | 0.52 | 20.82 | 0.00 | −4.06 | 30.61 | 0.00 | −20.00 | 0.00 | 55.15 | −1.99 | 0.00 | 0.00 | −4.53 | 0.00 | 0.00 | −0.56 | −0.09 | 0.00 | 0.00 | 0.00 |
| 195 | ADHEr, ATPS4r, FBA, SUCD4 | 7.51 | 0.42 | 25.99 | 0.00 | 6.86 | 13.76 | 0.00 | −20.00 | 0.00 | 42.72 | 7.01 | 0.00 | 0.00 | −3.62 | −5.00 | 0.00 | −0.45 | −0.07 | 0.00 | 0.00 | 0.00 |
| 196 | ADHEr, ATPS4r, PFK, SUCD4 | 7.51 | 0.42 | 25.99 | 0.00 | 6.86 | 13.76 | 0.00 | −20.00 | 0.00 | 42.72 | 7.01 | 0.00 | 0.00 | −3.62 | −5.00 | 0.00 | −0.45 | −0.07 | 0.00 | 0.00 | 0.00 |
| 197 | ADHEr, ATPS4r, SUCD4, TPI | 7.51 | 0.42 | 25.99 | 0.00 | 6.86 | 13.76 | 0.00 | −20.00 | 0.00 | 42.72 | 7.01 | 0.00 | 0.00 | −3.62 | −5.00 | 0.00 | −0.45 | −0.07 | 0.00 | 0.00 | 0.00 |
| 198 | ADHEr, FBA, NADH6, PPCK | 7.50 | 0.24 | 28.80 | 0.00 | −0.03 | 22.54 | 0.00 | −20.00 | 0.00 | 53.03 | −3.17 | 0.00 | 0.00 | −2.06 | 0.00 | 0.00 | −0.25 | −0.04 | 0.00 | 0.00 | 0.00 |
| 199 | ADHEr, NADH6, PFK, PPCK | 7.50 | 0.24 | 28.80 | 0.00 | −0.03 | 22.54 | 0.00 | −20.00 | 0.00 | 53.03 | −3.17 | 0.00 | 0.00 | −2.06 | 0.00 | 0.00 | −0.25 | −0.04 | 0.00 | 0.00 | 0.00 |
| 200 | ADHEr, NADH6, PPCK, TPI | 7.50 | 0.24 | 28.80 | 0.00 | −0.03 | 22.54 | 0.00 | −20.00 | 0.00 | 53.03 | −3.17 | 0.00 | 0.00 | −2.06 | 0.00 | 0.00 | −0.25 | −0.04 | 0.00 | 0.00 | 0.00 |
| 201 | ADHEr, HEX1, PFLi, THD2 | 7.47 | 0.69 | 14.32 | 0.00 | 8.09 | 0.00 | 0.00 | −20.00 | 0.00 | 31.52 | 19.49 | 0.00 | 0.00 | −6.01 | 0.00 | 0.00 | −0.74 | −0.12 | 0.00 | 0.00 | 0.00 |
| 202 | ADHEr, HEX1, NADH6, PFK | 7.46 | 0.26 | 28.53 | 0.00 | −0.04 | 22.42 | 0.00 | −20.00 | 0.00 | 52.78 | −2.76 | 0.00 | 0.00 | −2.23 | 0.00 | 0.00 | −0.28 | −0.05 | 0.00 | 0.00 | 0.00 |
| 203 | ADHEr, FBA, HEX1, NADH6 | 7.46 | 0.26 | 28.53 | 0.00 | −0.04 | 22.42 | 0.00 | −20.00 | 0.00 | 52.78 | −2.76 | 0.00 | 0.00 | −2.23 | 0.00 | 0.00 | −0.28 | −0.05 | 0.00 | 0.00 | 0.00 |
| 204 | ADHEr, HEX1, NADH6, TPI | 7.46 | 0.26 | 28.53 | 0.00 | −0.04 | 22.42 | 0.00 | −20.00 | 0.00 | 52.78 | −2.76 | 0.00 | 0.00 | −2.23 | 0.00 | 0.00 | −0.28 | −0.05 | 0.00 | 0.00 | 0.00 |
| 205 | ADHEr, ATPS4r, G6PDHy, MDH | 7.44 | 0.58 | 13.04 | 0.00 | 6.96 | 0.00 | 0.00 | −20.00 | 0.00 | 33.76 | 18.41 | 0.00 | 0.00 | −4.99 | 0.00 | 0.00 | −0.62 | −0.10 | 8.31 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 206 | ADHEr, ATPS4r, MDH, PGL | 7.44 | 0.58 | 13.04 | 0.00 | 6.96 | 0.00 | 0.00 | −20.00 | 0.00 | 33.76 | 18.41 | 0.00 | 0.00 | −4.99 | 0.00 | 0.00 | −0.62 | −0.10 | 8.31 | 0.00 | 0.00 |
| 207 | ADHEr, GLUDy, NADH6, PGI | 7.43 | 0.32 | 27.55 | 0.00 | 0.24 | 21.78 | 0.00 | −20.00 | 0.00 | 51.58 | −1.39 | 0.00 | 0.00 | −2.74 | 0.00 | 0.00 | −0.34 | −0.06 | 0.00 | 0.00 | 0.00 |
| 208 | ADHEr, ACKr, FRD2, LDH_D | 7.42 | 0.97 | 7.95 | 0.00 | 15.46 | 13.33 | 0.00 | −20.00 | 0.00 | 29.24 | 26.90 | 0.00 | 0.00 | −9.46 | −20.00 | 0.00 | −1.04 | −0.17 | 0.00 | 0.00 | 1.06 |
| 209 | ADHEr, ACKr, LDH_D, SUCD4 | 7.42 | 0.97 | 7.95 | 2.12 | 14.40 | 13.33 | 0.00 | −20.00 | 0.00 | 30.30 | 26.90 | 0.00 | 0.00 | −10.53 | −20.00 | 0.00 | −1.04 | −0.17 | 0.00 | 0.00 | 0.00 |
| 210 | ADHEr, ATPS4r, FUM, GLUDy | 7.38 | 0.54 | 24.25 | 0.00 | 2.47 | 17.14 | 0.00 | −20.00 | 0.00 | 45.22 | 4.95 | 0.00 | 0.00 | −4.66 | 0.00 | 0.00 | −0.58 | −0.09 | 0.00 | 0.00 | 0.00 |
| 211 | ADHEr, NADH6, PFK, RPE | 7.34 | 0.36 | 27.05 | 0.00 | 0.21 | 21.57 | 0.00 | −20.00 | 0.00 | 51.14 | −0.62 | 0.00 | 0.00 | −3.08 | 0.00 | 0.00 | −0.38 | −0.06 | 0.00 | 0.00 | 0.00 |
| 212 | ADHEr, FBA, NADH6, RPE | 7.34 | 0.36 | 27.05 | 0.00 | 0.21 | 21.57 | 0.00 | −20.00 | 0.00 | 51.14 | −0.62 | 0.00 | 0.00 | −3.08 | 0.00 | 0.00 | −0.38 | −0.06 | 0.00 | 0.00 | 0.00 |
| 213 | ADHEr, NADH6, RPE, TPI | 7.34 | 0.36 | 27.05 | 0.00 | 0.21 | 21.57 | 0.00 | −20.00 | 0.00 | 51.14 | −0.62 | 0.00 | 0.00 | −3.08 | 0.00 | 0.00 | −0.38 | −0.06 | 0.00 | 0.00 | 0.00 |
| 214 | ADHEr, FBA, GLUDy, NADH6 | 7.33 | 0.32 | 27.69 | 0.00 | −0.04 | 22.04 | 0.00 | −20.00 | 0.00 | 52.00 | −1.50 | 0.00 | 0.00 | −2.77 | 0.00 | 0.00 | −0.34 | −0.06 | 0.00 | 0.00 | 0.00 |
| 215 | ADHEr, GLUDy, NADH6, PFK | 7.33 | 0.32 | 27.69 | 0.00 | −0.04 | 22.04 | 0.00 | −20.00 | 0.00 | 52.00 | −1.50 | 0.00 | 0.00 | −2.77 | 0.00 | 0.00 | −0.34 | −0.06 | 0.00 | 0.00 | 0.00 |
| 216 | ADHEr, GLUDy, NADH6, TPI | 7.33 | 0.32 | 27.69 | 0.00 | −0.04 | 22.04 | 0.00 | −20.00 | 0.00 | 52.00 | −1.50 | 0.00 | 0.00 | −2.77 | 0.00 | 0.00 | −0.34 | −0.06 | 0.00 | 0.00 | 0.00 |
| 217 | ADHEr, ATPS4r, FUM, HEX1 | 7.31 | 0.66 | 21.12 | 0.00 | 0.90 | 20.04 | 0.00 | −20.00 | 0.00 | 45.88 | 5.75 | 0.00 | 0.00 | −5.74 | 0.00 | 0.00 | −0.71 | −0.12 | 0.00 | 0.00 | 0.00 |
| 218 | ADHEr, NADH6, TAL, TPI | 7.30 | 0.36 | 27.10 | 0.00 | 0.09 | 21.68 | 0.00 | −20.00 | 0.00 | 51.32 | −0.66 | 0.00 | 0.00 | −3.09 | 0.00 | 0.00 | −0.38 | −0.06 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 219 | ADHEr, NADH6, PFK, TAL | 7.30 | 0.36 | 27.10 | 0.00 | 0.09 | 21.68 | 0.00 | −20.00 | 0.00 | 51.32 | −0.66 | 0.00 | 0.00 | −3.09 | 0.00 | 0.00 | −0.38 | −0.06 | 0.00 | 0.00 | 0.00 |
| 220 | ADHEr, FBA, NADH6, TAL | 7.30 | 0.36 | 27.10 | 0.00 | 0.09 | 21.68 | 0.00 | −20.00 | 0.00 | 51.32 | −0.66 | 0.00 | 0.00 | −3.09 | 0.00 | 0.00 | −0.38 | −0.06 | 0.00 | 0.00 | 0.00 |
| 221 | ADHEr, ATPS4r, MDH, THD2 | 7.27 | 0.62 | 19.64 | 0.00 | −1.10 | 22.88 | 0.00 | −20.00 | 0.00 | 49.00 | 4.01 | 0.00 | 0.00 | −5.35 | 0.00 | 0.00 | −0.66 | −0.11 | 1.04 | 0.00 | 0.00 |
| 222 | ADHEr, GLUDy, MDH, NADH6 | 7.06 | 0.45 | 25.98 | 0.00 | −0.06 | 21.26 | 0.00 | −20.00 | 0.00 | 50.42 | 1.07 | 0.00 | 0.00 | −3.87 | 0.00 | 0.00 | −0.48 | −0.08 | 0.00 | 0.00 | 0.00 |
| 223 | ADHEr, GLCpts, NADH6, PPCK | 7.06 | 0.45 | 25.94 | 0.00 | −0.06 | 21.24 | 0.00 | −20.00 | 0.00 | 50.38 | 1.14 | 0.00 | 0.00 | −3.90 | 0.00 | 0.00 | −0.48 | −0.08 | 0.00 | 0.00 | 0.00 |
| 224 | ADHEr, NADH6, PPCK, RPE | 7.05 | 0.52 | 24.82 | 0.00 | 0.30 | 20.47 | 0.00 | −20.00 | 0.00 | 48.96 | 2.70 | 0.00 | 0.00 | −4.46 | 0.00 | 0.00 | −0.55 | −0.09 | 0.00 | 0.00 | 0.00 |
| 225 | ADHEr, GLUDy, NADH6, PPCK | 7.02 | 0.47 | 25.73 | 0.00 | −0.06 | 21.14 | 0.00 | −20.00 | 0.00 | 50.18 | 1.46 | 0.00 | 0.00 | −4.03 | 0.00 | 0.00 | −0.50 | −0.08 | 0.00 | 0.00 | 0.00 |
| 226 | ADHEr, FUM, NADH6, PPCK | 7.01 | 0.47 | 25.63 | 0.00 | −0.06 | 21.10 | 0.00 | −20.00 | 0.00 | 50.09 | 1.61 | 0.00 | 0.00 | −4.10 | 0.00 | 0.00 | −0.51 | −0.08 | 0.00 | 0.00 | 0.00 |
| 227 | ADHEr, MDH, NADH6, PPCK | 7.01 | 0.47 | 25.63 | 0.00 | −0.06 | 21.10 | 0.00 | −20.00 | 0.00 | 50.09 | 1.61 | 0.00 | 0.00 | −4.10 | 0.00 | 0.00 | −0.51 | −0.08 | 0.00 | 0.00 | 0.00 |
| 228 | ADHEr, ATPS4r, FRD2, LDH_D | 7.00 | 0.32 | 0.00 | 0.00 | 17.78 | 8.35 | 0.00 | −20.00 | 0.00 | 21.13 | 27.21 | 0.00 | 0.00 | −13.29 | −2.00 | 0.00 | −0.35 | −0.06 | 0.00 | 0.00 | 10.48 |
| 229 | ADHEr, NADH6, PPCK, TAL | 6.98 | 0.52 | 24.92 | 0.00 | 0.12 | 20.64 | 0.00 | −20.00 | 0.00 | 49.23 | 2.61 | 0.00 | 0.00 | −4.47 | 0.00 | 0.00 | −0.55 | −0.09 | 0.00 | 0.00 | 0.00 |
| 230 | ADHEr, FUM, GLUDy, NADH6 | 6.92 | 0.52 | 25.04 | 0.00 | −0.07 | 20.83 | 0.00 | −20.00 | 0.00 | 49.55 | 2.48 | 0.00 | 0.00 | −4.47 | 0.00 | 0.00 | −0.55 | −0.09 | 0.00 | 0.00 | 0.00 |
| 231 | ADHEr, GLCpts, MDH, NADH6 | 6.91 | 0.52 | 24.98 | 0.00 | −0.07 | 20.80 | 0.00 | −20.00 | 0.00 | 49.49 | 2.59 | 0.00 | 0.00 | −4.52 | 0.00 | 0.00 | −0.56 | −0.09 | 0.00 | 0.00 | 0.00 |

TABLE 7-continued

Knockout strategies derived by OptKnock assuming PEP carboxykinase to be reversible.

| Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|
| 232 ADHEr, MDH, NADH6, RPE | 6.91 | 0.59 | 23.79 | 0.00 | 0.34 | 19.96 | 0.00 | −20.00 | 0.00 | 47.94 | 4.24 | 0.00 | 0.00 | −5.10 | 0.00 | 0.00 | −0.63 | −0.10 | 0.00 | 0.00 | 0.00 |
| 233 ADHEr, MDH, NADH6, TAL | 6.84 | 0.59 | 23.91 | 0.00 | 0.14 | 20.16 | 0.00 | −20.00 | 0.00 | 48.26 | 4.13 | 0.00 | 0.00 | −5.11 | 0.00 | 0.00 | −0.63 | −0.10 | 0.00 | 0.00 | 0.00 |
| 234 ADHEr, HEX1, NADH6, THD2 | 6.83 | 0.92 | 18.08 | 0.00 | 17.16 | 1.07 | 0.00 | −20.00 | 0.00 | 25.70 | 27.21 | 0.00 | 0.00 | −7.98 | −15.00 | 0.00 | −0.99 | −0.16 | 0.00 | 0.00 | 0.00 |
| 235 ADHEr, FUM, NADH6, RPE | 6.77 | 0.66 | 22.78 | 0.00 | 0.38 | 19.47 | 0.00 | −20.00 | 0.00 | 46.96 | 5.73 | 0.00 | 0.00 | −5.72 | 0.00 | 0.00 | −0.71 | −0.12 | 0.00 | 0.00 | 0.00 |
| 236 ADHEr, CBMK2, MDH, NADH6 | 6.77 | 0.59 | 24.11 | 0.00 | −0.08 | 20.40 | 0.00 | −20.00 | 0.00 | 48.68 | 3.90 | 0.00 | 0.00 | −5.08 | 0.00 | 0.00 | −0.63 | −0.10 | 0.00 | 0.00 | 0.00 |
| 237 ADHEr, FUM, ME2, NADH6 | 6.76 | 0.59 | 24.04 | 0.00 | −0.08 | 20.37 | 0.00 | −20.00 | 0.00 | 48.62 | 4.00 | 0.00 | 0.00 | −5.12 | 0.00 | 0.00 | −0.63 | −0.10 | 0.00 | 0.00 | 0.00 |
| 238 ADHEr, FUM, NADH6, TAL | 6.69 | 0.66 | 22.89 | 0.00 | 0.16 | 19.68 | 0.00 | −20.00 | 0.00 | 47.29 | 5.65 | 0.00 | 0.00 | −5.75 | 0.00 | 0.00 | −0.71 | −0.12 | 0.00 | 0.00 | 0.00 |
| 239 ADHEr, ATPS4r, MDH, PGDH | 6.64 | 0.60 | 16.99 | 0.00 | 6.42 | 0.00 | 0.00 | −20.00 | 0.00 | 35.28 | 17.83 | 0.00 | 0.00 | −5.22 | 0.00 | 0.00 | −0.65 | −0.11 | 7.01 | 0.00 | 0.00 |
| 240 ADHEr, FUM, HEX1, NADH6 | 6.64 | 0.65 | 23.23 | 0.00 | −0.09 | 20.01 | 0.00 | −20.00 | 0.00 | 47.87 | 5.22 | 0.00 | 0.00 | −5.64 | 0.00 | 0.00 | −0.70 | −0.11 | 0.00 | 0.00 | 0.00 |
| 241 ADHEr, CBMK2, FUM, NADH6 | 6.61 | 0.66 | 23.09 | 0.00 | −0.09 | 19.94 | 0.00 | −20.00 | 0.00 | 47.74 | 5.43 | 0.00 | 0.00 | −5.73 | 0.00 | 0.00 | −0.71 | −0.12 | 0.00 | 0.00 | 0.00 |
| 242 ADHEr, GLCpts, PPCK, THD2 | 6.56 | 0.49 | 24.86 | 0.00 | −3.91 | 27.44 | 0.00 | −20.00 | 0.00 | 55.80 | −1.43 | 0.00 | 0.00 | −4.27 | 0.00 | 0.00 | −0.53 | −0.09 | 0.00 | 0.00 | 0.00 |
| 243 ADHEr, GLUDy, PPCK, THD2 | 6.56 | 0.50 | 24.67 | 0.00 | −3.84 | 27.31 | 0.00 | −20.00 | 0.00 | 55.57 | −1.17 | 0.00 | 0.00 | −4.36 | 0.00 | 0.00 | −0.54 | −0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 244 | ADHEr, CBMK2, NADH6, TAL | 6.49 | 0.77 | 21.51 | 0.00 | 5.18 | 14.02 | 0.00 | −20.00 | 0.00 | 40.97 | 12.72 | 0.00 | 0.00 | −6.63 | −5.00 | 0.00 | −0.82 | −0.13 | 0.00 | 0.00 | 0.00 |
| 245 | ADHEr, ATPS4r, MDH, TAL | 6.48 | 0.61 | 16.56 | 0.00 | 5.95 | 0.00 | 0.00 | −20.00 | 0.00 | 35.78 | 18.04 | 0.00 | 0.00 | −5.25 | 0.00 | 0.00 | −0.65 | −0.11 | 7.45 | 0.00 | 0.00 |
| 246 | ADHEr, ATPS4r, GLUDy, NADH6 | 6.45 | 0.65 | 22.52 | 0.00 | 1.91 | 16.48 | 0.00 | −20.00 | 0.00 | 45.54 | 8.28 | 0.00 | 0.00 | −5.60 | −2.00 | 0.00 | −0.69 | −0.11 | 0.97 | 0.00 | 0.00 |
| 247 | ADHEr, PGI, PPCK, SUCD4 | 6.33 | 0.22 | 30.11 | 0.00 | −6.16 | 31.28 | 0.00 | −20.00 | 0.00 | 62.99 | −8.37 | 0.00 | 0.00 | −1.95 | 0.00 | 0.00 | −0.24 | −0.04 | 0.00 | 0.00 | 0.00 |
| 248 | ADHEr, ATPS4r, MDH, RPE | 6.33 | 0.61 | 16.17 | 0.00 | 5.52 | 0.00 | 0.00 | −20.00 | 0.00 | 36.25 | 18.24 | 0.00 | 0.00 | −5.28 | 0.00 | 0.00 | −0.65 | −0.11 | 7.87 | 0.00 | 0.00 |
| 249 | ADHEr, FBP, PGM, THD2 | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 250 | ADHEr, ENO, FBP, THD2 | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 251 | ADHEr, FBA, PGM, THD2 | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 252 | ADHEr, ENO, FBA, THD2 | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 253 | ADHEr, ENO, THD2, TPI | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 254 | ADHEr, PGM, THD2, TPI | 6.33 | 0.03 | 33.21 | 0.00 | −6.19 | 33.35 | 0.00 | −20.00 | 0.00 | 66.75 | −12.02 | 0.00 | 0.00 | −0.23 | −2.00 | 0.00 | −0.03 | 0.00 | 0.00 | 0.00 | 0.00 |
| 255 | ADHEr, GLCpts, PGI, PPCK | 6.28 | 0.26 | 29.59 | 0.00 | −6.08 | 30.96 | 0.00 | −20.00 | 0.00 | 62.41 | −7.58 | 0.00 | 0.00 | −2.25 | 0.00 | 0.00 | −0.28 | −0.05 | 0.00 | 0.00 | 0.00 |
| 256 | ADHEr, FBA, HEX1, PPCK | 6.28 | 0.22 | 30.24 | 0.00 | −6.31 | 31.41 | 0.00 | −20.00 | 0.00 | 63.24 | −8.47 | 0.00 | 0.00 | −1.94 | 0.00 | 0.00 | −0.24 | −0.04 | 0.00 | 0.00 | 0.00 |
| 257 | ADHEr, HEX1, PFK, PPCK | 6.28 | 0.22 | 30.24 | 0.00 | −6.31 | 31.41 | 0.00 | −20.00 | 0.00 | 63.24 | −8.47 | 0.00 | 0.00 | −1.94 | 0.00 | 0.00 | −0.24 | −0.04 | 0.00 | 0.00 | 0.00 |
| 258 | ADHEr, HEX1, PPCK, TPI | 6.28 | 0.22 | 30.24 | 0.00 | −6.31 | 31.41 | 0.00 | −20.00 | 0.00 | 63.24 | −8.47 | 0.00 | 0.00 | −1.94 | 0.00 | 0.00 | −0.24 | −0.04 | 0.00 | 0.00 | 0.00 |

TABLE 7-continued

Knockout strategies derived by OptKnock assuming PEP carboxykinase to be reversible.

| Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|
| 259 ADHEr, PPCK, SUCD4, TPI | 6.27 | 0.23 | 30.17 | 0.00 | −6.30 | 31.37 | 0.00 | −20.00 | 0.00 | 63.17 | −8.37 | 0.00 | 0.00 | −1.98 | 0.00 | 0.00 | −0.25 | −0.04 | 0.00 | 0.00 | 0.00 |
| 260 ADHEr, PFK, PPCK, SUCD4 | 6.27 | 0.23 | 30.17 | 0.00 | −6.30 | 31.37 | 0.00 | −20.00 | 0.00 | 63.17 | −8.37 | 0.00 | 0.00 | −1.98 | 0.00 | 0.00 | −0.25 | −0.04 | 0.00 | 0.00 | 0.00 |
| 261 ADHEr, FBA, PPCK, SUCD4 | 6.27 | 0.23 | 30.17 | 0.00 | −6.30 | 31.37 | 0.00 | −20.00 | 0.00 | 63.17 | −8.37 | 0.00 | 0.00 | −1.98 | 0.00 | 0.00 | −0.25 | −0.04 | 0.00 | 0.00 | 0.00 |
| 262 ADHEr, GLUDy, PGI, PPCK | 6.26 | 0.27 | 29.44 | 0.00 | −6.06 | 30.86 | 0.00 | −20.00 | 0.00 | 62.23 | −7.35 | 0.00 | 0.00 | −2.35 | 0.00 | 0.00 | −0.29 | −0.05 | 0.00 | 0.00 | 0.00 |
| 263 ADHEr, GLCpts, PGI, SUCD4 | 6.24 | 0.28 | 29.26 | 0.00 | −6.03 | 30.74 | 0.00 | −20.00 | 0.00 | 62.02 | −7.06 | 0.00 | 0.00 | −2.46 | 0.00 | 0.00 | −0.30 | −0.05 | 0.00 | 0.00 | 0.00 |
| 264 ADHEr, FUM, GLUDy, PGI | 6.24 | 0.29 | 29.24 | 0.00 | −6.02 | 30.73 | 0.00 | −20.00 | 0.00 | 62.00 | −7.03 | 0.00 | 0.00 | −2.47 | 0.00 | 0.00 | −0.31 | −0.05 | 0.00 | 0.00 | 0.00 |
| 265 ADHEr, GLUDy, MDH, PGI | 6.24 | 0.29 | 29.24 | 0.00 | −6.02 | 30.73 | 0.00 | −20.00 | 0.00 | 62.00 | −7.03 | 0.00 | 0.00 | −2.47 | 0.00 | 0.00 | −0.31 | −0.05 | 0.00 | 0.00 | 0.00 |
| 266 ADHEr, FBA, HEX1, SUCD4 | 6.24 | 0.25 | 29.95 | 0.00 | −6.27 | 31.23 | 0.00 | −20.00 | 0.00 | 62.93 | −8.02 | 0.00 | 0.00 | −2.12 | 0.00 | 0.00 | −0.26 | −0.04 | 0.00 | 0.00 | 0.00 |
| 267 ADHEr, HEX1, SUCD4, TPI | 6.24 | 0.25 | 29.95 | 0.00 | −6.27 | 31.23 | 0.00 | −20.00 | 0.00 | 62.93 | −8.02 | 0.00 | 0.00 | −2.12 | 0.00 | 0.00 | −0.26 | −0.04 | 0.00 | 0.00 | 0.00 |
| 268 ADHEr, HEX1, PFK, SUCD4 | 6.24 | 0.25 | 29.95 | 0.00 | −6.27 | 31.23 | 0.00 | −20.00 | 0.00 | 62.93 | −8.02 | 0.00 | 0.00 | −2.12 | 0.00 | 0.00 | −0.26 | −0.04 | 0.00 | 0.00 | 0.00 |
| 269 ADHEr, GLUDy, PGI, SUCD4 | 6.23 | 0.29 | 29.14 | 0.00 | −6.01 | 30.67 | 0.00 | −20.00 | 0.00 | 61.88 | −6.88 | 0.00 | 0.00 | −2.53 | 0.00 | 0.00 | −0.31 | −0.05 | 0.00 | 0.00 | 0.00 |
| 270 ADHEr, FUM, HEX1, THD2 | 6.21 | 0.69 | 22.25 | 0.00 | −3.64 | 25.83 | 0.00 | −20.00 | 0.00 | 52.95 | 2.71 | 0.00 | 0.00 | −5.93 | 0.00 | 0.00 | −0.73 | −0.12 | 0.00 | 0.00 | 0.00 |
| 271 ADHEr, FBA, GLCpts, PPCK | 6.21 | 0.26 | 29.69 | 0.00 | −6.24 | 31.07 | 0.00 | −20.00 | 0.00 | 62.64 | −7.61 | 0.00 | 0.00 | −2.29 | 0.00 | 0.00 | −0.28 | −0.05 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 272 | ADHEr, GLCpts, PFK, PPCK | 6.21 | 0.26 | 29.69 | 0.00 | −6.24 | 31.07 | 0.00 | −20.00 | 0.00 | 62.64 | −7.61 | 0.00 | 0.00 | −2.29 | 0.00 | 0.00 | −0.28 | −0.05 | 0.00 | 0.00 | 0.00 |
| 273 | ADHEr, GLCpts, PPCK, TPI | 6.21 | 0.26 | 29.69 | 0.00 | −6.24 | 31.07 | 0.00 | −20.00 | 0.00 | 62.64 | −7.61 | 0.00 | 0.00 | −2.29 | 0.00 | 0.00 | −0.28 | −0.05 | 0.00 | 0.00 | 0.00 |
| 274 | ADHEr, PFK, PPCK, RPE | 6.20 | 0.30 | 29.01 | 0.00 | −6.02 | 30.60 | 0.00 | −20.00 | 0.00 | 61.77 | −6.66 | 0.00 | 0.00 | −2.63 | 0.00 | 0.00 | −0.32 | −0.05 | 0.00 | 0.00 | 0.00 |
| 275 | ADHEr, PPCK, RPE, TPI | 6.20 | 0.30 | 29.01 | 0.00 | −6.02 | 30.60 | 0.00 | −20.00 | 0.00 | 61.77 | −6.66 | 0.00 | 0.00 | −2.63 | 0.00 | 0.00 | −0.32 | −0.05 | 0.00 | 0.00 | 0.00 |
| 276 | ADHEr, FBA, PPCK, RPE | 6.20 | 0.30 | 29.01 | 0.00 | −6.02 | 30.60 | 0.00 | −20.00 | 0.00 | 61.77 | −6.66 | 0.00 | 0.00 | −2.63 | 0.00 | 0.00 | −0.32 | −0.05 | 0.00 | 0.00 | 0.00 |
| 277 | ADHEr, GLUDy, PFK, PPCK | 6.19 | 0.27 | 29.54 | 0.00 | −6.23 | 30.98 | 0.00 | −20.00 | 0.00 | 62.47 | −7.38 | 0.00 | 0.00 | −2.38 | 0.00 | 0.00 | −0.29 | −0.05 | 0.00 | 0.00 | 0.00 |
| 278 | ADHEr, GLUDy, PPCK, TPI | 6.19 | 0.27 | 29.54 | 0.00 | −6.23 | 30.98 | 0.00 | −20.00 | 0.00 | 62.47 | −7.38 | 0.00 | 0.00 | −2.38 | 0.00 | 0.00 | −0.29 | −0.05 | 0.00 | 0.00 | 0.00 |
| 279 | ADHEr, FBA, GLUDy, PPCK | 6.19 | 0.27 | 29.54 | 0.00 | −6.23 | 30.98 | 0.00 | −20.00 | 0.00 | 62.47 | −7.38 | 0.00 | 0.00 | −2.38 | 0.00 | 0.00 | −0.29 | −0.05 | 0.00 | 0.00 | 0.00 |
| 280 | ADHEr, ATPS4r, ME2, THD2 | 6.19 | 0.71 | 21.49 | 0.00 | −2.37 | 25.20 | 0.00 | −20.00 | 0.00 | 51.73 | 4.44 | 0.00 | 0.00 | −6.13 | −2.00 | 0.00 | −0.76 | −0.12 | 0.00 | 0.00 | 0.00 |
| 281 | ADHEr, HEX1, PFK, RPE | 6.18 | 0.32 | 28.82 | 0.00 | −5.99 | 30.48 | 0.00 | −20.00 | 0.00 | 61.55 | −6.36 | 0.00 | 0.00 | −2.74 | 0.00 | 0.00 | −0.34 | −0.06 | 0.00 | 0.00 | 0.00 |
| 282 | ADHEr, HEX1, RPE, TPI | 6.18 | 0.32 | 28.82 | 0.00 | −5.99 | 30.48 | 0.00 | −20.00 | 0.00 | 61.55 | −6.36 | 0.00 | 0.00 | −2.74 | 0.00 | 0.00 | −0.34 | −0.06 | 0.00 | 0.00 | 0.00 |
| 283 | ADHEr, FBA, HEX1, RPE | 6.18 | 0.32 | 28.82 | 0.00 | −5.99 | 30.48 | 0.00 | −20.00 | 0.00 | 61.55 | −6.36 | 0.00 | 0.00 | −2.74 | 0.00 | 0.00 | −0.34 | −0.06 | 0.00 | 0.00 | 0.00 |
| 284 | ADHEr, FBA, PPCK, TAL | 6.17 | 0.31 | 29.05 | 0.00 | −6.09 | 30.65 | 0.00 | −20.00 | 0.00 | 61.87 | −6.67 | 0.00 | 0.00 | −2.64 | 0.00 | 0.00 | −0.33 | −0.05 | 0.00 | 0.00 | 0.00 |
| 285 | ADHEr, PPCK, TAL, TPI | 6.17 | 0.31 | 29.05 | 0.00 | −6.09 | 30.65 | 0.00 | −20.00 | 0.00 | 61.87 | −6.67 | 0.00 | 0.00 | −2.64 | 0.00 | 0.00 | −0.33 | −0.05 | 0.00 | 0.00 | 0.00 |
| 286 | ADHEr, PFK, PPCK, TAL | 6.17 | 0.31 | 29.05 | 0.00 | −6.09 | 30.65 | 0.00 | −20.00 | 0.00 | 61.87 | −6.67 | 0.00 | 0.00 | −2.64 | 0.00 | 0.00 | −0.33 | −0.05 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 287 | ADHEr, ATPS4r, GLUDy, PPCK | 6.17 | 0.55 | 24.36 | 0.00 | −3.40 | 27.23 | 0.00 | −20.00 | 0.00 | 55.50 | 0.48 | 0.00 | 0.00 | −4.75 | −2.00 | 0.00 | −0.59 | −0.10 | 0.00 | 0.00 | 0.00 |
| 288 | ADHEr, FBA, GLUDy, HEX1 | 6.17 | 0.29 | 29.36 | 0.00 | −6.20 | 30.87 | 0.00 | −20.00 | 0.00 | 62.28 | −7.10 | 0.00 | 0.00 | −2.49 | 0.00 | 0.00 | −0.31 | −0.05 | 0.00 | 0.00 | 0.00 |
| 289 | ADHEr, GLUDy, HEX1, TPI | 6.17 | 0.29 | 29.36 | 0.00 | −6.20 | 30.87 | 0.00 | −20.00 | 0.00 | 62.28 | −7.10 | 0.00 | 0.00 | −2.49 | 0.00 | 0.00 | −0.31 | −0.05 | 0.00 | 0.00 | 0.00 |
| 290 | ADHEr, GLUDy, HEX1, PFK | 6.17 | 0.29 | 29.36 | 0.00 | −6.20 | 30.87 | 0.00 | −20.00 | 0.00 | 62.28 | −7.10 | 0.00 | 0.00 | −2.49 | 0.00 | 0.00 | −0.31 | −0.05 | 0.00 | 0.00 | 0.00 |
| 291 | ADHEr, GLCpts, SUCD4, TPI | 6.16 | 0.29 | 29.36 | 0.00 | −6.20 | 30.86 | 0.00 | −20.00 | 0.00 | 62.27 | −7.09 | 0.00 | 0.00 | −2.49 | 0.00 | 0.00 | −0.31 | −0.05 | 0.00 | 0.00 | 0.00 |
| 292 | ADHEr, FBA, GLCpts, SUCD4 | 6.16 | 0.29 | 29.36 | 0.00 | −6.20 | 30.86 | 0.00 | −20.00 | 0.00 | 62.27 | −7.09 | 0.00 | 0.00 | −2.49 | 0.00 | 0.00 | −0.31 | −0.05 | 0.00 | 0.00 | 0.00 |
| 293 | ADHEr, GLCpts, PFK, SUCD4 | 6.16 | 0.29 | 29.36 | 0.00 | −6.20 | 30.86 | 0.00 | −20.00 | 0.00 | 62.27 | −7.09 | 0.00 | 0.00 | −2.49 | 0.00 | 0.00 | −0.31 | −0.05 | 0.00 | 0.00 | 0.00 |
| 294 | ADHEr, GLUDy, MDH, PFK | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |
| 295 | ADHEr, FBA, GLUDy, MDH | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |
| 296 | ADHEr, FBA, FUM, GLUDy | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |
| 297 | ADHEr, FUM, GLUDy, PFK | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |
| 298 | ADHEr, GLUDy, MDH, TPI | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |
| 299 | ADHEr, FUM, GLUDy, TPI | 6.16 | 0.29 | 29.34 | 0.00 | −6.20 | 30.85 | 0.00 | −20.00 | 0.00 | 62.25 | −7.06 | 0.00 | 0.00 | −2.50 | 0.00 | 0.00 | −0.31 | −0.05 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 300 | ADHEr, RPE, SUCD4, TPI | 6.16 | 0.33 | 28.65 | 0.00 | −5.97 | 30.37 | 0.00 | −20.00 | 0.00 | 61.36 | −6.11 | 0.00 | 0.00 | −2.84 | 0.00 | 0.00 | −0.35 | −0.06 | 0.00 | 0.00 | 0.00 |
| 301 | ADHEr, PFK, RPE, SUCD4 | 6.16 | 0.33 | 28.65 | 0.00 | −5.97 | 30.37 | 0.00 | −20.00 | 0.00 | 61.36 | −6.11 | 0.00 | 0.00 | −2.84 | 0.00 | 0.00 | −0.35 | −0.06 | 0.00 | 0.00 | 0.00 |
| 302 | ADHEr, FBA, RPE, SUCD4 | 6.16 | 0.33 | 28.65 | 0.00 | −5.97 | 30.37 | 0.00 | −20.00 | 0.00 | 61.36 | −6.11 | 0.00 | 0.00 | −2.84 | 0.00 | 0.00 | −0.35 | −0.06 | 0.00 | 0.00 | 0.00 |
| 303 | ADHEr, GLUDy, PFK, SUCD4 | 6.15 | 0.30 | 29.25 | 0.00 | −6.19 | 30.80 | 0.00 | −20.00 | 0.00 | 62.15 | −6.91 | 0.00 | 0.00 | −2.56 | 0.00 | 0.00 | −0.32 | −0.05 | 0.00 | 0.00 | 0.00 |
| 304 | ADHEr, FBA, GLUDy, SUCD4 | 6.15 | 0.30 | 29.25 | 0.00 | −6.19 | 30.80 | 0.00 | −20.00 | 0.00 | 62.15 | −6.91 | 0.00 | 0.00 | −2.56 | 0.00 | 0.00 | −0.32 | −0.05 | 0.00 | 0.00 | 0.00 |
| 305 | ADHEr, GLUDy, SUCD4, TPI | 6.15 | 0.30 | 29.25 | 0.00 | −6.19 | 30.80 | 0.00 | −20.00 | 0.00 | 62.15 | −6.91 | 0.00 | 0.00 | −2.56 | 0.00 | 0.00 | −0.32 | −0.05 | 0.00 | 0.00 | 0.00 |
| 306 | ADHEr, HEX1, PFK, TAL | 6.14 | 0.32 | 28.86 | 0.00 | −6.07 | 30.53 | 0.00 | −20.00 | 0.00 | 61.66 | −6.37 | 0.00 | 0.00 | −2.76 | 0.00 | 0.00 | −0.34 | −0.06 | 0.00 | 0.00 | 0.00 |
| 307 | ADHEr, FBA, HEX1, TAL | 6.14 | 0.32 | 28.86 | 0.00 | −6.07 | 30.53 | 0.00 | −20.00 | 0.00 | 61.66 | −6.37 | 0.00 | 0.00 | −2.76 | 0.00 | 0.00 | −0.34 | −0.06 | 0.00 | 0.00 | 0.00 |
| 308 | ADHEr, HEX1, TAL, TPI | 6.14 | 0.32 | 28.86 | 0.00 | −6.07 | 30.53 | 0.00 | −20.00 | 0.00 | 61.66 | −6.37 | 0.00 | 0.00 | −2.76 | 0.00 | 0.00 | −0.34 | −0.06 | 0.00 | 0.00 | 0.00 |
| 309 | ADHEr, PFK, SUCD4, TAL | 6.13 | 0.33 | 28.70 | 0.00 | −6.05 | 30.43 | 0.00 | −20.00 | 0.00 | 61.47 | −6.12 | 0.00 | 0.00 | −2.86 | 0.00 | 0.00 | −0.35 | −0.06 | 0.00 | 0.00 | 0.00 |
| 310 | ADHEr, FBA, SUCD4, TAL | 6.13 | 0.33 | 28.70 | 0.00 | −6.05 | 30.43 | 0.00 | −20.00 | 0.00 | 61.47 | −6.12 | 0.00 | 0.00 | −2.86 | 0.00 | 0.00 | −0.35 | −0.06 | 0.00 | 0.00 | 0.00 |
| 311 | ADHEr, SUCD4, TAL, TPI | 6.13 | 0.33 | 28.70 | 0.00 | −6.05 | 30.43 | 0.00 | −20.00 | 0.00 | 61.47 | −6.12 | 0.00 | 0.00 | −2.86 | 0.00 | 0.00 | −0.35 | −0.06 | 0.00 | 0.00 | 0.00 |
| 312 | ADHEr, FUM, ME2, THD2 | 6.10 | 0.62 | 14.90 | 0.00 | −3.07 | 18.16 | 0.00 | −20.00 | 0.00 | 49.89 | 8.45 | 0.00 | 2.99 | −5.39 | 0.00 | 0.00 | −0.67 | −0.11 | 6.20 | 0.00 | 0.00 |
| 313 | ADHEr, ATPS4r, ME2, SUCD4 | 6.04 | 0.65 | 18.68 | 0.00 | 0.48 | 22.08 | 0.00 | −20.00 | 0.00 | 48.37 | 6.33 | 0.00 | 0.00 | −5.62 | −5.00 | 0.00 | −0.69 | −0.11 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 314 | ADHEr, PPCK, PYK, SUCD4 | 6.00 | 0.38 | 28.04 | 0.00 | −6.05 | 30.04 | 0.00 | −20.00 | 0.00 | 60.81 | −5.01 | 0.00 | 0.00 | −3.32 | 0.00 | 0.00 | −0.41 | −0.07 | 0.00 | 0.00 | 0.00 |
| 315 | ADHEr, GLCpts, PPCK, SUCD4 | 5.97 | 0.40 | 27.84 | 0.00 | −6.03 | 29.92 | 0.00 | −20.00 | 0.00 | 60.59 | −4.70 | 0.00 | 0.00 | −3.45 | 0.00 | 0.00 | −0.43 | −0.07 | 0.00 | 0.00 | 0.00 |
| 316 | ADHEr, PPCK, RPE, SUCD4 | 5.95 | 0.46 | 26.74 | 0.00 | −5.68 | 29.16 | 0.00 | −20.00 | 0.00 | 59.19 | −3.14 | 0.00 | 0.00 | −4.01 | 0.00 | 0.00 | −0.50 | −0.08 | 0.00 | 0.00 | 0.00 |
| 317 | ADHEr, FUM, GLUDy, PPCK | 5.94 | 0.42 | 27.58 | 0.00 | −6.00 | 29.76 | 0.00 | −20.00 | 0.00 | 60.30 | −4.29 | 0.00 | 0.00 | −3.61 | 0.00 | 0.00 | −0.45 | −0.07 | 0.00 | 0.00 | 0.00 |
| 318 | ADHEr, GLUDy, MDH, PPCK | 5.94 | 0.42 | 27.58 | 0.00 | −6.00 | 29.76 | 0.00 | −20.00 | 0.00 | 60.30 | −4.29 | 0.00 | 0.00 | −3.61 | 0.00 | 0.00 | −0.45 | −0.07 | 0.00 | 0.00 | 0.00 |
| 319 | ADHEr, GLUDy, PPCK, SUCD4 | 5.94 | 0.42 | 27.54 | 0.00 | −5.99 | 29.74 | 0.00 | −20.00 | 0.00 | 60.27 | −4.24 | 0.00 | 0.00 | −3.63 | 0.00 | 0.00 | −0.45 | −0.07 | 0.00 | 0.00 | 0.00 |
| 320 | ADHEr, PPCK, SUCD4, TAL | 5.90 | 0.46 | 26.81 | 0.00 | −5.79 | 29.24 | 0.00 | −20.00 | 0.00 | 59.36 | −3.18 | 0.00 | 0.00 | −4.02 | 0.00 | 0.00 | −0.50 | −0.08 | 0.00 | 0.00 | 0.00 |
| 321 | ADHEr, GLCpts, GLUDy, MDH | 5.89 | 0.45 | 27.19 | 0.00 | −5.95 | 29.52 | 0.00 | −20.00 | 0.00 | 59.87 | −3.68 | 0.00 | 0.00 | −3.85 | 0.00 | 0.00 | −0.48 | −0.08 | 0.00 | 0.00 | 0.00 |
| 322 | ADHEr, GLCpts, PPCK, RPE | 5.89 | 0.51 | 26.14 | 0.00 | −5.59 | 28.78 | 0.00 | −20.00 | 0.00 | 58.51 | −2.22 | 0.00 | 0.00 | −4.37 | 0.00 | 0.00 | −0.54 | −0.09 | 0.00 | 0.00 | 0.00 |
| 323 | ADHEr, GLUDy, MDH, RPE | 5.88 | 0.51 | 26.12 | 0.00 | −5.59 | 28.77 | 0.00 | −20.00 | 0.00 | 58.49 | −2.19 | 0.00 | 0.00 | −4.39 | 0.00 | 0.00 | −0.54 | −0.09 | 0.00 | 0.00 | 0.00 |
| 324 | ADHEr, GLUDy, PPCK, RPE | 5.87 | 0.52 | 26.00 | 0.00 | −5.57 | 28.69 | 0.00 | −20.00 | 0.00 | 58.35 | −2.00 | 0.00 | 0.00 | −4.46 | 0.00 | 0.00 | −0.55 | −0.09 | 0.00 | 0.00 | 0.00 |
| 325 | ADHEr, GLUDy, PPCK | 5.87 | 0.46 | 27.02 | 0.00 | −5.93 | 29.42 | 0.00 | −20.00 | 0.00 | 59.69 | −3.42 | 0.00 | 0.00 | −3.96 | 0.00 | 0.00 | −0.49 | −0.08 | 0.00 | 0.00 | 0.00 |
| 326 | ADHEr, GLCpts, MDH, SUCD4 | 5.86 | 0.46 | 26.97 | 0.00 | −5.93 | 29.38 | 0.00 | −20.00 | 0.00 | 59.63 | −3.35 | 0.00 | 0.00 | −3.99 | 0.00 | 0.00 | −0.49 | −0.08 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 327 | ADHEr, MDH, RPE, SUCD4 | 5.85 | 0.53 | 25.81 | 0.00 | −5.54 | 28.57 | 0.00 | −20.00 | 0.00 | 58.14 | −1.71 | 0.00 | 0.00 | −4.57 | 0.00 | 0.00 | −0.57 | −0.09 | 0.00 | 0.00 | 0.00 |
| 328 | ADHEr, GLCpts, MDH, PPCK | 5.85 | 0.47 | 26.83 | 0.00 | −5.91 | 29.29 | 0.00 | −20.00 | 0.00 | 59.47 | −3.12 | 0.00 | 0.00 | −4.08 | 0.00 | 0.00 | −0.50 | −0.08 | 0.00 | 0.00 | 0.00 |
| 329 | ADHEr, FUM, GLCpts, PPCK | 5.85 | 0.47 | 26.83 | 0.00 | −5.91 | 29.29 | 0.00 | −20.00 | 0.00 | 59.47 | −3.12 | 0.00 | 0.00 | −4.08 | 0.00 | 0.00 | −0.50 | −0.08 | 0.00 | 0.00 | 0.00 |
| 330 | ADHEr, MDH, PPCK, RPE | 5.84 | 0.54 | 25.70 | 0.00 | −5.53 | 28.50 | 0.00 | −20.00 | 0.00 | 58.02 | −1.54 | 0.00 | 0.00 | −4.64 | 0.00 | 0.00 | −0.57 | −0.09 | 0.00 | 0.00 | 0.00 |
| 331 | ADHEr, FUM, PPCK, RPE | 5.84 | 0.54 | 25.70 | 0.00 | −5.53 | 28.50 | 0.00 | −20.00 | 0.00 | 58.02 | −1.54 | 0.00 | 0.00 | −4.64 | 0.00 | 0.00 | −0.57 | −0.09 | 0.00 | 0.00 | 0.00 |
| 332 | ADHEr, GLCpts, PPCK, TAL | 5.84 | 0.51 | 26.23 | 0.00 | −5.72 | 28.88 | 0.00 | −20.00 | 0.00 | 58.71 | −2.28 | 0.00 | 0.00 | −4.38 | 0.00 | 0.00 | −0.54 | −0.09 | 0.00 | 0.00 | 0.00 |
| 333 | ADHEr, GLUDy, MDH, TAL | 5.83 | 0.51 | 26.21 | 0.00 | −5.71 | 28.86 | 0.00 | −20.00 | 0.00 | 58.68 | −2.24 | 0.00 | 0.00 | −4.40 | 0.00 | 0.00 | −0.54 | −0.09 | 0.00 | 0.00 | 0.00 |
| 334 | ADHEr, MDH, PPCK, PYK | 5.82 | 0.47 | 26.84 | 0.00 | −5.98 | 29.28 | 0.00 | −20.00 | 0.00 | 58.71 | −3.17 | 0.00 | 0.00 | −4.03 | 0.00 | 0.00 | −0.50 | −0.08 | 0.00 | 0.00 | 0.00 |
| 335 | ADHEr, FUM, PPCK, PYK | 5.82 | 0.47 | 26.84 | 0.00 | −5.98 | 29.28 | 0.00 | −20.00 | 0.00 | 59.61 | −3.17 | 0.00 | 0.00 | −4.03 | 0.00 | 0.00 | −0.50 | −0.08 | 0.09 | 0.00 | 0.00 |
| 336 | ADHEr, GLUDy, PPCK, TAL | 5.82 | 0.52 | 26.09 | 0.00 | −5.70 | 28.79 | 0.00 | −20.00 | 0.00 | 58.55 | −2.06 | 0.00 | 0.00 | −4.47 | 0.00 | 0.00 | −0.55 | −0.09 | 0.00 | 0.00 | 0.00 |
| 337 | ADHEr, FUM, GLUDy, SUCD4 | 5.81 | 0.49 | 26.51 | 0.00 | −5.87 | 29.10 | 0.00 | −20.00 | 0.00 | 59.12 | −2.62 | 0.00 | 0.00 | −4.28 | 0.00 | 0.00 | −0.53 | −0.09 | 0.00 | 0.00 | 0.00 |
| 338 | ADHEr, MDH, SUCD4, TAL | 5.80 | 0.53 | 25.90 | 0.00 | −5.67 | 28.67 | 0.00 | −20.00 | 0.00 | 58.33 | −1.76 | 0.00 | 0.00 | −4.59 | 0.00 | 0.00 | −0.57 | −0.09 | 0.00 | 0.00 | 0.00 |
| 339 | ADHEr, GLCpts, ME2, SUCD4 | 5.80 | 0.50 | 26.45 | 0.00 | −5.86 | 29.06 | 0.00 | −20.00 | 0.00 | 59.05 | −2.52 | 0.00 | 0.00 | −4.32 | 0.00 | 0.00 | −0.53 | −0.09 | 0.00 | 0.00 | 0.00 |
| 340 | ADHEr, ME2, RPE, SUCD4 | 5.79 | 0.57 | 25.28 | 0.00 | −5.46 | 28.24 | 0.00 | −20.00 | 0.00 | 57.53 | −0.89 | 0.00 | 0.00 | −4.90 | 0.00 | 0.00 | −0.61 | −0.10 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 341 | ADHEr, FUM, PPCK, TAL | 5.79 | 0.54 | 25.79 | 0.00 | −5.66 | 28.61 | 0.00 | −20.00 | 0.00 | 58.22 | −1.60 | 0.00 | 0.00 | −4.65 | 0.00 | 0.00 | −0.58 | −0.09 | 0.00 | 0.00 | 0.00 |
| 342 | ADHEr, FUM, MDH, PPCK, TAL | 5.79 | 0.54 | 25.79 | 0.00 | −5.66 | 28.61 | 0.00 | −20.00 | 0.00 | 58.22 | −1.60 | 0.00 | 0.00 | −4.65 | 0.00 | 0.00 | −0.58 | −0.09 | 0.00 | 0.00 | 0.00 |
| 343 | ADHEr, GLUDy, PRO1z, SUCD4 | 5.78 | 0.51 | 26.35 | 0.00 | −5.85 | 29.00 | 0.00 | −20.00 | 0.00 | 58.95 | −2.37 | 0.00 | 0.00 | −4.38 | 0.00 | 0.00 | −0.54 | −0.09 | 0.00 | 0.00 | 0.00 |
| 344 | ADHEr, FUM, GLUDy, RPE | 5.78 | 0.57 | 25.18 | 0.00 | −5.45 | 28.18 | 0.00 | −20.00 | 0.00 | 57.43 | −0.74 | 0.00 | 0.00 | −4.95 | 0.00 | 0.00 | −0.61 | −0.10 | 0.00 | 0.00 | 0.00 |
| 345 | ADHEr, GLUDy, RPE, SUCD4 | 5.78 | 0.57 | 25.17 | 0.00 | −5.45 | 28.17 | 0.00 | −20.00 | 0.00 | 57.41 | −0.72 | 0.00 | 0.00 | −4.96 | 0.00 | 0.00 | −0.61 | −0.10 | 0.00 | 0.00 | 0.00 |
| 346 | ADHEr, GLCpts, RPE, SUCD4 | 5.78 | 0.57 | 25.15 | 0.00 | −5.44 | 28.15 | 0.00 | −20.00 | 0.00 | 57.39 | −0.69 | 0.00 | 0.00 | −4.98 | 0.00 | 0.00 | −0.62 | −0.10 | 0.00 | 0.00 | 0.00 |
| 347 | ADHEr, FUM, GLUDy, ME2 | 5.78 | 0.51 | 26.30 | 0.00 | −5.85 | 28.97 | 0.00 | −20.00 | 0.00 | 58.89 | −2.29 | 0.00 | 0.00 | −4.41 | 0.00 | 0.00 | −0.55 | −0.09 | 0.00 | 0.00 | 0.00 |
| 348 | ADHEr, GLUDy, ME2, SUCD4 | 5.78 | 0.51 | 26.30 | 0.00 | −5.85 | 28.96 | 0.00 | −20.00 | 0.00 | 58.88 | −2.28 | 0.00 | 0.00 | −4.41 | 0.00 | 0.00 | −0.55 | −0.09 | 0.00 | 0.00 | 0.00 |
| 349 | ADHEr, FUM, GLCpts, GLUDy | 5.77 | 0.52 | 26.22 | 0.00 | −5.84 | 28.91 | 0.00 | −20.00 | 0.00 | 58.80 | −2.16 | 0.00 | 0.00 | −4.46 | 0.00 | 0.00 | −0.55 | −0.09 | 0.00 | 0.00 | 0.00 |
| 350 | ADHEr, GLCpts, GLUDy, SUCD4 | 5.76 | 0.52 | 26.17 | 0.00 | −5.83 | 28.88 | 0.00 | −20.00 | 0.00 | 58.74 | −2.08 | 0.00 | 0.00 | −4.49 | 0.00 | 0.00 | −0.56 | −0.09 | 0.00 | 0.00 | 0.00 |
| 351 | ADHEr, FUM, ME2, SUCD4 | 5.74 | 0.53 | 25.99 | 0.00 | −5.81 | 28.78 | 0.00 | −20.00 | 0.00 | 58.55 | −1.81 | 0.00 | 0.00 | −4.60 | 0.00 | 0.00 | −0.57 | −0.09 | 0.00 | 0.00 | 0.00 |
| 352 | ADHEr, ME2, SUCD4, TAL | 5.74 | 0.57 | 25.38 | 0.00 | −5.60 | 28.34 | 0.00 | −20.00 | 0.00 | 57.75 | −0.95 | 0.00 | 0.00 | −4.91 | 0.00 | 0.00 | −0.61 | −0.10 | 0.00 | 0.00 | 0.00 |
| 353 | ADHEr, FUM, GLUDy, TAL | 5.72 | 0.58 | 25.26 | 0.00 | −5.59 | 28.27 | 0.00 | −20.00 | 0.00 | 57.62 | −0.77 | 0.00 | 0.00 | −4.98 | 0.00 | 0.00 | −0.62 | −0.10 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 354 | ADHEr, GLUDy, SUCD4, TAL | 5.72 | 0.58 | 25.25 | 0.00 | -5.58 | 28.26 | 0.00 | -20.00 | 0.00 | 57.61 | -0.75 | 0.00 | 0.00 | -4.99 | 0.00 | 0.00 | -0.62 | -0.10 | 0.00 | 0.00 | 0.00 |
| 355 | ADHEr, GLCpts, SUCD4, TAL | 5.72 | 0.58 | 25.21 | 0.00 | -5.58 | 28.24 | 0.00 | -20.00 | 0.00 | 57.57 | -0.69 | 0.00 | 0.00 | -5.01 | 0.00 | 0.00 | -0.62 | -0.10 | 0.00 | 0.00 | 0.00 |
| 356 | ADHEr, ME2, PGL, THD2 | 5.71 | 0.95 | 0.00 | 0.00 | 6.29 | 15.52 | 0.00 | -20.00 | 0.00 | 40.16 | 26.98 | 0.00 | 0.00 | -8.25 | -20.00 | 0.00 | -1.02 | -0.17 | 8.93 | 0.00 | 0.00 |
| 357 | ADHEr, G6PDHy, ME2, THD2 | 5.71 | 0.95 | 0.00 | 0.00 | 6.29 | 15.52 | 0.00 | -20.00 | 0.00 | 40.16 | 26.98 | 0.00 | 0.00 | -8.25 | -20.00 | 0.00 | -1.02 | -0.17 | 8.93 | 0.00 | 0.00 |
| 358 | ADHEr, FUM, RPE, SUCD4 | 5.71 | 0.62 | 24.48 | 0.00 | -5.35 | 27.73 | 0.00 | -20.00 | 0.00 | 56.63 | 0.34 | 0.00 | 0.00 | -5.38 | 0.00 | 0.00 | -0.67 | -0.11 | 0.00 | 0.00 | 0.00 |
| 359 | ADHEr, HEX1, RPE, SUCD4 | 5.69 | 0.63 | 24.34 | 0.00 | -5.32 | 27.64 | 0.00 | -20.00 | 0.00 | 56.47 | 0.56 | 0.00 | 0.00 | -5.47 | 0.00 | 0.00 | -0.68 | -0.11 | 0.00 | 0.00 | 0.00 |
| 360 | ADHEr, CBMK2, GLU5K, PPCK | 5.68 | 0.57 | 25.51 | 0.00 | -5.76 | 28.48 | 0.00 | -20.00 | 0.00 | 58.02 | -1.05 | 0.00 | 0.00 | -4.90 | 0.00 | 0.00 | -0.61 | -0.10 | 0.00 | 0.00 | 0.00 |
| 361 | ADHEr, CBMK2, G5SD, PPCK | 5.68 | 0.57 | 25.51 | 0.00 | -5.76 | 28.48 | 0.00 | -20.00 | 0.00 | 58.02 | -1.05 | 0.00 | 0.00 | -4.90 | 0.00 | 0.00 | -0.61 | -0.10 | 0.00 | 0.00 | 0.00 |
| 362 | ADHEr, ASNS2, CBMK2, PPCK | 5.68 | 0.57 | 25.51 | 0.00 | -5.76 | 28.48 | 0.00 | -20.00 | 0.00 | 58.02 | -1.05 | 0.00 | 0.00 | -4.90 | 0.00 | 0.00 | -0.61 | -0.10 | 0.00 | 0.00 | 0.00 |
| 363 | ADHEr, CBMK2, PPCK, SO4t2 | 5.68 | 0.57 | 25.50 | 0.00 | -5.75 | 28.47 | 0.00 | -20.00 | 0.00 | 58.00 | -1.03 | 0.00 | 0.00 | -4.91 | 0.00 | 0.00 | -0.61 | -0.10 | 0.00 | 0.00 | 0.00 |
| 364 | ADHEr, GLUDy, HEX1, SUCD4 | 5.67 | 0.57 | 25.42 | 0.00 | -5.75 | 28.42 | 0.00 | -20.00 | 0.00 | 57.92 | -0.91 | 0.00 | 0.00 | -4.96 | 0.00 | 0.00 | -0.61 | -0.10 | 0.00 | 0.00 | 0.00 |
| 365 | ADHEr, FUM, SUCD4, TAL | 5.64 | 0.63 | 24.56 | 0.00 | -5.49 | 27.83 | 0.00 | -20.00 | 0.00 | 56.84 | 0.32 | 0.00 | 0.00 | -5.41 | 0.00 | 0.00 | -0.67 | -0.11 | 0.00 | 0.00 | 0.00 |
| 366 | ADHEr, HEX1, SUCD4, TAL | 5.63 | 0.63 | 24.44 | 0.00 | -5.48 | 27.75 | 0.00 | -20.00 | 0.00 | 56.70 | 0.52 | 0.00 | 0.00 | -5.49 | 0.00 | 0.00 | -0.68 | -0.11 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 367 | ADHEr, FUM, HEX1, SUCD4 | 5.62 | 0.60 | 25.02 | 0.00 | -5.70 | 28.17 | 0.00 | -20.00 | 0.00 | 57.47 | -0.27 | 0.00 | 0.00 | -5.21 | 0.00 | 0.00 | -0.65 | -0.11 | 0.00 | 0.00 | 0.00 |
| 368 | ADHEr, FUM, HEX1, RPE | 5.58 | 0.70 | 23.35 | 0.00 | -5.18 | 27.02 | 0.00 | -20.00 | 0.00 | 55.35 | 2.09 | 0.00 | 0.00 | -6.07 | 0.00 | 0.00 | -0.75 | -0.12 | 0.00 | 0.00 | 0.00 |
| 369 | ADHEr, CBMK2, FUM, SUCD4 | 5.58 | 0.62 | 24.73 | 0.00 | -5.67 | 27.99 | 0.00 | -20.00 | 0.00 | 57.15 | 0.18 | 0.00 | 0.00 | -5.39 | 0.00 | 0.00 | -0.67 | -0.11 | 0.00 | 0.00 | 0.00 |
| 370 | ADHEr, HEX1, PFLi, RPE | 5.54 | 0.72 | 14.12 | 0.00 | 3.77 | 0.00 | 0.00 | -20.00 | 0.00 | 37.22 | 20.40 | 0.00 | 0.00 | -6.22 | 0.00 | 0.00 | -0.77 | -0.13 | 8.99 | 0.00 | 0.00 |
| 371 | ADHEr, FUM, HEX1, TAL | 5.51 | 0.70 | 23.47 | 0.00 | -5.35 | 27.15 | 0.00 | -20.00 | 0.00 | 55.62 | 2.02 | 0.00 | 0.00 | -6.08 | 0.00 | 0.00 | -0.75 | -0.12 | 0.00 | 0.00 | 0.00 |
| 372 | ADHEr, CBMK2, FUM, HEX1 | 5.45 | 0.70 | 23.69 | 0.00 | -5.54 | 27.34 | 0.00 | -20.00 | 0.00 | 56.00 | 1.81 | 0.00 | 0.00 | -6.05 | 0.00 | 0.00 | -0.75 | -0.12 | 0.00 | 0.00 | 0.00 |
| 373 | ADHEr, HEX1, PFLi, TAL | 5.40 | 0.72 | 14.11 | 0.00 | 3.45 | 0.00 | 0.00 | -20.00 | 0.00 | 37.64 | 20.46 | 0.00 | 0.00 | -6.24 | 0.00 | 0.00 | -0.77 | -0.13 | 9.20 | 0.00 | 0.00 |
| 374 | ADHEr, GLYCL, HEX1, PFLi | 5.25 | 0.72 | 14.10 | 0.00 | 3.09 | 0.00 | 0.00 | -20.00 | 0.09 | 38.10 | 20.54 | 0.00 | 0.00 | -6.33 | 0.00 | 0.00 | -0.77 | -0.13 | 9.39 | 0.00 | 0.00 |
| 375 | ADHEr, ATPS4r, GLUDy, PGI | 5.14 | 0.46 | 27.54 | 0.00 | -4.79 | 29.95 | 0.00 | -20.00 | 0.00 | 60.78 | -1.47 | 0.00 | 0.00 | -4.00 | -5.00 | 0.00 | -0.49 | -0.08 | 0.00 | 0.00 | 0.00 |
| 376 | ADHEr, PFLi, PGDH, PGI | 5.08 | 0.43 | 16.39 | 0.00 | 1.66 | 0.00 | 0.00 | -20.00 | 0.00 | 43.14 | 16.32 | 0.00 | 0.00 | -3.72 | 0.00 | 0.00 | -0.46 | -0.08 | 11.84 | 0.00 | 0.00 |
| 377 | ADHEr, PFLi, PGI, TAL | 5.05 | 0.43 | 16.21 | 0.00 | 1.57 | 0.00 | 0.00 | -20.00 | 0.00 | 43.21 | 16.41 | 0.00 | 0.00 | -3.75 | 0.00 | 0.00 | -0.46 | -0.08 | 11.96 | 0.00 | 0.00 |
| 378 | ADHEr, ATPS4r, PFK, RPE | 5.03 | 0.52 | 26.76 | 0.00 | -4.73 | 29.48 | 0.00 | -20.00 | 0.00 | 59.94 | -0.22 | 0.00 | 0.00 | -4.50 | -5.00 | 0.00 | -0.56 | -0.09 | 0.00 | 0.00 | 0.00 |
| 379 | ADHEr, ATPS4r, FBA, RPE | 5.03 | 0.52 | 26.76 | 0.00 | -4.73 | 29.48 | 0.00 | -20.00 | 0.00 | 59.94 | -0.22 | 0.00 | 0.00 | -4.50 | -5.00 | 0.00 | -0.56 | -0.09 | 0.00 | 0.00 | 0.00 |
| 380 | ADHEr, ATPS4r, RPE, TPI | 5.03 | 0.52 | 26.76 | 0.00 | -4.73 | 29.48 | 0.00 | -20.00 | 0.00 | 59.94 | -0.22 | 0.00 | 0.00 | -4.50 | -5.00 | 0.00 | -0.56 | -0.09 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 381 | ADHEr, PFLi, PGI, RPE | 5.02 | 0.43 | 16.04 | 0.00 | 1.47 | 0.00 | 0.00 | −20.00 | 0.00 | 43.27 | 16.49 | 0.00 | 0.00 | −3.76 | 0.00 | 0.00 | −0.47 | −0.08 | 12.07 | 0.00 | 0.00 |
| 382 | ADHEr, ATPS4r, GLUDy, TPI | 5.02 | 0.47 | 27.70 | 0.00 | −5.08 | 30.15 | 0.00 | −20.00 | 0.00 | 61.18 | −1.51 | 0.00 | 0.00 | −4.05 | −5.00 | 0.00 | −0.50 | −0.08 | 0.00 | 0.00 | 0.00 |
| 383 | ADHEr, ATPS4r, FBA, GLUDy | 5.02 | 0.47 | 27.70 | 0.00 | −5.08 | 30.15 | 0.00 | −20.00 | 0.00 | 61.18 | −1.51 | 0.00 | 0.00 | −4.05 | −5.00 | 0.00 | −0.50 | −0.08 | 0.00 | 0.00 | 0.00 |
| 384 | ADHEr, ATPS4r, GLUDy, PFK | 5.02 | 0.47 | 27.70 | 0.00 | −5.08 | 30.15 | 0.00 | −20.00 | 0.00 | 61.18 | −1.51 | 0.00 | 0.00 | −4.05 | −5.00 | 0.00 | −0.50 | −0.08 | 0.00 | 0.00 | 0.00 |
| 385 | ADHEr, FBA, PFLi, PGI | 5.01 | 0.44 | 15.95 | 0.00 | 1.43 | 0.00 | 0.00 | −20.00 | 0.00 | 43.31 | 16.53 | 0.00 | 0.00 | −3.77 | 0.00 | 0.00 | −0.47 | −0.08 | 12.13 | 0.00 | 0.00 |
| 386 | ADHEr, PFK, PFLi, PGI | 5.01 | 0.44 | 15.95 | 0.00 | 1.43 | 0.00 | 0.00 | −20.00 | 0.00 | 43.31 | 16.53 | 0.00 | 0.00 | −3.77 | 0.00 | 0.00 | −0.47 | −0.08 | 12.13 | 0.00 | 0.00 |
| 387 | ADHEr, PFLi, PGI, TPI | 5.01 | 0.44 | 15.95 | 0.00 | 1.43 | 0.00 | 0.00 | −20.00 | 0.00 | 43.31 | 16.53 | 0.00 | 0.00 | −3.77 | 0.00 | 0.00 | −0.47 | −0.08 | 12.13 | 0.00 | 0.00 |
| 388 | ADHEr, PFLi, RPE, TPI | 4.99 | 0.44 | 15.97 | 0.00 | 1.38 | 0.00 | 0.00 | −20.00 | 0.00 | 43.37 | 16.55 | 0.00 | 0.00 | −3.78 | 0.00 | 0.00 | −0.47 | −0.08 | 12.15 | 0.00 | 0.00 |
| 389 | ADHEr, PFK, PFLi, TPI | 4.99 | 0.44 | 15.97 | 0.00 | 1.38 | 0.00 | 0.00 | −20.00 | 0.00 | 43.37 | 16.55 | 0.00 | 0.00 | −3.78 | 0.00 | 0.00 | −0.47 | −0.08 | 12.15 | 0.00 | 0.00 |
| 390 | ADHEr, FBA, PFLi, RPE | 4.99 | 0.44 | 15.97 | 0.00 | 1.38 | 0.00 | 0.00 | −20.00 | 0.00 | 43.37 | 16.55 | 0.00 | 0.00 | −3.78 | 0.00 | 0.00 | −0.47 | −0.08 | 12.15 | 0.00 | 0.00 |
| 391 | ADHEr, ATPS4r, PFK, TAL | 4.98 | 0.52 | 26.82 | 0.00 | −4.85 | 29.56 | 0.00 | −20.00 | 0.00 | 60.10 | −0.23 | 0.00 | 0.00 | −4.53 | −5.00 | 0.00 | −0.56 | −0.09 | 0.00 | 0.00 | 0.00 |
| 392 | ADHEr, ATPS4r, FBA, TAL | 4.98 | 0.52 | 26.82 | 0.00 | −4.85 | 29.56 | 0.00 | −20.00 | 0.00 | 60.10 | −0.23 | 0.00 | 0.00 | −4.53 | −5.00 | 0.00 | −0.56 | −0.09 | 0.00 | 0.00 | 0.00 |
| 393 | ADHEr, ATPS4r, TAL, TPI | 4.98 | 0.52 | 26.82 | 0.00 | −4.85 | 29.56 | 0.00 | −20.00 | 0.00 | 60.10 | −0.23 | 0.00 | 0.00 | −4.53 | −5.00 | 0.00 | −0.56 | −0.09 | 0.00 | 0.00 | 0.00 |
| 394 | ADHEr, FBA, PFLi, TAL | 4.94 | 0.44 | 16.00 | 0.00 | 1.28 | 0.00 | 0.00 | −20.00 | 0.00 | 43.49 | 16.58 | 0.00 | 0.00 | −3.80 | 0.00 | 0.00 | −0.47 | −0.08 | 12.18 | 0.00 | 0.00 |
| 395 | ADHEr, PFLi, TAL, TPI | 4.94 | 0.44 | 16.00 | 0.00 | 1.28 | 0.00 | 0.00 | −20.00 | 0.00 | 43.49 | 16.58 | 0.00 | 0.00 | −3.80 | 0.00 | 0.00 | −0.47 | −0.08 | 12.18 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 396 | ADHEr, PFK, PFLi, TAL | 4.94 | 0.44 | 16.00 | 0.00 | 1.28 | 0.00 | 0.00 | −20.00 | 0.00 | 43.49 | 16.58 | 0.00 | 0.00 | −3.80 | 0.00 | 0.00 | −0.47 | −0.08 | 12.18 | 0.00 | 0.00 |
| 397 | ADHEr, GLYCL, HEX1, THD2 | 4.90 | 0.74 | 22.16 | 0.00 | −6.47 | 26.02 | 0.00 | −20.00 | 0.09 | 56.37 | 3.67 | 0.00 | 0.00 | −6.47 | 0.00 | 0.00 | −0.79 | −0.13 | 1.43 | 0.00 | 0.00 |
| 398 | ADHEr, GLUDy, PFK, PFLi | 4.89 | 0.39 | 16.45 | 0.00 | 1.06 | 0.00 | 0.00 | −20.00 | 0.00 | 44.29 | 15.92 | 0.00 | 0.00 | −3.42 | 0.00 | 0.00 | −0.42 | −0.07 | 12.52 | 0.00 | 0.00 |
| 399 | ADHEr, GLUDy, PFLi, TPI | 4.89 | 0.39 | 16.45 | 0.00 | 1.06 | 0.00 | 0.00 | −20.00 | 0.00 | 44.29 | 15.92 | 0.00 | 0.00 | −3.42 | 0.00 | 0.00 | −0.42 | −0.07 | 12.52 | 0.00 | 0.00 |
| 400 | ADHEr, FBA, GLUDy, PFLi | 4.89 | 0.39 | 16.45 | 0.00 | 1.06 | 0.00 | 0.00 | −20.00 | 0.00 | 44.29 | 15.92 | 0.00 | 0.00 | −3.42 | 0.00 | 0.00 | −0.42 | −0.07 | 12.52 | 0.00 | 0.00 |
| 401 | ADHEr, EDA, PFLi, PGI | 4.83 | 0.50 | 0.00 | 0.00 | −3.17 | 0.00 | 0.00 | −20.00 | 0.00 | 45.11 | 21.92 | 0.00 | 0.00 | −4.32 | 0.00 | 0.00 | −0.53 | −0.09 | 20.78 | 0.00 | 0.00 |
| 402 | ADHEr, ATPS4r, GLUDy, RPE | 4.72 | 0.72 | 23.93 | 0.00 | −4.31 | 27.69 | 0.00 | −20.00 | 0.00 | 56.73 | 4.15 | 0.00 | 0.00 | −6.22 | −5.00 | 0.00 | −0.77 | −0.13 | 0.00 | 0.00 | 0.00 |
| 403 | ADHEr, ATPS4r, GLUDy, TAL | 4.65 | 0.72 | 24.01 | 0.00 | −4.47 | 27.80 | 0.00 | −20.00 | 0.00 | 56.96 | 4.14 | 0.00 | 0.00 | −6.26 | −5.00 | 0.00 | −0.77 | −0.13 | 0.00 | 0.00 | 0.00 |
| 404 | ADHEr, ATPS4r, CBMK2, RPE | 4.60 | 0.80 | 22.80 | 0.00 | −4.14 | 26.97 | 0.00 | −20.00 | 0.00 | 55.45 | 5.89 | 0.00 | 0.00 | −6.91 | −5.00 | 0.00 | −0.85 | −0.14 | 0.00 | 0.00 | 0.00 |
| 405 | ADHEr, ATPS4r, CBMK2, GLUDy | 4.57 | 0.72 | 24.19 | 0.00 | −4.67 | 27.97 | 0.00 | −20.00 | 0.00 | 57.30 | 4.00 | 0.00 | 0.00 | −6.26 | −5.00 | 0.00 | −0.77 | −0.13 | 0.00 | 0.00 | 0.00 |
| 406 | ADHEr, ATPS4r, CBMK2, TAL | 4.51 | 0.80 | 22.88 | 0.00 | −4.32 | 27.09 | 0.00 | −20.00 | 0.00 | 55.69 | 5.90 | 0.00 | 0.00 | −6.96 | −5.00 | 0.00 | −0.86 | −0.14 | 0.00 | 0.00 | 0.00 |
| 407 | ADHEr, ASNS2, ATPS4r, GLU5K | 4.42 | 0.81 | 22.95 | 0.00 | −4.53 | 27.20 | 0.00 | −20.00 | 0.00 | 55.93 | 5.95 | 0.00 | 0.00 | −7.03 | −5.00 | 0.00 | −0.87 | −0.14 | 0.00 | 0.00 | 0.00 |
| 408 | ADHEr, ASNS2, ATPS4r, G5SD | 4.42 | 0.81 | 22.95 | 0.00 | −4.53 | 27.20 | 0.00 | −20.00 | 0.00 | 55.93 | 5.95 | 0.00 | 0.00 | −7.03 | −5.00 | 0.00 | −0.87 | −0.14 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 409 | ADHEr, ACKr, PFLi, PGI | 3.00 | 0.50 | 3.27 | 0.00 | −6.43 | 0.00 | 0.00 | −20.00 | 0.00 | 50.40 | 21.51 | 0.00 | 0.00 | −4.32 | 0.00 | 0.00 | −0.53 | −0.09 | 21.79 | 0.00 | 0.00 |
| 410 | ADHEr, ACKr, AKGD, FRD2 | 2.76 | 1.03 | 3.32 | 0.00 | 14.07 | 0.00 | 0.00 | −20.00 | 0.00 | 25.81 | 30.15 | 0.00 | 15.19 | −8.90 | −20.00 | 0.00 | −1.10 | −0.18 | 0.00 | 0.00 | 0.00 |
| 411 | ADHEr, ACKr, FRD2, SUCOAS | 1.91 | 1.03 | 2.47 | 0.00 | 12.55 | 0.00 | 0.00 | −20.00 | 0.00 | 27.45 | 30.09 | 0.00 | 16.64 | −8.95 | −20.00 | 0.00 | −1.11 | −0.18 | 0.49 | 0.00 | 0.00 |
| 412 | ADHEr, FUM, G6PDHy, TAL | 1.40 | 0.71 | 14.98 | 0.00 | −12.86 | 18.72 | 0.00 | −20.00 | 0.00 | 62.31 | 11.80 | 0.00 | 0.00 | −6.44 | 0.00 | 0.27 | −0.76 | −0.12 | 11.63 | 0.00 | 0.00 |
| 413 | ADHEr, FUM, PGDH, TAL | 1.40 | 0.71 | 14.98 | 0.00 | −12.86 | 18.72 | 0.00 | −20.00 | 0.00 | 62.31 | 11.80 | 0.00 | 0.00 | −6.44 | 0.00 | 0.27 | −0.76 | −0.12 | 11.63 | 0.00 | 0.00 |
| 414 | ADHEr, FUM, PGL, TAL | 1.40 | 0.71 | 14.98 | 0.00 | −12.86 | 18.72 | 0.00 | −20.00 | 0.00 | 62.31 | 11.80 | 0.00 | 0.00 | −6.44 | 0.00 | 0.27 | −0.76 | −0.12 | 11.63 | 0.00 | 0.00 |
| 415 | ADHEr, FUM, ME2, TPI | 1.36 | 0.47 | 17.83 | 0.00 | −14.86 | 20.31 | 0.00 | −20.00 | 0.00 | 68.38 | 5.91 | 0.00 | 0.00 | −4.11 | 0.00 | 0.00 | −0.51 | −0.08 | 13.43 | 0.00 | 0.00 |
| 416 | ADHEr, FUM, ME2, PFK | 1.36 | 0.47 | 17.83 | 0.00 | −14.86 | 20.31 | 0.00 | −20.00 | 0.00 | 68.38 | 5.91 | 0.00 | 0.00 | −4.11 | 0.00 | 0.00 | −0.51 | −0.08 | 13.43 | 0.00 | 0.00 |
| 417 | ADHEr, FBA, FUM, ME2 | 1.36 | 0.47 | 17.83 | 0.00 | −14.86 | 20.31 | 0.00 | −20.00 | 0.00 | 68.38 | 5.91 | 0.00 | 0.00 | −4.11 | 0.00 | 0.00 | −0.51 | −0.08 | 13.43 | 0.00 | 0.00 |
| 418 | ADHEr, FRD2, GLUDy, LDH_D | 1.22 | 0.24 | 0.00 | 0.00 | −33.89 | 3.68 | 33.86 | −20.00 | 0.00 | 73.09 | 36.99 | 0.00 | 0.00 | −2.07 | 0.00 | 0.00 | −0.26 | −0.04 | 0.00 | 0.00 | 0.00 |
| 419 | ADHEr, FRD2, LDH_D, THD2 | 1.15 | 0.40 | 0.00 | 0.00 | 15.41 | 4.39 | 0.00 | −20.00 | 0.00 | 22.97 | 37.30 | 0.29 | 0.00 | −19.20 | 0.00 | 0.00 | −0.43 | −0.07 | 0.00 | 0.00 | 15.46 |
| 420 | ADHEr, G6PDHy, HEX1, TAL | 1.01 | 0.73 | 14.02 | 0.00 | −13.53 | 17.85 | 0.00 | −20.00 | 0.00 | 62.73 | 12.92 | 0.00 | 0.00 | −6.60 | 0.00 | 0.27 | −0.78 | −0.13 | 12.69 | 0.00 | 0.00 |
| 421 | ADHEr, HEX1, PGDH, TAL | 1.01 | 0.73 | 14.02 | 0.00 | −13.53 | 17.85 | 0.00 | −20.00 | 0.00 | 62.73 | 12.92 | 0.00 | 0.00 | −6.60 | 0.00 | 0.27 | −0.78 | −0.13 | 12.69 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 422 | ADHEr, HEX1, PGL, TAL | 1.01 | 0.73 | 14.02 | 0.00 | −13.53 | 17.85 | 0.00 | −20.00 | 0.00 | 62.73 | 12.92 | 0.00 | 0.00 | −6.60 | 0.00 | 0.27 | −0.78 | −0.13 | 12.69 | 0.00 | 0.00 |
| 423 | ADHEr, MDH, PGDH, TAL | 0.89 | 0.65 | 14.71 | 0.00 | −14.28 | 18.10 | 0.00 | −20.00 | 0.00 | 64.72 | 11.43 | 0.00 | 0.00 | −5.84 | 0.00 | 0.24 | −0.69 | −0.11 | 13.54 | 0.00 | 0.00 |
| 424 | ADHEr, G6PDHy, MDH, TAL | 0.89 | 0.65 | 14.71 | 0.00 | −14.28 | 18.10 | 0.00 | −20.00 | 0.00 | 64.72 | 11.43 | 0.00 | 0.00 | −5.84 | 0.00 | 0.24 | −0.69 | −0.11 | 13.54 | 0.00 | 0.00 |
| 425 | ADHEr, MDH, PGL, TAL | 0.89 | 0.65 | 14.71 | 0.00 | −14.28 | 18.10 | 0.00 | −20.00 | 0.00 | 64.72 | 11.43 | 0.00 | 0.00 | −5.84 | 0.00 | 0.24 | −0.69 | −0.11 | 13.54 | 0.00 | 0.00 |
| 426 | ADHEr, PGDH, TAL, TPI | 0.43 | 0.47 | 15.73 | 0.00 | −16.28 | 18.18 | 0.00 | −20.00 | 0.00 | 69.35 | 8.73 | 0.00 | 0.00 | −4.23 | 0.00 | 0.18 | −0.50 | −0.08 | 15.97 | 0.00 | 0.00 |
| 427 | ADHEr, FBA, PGDH, TAL | 0.43 | 0.47 | 15.73 | 0.00 | −16.28 | 18.18 | 0.00 | −20.00 | 0.00 | 69.35 | 8.73 | 0.00 | 0.00 | −4.23 | 0.00 | 0.18 | −0.50 | −0.08 | 15.97 | 0.00 | 0.00 |
| 428 | ADHEr, PFK, PGDH, TAL | 0.43 | 0.47 | 15.73 | 0.00 | −16.28 | 18.18 | 0.00 | −20.00 | 0.00 | 69.35 | 8.73 | 0.00 | 0.00 | −4.23 | 0.00 | 0.18 | −0.50 | −0.08 | 15.97 | 0.00 | 0.00 |
| 429 | ADHEr, GLYCL, TAL, TPI | 0.41 | 0.49 | 15.57 | 0.00 | −16.70 | 18.12 | 0.00 | −20.00 | 0.06 | 69.95 | 8.24 | 0.00 | 0.00 | −4.26 | 0.00 | 0.00 | −0.52 | −0.09 | 16.38 | 0.00 | 0.00 |
| 430 | ADHEr, TAL, THD5, TPI | 0.40 | 0.49 | 15.57 | 0.00 | −16.69 | 18.11 | 0.00 | −20.00 | 0.00 | 69.95 | 8.24 | 0.00 | 0.00 | −4.21 | 0.00 | 0.00 | −0.52 | −0.09 | 16.41 | 0.00 | 0.00 |
| 431 | ADHEr, LDH_D, TAL, TPI | 0.40 | 0.49 | 15.57 | 0.00 | −16.69 | 18.11 | 0.00 | −20.00 | 0.00 | 69.95 | 8.24 | 0.00 | 0.00 | −4.21 | 0.00 | 0.00 | −0.52 | −0.09 | 16.41 | 0.00 | 0.00 |
| 432 | ADHEr, ASPT, EDA, MDH, PGI | 16.17 | 0.05 | 8.39 | 0.00 | 11.88 | 24.76 | 0.00 | −20.00 | 0.00 | 33.47 | −3.46 | 0.00 | 0.00 | −0.39 | 0.00 | 0.00 | −0.05 | −0.01 | 0.00 | 0.00 | 0.00 |
| 433 | ADHEr, ATPS4r, FRD2, LDH_D, ME2 | 15.11 | 0.23 | 0.00 | 0.00 | 23.25 | 9.12 | 0.00 | −20.00 | 0.00 | 13.86 | 15.46 | 2.12 | 0.00 | −5.10 | −2.00 | 0.00 | −0.25 | −0.04 | 0.00 | 0.00 | 0.99 |
| 434 | ADHEr, EDA, PFLi, PGI, PPCK | 14.76 | 0.16 | 16.11 | 0.00 | 22.13 | 0.00 | 0.00 | −20.00 | 0.00 | 17.24 | 10.28 | 0.00 | 0.00 | −1.38 | 0.00 | 0.00 | −0.17 | −0.03 | 0.00 | 0.00 | 0.00 |
| 435 | ADHEr, ATPS4r, FRD2, | 15.02 | 0.23 | 0.00 | 0.00 | 23.19 | 9.11 | 0.00 | −20.00 | 0.00 | 13.93 | 15.60 | 2.10 | 0.00 | −5.18 | −2.00 | 0.00 | −0.25 | −0.04 | 0.00 | 0.00 | 1.08 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 436 | LDH_D, MDH | 14.65 | 0.19 | 15.67 | 0.00 | 21.97 | 0.00 | 0.00 | −20.00 | 0.00 | 17.05 | 10.88 | 0.00 | 0.00 | −1.68 | 0.00 | 0.00 | −0.21 | −0.03 | 0.00 | 0.00 | 0.00 |
| 437 | ADHEr, EDA, PFLi, PGI, SUCD4 | 14.65 | 0.19 | 15.67 | 0.00 | 21.97 | 0.00 | 0.00 | −20.00 | 0.00 | 17.05 | 10.88 | 0.00 | 0.00 | −1.68 | 0.00 | 0.00 | −0.21 | −0.03 | 0.00 | 0.00 | 0.00 |
| 438 | ADHEr, EDA, NADH6, PFLi, PGI | 14.47 | 0.09 | 17.44 | 0.00 | 19.97 | 3.46 | 0.00 | −20.00 | 0.00 | 21.55 | 7.19 | 0.00 | 0.00 | −0.80 | 0.00 | 0.00 | −0.10 | −0.02 | 0.00 | 0.00 | 0.00 |
| 439 | ADHEr, EDA, NADH6, PGI, PPCK | 14.38 | 0.36 | 13.01 | 0.00 | 21.55 | 0.00 | 0.00 | −20.00 | 0.00 | 15.56 | 13.74 | 0.00 | 0.00 | −3.10 | 0.00 | 0.00 | −0.38 | −0.06 | 0.00 | 0.00 | 0.00 |
| 440 | ADHEr, ASPT, LDH_D, MDH, PFLi | 14.31 | 0.31 | 14.25 | 0.00 | 21.45 | 0.00 | 0.00 | −20.00 | 0.00 | 16.44 | 12.79 | 0.00 | 0.00 | −2.67 | 0.00 | 0.00 | −0.33 | −0.05 | 0.00 | 0.00 | 0.00 |
| 441 | ADHEr, GLUDy, HEX1, PFLi, PGI | 14.23 | 0.27 | 14.38 | 0.00 | 22.22 | 0.00 | 0.00 | −20.00 | 0.00 | 16.72 | 13.18 | 0.00 | 0.00 | −2.35 | −2.00 | 0.00 | −0.29 | −0.05 | 0.00 | 0.00 | 0.00 |
| 442 | ADHEr, ACKr, GLCpts, NADH6, PGI | 14.13 | 0.25 | 15.36 | 0.00 | 19.91 | 2.53 | 0.00 | −20.00 | 0.00 | 19.65 | 10.34 | 0.00 | 0.00 | −2.15 | 0.00 | 0.00 | −0.27 | −0.04 | 0.00 | 0.00 | 0.00 |
| 443 | ADHEr, EDA, GLUDy, NADH6, PGI | 14.07 | 0.27 | 15.02 | 0.00 | 19.91 | 2.38 | 0.00 | −20.00 | 0.00 | 19.34 | 10.85 | 0.00 | 0.00 | −2.37 | 0.00 | 0.00 | −0.29 | −0.05 | 0.00 | 0.00 | 0.00 |
| 444 | ADHEr, ACKr, PFLi, PGI, SUCD4 | 14.04 | 0.19 | 14.14 | 0.00 | 21.04 | 0.00 | 0.00 | −20.00 | 0.00 | 17.69 | 10.52 | 0.00 | 2.18 | −1.66 | 0.00 | 0.00 | −0.21 | −0.03 | 0.20 | 0.00 | 0.00 |
| 445 | ADHEr, ACKr, NADH6, PFLi, PGI | 14.04 | 0.19 | 14.14 | 0.00 | 22.14 | 0.00 | 0.00 | −20.00 | 0.00 | 16.60 | 12.71 | 0.00 | 0.00 | −2.75 | 0.00 | 0.00 | −0.21 | −0.03 | 0.00 | 0.00 | 1.09 |
| 446 | ADHEr, ACKr, GLUDy, NADH6, PGI | 14.03 | 0.30 | 14.19 | 0.00 | 22.02 | 0.00 | 0.00 | −20.00 | 0.00 | 16.65 | 13.53 | 0.00 | 0.31 | −2.61 | −2.00 | 0.00 | −0.32 | −0.05 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 447 | ADHEr, EDA, GLCpts, NADH6, PGI | 14.02 | 0.28 | 14.76 | 0.00 | 21.90 | 0.00 | 0.00 | −20.00 | 0.00 | 17.17 | 13.25 | 0.00 | 0.00 | −2.43 | −2.00 | 0.00 | −0.30 | −0.05 | 0.21 | 0.00 | 0.00 |
| 448 | ADHEr, ACKr, CBMK2, NADH6, PGI | 13.94 | 0.34 | 14.12 | 0.00 | 21.89 | 0.00 | 0.00 | −20.00 | 0.00 | 16.54 | 14.17 | 0.00 | 0.00 | −2.94 | −2.00 | 0.00 | −0.36 | −0.06 | 0.00 | 0.00 | 0.00 |
| 449 | ADHEr, ATPS4r, FDH2, NADH6, PGI | 13.86 | 0.22 | 14.56 | 0.00 | 21.78 | 0.00 | 0.00 | −20.00 | 0.00 | 17.62 | 11.98 | 0.00 | 1.48 | −1.92 | −2.00 | 0.00 | −0.24 | −0.04 | 0.00 | 0.00 | 0.00 |
| 450 | ADHEr, ATPS4r, NADH6, PFLi, PGI | 13.86 | 0.22 | 14.56 | 0.00 | 21.78 | 0.00 | 0.00 | −20.00 | 0.00 | 17.62 | 11.98 | 0.00 | 1.48 | −1.92 | −2.00 | 0.00 | −0.24 | −0.04 | 0.00 | 0.00 | 0.00 |
| 451 | ADHEr, ATPS4r, GLCpts, NADH6, PFLi | 13.80 | 0.27 | 16.36 | 0.00 | 20.68 | 0.00 | 0.00 | −20.00 | 0.00 | 18.31 | 11.92 | 0.00 | 0.00 | −2.38 | 0.00 | 0.00 | −0.29 | −0.05 | 0.00 | 0.00 | 0.00 |
| 452 | ADHEr, ATPS4r, MDH, NADH6, PGL | 13.69 | 0.43 | 13.35 | 0.00 | 20.51 | 0.00 | 0.00 | −20.00 | 0.00 | 16.43 | 14.76 | 0.00 | 0.00 | −3.75 | 0.00 | 0.00 | −0.46 | −0.08 | 0.00 | 0.00 | 0.00 |
| 453 | ADHEr, ATPS4r, G6PDHy, MDH, NADH6 | 13.69 | 0.43 | 13.35 | 0.00 | 20.51 | 0.00 | 0.00 | −20.00 | 0.00 | 16.43 | 14.76 | 0.00 | 0.00 | −3.75 | 0.00 | 0.00 | −0.46 | −0.08 | 0.00 | 0.00 | 0.00 |
| 454 | ADHEr, ACKr, FUM, GLUDy, LDH_D | 13.68 | 0.36 | 13.87 | 0.00 | 18.43 | 4.12 | 0.00 | −20.00 | 0.00 | 20.56 | 11.37 | 0.00 | 0.00 | −3.12 | 0.00 | 0.00 | −0.39 | −0.06 | 0.00 | 0.00 | 0.00 |
| 455 | ADHEr, ATPS4r, NADH6, PGI, SUCD4 | 13.66 | 0.25 | 15.79 | 0.00 | 19.61 | 3.75 | 0.00 | −20.00 | 0.00 | 21.32 | 10.53 | 0.00 | 0.00 | −2.17 | −2.00 | 0.00 | −0.27 | −0.04 | 0.00 | 0.00 | 0.00 |
| 456 | ADHEr, ACKr, GLUDy, LDH_D, SUCD4 | 13.56 | 0.37 | 13.76 | 0.00 | 17.71 | 5.22 | 0.00 | −20.00 | 0.00 | 21.60 | 10.89 | 0.00 | 0.00 | −3.19 | 0.00 | 0.00 | −0.39 | −0.06 | 0.00 | 0.00 | 0.00 |
| 457 | ADHEr, ATPS4r, G6PDHy, | 13.53 | 0.44 | 10.63 | 0.00 | 14.18 | 12.16 | 0.00 | −20.00 | 0.00 | 25.92 | 8.72 | 0.00 | 0.00 | −3.81 | 0.00 | 0.00 | −0.47 | −0.08 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 458 | MDH, THD2 | 13.53 | 0.44 | 10.63 | 0.00 | 14.18 | 12.16 | 0.00 | −20.00 | 0.00 | 25.92 | 8.72 | 0.00 | 0.00 | −3.81 | 0.00 | 0.00 | −0.47 | −0.08 | 0.00 | 0.00 | 0.00 |
| 459 | ADHEr, ATPS4r, MDH, PGL, THD2 | 13.44 | 0.26 | 11.28 | 0.00 | 7.24 | 25.83 | 0.00 | −20.00 | 0.00 | 38.92 | −1.53 | 0.00 | 0.00 | −2.21 | 0.00 | 0.00 | −0.27 | −0.04 | 0.00 | 0.00 | 0.00 |
| 460 | ADHEr, ASPT, G6PDHy, MDH, PYK | 13.44 | 0.26 | 11.28 | 0.00 | 7.24 | 25.83 | 0.00 | −20.00 | 0.00 | 38.92 | −1.53 | 0.00 | 0.00 | −2.21 | 0.00 | 0.00 | −0.27 | −0.04 | 0.00 | 0.00 | 0.00 |
| 461 | ADHEr, ASPT, EDA, MDH, PYK | 13.44 | 0.26 | 11.28 | 0.00 | 7.24 | 25.83 | 0.00 | −20.00 | 0.00 | 38.92 | −1.53 | 0.00 | 0.00 | −2.21 | 0.00 | 0.00 | −0.27 | −0.04 | 0.00 | 0.00 | 0.00 |
| 462 | ADHEr, FRD2, LDH_D, MDH, SUCOAS | 13.35 | 0.25 | 4.81 | 0.00 | 13.43 | 19.59 | 0.00 | −20.00 | 0.00 | 28.60 | 6.97 | 2.19 | 0.00 | −4.35 | 0.00 | 0.00 | −0.27 | −0.04 | 0.12 | 0.00 | 0.00 |
| 463 | ADHEr, ASPT, LDH_D, MDH, SUCOAS | 13.27 | 0.26 | 4.78 | 0.00 | 13.14 | 19.51 | 0.00 | −20.00 | 0.00 | 28.92 | 7.01 | 2.11 | 0.00 | −4.33 | 0.00 | 0.00 | −0.27 | −0.04 | 0.35 | 0.00 | 0.00 |
| 464 | ADHEr, ACt6, LDH_D, MDH, SUCD4 | 13.22 | 0.26 | 0.00 | 0.00 | 17.54 | 14.32 | 0.00 | −20.00 | 0.00 | 21.06 | 13.99 | 0.00 | 0.00 | −7.14 | 0.00 | 0.00 | −0.28 | −0.05 | 0.00 | 0.00 | 4.89 |
| 465 | ADHEr, ATPS4r, GLUDy, PGI, SUCD4 | 13.17 | 0.24 | 16.40 | 0.00 | 17.06 | 7.36 | 0.00 | −20.00 | 0.00 | 25.48 | 8.35 | 0.00 | 0.00 | −2.11 | −2.00 | 0.00 | −0.26 | −0.04 | 0.00 | 0.00 | 0.00 |
| 466 | ADHEr, ASPT, FUM, LDH_D, MDH | 13.15 | 0.27 | 5.76 | 0.00 | 12.63 | 20.09 | 0.00 | −20.00 | 0.00 | 29.76 | 6.45 | 1.98 | 0.00 | −4.33 | 0.00 | 0.00 | −0.29 | −0.05 | 0.00 | 0.00 | 0.00 |
| 467 | ADHEr, ASPT, LDH_D, MALS, MDH | 13.15 | 0.27 | 5.76 | 0.00 | 12.63 | 20.09 | 0.00 | −20.00 | 0.00 | 29.76 | 6.45 | 1.98 | 0.00 | −4.33 | 0.00 | 0.00 | −0.29 | −0.05 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 468 | ADHEr, ASPT, ICL, LDH_D, MDH | 13.15 | 0.27 | 5.76 | 0.00 | 12.63 | 20.09 | 0.00 | −20.00 | 0.00 | 29.76 | 6.45 | 1.98 | 0.00 | −4.33 | 0.00 | 0.00 | −0.29 | −0.05 | 0.00 | 0.00 | 0.00 |
| 469 | ADHEr, ACt6, LDH_D, MDH, NADH6 | 13.07 | 0.51 | 0.00 | 0.00 | 23.45 | 0.00 | 0.00 | −20.00 | 0.00 | 13.57 | 25.20 | 0.00 | 0.00 | −5.48 | −10.00 | 0.00 | −0.54 | −0.09 | 4.43 | 0.00 | 1.10 |
| 470 | ADHEr, FRD2, GLUDy, LDH_D, PPCK | 12.91 | 0.12 | 12.29 | 0.00 | −0.02 | 38.75 | 0.00 | −20.00 | 0.00 | 51.90 | −10.70 | 0.00 | 0.00 | −1.05 | 0.00 | 0.00 | −0.13 | −0.02 | 0.00 | 0.00 | 0.00 |
| 471 | ADHEr, FRD2, LDH_D, PPCK, THD2 | 12.89 | 0.13 | 12.25 | 0.00 | −0.02 | 38.70 | 0.00 | −20.00 | 0.00 | 51.85 | −10.60 | 0.00 | 0.00 | −1.09 | 0.00 | 0.00 | −0.13 | −0.02 | 0.00 | 0.00 | 0.00 |
| 472 | ADHEr, ACKr, ATPS4r, LDH_D, SUCD4 | 12.73 | 0.47 | 12.99 | 0.00 | 16.72 | 6.70 | 0.00 | −20.00 | 0.00 | 23.06 | 12.66 | 0.00 | 0.00 | −4.09 | −2.00 | 0.00 | −0.51 | −0.08 | 0.00 | 0.00 | 0.00 |
| 473 | ADHEr, ACKr, ACS, PPC, PPCK | 12.62 | 0.11 | 12.68 | 0.00 | 0.33 | 39.20 | 0.00 | −20.00 | 0.00 | 52.67 | −10.25 | 0.00 | 0.00 | −0.96 | −2.00 | 0.00 | −0.12 | −0.02 | 0.00 | 0.00 | 0.00 |
| 474 | ADHEr, GLUDy, LDH_D, PPC, PPCK | 12.60 | 0.16 | 11.81 | 0.00 | 0.47 | 38.84 | 0.00 | −20.00 | 0.00 | 51.79 | −9.20 | 0.00 | 0.00 | −1.38 | −2.00 | 0.00 | −0.17 | −0.03 | 0.00 | 0.00 | 0.00 |
| 475 | ADHEr, ATPS4r, FDH2, NADH6, SULabc | 12.60 | 0.48 | 14.92 | 0.00 | 19.87 | 0.00 | 0.00 | −20.00 | 0.00 | 18.32 | 16.04 | 0.00 | 0.00 | −4.14 | −2.00 | 0.00 | −0.51 | −0.08 | 0.00 | 0.00 | 0.00 |
| 476 | ADHEr, LDH_D, PPC, PPCK, THD2 | 12.60 | 0.16 | 11.72 | 0.00 | 0.49 | 38.81 | 0.00 | −20.00 | 0.00 | 51.71 | −9.09 | 0.00 | 0.00 | −1.43 | −2.00 | 0.00 | −0.18 | −0.03 | 0.00 | 0.00 | 0.00 |
| 477 | ADHEr, ASPT, ATPS4r, GLCpts, MDH | 12.57 | 0.29 | 9.83 | 0.00 | 18.83 | 0.00 | 0.00 | −20.00 | 0.00 | 18.28 | 11.62 | 0.00 | 6.37 | −2.53 | 0.00 | 0.00 | −0.31 | −0.05 | 0.00 | 0.00 | 0.00 |
| 478 | ADHEr, G6PDHy, MDH, | 12.37 | 0.68 | 7.32 | 0.00 | 24.57 | 2.87 | 0.00 | −20.00 | 0.00 | 15.06 | 24.76 | 0.00 | 0.00 | −5.93 | −15.00 | 0.00 | −0.73 | −0.12 | 0.00 | 0.00 | 0.00 |

TABLE 7-continued

Knockout strategies derived by OptKnock assuming PEP carboxykinase to be reversible.

| # | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| 479 | ADHEr, MDH, NADH6, PGL, THD2 | 12.37 | 0.68 | 7.32 | 0.00 | 24.57 | 2.87 | 0.00 | −20.00 | 0.00 | 15.06 | 24.76 | 0.00 | 0.00 | −5.93 | −15.00 | 0.00 | −0.73 | −0.12 | 0.00 | 0.00 | 0.00 |
| 480 | ADHEr, ACKr, FBA, GLUDy, NADH6 | 12.36 | 0.41 | 12.58 | 0.00 | 28.51 | 0.00 | 0.00 | −20.00 | 0.00 | 15.47 | 23.61 | 0.00 | 0.00 | −3.52 | −20.00 | 0.00 | −0.44 | −0.07 | 0.00 | 0.00 | 0.00 |
| 481 | ADHEr, ACKr, GLUDy, NADH6, PFK | 12.36 | 0.41 | 12.58 | 0.00 | 28.51 | 0.00 | 0.00 | −20.00 | 0.00 | 15.47 | 23.61 | 0.00 | 0.00 | −3.52 | −20.00 | 0.00 | −0.44 | −0.07 | 0.00 | 0.00 | 0.00 |
| 482 | ADHEr, ACKr, GLUDy, NADH6, TPI | 12.36 | 0.41 | 12.58 | 0.00 | 28.51 | 0.00 | 0.00 | −20.00 | 0.00 | 15.47 | 23.61 | 0.00 | 0.00 | −3.52 | −20.00 | 0.00 | −0.44 | −0.07 | 0.00 | 0.00 | 0.00 |
| 483 | ADHEr, ATPS4r, MTHFC, NADH6, PFLi | 12.33 | 0.49 | 15.46 | 0.00 | 19.46 | 0.00 | 0.00 | −20.00 | 0.00 | 18.94 | 16.09 | 0.00 | 0.00 | −4.23 | −2.00 | 0.00 | −0.52 | −0.09 | 0.00 | 0.00 | 0.00 |
| 484 | ADHEr, ATPS4r, FTHFD, NADH6, PFLi | 12.33 | 0.49 | 15.46 | 0.00 | 19.46 | 0.00 | 0.00 | −20.00 | 0.00 | 18.94 | 16.09 | 0.00 | 0.00 | −4.23 | −2.00 | 0.00 | −0.52 | −0.09 | 0.00 | 0.00 | 0.00 |
| 485 | ADHEr, ATPS4r, G6PDHy, GLCpts, MDH | 12.30 | 0.34 | 0.00 | 0.00 | 12.96 | 0.00 | 0.00 | −20.00 | 0.00 | 24.29 | 17.81 | 0.00 | 0.00 | −2.93 | 0.00 | 0.00 | −0.36 | −0.06 | 10.94 | 0.00 | 0.00 |
| 486 | ADHEr, ATPS4r, GLCpts, MDH, PGL | 12.30 | 0.34 | 0.00 | 0.00 | 12.96 | 0.00 | 0.00 | −20.00 | 0.00 | 24.29 | 17.81 | 0.00 | 0.00 | −2.93 | 0.00 | 0.00 | −0.36 | −0.06 | 10.94 | 0.00 | 0.00 |
| 487 | ADHEr, ACKr, FBA, GLCpts, NADH6 | 12.15 | 0.44 | 12.39 | 0.00 | 28.20 | 0.00 | 0.00 | −20.00 | 0.00 | 15.54 | 24.17 | 0.00 | 0.00 | −3.83 | −20.00 | 0.00 | −0.47 | −0.08 | 0.00 | 0.00 | 0.00 |
| 488 | ADHEr, ACKr, GLCpts, NADH6, TPI | 12.15 | 0.44 | 12.39 | 0.00 | 28.20 | 0.00 | 0.00 | −20.00 | 0.00 | 15.54 | 24.17 | 0.00 | 0.00 | −3.83 | −20.00 | 0.00 | −0.47 | −0.08 | 0.00 | 0.00 | 0.00 |
| 489 | ADHEr, ACKr, | 12.15 | 0.44 | 12.39 | 0.00 | 28.20 | 0.00 | 0.00 | −20.00 | 0.00 | 15.54 | 24.17 | 0.00 | 0.00 | −3.83 | −20.00 | 0.00 | −0.47 | −0.08 | 0.00 | 0.00 | 0.00 |

TABLE 7-continued

Knockout strategies derived by OptKnock assuming PEP carboxykinase to be reversible.

| | Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|---|
| | GLCpts, NADH6, PFK | | | | | | | | | | | | | | | | | | | | | |
| 490 | ADHEr, ACKr, LDH_D, MDH, SUCD4 | 12.15 | 0.40 | 12.37 | 0.00 | 6.33 | 23.73 | 0.00 | −20.00 | 0.00 | 38.94 | 1.52 | 0.00 | 0.00 | −3.46 | 0.00 | 0.00 | −0.43 | −0.07 | 0.00 | 0.00 | 0.00 |
| 491 | ADHEr, ACKr, AKGD, ATPS4r, FBA | 12.13 | 0.22 | 12.25 | 0.00 | 37.66 | 0.00 | 0.00 | −20.00 | 0.00 | 13.85 | 29.63 | 0.00 | 0.00 | −1.94 | −38.95 | 0.00 | −0.24 | −0.04 | 0.00 | 0.00 | 0.00 |
| 492 | ADHEr, ACKr, AKGD, ATPS4r, PFK | 12.13 | 0.22 | 12.25 | 0.00 | 37.66 | 0.00 | 0.00 | −20.00 | 0.00 | 13.85 | 29.63 | 0.00 | 0.00 | −1.94 | −38.95 | 0.00 | −0.24 | −0.04 | 0.00 | 0.00 | 0.00 |
| 493 | ADHEr, ACKr, AKGD, ATPS4r, TPI | 12.13 | 0.22 | 12.25 | 0.00 | 12.10 | 25.56 | 0.00 | −20.00 | 0.00 | 39.40 | 4.07 | 0.00 | 0.00 | −1.94 | −13.39 | 0.00 | −0.24 | −0.04 | 0.00 | 0.00 | 0.00 |
| 494 | ADHEr, EDA, PGI, PPCK, SUCD4 | 12.09 | 0.07 | 20.13 | 0.00 | 7.88 | 20.50 | 0.00 | −20.00 | 0.00 | 41.14 | −2.89 | 0.00 | 0.00 | −0.62 | 0.00 | 0.00 | −0.08 | −0.01 | 0.00 | 0.00 | 0.00 |
| 495 | ADHEr, ACKr, ATPS4r, FBA, SUCOAS | 12.09 | 0.23 | 12.21 | 0.00 | 12.27 | 25.58 | 0.00 | −20.00 | 0.00 | 39.40 | 4.32 | 0.00 | 0.00 | −1.95 | −13.90 | 0.00 | −0.24 | −0.04 | 0.00 | 0.00 | 0.00 |
| 496 | ADHEr, ACKr, ATPS4r, PFK, SUCOAS | 12.09 | 0.23 | 12.21 | 0.00 | 12.27 | 25.58 | 0.00 | −20.00 | 0.00 | 39.40 | 4.32 | 0.00 | 0.00 | −1.95 | −13.90 | 0.00 | −0.24 | −0.04 | 0.00 | 0.00 | 0.00 |
| 497 | ADHEr, ACKr, ATPS4r, SUCOAS, TPI | 12.09 | 0.23 | 12.21 | 0.00 | 37.86 | 0.00 | 0.00 | −20.00 | 0.00 | 13.82 | 29.91 | 0.00 | 0.00 | −1.95 | −39.48 | 0.00 | −0.24 | −0.04 | 0.00 | 0.00 | 0.00 |
| 498 | ADHEr, FRD2, LDH_D, ME2, SUCOAS | 12.08 | 0.26 | 3.82 | 0.00 | 8.14 | 17.37 | 4.03 | −20.00 | 0.00 | 33.19 | 10.83 | 1.87 | 0.00 | −4.10 | 0.00 | 0.00 | −0.28 | −0.05 | 0.12 | 0.00 | 0.00 |
| 499 | ADHEr, ACKr, CBMK2, FBA, NADH6 | 12.06 | 0.46 | 12.31 | 0.00 | 28.06 | 0.00 | 0.00 | −20.00 | 0.00 | 15.57 | 24.41 | 0.00 | 0.00 | −3.97 | −20.00 | 0.00 | −0.49 | −0.08 | 0.00 | 0.00 | 0.00 |

TABLE 7-continued

Knockout strategies derived by OptKnock assuming PEP carboxykinase to be reversible.

| Metabolic Transformations Targeted For Removal †, ‡, # | BDO | BIO | AC | ALA | CO2 | FOR | FUM | GLC | GLY | H+ | H2O | ILE | LAC | NH4 | NO3 | PHE | PI | SO4 | SUC | THR | VAL |
|---|---|---|---|---|---|---|---|---|---|---|---|---|---|---|---|---|---|---|---|---|---|
| 500 ADHEr, ACKr, CBMK2, NADH6, PFK | 12.06 | 0.46 | 12.31 | 0.00 | 28.06 | 0.00 | 0.00 | −20.00 | 0.00 | 15.57 | 24.41 | 0.00 | 0.00 | −3.97 | −20.00 | 0.00 | −0.49 | −0.08 | 0.00 | 0.00 | 0.00 |
| 501 ADHEr, ACKr, CBMK2, NADH6, TPI | 12.06 | 0.46 | 12.31 | 0.00 | 28.06 | 0.00 | 0.00 | −20.00 | 0.00 | 15.57 | 24.41 | 0.00 | 0.00 | −3.97 | −20.00 | 0.00 | −0.49 | −0.08 | 0.00 | 0.00 | 0.00 |
| 502 ADHEr, ACKr, NADH6, RPE, TPI | 12.05 | 0.46 | 12.30 | 0.00 | 28.05 | 0.00 | 0.00 | −20.00 | 0.00 | 15.58 | 24.45 | 0.00 | 0.00 | −3.99 | −20.00 | 0.00 | −0.49 | −0.08 | 0.00 | 0.00 | 0.00 |
| 503 ADHEr, ACKr, NADH6, PFK, RPE | 12.05 | 0.46 | 12.30 | 0.00 | 28.05 | 0.00 | 0.00 | −20.00 | 0.00 | 15.58 | 24.45 | 0.00 | 0.00 | −3.99 | −20.00 | 0.00 | −0.49 | −0.08 | 0.00 | 0.00 | 0.00 |
| 504 ADHEr, ACKr, FBA, NADH6, RPE | 12.05 | 0.46 | 12.30 | 0.00 | 28.05 | 0.00 | 0.00 | −20.00 | 0.00 | 15.58 | 24.45 | 0.00 | 0.00 | −3.99 | −20.00 | 0.00 | −0.49 | −0.08 | 0.00 | 0.00 | 0.00 |
| 505 ADHEr, ACKr, ASNS2, FBA, NADH6 | 12.05 | 0.46 | 12.30 | 0.00 | 28.04 | 0.00 | 0.00 | −20.00 | 0.00 | 15.58 | 24.46 | 0.00 | 0.00 | −4.00 | −20.00 | 0.00 | −0.49 | −0.08 | 0.00 | 0.00 | 0.00 |

TABLE 8

Corresponding genes to be knocked out to prevent a particular reaction from occurring in E. coli.

| Reaction Abbreviation | Reaction Stoichiometry* | Genes Encoding the Enzyme(s) Catalyzing Each Reaction& |
|---|---|---|
| ACKr | [c]: ac + atp <==> actp + adp | (b3115 or b2296 or b1849) |
| ACS | [c]: ac + atp + coa --> accoa + amp + ppi | b4069 |
| ACt6 | ac[p] + h[p] <==> ac[c] + h[c] | Non-gene associated |
| ADHEr | [c]: etoh + nad <==> acald + h + nadh | (b0356 or b1478 or b1241) |
|  | [c]: acald + coa + nad <==> accoa + h + nadh | (b1241 or b0351) |
| AKGD | [c]: akg + coa + nad --> co2 + nadh + succoa | (b0116 and b0726 and b0727) |
| ASNS2 | [c]: asp-L + atp + nh4 --> amp + asn-L + h + ppi | b3744 |
| ASPT | [c]: asp-L --> fum + nh4 | b4139 |
| ATPS4r | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | [c]: atp + co2 + nh4 <==> adp + cbp + (2) h | (b0521 or b0323 or b2874) |
| EDA | [c]: 2ddg6p --> g3p + pyr | b1850 |
| ENO | [c]: 2pg <==> h2o + pep | b2779 |
| FBA | [c]: fdp <==> dhap + g3p | (b2097 or b2925 or b1773) |
| FBP | [c]: fdp + h2o --> f6p + pi | (b4232 or b3925) |
| FDH2 | for[p] + (2) h[c] + q8[c] --> co2[c] + h[p] + q8h2[c] | ((b3892 and b3893 and b3894) or (b1474 and b1475 and b1476)) |
|  | for[p] + (2) h[c] + mqn8[c] --> co2[c] + h[p] + mql8[c] |  |
| FRD2 | [c]: fum + mql8 --> mqn8 + succ | (b4151 and b4152 and b4153 and b4154) |
|  | [c]: 2dmmql8 + fum --> 2dmmq8 + succ |  |
| FTHFD | [c]: 10fthf + h2o --> for + h + thf | b1232 |
| FUM | [c]: fum + h2o <==> mal-L | (b1612 or b4122 or b1611) |
| G5SD | [c]: glu5p + h + nadph --> glu5sa + nadp + pi | b0243 |
| G6PDHy | [c]: g6p + nadp <==> 6pgl + h + nadph | b1852 |
| GLCpts | glc-D[p] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | [c]: atp + glu-L --> adp + glu5p | b0242 |
| GLUDy | [c]: glu-L + h2o + nadp <==> akg + h + nadph + nh4 | b1761 |
| GLYCL | [c]: gly + nad + thf --> co2 + mlthf + nadh + nh4 | (b2904 and b2903 and b2905 and b0116) |
| HEX1 | [c]: atp + glc-D --> adp + g6p + h | b2388 |
| ICL | [c]: icit --> glx + succ | b4015 |
| LDH_D | [c]: lac-D + nad <==> h + nadh + pyr | (b2133 or b1380) |
| MALS | [c]: accoa + glx + h2o --> coa + h + mal-L | (b4014 or b2976) |
| MDH | [c]: mal-L + nad <==> h + nadh + oaa | b3236 |
| ME2 | [c]: mal-L + nadp --> co2 + nadph + pyr | b2463 |
| MTHFC | [c]: h2o + methf <==> 10fthf + h | b0529 |
| NADH12 | [c]: h + mqn8 + nadh --> mql8 + nad | b1109 |
|  | [c]: h + nadh + q8 --> nad + q8h2 |  |
|  | [c]: 2dmmq8 + h + nadh --> 2dmmql8 + nad |  |
| NADH6 | (4) h[c] + nadh[c] + q8[c] --> (3) h[p] + nad[c] + q8h2[c] | (b2276 and b2277 and b2278 and b2279 and b2280 and b2281 and b2282 and b2283 and b2284 and b2285 and b2286 and b2287 and b2288) |
|  | (4) h[c] + mqn8[c] + nadh[c] --> (3) h[p] + mql8[c] + nad[c] |  |
|  | 2dmmq8[c] + (4) h[c] + nadh[c] --> 2dmmql8[c] + (3) h[p] + nad[c] |  |

TABLE 8-continued

Corresponding genes to be knocked out to prevent a particular reaction from occurring in *E. coli*.

| Reaction Abbreviation | Reaction Stoichiometry* | Genes Encoding the Enzyme(s) Catalyzing Each Reaction& |
|---|---|---|
| PFK | [c]: atp + f6p --> adp + fdp + h | (b3916 or b1723) |
| PFLi | [c]: coa + pyr --> accoa + for | (((b0902 and b0903) and b2579) or (b0902 and b0903) or (b0902 and b3114) or (b3951 and b3952)) |
| PGDH | [c]: 6pgc + nadp --> co2 + nadph + ru5p-D | b2029 |
| PGI | [c]: g6p <==> f6p | b4025 |
| PGL | [c]: 6pgl + h2o --> 6pgc + h | b0767 |
| PGM | [c]: 2pg <==> 3pg | (b3612 or b4395 or b0755) |
| PPC | [c]: co2 + h2o + pep --> h + oaa + pi | b3956 |
| PPCK | [c]: atp + oaa --> adp + co2 + pep | b3403 |
| PRO1z | [c]: fad + pro-L --> 1pyr5c + fadh2 + h | b1014 |
| PYK | [c]: adp + h + pep --> atp + pyr | b1854 or b1676) |
| PYRt2 | h[p] + pyr[p] <==> h[c] + pyr[c] | Non-gene associated |
| RPE | [c]: ru5p-D <==> xu5p-D | (b4301 or b3386) |
| SO4t2 | so4[e] <==> so4[p] | (b0241 or b0929 or b1377 or b2215) |
| SUCD4 | [c]: q8 + succ --> fum + q8h2 | (b0721 and b0722 and b0723 and b0724) |
| SUCOAS | [c]: atp + coa + succ <==> adp + pi + succoa | (b0728 and b0729) |
| SULabc | atp[c] + h2o[c] + so4[p] --> adp[c] + h[c] + pi[c] + so4[c] | ((b2422 and b2425 and b2424 and b2423) or (b0763 and b0764 and b0765) or (b2422 and b2424 and b2423 and b3917)) |
| TAL | [c]: g3p + s7p <==> e4p + f6p | (b2464 and b0008) |
| THD2 | (2) h[p] + nadh[c] + nadp[c] --> (2) h[c] + nad[c] + nadph[c] | (b1602 and b1603) |
| THD5 | [c]: nad + nadph --> nadh + nadp | (b3962 or (b1602 and b1603)) |
| TPI | [c]: dhap <==> g3p | b3919 |

TABLE 9

Metabolite names corresponding to abbreviations used in Table 8.

| Metabolite Abbreviation | Metabolite Name |
|---|---|
| 10fthf | 10-Formyltetrahydrofolate |
| 1pyr5c | 1-Pyrroline-5-carboxylate |
| 2ddg6p | 2-Dehydro-3-deoxy-D-gluconate 6-phosphate |
| 2dmmq8 | 2-Demethylmenaquinone 8 |
| 2dmmql8 | 2-Demethylmenaquinol 8 |
| 2pg | D-Glycerate 2-phosphate |
| 3pg | 3-Phospho-D-glycerate |
| 6pgc | 6-Phospho-D-gluconate |
| 6pgl | 6-phospho-D-glucono-1,5-lactone |
| ac | Acetate |
| acald | Acetaldehyde |
| accoa | Acetyl-CoA |
| actp | Acetyl phosphate |
| adp | ADP |
| akg | 2-Oxoglutarate |
| amp | AMP |
| asn-L | L-Asparagine |
| asp-L | L-Aspartate |
| atp | ATP |
| cbp | Carbamoyl phosphate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | Flavin adenine dinucleotide oxidized |
| fadh2 | Flavin adenine dinucleotide reduced |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |
| glu5p | L-Glutamate 5-phosphate |
| glu5sa | L-Glutamate 5-semialdehyde |
| glu-L | L-Glutamate |
| glx | Glyoxylate |
| gly | Glycine |
| h | H+ |
| h2o | H2O |
| icit | Isocitrate |
| lac-D | D-Lactate |
| mal-L | L-Malate |
| methf | 5,10-Methenyltetrahydrofolate |
| mlthf | 5,10-Methylenetetrahydrofolate |
| mql8 | Menaquinol 8 |
| mqn8 | Menaquinone 8 |
| nad | Nicotinamide adenine dinucleotide |
| nadh | Nicotinamide adenine dinucleotide - reduced |
| nadp | Nicotinamide adenine dinucleotide phosphate |
| nadph | Nicotinamide adenine dinucleotide phosphate - reduced |

TABLE 9-continued

Metabolite names corresponding to abbreviations used in Table 8.

| Metabolite Abbreviation | Metabolite Name |
|---|---|
| nh4 | Ammonium |
| oaa | Oxaloacetate |
| pep | Phosphoenolpyruvate |
| pi | Phosphate |
| ppi | Diphosphate |
| pro-L | L-Proline |
| pyr | Pyruvate |
| q8 | Ubiquinone-8 |
| q8h2 | Ubiquinol-8 |
| ru5p-D | D-Ribulose 5-phosphate |
| s7p | Sedoheptulose 7-phosphate |
| so4 | Sulfate |
| succ | Succinate |
| succoa | Succinyl-CoA |
| thf | 5,6,7,8-Tetrahydrofolate |
| xu5p-D | D-Xylulose 5-phosphate |

A number of criteria were applied to select the most practical sets of genes to target for removal. First, the designs were limited to include only knockouts that would not significantly (that is, >5%) reduce the maximum theoretical yield of BDO under anaerobic conditions with or without the presence of nitrate as an electron acceptor. Such knockouts would create an artificial ceiling on any future metabolic engineering efforts and are thus undesirable. To this end, a series of linear programming (LP) problems were solved that maximized the BDO yield for the wild-type *E. coli* metabolic network assuming every reaction was individually deleted from the network. As used herein, reference to the wild-type *E. coli* network assumes that the BDO pathway is available. The term "wild-type" is thus a surrogate name for the undeleted *E. coli* network. Reactions whose deletion negatively affects the maximum BDO yield assuming PEP carboxykinase to be irreversible or reversible are shown in Tables 10 and 11, respectively. Table 10 shows reactions which, when deleted, reduce the maximum theoretical BDO yield under anaerobic conditions with or without the presence of nitrate, assuming that PEP carboxykinase cannot be used to produce oxaloacetate. Strain AB3 contains deletions in ADHE, LDH_D, and PFLi. 'Inf' indicates that the non-growth associated energetic requirements cannot be satisfied.

TABLE 10

Reactions which, when deleted, reduce the maximum theoretical BDO yield under anaerobic conditions with or without the presence of nitrate, assuming that PEP carboxykinase cannot be used to produce oxaloacetate.

| | | WT, Anaerobic | | WT, Nitrate | | AB3, Anaerobic | | AB3, Nitrate | | AB3 MDH ASPT, Anaerobic | | AB3 MDH ASPT, Nitrate | |
|---|---|---|---|---|---|---|---|---|---|---|---|---|---|
| | | MAXIMUM MASS YIELD | | | | | | | | | | | |
| | | 0.477 g/g | | 0.528 g/g | | 0.477 g/g | | 0.528 g/g | | 0.477 g/g | | 0.528 g/g | |
| Abbreviation | Reaction Name | BDO Yield | % of Max Yield | BDO Yield | % of Max Yield | BDO Yield | % of Max Yield | BDO Yield | % of Max Yield | BDO Yield | % of Max Yield | BDO Yield | % of Max Yield |
| 4HBACT | 4-hydroxybutyrate acetyl-CoA transferase | 0.00 | 0% | 0.00 | 0% | 0.00 | 0% | 0.00 | 0% | 0.00 | 0% | 0.00 | 0% |
| 4HBDH | 4-hydroxybutyrate dehydrogenase | 0.00 | 0% | 0.00 | 0% | 0.00 | 0% | 0.00 | 0% | 0.00 | 0% | 0.00 | 0% |
| 4HBTALDDH | 4-hydroxybutyraldehyde dehydrogenase | 0.00 | 0% | 0.00 | 0% | 0.00 | 0% | 0.00 | 0% | 0.00 | 0% | 0.00 | 0% |
| ACKr | acetate kinase | 0.44 | 93% | 0.50 | 95% | 0.44 | 93% | 0.50 | 95% | 0.44 | 93% | 0.50 | 95% |
| ACONT | aconitase | 0.41 | 86% | 0.48 | 91% | 0.41 | 86% | 0.48 | 91% | 0.32 | 67% | 0.43 | 81% |
| ACt6 | acetate transport in/out via proton symport | 0.42 | 89% | 0.53 | 100% | 0.40 | 83% | 0.53 | 100% | 0.39 | 83% | 0.53 | 100% |
| ATPS4r | ATP synthase (four protons for one ATP) | 0.45 | 95% | 0.45 | 86% | 0.45 | 95% | 0.45 | 86% | 0.45 | 95% | 0.45 | 86% |
| BTDP2 | 1,4 butanediol dehydrogenase | 0.00 | 0% | 0.00 | 0% | 0.00 | 0% | 0.00 | 0% | 0.00 | 0% | 0.00 | 0% |
| BTDt1 | 1,4-butanediol transport (Diffusion) | 0.00 | 0% | 0.00 | 0% | 0.00 | 0% | 0.00 | 0% | 0.00 | 0% | 0.00 | 0% |
| CO2t | CO2 transport out via diffusion | 0.36 | 75% | 0.36 | 68% | 0.27 | 57% | 0.27 | 52% | 0.26 | 54% | 0.26 | 49% |
| CS | citrate synthase | 0.41 | 86% | 0.48 | 91% | 0.41 | 86% | 0.48 | 91% | 0.32 | 67% | 0.43 | 81% |
| ENO | enolase | 0.03 | 7% | 0.46 | 88% | Inf | Inf | 0.46 | 88% | Inf | Inf | 0.45 | 85% |
| FBA | fructose-bisphosphate aldolase | 0.47 | 98% | 0.53 | 100% | 0.47 | 98% | 0.53 | 100% | 0.46 | 96% | 0.52 | 99% |
| FRD3 | fumarate reductase | 0.47 | 99% | 0.53 | 100% | 0.47 | 99% | 0.53 | 100% | 0.47 | 99% | 0.53 | 100% |
| FUM | fumarase | 0.48 | 100% | 0.53 | 100% | 0.48 | 100% | 0.53 | 100% | 0.40 | 84% | 0.52 | 99% |
| GAPD | glyceraldehyde-3-phosphate dehydrogenase (NAD) | Inf | Inf | 0.44 | 82% | Inf | Inf | 0.44 | 82% | Inf | Inf | 0.42 | 79% |
| GLCpts | D-glucose transport via PEP: Pyr PTS | 0.45 | 94% | 0.52 | 99% | 0.45 | 94% | 0.52 | 99% | 0.45 | 94% | 0.52 | 99% |
| H2Ot5 | H2O transport via diffusion | 0.44 | 91% | 0.47 | 88% | 0.39 | 81% | 0.39 | 73% | 0.36 | 76% | 0.37 | 70% |
| ICDHy | isocitrate dehydrogenase (NADP) | 0.48 | 100% | 0.53 | 100% | 0.48 | 100% | 0.53 | 100% | 0.46 | 96% | 0.51 | 97% |
| ICL | Isocitrate lyase | 0.48 | 100% | 0.53 | 100% | 0.48 | 100% | 0.53 | 100% | 0.37 | 78% | 0.52 | 99% |
| MALS | malate synthase | 0.48 | 100% | 0.53 | 100% | 0.48 | 100% | 0.53 | 100% | 0.40 | 84% | 0.52 | 99% |
| NADH6 | NADH dehydrogenase (ubiquinone-8 & 3.5 protons) | 0.48 | 100% | 0.53 | 100% | 0.48 | 100% | 0.53 | 100% | 0.48 | 100% | 0.53 | 100% |

TABLE 10-continued

Reactions which, when deleted, reduce the maximum theoretical BDO yield under anaerobic conditions with or without the presence of nitrate, assuming that PEP carboxykinase cannot be used to produce oxaloacetate.

| | | WT, Anaerobic | | WT, Nitrate | | AB3, Anaerobic | | AB3, Nitrate | | AB3 MDH ASPT, Anaerobic | | AB3 MDH ASPT, Nitrate | |
|---|---|---|---|---|---|---|---|---|---|---|---|---|---|
| | | \multicolumn{12}{c}{MAXIMUM MASS YIELD} |
| | | 0.477 g/g | | 0.528 g/g | | 0.477 g/g | | 0.528 g/g | | 0.477 g/g | | 0.528 g/g | |
| Abbreviation | Reaction Name | BDO Yield | % of Max Yield | BDO Yield | % of Max Yield | BDO Yield | % of Max Yield | BDO Yield | % of Max Yield | BDO Yield | % of Max Yield | BDO Yield | % of Max Yield |
| NADH8 | NADH dehydrogenase (demethylmenaquinone-8 & 2.8 protons) | 0.47 | 99% | 0.53 | 100% | 0.47 | 99% | 0.53 | 100% | 0.47 | 99% | 0.53 | 100% |
| NO3R1 | Nitrate reductase (Ubiquinol-8) | 0.48 | 100% | 0.52 | 99% | 0.48 | 100% | 0.52 | 99% | 0.48 | 100% | 0.52 | 99% |
| NO3t7 | nitrate transport in via nitrite antiport | 0.48 | 100% | 0.48 | 90% | 0.48 | 100% | 0.48 | 90% | 0.48 | 100% | 0.48 | 90% |
| PDH | pyruvate dehydrogenase | 0.43 | 89% | 0.51 | 97% | 0.29 | 60% | 0.48 | 91% | 0.22 | 46% | 0.47 | 90% |
| PFK | phosphofructokinase | 0.47 | 98% | 0.53 | 100% | 0.47 | 98% | 0.53 | 100% | 0.46 | 96% | 0.52 | 99% |
| PGI | glucose-6-phosphate isomerase | 0.43 | 90% | 0.52 | 98% | 0.43 | 90% | 0.52 | 98% | 0.24 | 51% | 0.52 | 98% |
| PGK | phosphoglycerate kinase | Inf | Inf | 0.44 | 82% | Inf | Inf | 0.44 | 82% | Inf | Inf | 0.42 | 79% |
| PGM | phosphoglycerate mutase | 0.03 | 7% | 0.46 | 88% | Inf | Inf | 0.46 | 88% | Inf | Inf | 0.45 | 85% |
| PPC | phosphoenolpyruvate carboxylase | 0.40 | 84% | 0.52 | 98% | 0.14 | 30% | 0.52 | 98% | 0.00 | 0% | 0.00 | 0% |
| PTAr | phosphotransacetylase | 0.44 | 93% | 0.50 | 95% | 0.44 | 93% | 0.50 | 95% | 0.44 | 93% | 0.50 | 95% |
| SSALcoax | CoA-dependant succinate semialdehyde dehydrogenase | 0.40 | 83% | 0.52 | 98% | 0.31 | 64% | 0.52 | 98% | 0.19 | 39% | 0.52 | 98% |
| TPI | triose-phosphate isomerase | 0.35 | 74% | 0.50 | 95% | 0.35 | 74% | 0.50 | 95% | 0.28 | 58% | 0.49 | 93% |

Table 11 shows reactions which, when deleted, reduce the maximum theoretical BDO yield under anaerobic conditions with or without the presence of nitrate, assuming that PEP carboxykinase can be used to produce oxaloacetate. 'Inf' indicates that the non-growth associated energetic requirements cannot be satisfied.

TABLE 11

Reactions which, when deleted, reduce the maximum theoretical BDO yield under anaerobic conditions with or without the presence of nitrate, assuming that PEP carboxykinase can be used to produce oxaloacetate.

| | | WT, Anaerobic | | WT, Nitrate | | AB3, Anaerobic | | AB3, Nitrate | | AB3 MDH ASPT, Anaerobic | | AB3 MDH ASPT, Nitrate | |
|---|---|---|---|---|---|---|---|---|---|---|---|---|---|
| | | \multicolumn{12}{c}{MAXIMUM MASS YIELD} |
| | | 0.545 g/g | | 0.545 g/g | | 0.545 g/g | | 0.545 g/g | | 0.545 g/g | | 0.545 g/g | |
| Abbreviation | Reaction Name | BDO Yield | % of Max Yield | BDO Yield | % of Max Yield | BDO Yield | % of Max Yield | BDO Yield | % of Max Yield | BDO Yield | % of Max Yield | BDO Yield | % of Max Yield |
| 4HBACT | 4-hydroxybutyrate acetyl-CoA transferase | 0.00 | 0% | 0.00 | 0% | 0.00 | 0% | 0.00 | 0% | 0.00 | 0% | 0.00 | 0% |
| 4HBDH | 4-hydroxybutyrate dehydrogenase | 0.00 | 0% | 0.00 | 0% | 0.00 | 0% | 0.00 | 0% | 0.00 | 0% | 0.00 | 0% |
| 4HBTALDDH | 4-hydroxybutyraldehyde dehydrogenase | 0.00 | 0% | 0.00 | 0% | 0.00 | 0% | 0.00 | 0% | 0.00 | 0% | 0.00 | 0% |
| ACKr | acetate kinase | 0.50 | 92% | 0.53 | 97% | 0.50 | 92% | 0.53 | 97% | 0.48 | 89% | 0.53 | 96% |
| ACONT | aconitase | 0.47 | 86% | 0.51 | 94% | 0.47 | 86% | 0.51 | 94% | 0.36 | 66% | 0.45 | 83% |
| BTDP2 | 1,4 butanediol dehydrogenase | 0.00 | 0% | 0.00 | 0% | 0.00 | 0% | 0.00 | 0% | 0.00 | 0% | 0.00 | 0% |
| BTDt1 | 1,4-butanediol transport (Diffusion) | 0.00 | 0% | 0.00 | 0% | 0.00 | 0% | 0.00 | 0% | 0.00 | 0% | 0.00 | 0% |
| CO2t | CO2 transport out via diffusion | 0.36 | 67% | 0.36 | 67% | 0.33 | 61% | 0.33 | 61% | 0.29 | 54% | 0.30 | 54% |
| CS | citrate synthase | 0.47 | 86% | 0.51 | 94% | 0.47 | 86% | 0.51 | 94% | 0.36 | 66% | 0.45 | 83% |
| ENO | enolase | 0.07 | 14% | 0.46 | 85% | Inf | Inf | 0.46 | 85% | 0.00 | 0% | 0.46 | 85% |
| GAPD | glyceraldehyde-3-phosphate dehydrogenase (NAD) | Inf | Inf | 0.44 | 80% | Inf | Inf | 0.44 | 80% | 0.00 | 0% | 0.43 | 80% |

TABLE 11-continued

Reactions which, when deleted, reduce the maximum theoretical BDO yield under anaerobic conditions with or without the presence of nitrate, assuming that PEP carboxykinase can be used to produce oxaloacetate.

| Abbreviation | Reaction Name | WT, Anaerobic | | WT, Nitrate | | AB3, Anaerobic | | AB3, Nitrate | | AB3 MDH ASPT, Anaerobic | | AB3 MDH ASPT, Nitrate | |
|---|---|---|---|---|---|---|---|---|---|---|---|---|---|
| | | \multicolumn{12}{c}{MAXIMUM MASS YIELD} |
| | | 0.545 g/g | | 0.545 g/g | | 0.545 g/g | | 0.545 g/g | | 0.545 g/g | | 0.545 g/g | |
| | | BDO Yield | % of Max Yield | BDO Yield | % of Max Yield | BDO Yield | % of Max Yield | BDO Yield | % of Max Yield | BDO Yield | % of Max Yield | BDO Yield | % of Max Yield |
| H2Ot5 | H2O transport via diffusion | 0.50 | 92% | 0.50 | 92% | 0.46 | 84% | 0.46 | 84% | 0.44 | 81% | 0.44 | 81% |
| ICDHy | isocitrate dehydrogenase (NADP) | 0.50 | 92% | 0.53 | 97% | 0.50 | 92% | 0.53 | 97% | 0.50 | 92% | 0.53 | 97% |
| PDH | pyruvate dehydrogenase | 0.53 | 97% | 0.54 | 99% | 0.39 | 71% | 0.51 | 94% | 0.31 | 57% | 0.50 | 92% |
| PGI | glucose-6-phosphate isomerase | 0.54 | 98% | 0.54 | 100% | 0.54 | 98% | 0.54 | 100% | 0.40 | 73% | 0.53 | 98% |
| PGK | phosphoglycerate kinase | Inf | Inf | 0.44 | 80% | Inf | Inf | 0.44 | 80% | 0.00 | 0% | 0.43 | 80% |
| PGM | phosphoglycerate mutase | 0.07 | 14% | 0.46 | 85% | Inf | Inf | 0.46 | 85% | 0.00 | 0% | 0.46 | 85% |
| PPCK | Phosphoenol-pyruvate carboxykinase | 0.48 | 88% | 0.53 | 97% | 0.48 | 88% | 0.53 | 97% | 0.48 | 88% | 0.53 | 97% |
| PTAr | Phosphotrans-acetylase | 0.50 | 92% | 0.53 | 97% | 0.50 | 92% | 0.53 | 97% | 0.48 | 89% | 0.53 | 96% |
| SSALcoax | CoA-dependant succinate semialdehyde dehydrogenase | 0.52 | 95% | 0.54 | 98% | 0.48 | 89% | 0.54 | 98% | 0.46 | 84% | 0.54 | 98% |
| TPI | triose-phosphate isomerase | 0.44 | 81% | 0.52 | 96% | 0.44 | 81% | 0.52 | 96% | 0.40 | 73% | 0.52 | 95% |

The above-described analysis led to three critical observations. One critical observation was that acetate kinase and phosphotransacetylase are required to achieve the maximum BDO yields under all conditions by regenerating acetyl-CoA from the acetate produced by 4-hydroxybutyrate:acetyl-CoA transferase. This finding strongly suggests that eliminating acetate formation by deleting ackA-pta may not be a viable option. Thus a successful strain will likely have to provide an intracellular environment where converting acetate to acetyl-CoA is beneficial and thermodynamically feasible. Otherwise, a set of enzymes capable of performing the required BDO reductions without passing through a CoA derivative would have to be found or the co-production of 1 mol of acetate per mol of BDO would have to be accepted.

A second critical observation was that the TCA cycle enzymes citrate synthase (CS), aconitase (ACONT), and isocitrate dehydrogenase (ICDHy) are required to achieve the maximum BDO yields under all conditions. This indicates that the reverse TCA cycle flux from oxaloacetate to succinate to succinyl-CoA must be complemented to some extent by CS, ACONT, and ICDHy for maximum production.

A third critical observation was that supplanting PEP carboxylase with PEP carboxykinase in E. coli can positively impact the BDO program. The maximum BDO yield under anaerobic conditions with and without the presence of nitrate is 3% and 12% lower, respectively, if PEP carboxylase carries out the PEP to oxaloacetate conversion as compared to if PEP carboxykinase carries out the conversion. Furthermore, under anaerobic conditions without nitrate addition, PEP carboxykinase can lessen the requirement for pyruvate dehydrogenase activity for maximum BDO production. Specifically, the maximum BDO yield drops 11% if this typically aerobic enzyme has no activity if PEP carboxykinase is assumed irreversible as compared to a 3% reduction if PEP carboxykinase can catalyze the production of oxaloacetate. An alternative to pyruvate dehydrogenase activity can be utilized by coupling non-native formate dehydrogenase, capable of catalyzing the reduction of formate to carbon dioxide, to pyruvate formate lyase activity.

The next two criteria applied to evaluate the OptKnock designs were the number of required knockouts and the predicted BDO yield at maximum growth. Analysis of the one, two, and three reaction deletion strategies in Table 6 (that is, PEP carboxykinase assumed irreversible) revealed that so few knockouts were insufficient to prevent high acetate yields. The predicted acetate/BDO ratios for all one, two, or three deletion designs, was at least 1.5. Even allowing for four deletions led to only two designs, #99 and #100, with predicted BDO yields above 0.35 g/g, and those designs suggest the removal of the glycolysis gene, pgi, which encodes phosphoglucoisomerase. Given the anticipated importance of glycolysis in the fermentation of E. coli, it was decided to pursue such high-risk designs only as a last resort. Furthermore, the suggested deletions lower the maximum theoretical yield in designs #99 and #100 by 8% and 15%, respectively. The highest producing four deletion strategy that did not negatively impact the maximum theoretical yield was design #129, which had a predicted BDO yield at maximum growth of only 0.26 g/g.

Only one five deletion design in Table 6 satisfies all criteria for a successful design. This knockout strategy involves the removal of ADHEr (alcohol dehydrogenase), PFLi (pyruvate formate lyase), LDH_D (lactate dehydrogenase), MDH (malate dehydrogenase), and ASPT (aspartate transaminase). The suggested knockouts do not reduce the maximum theoretical BDO yield under any of the conditions examined. A strain engineered with these knockouts is predicted to achieve a BDO yield at maximum growth of 0.37 g/g assuming anaerobic conditions and PEP carboxykinase irreversibility. This design has several desirable properties. Most notably, it prevents the network from producing high yields of the natural fermentation products, ethanol, formate, lactate, and succinate. The prevention of homosuccinate production via the MDH deletion as opposed to removing PEP carboxylase, fumarase, or fumarate reductase, is particularly intriguing because it blocks the energy-yielding fermentation pathway from oxaloacetate to succinate that could arise if PEP carboxykinase is assumed reversible without negatively impacting the maximum BDO yield. In this design, succinate semialdehyde can be made via succinyl-CoA or alpha-ketoglutarate. The succinyl-CoA is formed from succinate via succinyl-CoA synthetase. The succinate can be formed from both the reverse TCA cycle reactions (PEP carboxylase, PEP carboxykinase, fumarase, fumarate reductase) and the glyoxylate shunt (malate synthase, isocitrate lyase).

Figure 7A:
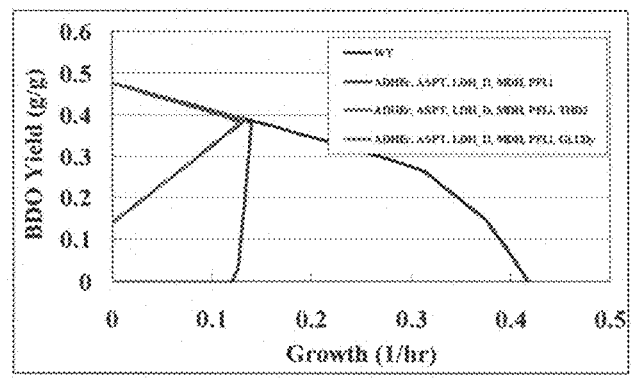
FIGS. 7A and 7B show the anaerobic growth rate versus BDO yield solution boundaries for an *E. coli* strain possessing the BDO production pathways shown and OptKnock predicted knockouts in FIG. 5 assuming in FIG. 7A PEP carboxykinase irreversibility and in FIG. 7B PEP carboxykinase reversibility. A basis glucose uptake rate of 20 mmol/gDW/hr is assumed along with a non-growth associated ATP maintenance requirement of 7.6 mmol/gDW/hr.
Figure 7B:
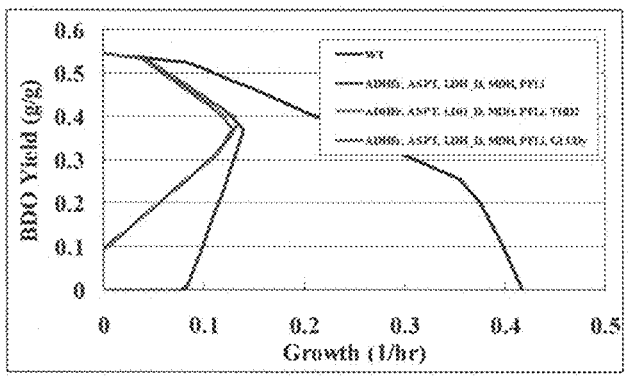

The BDO versus biomass solution boundaries for the ADHEr, PFLi, LDH_D, MDH, ASPT knockout strategy are shown in FIGS. 7A and 7B, assuming PEP carboxykinase irreversibility or reversibility, respectively. Note that the solution boundaries are obtained using a genome-scale model of *E. coli* metabolism as opposed to the reduced model because these calculations are not CPU-intensive. The solution boundaries reveal that the growth coupling of BDO is robust with respect to the assumption of PEP carboxykinase reversibility. However, the deletion of the proton-pumping transhydrogenase (THD2) or glutamate dehydrogenase (GLUDy) may be necessary to achieve an obligatory coupling of cell growth with BDO production. The only negative aspect of the design is that the MDH and ASPT deletions drop the maximum ATP yield of BDO production slightly (~20%) if PEP carboxykinase reversibility is assumed. This causes the optimal growth solution of the design strategy to drop below the black BDO vs. biomass line of the wild-type network in FIG. 7B. However, this finding suggests the possibility of engineering an optimal balance of MDH activity where enough is present to ensure efficient BDO production while also being limited enough to prevent succinate from becoming the major fermentation product. Note that succinate is predicted to be the major fermentation product of the wild-type network if PEP carboxykinase reversibility is assumed.

Tables 10 and 11 list reactions whose deletion negatively impacts the maximum BDO yield in an intermediate strain, referred to as AB3, which lacks ADHEr, LDH_D, and PFLi as well as a strain lacking ASPT and MDH in addition to the AB3 deletions. Note that the suggested deletions place a very high importance on obtaining pyruvate dehydrogenase, citrate synthase, and aconitase activity under completely anaerobic conditions. If sufficient pyruvate dehydrogenase activity cannot be attained, an alternative is to leave PFLi intact and supplement its activity with a non-native formate dehydrogenase that can capture one reducing equivalent while converting formate to carbon dioxide.

Figure 8:
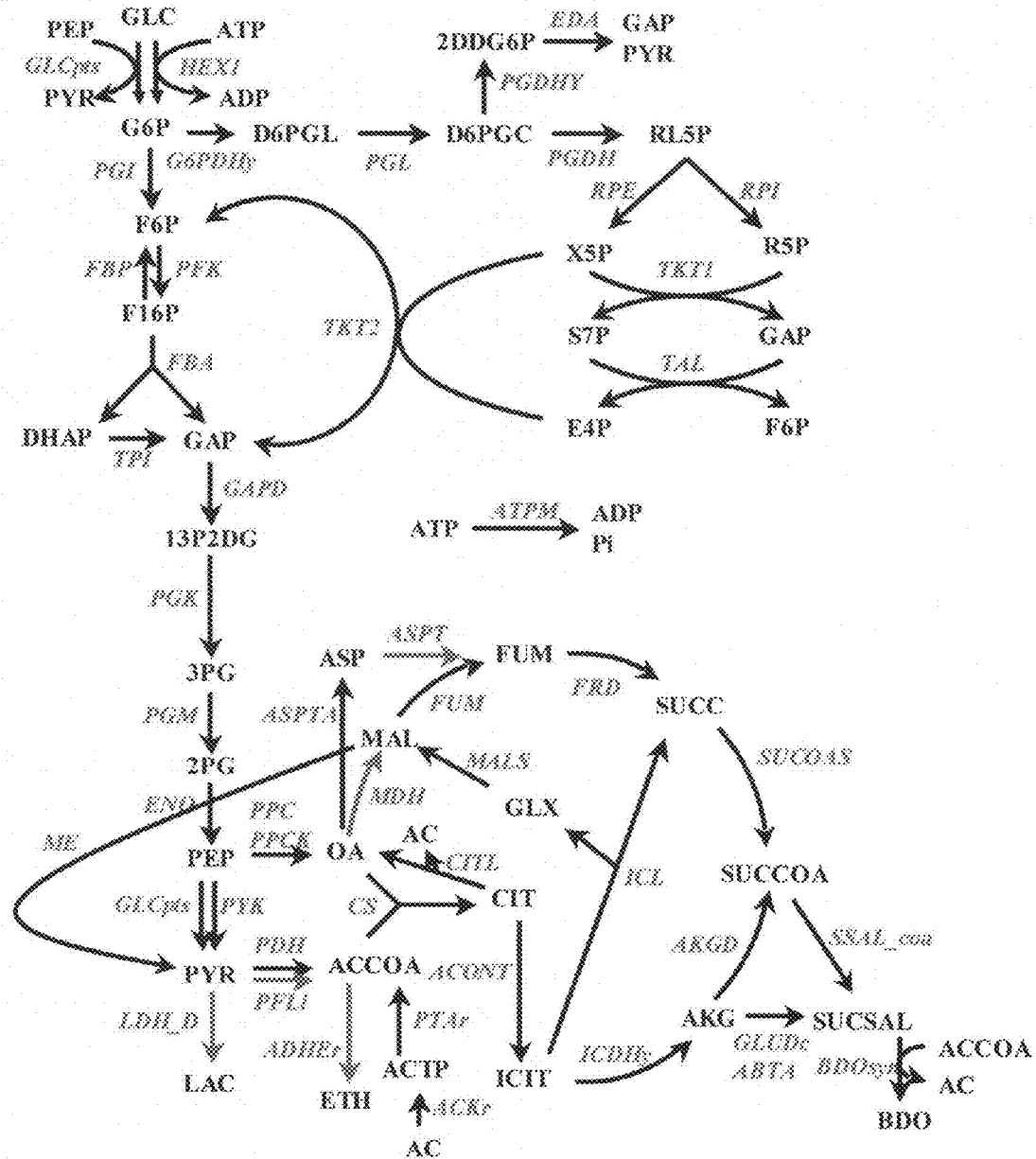
FIG. 8 shows a pictorial representation of *E. coli* central metabolism.

FIG. 8 and Table 12 depict the flux ranges that the *E. coli* network can attain while reaching either the maximum BDO yield (cases 1-4) or the maximum biomass yield (case 5) under anaerobic conditions. Cases 1 and 2 assume that no gene deletions have taken place. Case 2 exhibits tighter flux ranges than case 1 due to the fact that an additional constraint enforcing the maximum ATP yield at the maximum BDO yield is imposed. Cases 3 and 4 are analogous to cases 1 and 2 except that the fluxes encoding the reactions for ADHEr, ASPT, LDH_D, MDH, and PFLi have been set to zero. The flux ranges assuming biomass yield maximization in the presence of the ADHEr, ASPT, LDH_D, MDH, and PFLi knockouts are shown in case 5.

Table 12 shows achievable ranges of central metabolic fluxes under anaerobic conditions assuming PEP carboxykinase to be reversible. Bold flux values were set as constraints on the system. Five cases are considered: Case 1, maximum BDO yield of the wild-type network; Case 2, maximum ATP yield assuming the maximum BDO yield of the wild-type network; Case 3, maximum BDO yield of the network with fluxes through ADHEr, ASPT, LDH_D, MDH, and PFLi set to zero; Case 4, maximum ATP yield assuming the maximum BDO yield of the network with fluxes through ADHEr, ASPT, LDH_D, MDH, and PFLi set to zero; and Case 5, maximum biomass yield of the network with fluxes through ADHEr, ASPT, LDH_D, MDH, and PFLi set to zero.

TABLE 12

Achievable ranges of central metabolic fluxes under anaerobic conditions assuming PEP carboxykinase to be reversible. Reactions that are assumed inactive in cases 3, 4, and 5 are indicated with bold font.

| Reaction Abbreviation | CASE 1 | | CASE 2 | | CASE 3 | | CASE 4 | | CASE 5 | |
|---|---|---|---|---|---|---|---|---|---|---|
| | MIN | MAX | MIN | MAX | MIN | MAX | MIN | MAX | MIN | MAX |
| | mmol/gDW/hr | | | | | | | | | |
| GLCpts | 0.0 | 20.0 | 18.2 | 18.2 | 0.0 | 20.0 | 20.0 | 20.0 | 20.0 | 20.0 |
| HEX1 | 0.0 | 20.0 | 1.8 | 1.8 | 0.0 | 20.0 | 0.0 | 0.0 | 0.0 | 0.0 |
| G6PDHy | 0.0 | 27.3 | 0.0 | 0.0 | 0.0 | 15.3 | 0.0 | 0.0 | 0.0 | 0.0 |
| PGL | 0.0 | 27.3 | 0.0 | 0.0 | 0.0 | 15.3 | 0.0 | 0.0 | 0.0 | 0.0 |
| PGDH | 0.0 | 27.3 | 0.0 | 0.0 | 0.0 | 15.3 | 0.0 | 0.0 | 0.0 | 0.0 |
| RPE | −6.4 | 18.2 | 0.0 | 0.0 | −6.2 | 10.2 | 0.0 | 0.0 | −0.2 | −0.2 |
| RPI | −9.1 | 0.0 | 0.0 | 0.0 | −6.2 | 0.0 | 0.0 | 0.0 | −0.2 | −0.2 |
| TKT1 | −3.2 | 9.1 | 0.0 | 0.0 | −3.1 | 5.1 | 0.0 | 0.0 | −0.1 | −0.1 |
| TKT2 | −3.2 | 9.1 | 0.0 | 0.0 | −3.1 | 5.1 | 0.0 | 0.0 | −0.2 | −0.2 |
| TAL | −3.2 | 9.1 | 0.0 | 0.0 | −3.1 | 5.1 | 0.0 | 0.0 | −0.1 | −0.1 |
| EDA | 0.0 | 12.7 | 0.0 | 0.0 | 0.0 | 10.5 | 0.0 | 0.0 | 0.0 | 0.0 |
| PGDHY | 0.0 | 12.7 | 0.0 | 0.0 | 0.0 | 10.5 | 0.0 | 0.0 | 0.0 | 0.0 |
| PGI | −7.3 | 20.0 | 20.0 | 20.0 | 4.7 | 20.0 | 20.0 | 20.0 | 20.0 | 20.0 |
| FBP | 0.0 | 15.9 | 0.0 | 0.0 | 0.0 | 12.7 | 0.0 | 0.0 | 0.0 | 0.0 |
| PFK | 7.3 | 35.9 | 20.0 | 20.0 | 9.5 | 32.7 | 20.0 | 20.0 | 19.7 | 19.7 |
| FBA | 7.3 | 20.0 | 20.0 | 20.0 | 9.5 | 20.0 | 20.0 | 20.0 | 19.7 | 19.7 |
| TPI | 7.3 | 20.0 | 20.0 | 20.0 | 9.5 | 20.0 | 20.0 | 20.0 | 19.7 | 19.7 |
| GAPD | 27.3 | 40.0 | 40.0 | 40.0 | 29.5 | 40.0 | 40.0 | 40.0 | 39.3 | 39.3 |

TABLE 12-continued

Achievable ranges of central metabolic fluxes under anaerobic conditions assuming PEP carboxykinase to be reversible. Reactions that are assumed inactive in cases 3, 4, and 5 are indicated with bold font.

| Reaction Abbreviation | CASE 1 MIN | CASE 1 MAX | CASE 2 MIN | CASE 2 MAX | CASE 3 MIN | CASE 3 MAX | CASE 4 MIN | CASE 4 MAX | CASE 5 MIN | CASE 5 MAX |
|---|---|---|---|---|---|---|---|---|---|---|
| PGK | 27.3 | 40.0 | 40.0 | 40.0 | 29.5 | 40.0 | 40.0 | 40.0 | 39.3 | 39.3 |
| PGM | 27.3 | 43.6 | 40.0 | 40.0 | 29.5 | 43.6 | 40.0 | 40.0 | 39.0 | 39.0 |
| ENO | 27.3 | 43.6 | 40.0 | 40.0 | 29.5 | 43.6 | 40.0 | 40.0 | 39.0 | 39.0 |
| PYK | 0.0 | 29.5 | 0.0 | 0.0 | 0.0 | 29.5 | 1.8 | 1.8 | 10.7 | 10.7 |
| PDH | 0.0 | 34.5 | 14.5 | 18.2 | 12.0 | 34.5 | 21.8 | 21.8 | 30.1 | 30.1 |
| PFLi | 0.0 | 11.9 | 0.0 | 3.6 | 0.0 | 0.0 | 0.0 | 0.0 | 0.0 | 0.0 |
| PPC | 0.0 | 15.9 | 0.0 | 0.0 | 0.0 | 12.7 | 0.0 | 0.0 | 0.0 | 0.0 |
| PPCK | 5.5 | 51.4 | 21.8 | 21.8 | 5.5 | 30.9 | 18.2 | 18.2 | 8.1 | 8.1 |
| CS | 9.1 | 34.1 | 18.2 | 18.2 | 13.1 | 32.7 | 18.2 | 18.2 | 7.5 | 7.5 |
| CITL | 0.0 | 15.9 | 0.0 | 0.0 | 0.0 | 12.7 | 0.0 | 0.0 | 0.0 | 0.0 |
| ACONT | 9.1 | 21.8 | 18.2 | 18.2 | 13.1 | 21.8 | 18.2 | 18.2 | 7.5 | 7.5 |
| ICDHy | 1.8 | 21.4 | 18.2 | 18.2 | 1.8 | 21.3 | 14.5 | 14.5 | 0.2 | 0.2 |
| AKGD | 0.0 | 21.4 | 0.0 | 18.2 | 0.0 | 21.3 | 0.0 | 14.5 | 0.0 | 0.0 |
| SUCOAS | 0.5 | 20.0 | 3.6 | 3.6 | 0.6 | 20.0 | 7.3 | 7.3 | 14.9 | 14.9 |
| FRD | 0.0 | 12.7 | 3.6 | 3.6 | 0.0 | 8.7 | 3.6 | 3.6 | 7.5 | 7.5 |
| FUM | −55.5 | 12.7 | −14.5 | 3.6 | −5.1 | 8.7 | 3.6 | 3.6 | 7.2 | 7.2 |
| MDH | −50.9 | 33.2 | −14.5 | 3.6 | 0.0 | 0.0 | 0.0 | 0.0 | 0.0 | 0.0 |
| ICL | 0.0 | 18.2 | 0.0 | 0.0 | 0.0 | 18.2 | 3.6 | 3.6 | 7.2 | 7.2 |
| MALS | 0.0 | 16.4 | 0.0 | 0.0 | 0.0 | 16.4 | 3.6 | 3.6 | 7.2 | 7.2 |
| ME | 0.0 | 29.5 | 0.0 | 0.0 | 0.0 | 12.7 | 0.0 | 0.0 | 0.0 | 0.0 |
| ASPTA | 0.0 | 66.7 | 0.0 | 18.2 | 0.0 | 7.5 | 0.0 | 0.0 | 0.6 | 0.6 |
| ASPT | 0.0 | 66.7 | 0.0 | 18.2 | 0.0 | 0.0 | 0.0 | 0.0 | 0.0 | 0.0 |
| LDH_D | 0.0 | 0.0 | 0.0 | 0.0 | 0.0 | 0.0 | 0.0 | 0.0 | 0.0 | 0.0 |
| ADHEr | 0.0 | 0.0 | 0.0 | 0.0 | 0.0 | 0.0 | 0.0 | 0.0 | 0.0 | 0.0 |
| PTAr | 5.9 | 37.7 | 21.8 | 21.8 | 9.1 | 34.5 | 21.8 | 21.8 | 0.1 | 0.1 |
| ACKr | 5.9 | 37.7 | 21.8 | 21.8 | 9.1 | 34.5 | 21.8 | 21.8 | 0.1 | 0.1 |
| GLUDc | 0.0 | 21.4 | 0.0 | 18.2 | 0.0 | 21.3 | 0.0 | 14.5 | 0.0 | 0.0 |
| ABTA | 0.0 | 21.4 | 0.0 | 18.2 | 0.0 | 21.2 | 0.0 | 14.5 | 0.0 | 0.0 |
| SSAL_coa | 0.5 | 37.7 | 3.6 | 21.8 | 0.6 | 34.5 | 7.3 | 21.8 | 14.8 | 14.8 |
| ATPM | 0.0 | 15.9 | 15.9 | 15.9 | 0.0 | 12.7 | 12.7 | 12.7 | 7.6 | 7.6 |
| BDOsyn | 21.8 | 21.8 | 21.8 | 21.8 | 21.8 | 21.8 | 21.8 | 21.8 | 14.8 | 14.8 | l/hr

| | | | | | | | | | | |
|---|---|---|---|---|---|---|---|---|---|---|
| BIOMASS | 0.0 | 0.0 | 0.0 | 0.0 | 0.0 | 0.0 | 0.0 | 0.0 | 0.21 | 0.21 |

The first two four deletion designs (#92 and #93) listed in Table 7 (that is, PEP carboxykinase assumed reversible) were considered next due to their relatively high predicted BDO yields. Design #92 (ADHEr, HEX1, PFLi, and PGI) would need additional knockouts that eliminate succinate and lactate production and the maximum BDO yield of design #93 (ADHEr, EDA, NADH6, PGI) was only 90% of the theoretical maximum of the wild-type network. Both designs called for the removal of PGI which, as mentioned above, was ruled undesirable due to the anticipated importance of glycolysis on fermentation. Design #98 (ADHEr, ATPS4r, FDH2, NADH6) was the first four deletion design to require the removal of ATP synthase without additionally requiring the PGI knockout. However, this design would also require the deletion of genes to prevent lactate and succinate production in order to raise the predicted BDO yield at maximum growth. Upon further analysis, it was found that nearly all promising designs in Table 7 could be improved by ensuring that the deletions (i.e, ADHEr, LDH_D, MDH, ASPT, and PFLi) were also implemented if not already specified.

Figure 9:
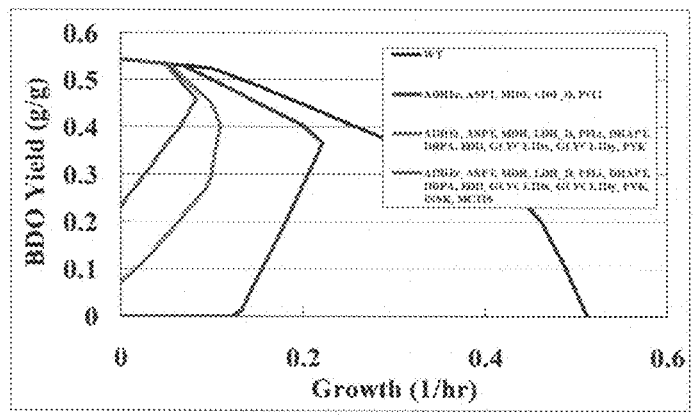
FIG. 9 shows the anaerobic growth rate versus BDO yield solution boundaries for an *E. coli* strain possessing the BDO production pathways shown and OptKnock predicted knockouts in FIG. 5 assuming PEP carboxykinase reversibility. A basis glucose uptake rate of 20 mmol/gDW/hr is assumed along with a non-growth associated ATP maintenance requirement of 7.6 mmol/gDW/hr.

Efforts were next focused on identifying reaction deletions that could supplement the core set (that is, ADHEr, LDH_D, MDH, ASPT, PFLi). Table 13 shows known *E. coli* genes responsible for catalyzing the reactions targeted for removal. The designation "[c]" refers to cytosolic. The genes encoding these reactions along with the reactions of the core set are provided in Table 13. The effect of the additional deletions on the BDO versus biomass solution boundaries is shown in FIG. 9. Notably, the coupling between BDO and biomass production becomes more and more pronounced as additional deletions are accumulated. The predicted BDO yield at maximum growth after accumulating all deletions is 0.46 g/g. Lastly, none of the deletions negatively impact the maximum theoretical BDO yield.

TABLE 13

Known *E. coli* genes responsible for catalyzing the reactions targeted for removal.

| Reaction Abbreviation | Reaction Stoichiometry | Genes Encoding the Enzyme(s) Catalyzing Each Reaction& |
|---|---|---|
| ADHEr | [c]: etoh + nad <==> acald + h + nadh<br>[c]: acald + coa + nad <==> accoa + h + nadh | (b0356 or b1478 or b1241)<br>(b1241 or b0351) |
| PFLi | [c]: coa + pyr --> accoa + for | (((b0902 and b0903) and b2579) or |

TABLE 13-continued

Known E. coli genes responsible for catalyzing the reactions targeted for removal.

| Reaction Abbreviation | Reaction Stoichiometry | Genes Encoding the Enzyme(s) Catalyzing Each Reaction& |
|---|---|---|
| | | (b0902 and b0903) or (b0902 and b3114) or (b3951 and b3952)) |
| MDH | [c]: mal-L + nad <==> h + nadh + oaa | b3236 |
| ASPT | [c]: asp-L --> fum + nh4 | b4139 |
| LDH_D | [c]: lac-D + nad <==> h + nadh + pyr | (b2133 or b1380) |
| DHAPT | [c]: dha + pep --> dhap + pyr | (b1200 and b1199 and b1198 and b2415 and b2416) |
| DRPA | [c]: 2dr5p --> acald + g3p | b4381 |
| PYK | [c]: adp + h + pep --> atp + pyr | (b1854 or b1676) |
| EDD | [c]: 6pgc --> 2ddg6p + h2o | b1851 |
| GLYCLTDx | [c]: glx + h + nadh --> glyclt + nad | (b3553 or b1033) |
| GLYCLTDy | [c]: glx + h + nadph --> glyclt + nadp | |
| MCITS | [c]: h2o + oaa + ppcoa --> 2mcit + coa + h | b0333 |
| INSK | [c]: atp + ins --> adp + h + imp | b0477 |

In the results shown in Table 13, OptKnock identifies reactions to be eliminated from an organism to enhance biochemical production. Any combination (that is, at least one and at most all) of the listed gene deletions could conceivably have the desired effect of ensuring that the corresponding reaction is non-functional in E. coli. The most practical experimental strategy for eliminating the reactions targeted for removal must be determined on a case-by-case basis.

Example VI

Generation of Engineered Strains

In order to validate the computational predictions of Example V, the strains are constructed, evolved, and tested. Escherichia coli K-12 MG1655 serves as the wild-type strain into which the deletions are introduced. The strains are constructed by incorporating in-frame deletions using homologous recombination via the λ Red recombinase system of (Datsenko and Wanner, Proc. Natl. Acad. Sci. USA 97:6640-6645 (2000)). The approach involves replacing a chromosomal sequence (that is, the gene targeted for removal) with a selectable antibiotic resistance gene, which itself is later removed. The knockouts are integrated one by one into the recipient strain. No drug resistance markers or scars will remain after each deletion, allowing accumulation of multiple mutations in each target strain. The deletion technology completely removes the gene targeted for removal so as to substantially reduce the possibility of the constructed mutants reverting back to the wild-type. During the initial stages of strain development, non-native genes enabling BDO production are expressed in a synthetic operon behind an inducible promoter on a medium- or high-copy plasmid; for example the PBAD promoter which is induced by arabinose, on a plasmid of the pBAD series (Guzman et al., J. Bacteriol. 177:4121-4130 (1995)). This promoter is known to be very easily titratable, allowing expression to be fine tuned over a 1000-fold range of arabinose concentrations. If BDO production is successful, these genes are then be integrated into the chromosome to promote stability.

The engineered strains are characterized by measuring growth rate, substrate uptake rate, and product/byproduct secretion rate. These strains are initially anticipated to exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several E. coli mutants that had been adaptively evolved on various substrates to reach the growth rates predicted a priori by an in silico model (Fong and Palsson, Nat. Genet. 36:1056-1058 (2004)). Should the OptKnock predictions prove successful, the growth improvements brought about by adaptive evolution are accompanied by enhanced rates of BDO production. Adaptive evolution is performed in triplicate (running in parallel) due to differences in the evolutionary patterns witnessed previously in E. coli (Fong and Palsson, supra, 2004; Fong et al., J. Bacteriol. 185:6400-6408 (2003); Ibarra et al., Nature 420:186-189 (2002)) that could potentially result in one strain having superior production qualities over the others. Evolutions iw run for a period of 2-6 weeks, depending on the rate of growth improvement obtained. In general, evolutions q43 stopped once a stable growth phenotype is obtained.

Following the adaptive evolution process, the new strains are again characterized by measuring growth rate, substrate uptake rate, and product/byproduct secretion rate. These results are compared to the OptKnock predictions by plotting actual growth and production yields along side the production described above. The most successful OptKnock design/evolution combinations are chosen to pursue further, and are characterized in lab-scale batch and continuous fermentations. The growth-coupled biochemical production concept behind the OptKnock approach salso results in the generation of genetically stable overproducers. Thus, the cultures are maintained in continuous mode for one month to evaluate long-term stability. Periodic samples are taken to ensure that yield and productivity are maintained throughout the process.

Example VII

OptKnock Strains for Production of BDO

As described in Examples V and VI, the application of the OptKnock methodology has been applied for generating promising deletion targets to generate BDO producing strains. OptKnock identifies reactions to be eliminated from an organism to couple the biochemical production and biomass yields. The designs provide a list of the metabolic reactions to be targeted for removal by OptKnock. The *E. coli* genes known to encode the enzymes that catalyze each reaction were also provided to describe which genetic modifications must be implemented to realize the predicted growth-coupled production phenotypes. Obviously, if new discoveries reveal that additional genes in the *E. coli* genome can confer one or more of the reaction functionalities targeted for removal in a given design, then these genes should be removed as well as the ones described herein. Note that preventing the activity of only a subset (that is, at least one and at most all) of the reactions in each of the designs may sometimes be sufficient to confer a growth-coupled producing phenotype. For example, if a design calls for the removal of a particular reaction whose activity in vivo is not sufficient to uncouple growth from BDO production, then the genes encoding the enzymes that catalyze this reaction can be left intact. In addition, any combination (that is, at least one and at most all) of the listed gene deletions for a given reaction could conceivably have the desired effect of ensuring that the reaction is non-functional in *E. coli*.

Multiple deletion strategies are listed in Table 6 and 7 for enhancing the coupling between 1,4-butanediol production and *E. coli* growth assuming PEP carboxykinase to be irreversible and reversible, respectively. One design (that is, ADHEr, ASPT, MDH, LDH_D, PFLi) emerged as the most promising upon satisfying multiple criteria. The suggested deletions 1) led to a high predicted BDO yield at maximum growth, 2) required a reasonable number of knockouts, 3) had no detrimental effect on the maximum theoretical BDO yield, 4) brought about a tight coupling of BDO production with cell growth, and 5) was robust with respect to the irreversibility/reversibility of PEP carboxykinase. The following list specifies the minimal set of required gene deletions predicted to render BDO the major fermentation product of *E. coli:* adhE (b1421), ldhA (b1380).

pflAB (b0902, b0903) is not included in the minimal set because its deletion forces a reliance on pyruvate dehydrogenase to provide sufficient acetyl-CoA for cell growth and one reducing equivalent from pyruvate. As pyruvate dehydrogenase activity is low under anaerobic conditions and inhibited by high NADH concentrations, a plausible alternative to the pflAB deletion is to add a non-native formate dehydrogenase to *E. coli* that can capture the reducing power that is otherwise lost via formate secretion. Nevertheless, adding pflAB to the minimal deletion set yields:

adhE (b1421), ldhA (b1380), pflAB (b0902, b0903).

mdh (b3236) is not included in the minimal set because there are multiple deletions capable of preventing succinate from becoming the major fermentation product of *E. coli* as opposed to BDO. Examples include the genes encoding fumarase and/or fumarate reductase. However, eliminating malate dehydrogenase appears to be the most logical choice to attenuate succinate production as it leaves intact a pathway for the conversion of the glyoxylate shunt product, malate, to BDO. Adding the malate dehydrogenase deletion to the minimal set above yields:

adhE (b1421), ldhA (b1380), pflAB (b0902, b0903), mdh (b3236).

The gene, mqo, which encodes a malate:quinone-oxidoreductase, is believed to catalyze the oxidation of malate to oxaloactate (van der Rest et al., *J. Bacteriol.* 182:6892-6899 (2000)). However, if it is shown to also catalyze the formation of malate from oxaloacetate, its removal will be necessary to ensure that it does not circumvent the mdh deletion. This leads to the deletion set:

adhE (b1421), ldhA (b1380), pflAB (b0902, b0903), mdh (b3236), mqo (b2210).

aspA is left out of the minimal set as it is questionable whether or not aspartate deaminase can carry enough flux to circumvent the malate dehydrogenase deletion. However, if this scenario is indeed possible, then the minimal list of required deletions becomes:

adhE (b1421), ldhA (b1380), pflAB (b0902, b0903), mdh (b3236), aspA (b4139).

For the calculations above, NADH and NADPH-dependent malic enzymes of *E. coli* were assumed to operate irreversibly catalyzing only the conversion of malate to carbon dioxide and pyruvate. If these enzymes can also catalyze the formation of malate from pyruvate and carbon dioxide, the genes encoding one or both malic enzymes will have to be removed to prevent succinate from becoming the major fermentation product. This leads to the following sets of deletions:

adhE (b1421), mdh (b3236), ldhA (b1380), pflAB (b0902, b0903), sfcA (b1479)

adhE (b1421), mdh (b3236), ldhA (b1380), pflAB (b0902, b0903), maeB (b2463)

adhE (b1421), mdh (b3236), ldhA (b1380), pflAB (b0902, b0903), sfcA (b1479), maeB (b2463)

The minimal set of deletions can be supplemented with additional deletions aimed at tightening the coupling of BDO production to cell growth. These sets of the deletions are listed below.

adhE (b1421), ldhA (b1380), pflAB (b0902, b0903), mdh (b3236), pntAB (b1602, b1603)

adhE (b1421), ldhA (b1380), pflAB (b0902, b0903), mdh (b3236), gdhA (b1761)

adhE (b1421), ldhA (b1380), pflAB (b0902, b0903), mdh (b3236), pykA (b1854), pykF (b1676), dhaKLM (b1198, b1199, b1200), deoC (b4381), edd (b1851), yiaE (b3553), ycdW (b1033) adhE (b1421), ldhA (b1380), pflAB (b0902, b0903), mdh (b3236), pykA (b1854), pykF (b1676), dhaKLM (b1198, b1199, b1200), deoC (b4381), edd (b1851), yiaE (b3553), ycdW (b1033), prpC (b0333), gsk (b0477)

Strains possessing the deletions listed in this Example can be supplemented with additional deletions if it is found that the suggested deletions do not reduce the activity of their corresponding reactions to the extent required to attain growth coupled BDO production or if native *E. coli* genes, through adaptive evolution or mutagenesis, attain mutations conferring activities capable of circumventing the proposed design strategies.

Throughout this application various publications have been referenced within parentheses. The disclosures of these publications in their entireties are hereby incorporated by reference in this application in order to more fully describe the state of the art to which this invention pertains. Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring *Escherichia coli* microorganism comprising a set of metabolic modifications, said set of metabolic modifications comprising disruption of genes encoding alcohol dehydrogenase, malate dehydrogenase, aspartate transaminase, lactate dehydrogenase and succinyl- CoA synthetase, wherein said microorganism expresses heterologous enzymes that provide production of 1,4-butanediol.

2. The non-naturally occurring microorganism of claim 1, wherein one or more of said gene disruptions comprise a deletion of one or more of said genes.

3. The non-naturally occurring microorganism of claim 2, wherein each of said gene disruptions comprise a deletion.

4. A method of producing 1,4-butanediol, comprising:
   (a) culturing the non-naturally occurring microorganism of claim 1; and
   (b) isolating 1,4-butanediol produced from said non-naturally occurring microorganism.

5. The method of claim 4, wherein one or more of said gene disruptions comprise a deletion of one or more of said genes.

6. The method of claim 5, wherein each of said gene disruptions comprise a deletion.

* * * * *